US012387819B2

(12) United States Patent
Mouliere et al.

(10) Patent No.: US 12,387,819 B2
(45) Date of Patent: Aug. 12, 2025

(54) ENHANCED DETECTION OF TARGET DNA BY FRAGMENT SIZE ANALYSIS

(71) Applicant: Cancer Research Technology Limited, London (GB)

(72) Inventors: Florent Mouliere, London (GB); Dineika Chandrananda, London (GB); Anna Piskorz, London (GB); James Brenton, London (GB); Nitzan Rosenfeld, London (GB)

(73) Assignee: Cancer Research Technology Limited, London (GB)

( * ) Notice: Subject to any disclaimer, the term of this patent is extended or adjusted under 35 U.S.C. 154(b) by 1104 days.

(21) Appl. No.: 17/290,924

(22) PCT Filed: Nov. 7, 2019

(86) PCT No.: PCT/EP2019/080506
§ 371 (c)(1),
(2) Date: May 3, 2021

(87) PCT Pub. No.: WO2020/094775
PCT Pub. Date: May 14, 2020

(65) Prior Publication Data
US 2023/0014674 A1    Jan. 19, 2023

(30) Foreign Application Priority Data
Nov. 7, 2018    (GB) .................................... 1818159

(51) Int. Cl.
*G16B 40/20*    (2019.01)
*C12N 15/10*    (2006.01)
(Continued)

(52) U.S. Cl.
CPC ......... *G16B 40/20* (2019.02); *C12N 15/1093* (2013.01); *G16B 30/00* (2019.02);
(Continued)

(58) Field of Classification Search
CPC ........ G16B 40/20; G16B 30/00; G16B 40/00; C12N 15/1093; G16H 10/40; G16H 50/20; G16H 50/70; G16H 70/60; C12Q 1/6886

See application file for complete search history.

(56) References Cited

U.S. PATENT DOCUMENTS

2018/0307796 A1   10/2018  Jiang et al.
2019/0287645 A1*   9/2019  Abdueva ................ G16B 30/10
(Continued)

FOREIGN PATENT DOCUMENTS

WO    WO 2018/009723 A1    1/2018
WO    WO-2019222657 A1 *   11/2019    .............. A61P 35/00

OTHER PUBLICATIONS

Hovelson, Daniel. Precision Oncology Opportunities and Disease Insights From Next-Generation-Sequencing Profiling of Routine Clinical Biospecimens. Diss. 2017. (Year: 2017).*
(Continued)

*Primary Examiner* — Jesse P Frumkin
(74) *Attorney, Agent, or Firm* — Wolf, Greenfield & Sacks, P.C.

(57) ABSTRACT

The present invention provides a computer-implemented method for detecting variant nucleic acid from a cell-free nucleic acid-containing sample. The method comprises (a) providing data representing fragment sizes of nucleic acid fragments obtained from said sample and/or representing a measure of deviation from copy number neutrality of the nucleic acid fragments obtained from said sample; b) processing the data from step a) according to a classification algorithm, wherein said classification algorithm operates to classify sample data into one of at least a first class containing the variant nucleic acid and a second class not containing the variant nucleic acid, based on a plurality of cell-free nucleic acid fragment size features and/or a devia-
(Continued)

tion from copy number neutrality feature; and c) outputting the classification of the sample from step b, thereby determining whether the sample contains the variant nucleic acid or not, or a probability that the sample contains the variant nucleic acid. Related methods are also provided.

18 Claims, 32 Drawing Sheets

(51) Int. Cl.
　　　G16B 30/00　　　(2019.01)
　　　G16H 10/40　　　(2018.01)
　　　G16H 50/20　　　(2018.01)
　　　G16H 50/70　　　(2018.01)
　　　G16H 70/60　　　(2018.01)

(52) U.S. Cl.
　　　CPC .............. *G16H 10/40* (2018.01); *G16H 50/20* (2018.01); *G16H 50/70* (2018.01); *G16H 70/60* (2018.01)

(56) References Cited

U.S. PATENT DOCUMENTS

2021/0002728 A1*　1/2021　Landau .................. G16B 20/00
2021/0174958 A1*　6/2021　Drake .................... G16H 20/10

OTHER PUBLICATIONS

Kurtz, David M. Personalized Risk Assessment and Disease Monitoring in Non-Hodgkin Lymphoma from Circulating Tumor DNA. Diss. Stanford University, 2017. (Year: 2017).*
Lapin, Morten, et al. "Fragment size and level of cell-free DNA provide prognostic information in patients with advanced pancreatic cancer." Journal of translational medicine 16 (2018): 1-10. (Year: 2018).*
PCT/EP2019/080506, Feb. 26, 2020, International Search Report and Written Opinion.
PCT/EP2019/080506, May 20, 2021, International Preliminary Report on Patentability.
International Preliminary Report on Patentability for International Application No. PCT/EP2019/080506 mailed May 20, 2021.
Abbosh et al., Phylogenetic ctDNA analysis depicts early-stage lung cancer evolution. Nature. May 25, 2017;545(7655):446-51.
Adalsteinsson et al., Scalable whole-exome sequencing of cell-free DNA reveals high concordance with metastatic tumors. Nature communications. Nov. 6, 2017;8(1):1324. 13 pages.
Belic et al., Rapid identification of plasma DNA samples with increased ctDNA levels by a modified FAST-SeqS approach. Clinical chemistry. Jun. 1, 2015;61(6):838-49.
Best et al., RNA-Seq of tumor-educated platelets enables blood-based pan-cancer, multiclass, and molecular pathway cancer diagnostics. Cancer cell. Nov. 9, 2015;28(5):666-76.
Best et al., Swarm intelligence-enhanced detection of non-small-cell lung cancer using tumor-educated platelets. Cancer cell. Aug. 14, 2017;32(2):238-52.
Bettegowda et al., Detection of circulating tumor DNA in early-and late-stage human malignancies. Science translational medicine. Feb. 19, 2014;6(224):224ra24-. 12 pages.
Bronkhorst et al., Characterization of the cell-free DNA released by cultured cancer cells. Biochimica et Biophysica Acta (BBA)-Molecular Cell Research. Jan. 1, 2016;1863(1):157-65.
Burnham et al., Single-stranded DNA library preparation uncovers the origin and diversity of ultrashort cell-free DNA in plasma. Scientific reports. Jun. 14, 2016;6(1):27859. 9 pages.
Chandrananda et al., High-resolution characterization of sequence signatures due to non-random cleavage of cell-free DNA. BMC medical genomics. Dec. 2015;8:1-9.

Chaudhuri et al., Early detection of molecular residual disease in localized lung cancer by circulating tumor DNA profiling. Cancer discovery. Dec. 1, 2017;7(12):1394-403.
Cohen et al., Detection and localization of surgically resectable cancers with a multi-analyte blood test. Science. Feb. 23, 2018;359(6378):926-30. 5 pages.
Dawson et al., Analysis of circulating tumor DNA to monitor metastatic breast cancer. New England Journal of Medicine. Mar. 28, 2013;368(13):1199-209.
Diehl et al., Circulating mutant DNA to assess tumor dynamics. Nature medicine. Sep. 2008;14(9):985-90.
Diehl et al., Detection and quantification of mutations in the plasma of patients with colorectal tumors. Proceedings of the National Academy of Sciences. Nov. 8, 2005;102(45):16368-73.
Forshew et al., Noninvasive identification and monitoring of cancer mutations by targeted deep sequencing of plasma DNA. Science translational medicine. May 30, 2012;4(136):136ra68-. 13 pages.
Genovese et al., Clonal hematopoiesis and blood-cancer risk inferred from blood DNA sequence. New England Journal of Medicine. Dec. 25, 2014;371(26):2477-87.
Giacona et al., Cell-free DNA in human blood plasma: length measurements in patients with pancreatic cancer and healthy controls. Pancreas. Jul. 1, 1998;17(1):89-97.
Hanahan et al., Hallmarks of cancer: the next generation. cell. Mar. 4, 2011;144(5):646-74.
Haque et al., Challenges in using ctDNA to achieve early detection of cancer. BioRxiv. Dec. 21, 2017:237578. 20 pages.
Heitzer et al., Tumor-associated copy number changes in the circulation of patients with prostate cancer identified through whole-genome sequencing. Genome medicine. Dec. 2013;5(4):1-6.
Hu et al., False-positive plasma genotyping due to clonal hematopoiesis. Clinical Cancer Research. Sep. 15, 2018;24(18):4437-43.
Jahr et al., DNA fragments in the blood plasma of cancer patients: quantitations and evidence for their origin from apoptotic and necrotic cells. Cancer research. Feb. 2, 2001;61(4):1659-65.
Jiang et al., The long and short of circulating cell-free DNA and the ins and outs of molecular diagnostics. Trends in Genetics. Jun. 1, 2016;32(6):360-71.
Jiang et al., Lengthening and shortening of plasma DNA in hepatocellular carcinoma patients. Proceedings of the National Academy of Sciences. Mar. 17, 2015;112(11):E1317-25.
Li et al., Fast and accurate short read alignment with Burrows-Wheeler transform. bioinformatics. Jul. 15, 2009;25(14):1754-60.
Lo et al., Maternal plasma DNA sequencing reveals the genome-wide genetic and mutational profile of the fetus. Science translational medicine. Dec. 8, 2010;2(61):61ra91-. 14 pages.
Lun et al., Noninvasive prenatal diagnosis of monogenic diseases by digital size selection and relative mutation dosage on DNA in maternal plasma. Proceedings of the National Academy of Sciences. Dec. 16, 2008;105(50):19920-5.
Macintyre et al., Copy number signatures and mutational processes in ovarian carcinoma. Nature genetics. Sep. 2018;50(9):1262-70.
Minarik et al., Utilization of benchtop next generation sequencing platforms ion torrent PGM and MiSeq in noninvasive prenatal testing for chromosome 21 trisomy and testing of impact of in silico and physical size selection on its analytical performance. PloS one. Dec. 15, 2015;10(12):e0144811. 12 pages.
Mouliere et al., Multi-marker analysis of circulating cell-free DNA toward personalized medicine for colorectal cancer. Molecular oncology. Jul. 1, 2014;8(5):927-41.
Mouliere et al., High fragmentation characterizes tumour-derived circulating DNA. PloS one. Sep. 6, 2011;6(9):e23418. 10 pages.
Murtaza et al., Non-invasive analysis of acquired resistance to cancer therapy by sequencing of plasma DNA. Nature. May 2, 2013;497(7447):108-12.
Newman et al., Integrated digital error suppression for improved detection of circulating tumor DNA. Nature biotechnology. May 2016;34(5):547-55.
Parkinson et al., Exploratory analysis of TP53 mutations in circulating tumour DNA as biomarkers of treatment response for patients with relapsed high-grade serous ovarian carcinoma: a retrospective study. PLoS medicine. Dec. 20, 2016;13(12):e1002198. 25 pages.

(56) References Cited

OTHER PUBLICATIONS

Patel et al., Association of plasma and urinary mutant DNA with clinical outcomes in muscle invasive bladder cancer. Scientific reports. Jul. 17, 2017;7(1):5554. 12 pages.
Riediger et al., Mutation analysis of circulating plasma DNA to determine response to EGFR tyrosine kinase inhibitor therapy of lung adenocarcinoma patients. Scientific reports. Sep. 19, 2016;6(1):33505. 8 pages.
Routy et al., Gut microbiome influences efficacy of PD-1-based immunotherapy against epithelial tumors. Science. Jan. 5, 2018;359(6371):91-7. 8 pages.
Scheinin et al., DNA copy number analysis of fresh and formalin-fixed specimens by shallow whole-genome sequencing with identification and exclusion of problematic regions in the genome assembly. Genome research. Dec. 1, 2014;24(12):2022-32.
Siravegna et al., Integrating liquid biopsies into the management of cancer. Nature reviews Clinical oncology. Sep. 2017;14(9):531-48.
Snyder et al., Cell-free DNA comprises an in vivo nucleosome footprint that informs its tissues-of-origin. Cell. Jan. 14, 2016;164(1):57-68.
Stover et al., Association of cell-free DNA tumor fraction and somatic copy number alterations with survival in metastatic triple-negative breast cancer. Journal of Clinical Oncology. Feb. 2, 2018;36(6):543. 21 pages.
Thierry et al., Origins, structures, and functions of circulating DNA in oncology. Cancer and metastasis reviews. Sep. 2016;35:347-76.
Tie et al., Circulating tumor DNA analysis detects minimal residual disease and predicts recurrence in patients with stage II colon cancer. Science translational medicine. Jul. 6, 2016;8(346):346ra92-. 11 pages.
Ulz et al., Inferring expressed genes by whole-genome sequencing of plasma DNA. Nature genetics. Oct. 2016;48(10):1273-8.
Umetani et al., Prediction of breast tumor progression by integrity of free circulating DNA in serum. Journal of clinical oncology. Sep. 10, 2006;24(26):4270-6.
Underhill et al., Fragment length of circulating tumor DNA. PLoS genetics. Jul. 18, 2016;12(7):e1006162. 24 pages.
Wan et al., Liquid biopsies come of age: towards implementation of circulating tumour DNA. Nature Reviews Cancer. Apr. 2017;17(4):223-38.
Yu et al., Size-based molecular diagnostics using plasma DNA for noninvasive prenatal testing. Proceedings of the National Academy of Sciences. Jun. 10, 2014;111(23):8583-8.
Zill et al., The landscape of actionable genomic alterations in cell-free circulating tumor DNA from 21,807 advanced cancer patients. Clinical Cancer Research. Aug. 1, 2018;24(15):3528-38.
International Search Report and Written Opinion for International Application No. PCT/EP2019/080506 mailed Feb. 26, 2020.
Adalsteinsson et al., Scalable whole-exome sequencing of cell-free DNA reveals high concordance with metastatic tumors. Nature communications. Nov. 6, 2017;8(1):1-26. Together with Supplemental Materials available at https://www.nature.com/articles/s41467-017-00965-y:521 pages.
Mouliere et al., Selecting short DNA fragments in plasma improves detection of circulating tumour DNA. BioRxiv. Jan. 1, 2017:134437. Together with Supplemental Materials available at https://www.biorxiv.org/content/10.1101/134437v1:364 pages.
Underhill et al., Fragment length of circulating tumor DNA. PLoS genetics. Jul. 18, 2016;12(7):e1006162. 29 pages.

* cited by examiner

ENHANCED DETECTION OF TARGET DNA BY FRAGMENT SIZE ANALYSIS

RELATED APPLICATIONS

This Application is a National Stage filing under 35 U.S.C. § 371 of International Patent Application Serial No. PCT/EP2019/080506, filed Nov. 7, 2019, which claims priority from British Application No. GB1818159.4, filed Nov. 7, 2018, each of which is incorporated by reference herein in its entirety.

FIELD OF THE INVENTION

The present invention relates in part to methods for detecting the presence of target DNA, such as circulating tumour DNA (ctDNA) from, e.g., a cell-free DNA (cfDNA) source, such as blood plasma or other biological fluid. In particular, the methods of the invention find use in the diagnosis, treatment and especially monitoring of cancer.

BACKGROUND TO THE INVENTION

Blood plasma of cancer patients contains circulating tumor DNA (ctDNA), but this valuable source of information is diluted by much larger quantities of DNA of non-cancerous origins: ctDNA therefore represents only a small fraction of the total cell-free DNA (cfDNA) (1, 2). High-depth targeted sequencing of selected genomic regions can be used to detect low levels of ctDNA, but broader analysis with methods such as whole exome sequencing (WES) and shallow whole genome sequencing (sWGS) are only generally informative when ctDNA levels are ~10% or greater (3-5). The concentration of ctDNA can exceed 10% of the total cfDNA in patients with advanced-stage cancers (6-8), but is much lower in patients with low tumor burden (9-12) and in patients with some cancer types such as gliomas and renal cancers (6). Current strategies to improve ctDNA detection rely on increasing depth of sequencing coupled with various error-correction methods (2, 13, 14). However, approaches that focus only on mutation analysis do not take advantage of the potential differences in chromatin organization or fragment size in ctDNA (15-17). Results of ever-deeper sequencing are also confounded by the likelihood of false positive results from detection of mutations from non-cancerous cells or clonal expansions in normal epithelia, or clonal hematopoiesis of indeterminate potential (CHIP) (13, 18, 19).

The cell of origin and the mechanism of cfDNA release into blood can mark cfDNA with specific fragmentation signatures, potentially providing precise information about cell type, gene expression, oncogenic potential or action of treatment (15, 16, 20). cfDNA fragments commonly show a prominent mode at 167 bp, suggesting release from apoptotic caspase-dependent cleavage (21-24). Circulating fetal DNA has been shown to be shorter than maternal DNA in plasma, and these size differences have been used to improve sensitivity of non-invasive prenatal diagnosis (22, 25-27). The size distribution of tumor-derived cfDNA has only been investigated in a few studies, encompassing a small number of cancer types and patients, and shows conflicting results (28-33). A limitation of previous studies is that determining the specific sizes of tumor-derived DNA fragments requires detailed characterization of matched tumor-derived alterations (30, 33), and the broader understanding and implications of potential biological differences have not previously been explored. Mouliere, Pikorz, Chandrananda, Moore et al., 2017, BioRxiv Preprint, doi: dx.doi.org/10.1101/134437 reports that selecting short fragments in plasma improves detection of circulating tumour DNA (ctDNA) in patients having recurrent high-grade serous ovarian cancer.

While detection of ctDNA shows promise in the field of cancer care, there remains an unmet need for methods and systems that maximise signal-to-noise ratio in the context of ctDNA detection. A related problem is the need to distinguish somatic cancer mutations from mutations present in non-cancerous cells, clonal expansions of normal epithelia or CHIP. The present invention seeks to provide solutions to these needs and provides further related advantages.

BRIEF DESCRIPTION OF THE INVENTION

The present inventors hypothesised that differences in fragment lengths of circulating DNA could be exploited to enhance sensitivity for detecting the presence of ctDNA and for non-invasive genomic analysis of cancer. As described in detail herein, analysis of size-selected cfDNA identified clinically actionable mutations and copy number alterations that were otherwise not detected. Identification of patients with advanced cancer was improved by predictive models integrating fragment length and copy number analysis of cfDNA with AUC>0.99 compared to AUC<0.80 without fragmentation features. Increased detection of ctDNA from patients with glioma, renal and pancreatic cancer patients was achieved with AUC>0.91, compared to AUC<0.5 without fragmentation features. Detection of ctDNA from glioma, which does not metastasize beyond the central nervous system (CNS) has previously been reported to be very challenging (6). Fragment-size analysis and selective sequencing of specific fragment sizes can boost ctDNA detection, and could be an alternative to deeper mutation sequencing for clinical applications, earlier diagnosis and to study tumor biology.

Accordingly, in a first aspect the present invention provides a computer-implemented method for detecting variant nucleic acid (e.g. DNA or RNA) from a cell-free nucleic acid (e.g. DNA or RNA)-containing sample, comprising:
  a) providing data representing fragment sizes of nucleic acid fragments obtained from said sample and/or representing a measure of deviation from copy number neutrality of the nucleic acid fragments obtained from said sample;
  b) causing a processor of the computer to process the data from step a) according to a classification algorithm that has been trained on a training set comprising a plurality of samples of cell-free nucleic acid containing the variant nucleic acid and a plurality of samples not containing the variant nucleic acid, wherein said classification algorithm operates to classify sample data into one of at least two classes, the at least two classes comprising a first class containing the variant nucleic acid and a second class not containing the variant nucleic acid, based on a plurality of cell-free nucleic acid fragment size features and/or a deviation from copy number neutrality feature; and
  c) outputting the classification of the sample from step b) and thereby determining whether the sample contains the variant nucleic acid or not, or determining a probability that the sample contains the variant nucleic acid.

In some embodiments the cell-free nucleic acid-containing sample is a cell-free DNA (cfDNA)-containing sample, and wherein the variant nucleic acid is variant DNA. In particular, the variant DNA may be selected from the group consisting of: circulating tumour DNA (ctDNA), circulating bacterial DNA, circulating pathogen DNA, circulating mitochondrial DNA, circulating foetal DNA, circulating DNA derived from a donor organ or donor tissue, circulating DNA release by a cell or tissue with an altered physiology, circulating extra chromosomal DNA, and a double minute of circular DNA. In a particularly preferred embodiment the variant DNA is ctDNA.

In some embodiments the data representing fragment sizes of the nucleic acid fragments (e.g. DNA or RNA fragments) comprise fragment sizes inferred from sequence reads, fragment sizes determined by fluorimetry, or fragment sizes determined by densitometry.

In some embodiments the present invention provides a computer-implemented method for detecting variant DNA from a cell-free DNA (cfDNA)-containing sample, comprising:

a) providing sequence data representing fragment sizes of cfDNA fragments obtained from said sample and/or representing a measure of deviation from copy number neutrality of the cfDNA fragments obtained from said sample;

b) causing a processor of the computer to process the sequence data from step a) according to a classification algorithm that has been trained on a training set comprising a plurality of samples of cfDNA containing the variant DNA and a plurality of samples not containing the variant DNA, wherein said classification algorithm operates to classify sample data into one of at least two classes, the at least two classes comprising a first class containing the variant DNA and a second class not containing the variant DNA, based on a plurality of cfDNA fragment size features and/or a deviation from copy number neutrality feature; and c) outputting the classification of the sample from step b) and thereby determining whether the sample contains the variant DNA or not, or determining a probability that the sample contains the variant DNA. As described in the Examples herein, classification algorithms can learn from cfDNA fragmentation features and somatic copy number alterations (SCNAs) analysis and improve the detection of ctDNA with a relatively low-cost and shallow sequencing approach. Moreover, the cfDNA fragmentation features and/or SCNAs analysis can be leveraged to classify cancer and healthy samples with high accuracy.

In some embodiments the classification algorithm operates to classify sample data into one of said at least two, three, four, or at least five classes based on at least a plurality of cfDNA fragment size features selected from the group consisting of:

(i) the proportion of fragments in the size range 20-150 bp (P20-150);

(ii) the proportion of fragments in the size range 100-150 bp (P100-150);

(iii) the proportion of fragments in the size range 160-180 bp (P160-180);

(iv) the proportion of fragments in the size range 180-220 bp (P180-220);

(v) the proportion of fragments in the size range 250-320 bp (P250-320);

(vi) the ratio of the proportions P(20-150)/P(160-180);

(vii) the ratio of the proportion P(100-150) divided by the proportion of fragment in the size range 163-169 bp;

(viii) the ratio of the proportions P(20-150)/P180-220); and (ix) the amplitude oscillations in fragment size density with 10 bp periodicity. It will be appreciated that the sequence data representing fragment sizes of cfDNA fragments in step a) includes the cfDNA fragment size features used by the classification algorithm.

In some embodiments the plurality of cfDNA fragment size features comprise: P(160-180), P(180-220), P(250-320) and the amplitude oscillations in fragment size density with 10 bp periodicity. As described in the Examples herein, both a linear and a non-linear machine learning algorithm independently identified the same four fragment size features P(160-180), P(180-220), P(250-320) and the amplitude oscillations in fragment size density with 10 bp periodicity, along with the SCNA feature (i.e. trimmed Median Absolute Deviation from copy number neutrality (t-MAD) score), albeit with some differences in the rank order of the features. Classification with high accuracy was obtained using only the four fragmentation features (see FIG. 26).

In some embodiments the classification algorithm operates to classify sample data into one of said at least two classes based on at least a deviation from copy number neutrality feature which is a trimmed Median Absolute Deviation from copy number neutrality (t-MAD) score or an ichorCNA feature.

ichorCNA is a tool for estimating the fraction of tumor in cell-free DNA from ultra-low-pass whole genome sequencing (ULP-WGS, 0.1× coverage). The code for ichorCNA is available at the following URL: github.com/broadinstitute/ichorCNA. ichorCNA uses a probabilistic model, implemented as a hidden Markov model (HMM), to simultaneously segment the genome, predict large-scale copy number alterations, and estimate the tumor fraction of a ultra-low-pass whole genome sequencing sample (ULP-WGS). The methodology and probabilistic model are described in: Adalsteinsson, Ha, Freeman, et al. Scalable whole-exome sequencing of cell-free DNA reveals high concordance with metastatic tumors. (2017) Nature Communications November 6; 8(1):1324. doi: 10.1038/s41467-017-00965-y (the contents of which are incorporated herein by reference). The analysis workflow consists of 2 tasks:

GC-Content Bias Correction (Using HMMcopy)
  a. Computing read coverage from ULP-WGS
  b. Data correction and normalization
CNA Prediction and Estimation of Tumor Fraction of cfDNA.

In particular, when the deviation from copy number neutrality feature comprise a t-MAD score, the score may be determined by trimming regions of genome that exhibit high copy number variability in whole genome datasets derived from healthy subjects and then calculating the median absolute deviation from $\log_2 R=0$ of the non-trimmed regions of the genome.

In some embodiments in accordance with the present invention the classification algorithm performs random forests (RF) analysis, logistic regression (LR) analysis, or support vector machine (SVM) analysis. The classification algorithm may provide an output that is a probability of correct classification, e.g., a probability that the sample in question has been classified correctly to the healthy class or cancerous class per the training set on which the classification algorithm has been trained.

In some embodiments the performance of the classification algorithm when trained on the training set is assessed by the area under the curve (AUC) value from a receiver operating characteristic (ROC) analysis. Generally the classification algorithm model showing the highest AUC value is selected as having the best performance.

In some embodiments the classification algorithm has been trained on a training set comprising at least 10, 20, 30, 40 or at least 50 samples from healthy subjects and at least 10, 20, 30, 40 or at least 50 samples from subjects known to have a cancer. In particular, the samples employed in the training set may be those shown in Table 2.

In some embodiments the sequence data provided in step a) represent whole-genome sequence (WGS) reads, Tailored Panel Sequencing (TAPAS) sequence reads, Integration of Variant Reads (INVAR) TAPAS (see co-pending patent application GB1803596.4 filed 6 Mar. 2018, incorporated herein by reference), hybrid-capture sequence reads, Tagged-Amplicon Deep Sequencing (TAm-Seq) reads, focused-exome sequence reads or whole-exome sequence reads. In particular, the sequence data provided in step a) may represent shallow whole-genome sequence (sWGS) reads, optionally 0.4× depth WGS reads.

In some embodiments the data provided in step a) represent fragment sizes of multiple nucleic acid fragments (e.g. DNA fragments) from a substantially cell-free liquid sample from a subject having or suspected as having a cancer.

In some embodiments the sequence data provided in step a) represent sequence reads of multiple DNA fragments from a substantially cell-free liquid sample from a subject having or suspected as having a cancer.

In some embodiments, the cancer may be selected from melanoma, lung cancer, cholangiocarcinoma, bladder cancer, oesophageal cancer, colorectal cancer, ovarian cancer, glioma, pancreatic cancer, renal cancer and breast cancer.

In some embodiments the sample is a plasma sample, a urine sample, a saliva sample, a cerebrospinal fluid sample, a serum sample or other nucleic acid containing (e.g. DNA-containing) biological liquid sample.

In some embodiments, wherein the variant DNA is ctDNA, the method is for detecting the presence of, growth of, prognosis of, regression of, treatment response of, or recurrence of a cancer in a subject from which the sample has been obtained.

In some embodiments the presence of ctDNA in the sample is distinguished from cfDNA containing somatic mutations of non-cancerous origin. It is specifically contemplated herein that including fragment size information on each read may enhance mutation calling algorithms from high depth sequencing so as to distinguish tumour-derived mutations from other sources of somatic variants (including clonal expansions of non-cancerous cells) or background sequencing noise. In certain embodiments the method may distinguish variant sequence reads representing clonal expansions of normal epithelia or clonal haematopoiesis of indeterminate potential (CHIP) from variant sequence reads representing ctDNA.

In certain embodiments the fragment size data provided in step a) represent sequence reads of multiple DNA fragments from a substantially cell-free liquid sample from a subject and wherein the method is for determining whether the sample contains ctDNA or contains cfDNA from CHIP. In particular, the classification algorithm may have been trained on a training set further comprising a plurality of samples of cfDNA obtained from subjects having CHIP, and wherein said at least two classes further comprise a third class containing CHIP-derived cfDNA based on a plurality of cfDNA fragment size features and/or a deviation from copy number neutrality feature.

In a second aspect the present invention provides a method for detecting variant nucleic acid from a cell-free nucleic acid-containing sample, comprising:

analysing a cell-free nucleic acid-containing sample, or a library derived from a cell-free nucleic acid-containing sample, wherein the sample has been obtained from a subject, to determine fragment sizes of nucleic acid fragments in said sample or said library; and
carrying out the method of the first aspect of the invention using the fragment sizes.

In some embodiments said analysing comprises:
sequencing nucleic acids from the nucleic acid-containing sample or the library and inferring fragment sizes from the sequence reads;
measuring fragment sizes of nucleic acids from the nucleic acid-containing sample or the library by fluorimetry; and/or
measuring fragment sizes of nucleic acids from the nucleic acid-containing sample or the library by densitometry.

In some embodiments the present invention provides a method for detecting variant DNA from a cell-free DNA (cfDNA)-containing sample, comprising:
sequencing a cfDNA-containing sample, or a library derived from a cfDNA-containing sample, that has been obtained from a subject to obtain a plurality of sequence reads;
processing the sequence reads to determine sequence data representing fragment sizes of cfDNA fragments obtained from said sample and/or representing a measure of deviation from copy number neutrality of the cfDNA fragments obtained from said sample; and
carrying out the method of the first aspect of the invention using the sequence data.

In some embodiments the sequencing comprises generating a sequencing library from the sample and performing whole-genome sequencing, Tailored Panel Sequencing (TAPAS) sequencing, hybrid-capture sequencing, TAm-Seq sequencing, focused-exome sequencing or whole-exome sequencing, optionally generating an indexed sequencing library and performing shallow whole genome sequencing (e.g. to a depth of 0.4×).

In some embodiments processing the sequence reads comprises one or more of the following steps:
aligning sequence reads to a reference genome of the same species as the subject (e.g. the human reference genome GRCh37 for a human subject);
removal of contaminating adapter sequences;
removal of PCR and optical duplicates;
removal of sequence reads of low mapping quality; and
if multiplex sequencing, de-multiplexing by excluding mismatches in sequencing barcodes.

In some embodiments the variant DNA is selected from the group consisting of: circulating tumour DNA (ctDNA), circulating bacterial DNA, circulating pathogen DNA, circulating mitochondrial DNA, circulating foetal DNA, and circulating DNA derived from a donor organ or donor tissue, circulating DNA release by a cell or tissue with an altered physiology, circulating extra chromosomal DNA, and a double minute of circular DNA.

In some embodiments processing the sequence reads to determine sequence data representing fragment sizes of cfDNA fragments obtained from said sample and/or representing a measure of deviation from copy number neutrality of the cfDNA fragments obtained from said sample comprises determining one or more (e.g. 2, 3, 4, 5 or more) features selected from the group consisting of:
(i) the proportion of fragments in the size range 20-150 bp (P20-150);

(ii) the proportion of fragments in the size range 100-150 bp (P100-150);
(iii) the proportion of fragments in the size range 160-180 bp (P160-180);
(iv) the proportion of fragments in the size range 180-220 bp (P180-220);
(v) the proportion of fragments in the size range 250-320 bp (P250-320);
(vi) the ratio of the proportions P(20-150)/P(160-180);
(vii) the ratio of the proportion P(100-150) divided by the proportion of fragment in the size range 163-169 bp;
(viii) the ratio of the proportions P(20-150)/P180-220); and
(ix) the amplitude oscillations in fragment size density with 10 bp periodicity.

In some embodiments the plurality of cfDNA fragment size features comprise: P(160-180), P(180-220), P(250-320) and the amplitude oscillations in fragment size density with 10 bp periodicity.

In some embodiments the fragment sizes of cfDNA fragments are inferred from sequence reads using the mapping locations of the read ends in the genome following alignment of the sequence reads with the reference genome of the species from which the sample was obtained.

In some embodiments processing the sequence reads to determine sequence data representing a measure of deviation from copy number neutrality of the cfDNA fragments obtained from said sample comprises determining a trimmed Median Absolute Deviation from copy number neutrality (t-MAD) score or an ichorCNA score. In particular, the t-MAD score may be determined by trimming regions of genome that exhibit high copy number variability in whole genome datasets derived from healthy subjects and then calculating the median absolute deviation from $\log_2 R=0$ of the non-trimmed regions of the genome.

In some embodiments the sample contains multiple DNA fragments from a substantially cell-free liquid from a subject having or suspected as having a cancer. In particular cases, the cancer may be selected from melanoma, lung cancer, cholangiocarcinoma, bladder cancer, oesophageal cancer, colorectal cancer, ovarian cancer, glioma, pancreatic cancer, renal cancer and breast cancer.

In some embodiments the sample is a plasma sample, a urine sample, a saliva sample, a cerebrospinal fluid sample, a serum sample or other DNA-containing biological liquid sample.

In accordance with any aspect of the present invention the sample may be or may have been subjected to one or more processing steps to remove whole cells, for example by centrifugation.

In certain embodiments, wherein the variant DNA is ctDNA, the method may be for detecting the presence of, growth of, prognosis of, regression of, treatment response of, or recurrence of a cancer in a subject from which the sample has been obtained.

In some embodiments the presence of ctDNA is distinguished from the presence of cfDNA containing somatic mutations of non-cancerous origin, optionally from CHIP origin.

In some embodiments a somatic mutation containing cfDNA fragment is classified as being of tumour origin or being of CHIP origin based on a plurality of fragment size features determined from the sequence reads.

In some embodiments the variant DNA is ctDNA and the classification of the sample as containing ctDNA or not, or the determined probability that the sample contains ctDNA is used to predict whether said sample or a further sample from the same subject will be susceptible to further ctDNA analysis.

In some cases the further ctDNA analysis comprises sequencing to a greater sequencing depth and/or targeted sequencing of ctDNA in said sample.

In some embodiments, when the probability that the sample contains ctDNA as determined by the classification algorithm is at least 0.5 (e.g. at least 0.6 or at least 0.75), the sample is subjected to said further ctDNA analysis.

In some embodiments:
said sample is a plasma sample and the probability that the sample contains ctDNA as determined by the classification algorithm is used to determine whether ctDNA will be detectable in a urine sample; or
said sample is a urine sample and wherein the probability that the sample contains ctDNA as determined by the classification algorithm is used to determine whether ctDNA will be detectable in a plasma sample. As shown in Example 8, a relatively high probability shown by the classification algorithm that a plasma sample contains ctDNA was associated with an increased probability that useful detection of ctDNA was possible with a urine sample (see also FIG. 27).

In a third aspect the present invention provides a method for improving the detection of circulating tumour DNA (ctDNA) in a cell-free DNA (cfDNA) containing sample, comprising performing an in vitro and/or in silico size selection to enrich for DNA fragments of less than 167 bp in length and/or to enrich for DNA fragments in the size range 250 to 320 bp. In some embodiments the size selection is to enrich for DNA fragments in the range 90 to 150 bp in length. In some cases the size selection may comprise excluding high molecular weight DNA such as that derived from white blood cells when the sample comprises a serum sample.

In some embodiments the sample may have been obtained from a subject having or suspected as having a cancer selected from the group consisting of melanoma, cholangiocarcinoma, colorectal cancer, glioma, pancreatic cancer, renal cancer and breast cancer.

In some embodiments the size selection comprises an in vitro size selection that is performed on DNA extracted from a cfDNA containing sample and/or is performed on a library created from DNA extracted from a cfDNA containing sample. In particular, the in vitro size selection may comprise agarose gel electrophoresis.

In some embodiments the size selection comprises an in silico size selection that is performed on sequence reads.

In particular cases the sequence reads may comprise paired-end reads generated by sequencing DNA from both ends of the fragments present in a library generated from the cfDNA containing sample. The original length of the DNA fragments in the cfDNA containing sample may be inferred using the mapping locations of the read ends in the genome following alignment of the sequence reads with the reference genome of the species from which the sample was obtained (e.g. the human reference genome GRCh37 for a human subject).

In some embodiments DNA fragments outside the range 90 to 150 bp in length are substantially excluded (see, e.g., FIG. 6B).

In some embodiments the size selection is performed on a genome wide basis or an exome wide basis. As described herein, the present inventors identified size differences between mutant an non-mutant cfDNA on a genome-wide and pan-cancer scale in contrast to previous studies that were limited to specific genomic loci, cancer types or cases (30, 32, 33).

In certain embodiments the in vitro size selection is performed prior to shallow whole genome sequencing (sWGS) or the in silico size selection is performed on sWGS sequencing reads.

In certain embodiments the method further comprises performing somatic copy number aberration analysis and/or mutation calling on the sequence reads subsequent to the size selection. In particular cases somatic copy number aberration analysis may comprise processing the sequence reads to determine a trimmed Median Absolute Deviation from copy number neutrality (t-MAD) score or an ichorCNA score. For example, the t-MAD score may be determined by trimming regions of genome that exhibit high copy number variability in whole genome datasets derived from healthy subjects and then calculating the median absolute deviation from $\log_2 R=0$ of the non-trimmed regions of the genome.

In certain embodiments somatic copy number aberration analysis may comprise detecting amplifications in one or more genes selected from NF1, TERT, and MYC. As described in the Examples herein, analysis of plasma cfDNA after size selection revealed a large number of SCNAs that were not observed in the same samples without size selection.

In certain embodiments mutation calling comprises detecting mutations in one or more genes selected from BRAF, ARID1A, and NF1. As described in the Examples herein, size selection enriched the mutant allele fraction (MAF) for nearly all mutations.

In some embodiments the cancer is a high ctDNA cancer selected from the group consisting of: colorectal, cholangiocarcinoma, breast and melanoma.

In some embodiments the cancer is a low ctDNA cancer selected from the group consisting of: pancreatic cancer, renal cancer and glioma.

In certain embodiments the sample may be a plasma sample, a urine sample, a saliva sample, a cerebrospinal fluid sample, a serum sample or other DNA-containing biological liquid sample.

In some embodiments the method further comprises detecting the presence of, growth of, prognosis of, regression of, treatment response of, or recurrence of a cancer in a subject from which the sample has been obtained. Improving the detection of ctDNA, mutation calling and/or SCNA detection in accordance with the methods of this aspect of the invention may assist with the early detection of cancer and with ongoing cancer monitoring, and may inform treatment strategies.

In some embodiments the method may carried out on a sample obtained prior to a cancer treatment of the subject and on a sample obtained following the cancer treatment of the subject. As described herein, size selected samples indicated tumour progression 69 and 87 days before detection by imaging or non-size selected t-MAD analysis (see FIGS. 10E and F).

In accordance with any aspect of the present invention, the subject may be a human, a companion animal (e.g. a dog or cat), a laboratory animal (e.g. a mouse, rat, rabbit, pig or non-human primate), a domestic or farm animal (e.g. a pig, cow, horse or sheep).

Preferably, the subject is a human patient. In some cases, the subject is a human patient who has been diagnosed with, is suspected of having or has been classified as at risk of developing, a cancer.

Embodiments of the present invention will now be described by way of example and not limitation with reference to the accompanying figures. However various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
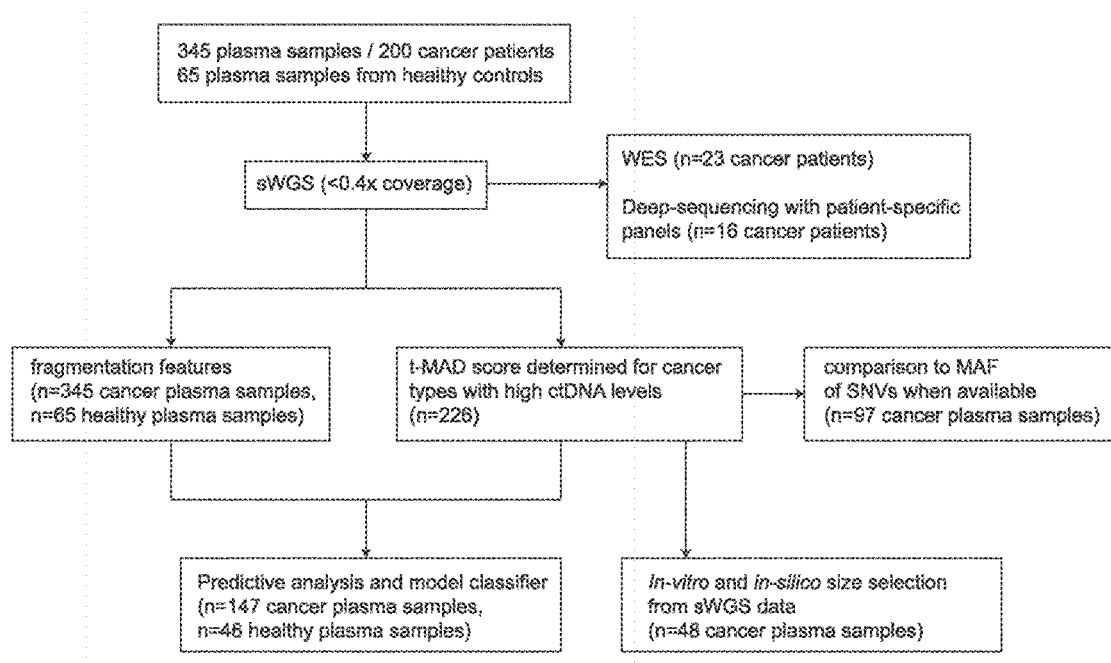
FIG. 1 shows a flowchart summarizing the different experiments done in this study and the corresponding samples numbers used at each step.

Aspects and embodiments of the present invention will now be discussed with reference to the accompanying figures. Further aspects and embodiments will be apparent to those skilled in the art. All documents mentioned in this text are incorporated herein by reference.

In describing the present invention, the following terms will be employed, and are intended to be defined as indicated below.

"Computer-implemented method" where used herein is to be taken as meaning a method whose implementation involves the use of a computer, computer network or other programmable apparatus, wherein one or more features of the method are realised wholly or partly by means of a computer program.

A "sample" as used herein may be a biological sample, such as a cell-free DNA sample, a cell (including a circulating tumour cell) or tissue sample (e.g. a biopsy), a biological fluid, an extract (e.g. a protein or DNA extract obtained from the subject). In particular, the sample may be a tumour sample, a biological fluid sample containing DNA, a blood sample (including plasma or serum sample), a urine sample, a cervical smear, a cerebrospinal fluid sample, or a non-tumour tissue sample. It has been found that urine and cervical smears contains cells, and so may provide a suitable sample for use in accordance with the present invention. Other sample types suitable for use in accordance with the present invention include fine needle aspirates, lymph nodes, surgical margins, bone marrow or other tissue from a tumour microenvironment, where traces of tumour DNA may be found or expected to be found. The sample may be one which has been freshly obtained from the subject (e.g. a blood draw) or may be one which has been processed and/or stored prior to making a determination (e.g. frozen, fixed or subjected to one or more purification, enrichment or extractions steps, including centrifugation). The sample may be derived from one or more of the above biological samples via a process of enrichment or amplification. For example, the sample may comprise a DNA library generated from the biological sample and may optionally be a barcoded or otherwise tagged DNA library. A plurality of samples may be taken from a single patient, e.g. serially during a course of treatment. Moreover, a plurality of samples may be taken from a plurality of patients. Sample preparation may be as described in the Materials and Methods section herein.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.
Providing Sequence Reads The sequence reads data may be provided or obtained directly, e.g., by sequencing the cfDNA sample or library or by obtaining or being provided with sequencing data that has already been generated, for example by retrieving sequence read data from a non-volatile or volatile computer memory, data store or network location. Where the sequence reads are obtained by sequencing a sample, the median mass of input DNA may in some cases be in the range 1-100 ng, e.g., 2-50 ng or 3-10 ng. The DNA may be amplified to obtain a library having, e.g. 100-1000 ng of DNA. The sequence reads may be in a suitable data format, such as FASTQ.
Sequence Data Processing and Error Suppression The sequence read data, e.g., FASTQ files, may be subjected to one or more processing or clean-up steps prior to or as part of the step of reads collapsing into read families. For example, the sequence data files may be processed using one or more tools selected from as FastQC v0.11.5, a tool to remove adaptor sequences (e.g. cutadapt v1.9.1). The sequence reads (e.g. trimmed sequence reads) may be aligned to an appropriate reference genome, for example, the human reference genome GRCh37 for a human subject.

As used herein "read" or "sequencing read" may be taken to mean the sequence that has been read from one molecule and read once. Each molecule can be read any number of times, depending on the sequencing performed.

"Classifier" or "classification algorithm" may be a model or algorithm that maps input data, such as a cfDNA fragment size features, to a category, such as cancerous or non-cancerous origin. In some embodiments, the present invention provides methods for detecting, classifying, prognosticating, or monitoring cancer in subjects. In particular, data obtained from sequence analysis, such as fragment length and/or copy number (e.g. trimmed median absolute deviation from copy-number neutrality "t-MAD") of may be evaluated using one or more pattern recognition algorithms. Such analysis methods may be used to form a predictive model, which can be used to classify test data. For example, one convenient and particularly effective method of classification employs multivariate statistical analysis modelling, first to form a model (a "predictive mathematical model") using data ("modelling data") from samples of known category (e.g., from subjects known to have a particular cancer), and second to classify an unknown sample (e.g., "test sample") according to category.

Pattern recognition is the use of multivariate statistics, both parametric and non-parametric, to analyse data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. However, this type of approach may not be suitable for developing a clinical assay that can be used to classify samples derived from subjects independent of the initial sample population used to train the prediction algorithm.

The other approach is termed "supervised" whereby a training set of samples with known class or outcome is used to produce a mathematical model which is then evaluated with independent validation data sets. Here, a "training set" of sequence information, e.g. fragmentation features and/or copy number features, is used to construct a statistical model that predicts correctly the class of each sample. This training set is then tested with independent data (referred to as a test or validation set) to determine the robustness of the computer-based model. These models are sometimes termed "expert systems," but may be based on a range of different mathematical procedures such as support vector machine (SVM), decision trees, k-nearest neighbour and naïve Bayes, each of which are contemplated herein for use in accordance with the present invention. As detailed in the Examples herein, logistic regression (LR) and Random Forests (RF) were used for variable selection and the classification of samples as "healthy" or "cancer". Supervised methods can use a data set with reduced dimensionality (for example, the first few principal components), but typically use unreduced data, with all dimensionality. The robustness of the predictive models can also be checked using cross-validation, by leaving out selected samples from the analysis.

Tailored Panel Sequencing (TAPAS)

As used herein tailored panel sequencing refers to sequencing of targeted regions and/or genes. This may employ selected or custom capture panels that target genes of interest, such as genes commonly mutated in cancer and/or genes found to carry mutations in a tumour of the subject of interest (e.g. identified by sequencing matched tumor tissue DNA and plasma DNA samples). In some cases the capture panels may range in size from 0.5-5 Mb, e.g. 1-3 Mb.

The following is presented by way of example and is not to be construed as a limitation to the scope of the claims.

EXAMPLES

Materials and Methods

Study Design 344 plasma samples from 200 patients with multiple cancer types, and 65 plasma samples from 65 healthy controls, were collected. Among the patients, 172 individuals were recruited through prospective clinical studies at Addenbrooke's Hospital, Cambridge, UK, approved by the local research ethics committee (REC reference numbers: 07/Q0106/63; and NRES Committee East of England—Cambridge Central 03/018). Written informed consent was obtained from all patients and blood samples were collected before and after initiation of treatment with surgery or chemotherapeutic agents. DNA was extracted from 2 mL of plasma using the QIAamp circulating nucleic acid kit (Qiagen) or QIAsymphony (Qiagen) according to the manufacturer's instructions. In addition, 28 patients were recruited as part of the Copenhagen Prospective Personalized Oncology (CoPPO) program (Ref: PMID: 25046202) at Rigshospitalet, Copenhagen, Denmark, approved by the local research ethics committee. Baseline tumor tissue biopsies were available from all 28 patients, together with re-biopsies collected at relapse from two patients, including matched plasma samples. Brain tumor patients were recruited at the Addenbrooke's Hospital, Cambridge, UK, as part of the BLING study (REC-15/EE/0094). Bladder cancer patients were recruited at the Netherlands Cancer Institute, Amsterdam, The Netherlands, and approval was in accordance with national guidelines (N13KCM/CFMPB250) (47). 65 plasma samples were obtained from healthy control individuals using a similar protocol (Seralab). Plasma samples were freeze-thawed no more than 2 times to reduce artifactual fragmentation of cfDNA. FIG. 1 describes the study as a flowchart.

In Vitro Size Selection

Between 8-20 ng of DNA were loaded into a 3% agarose cassette (HTC3010, Sage Bioscience) and size selection was performed on a PippinHT (Sage Bioscience) according to the manufacturer's protocol. Quality controls of in vitro size selection were performed on 20 healthy controls samples. Duplicate reads observed with in vitro selection were removed for any downstream size selection analysis. A QC metric called the median absolute pairwise difference (MAPD) algorithm was used to determine the sequencing noise. MAPD measured the absolute difference between the log 2 CN ratios of every pair of neighboring bins and determined the median across all bins. Higher MAPD scores reflected greater noise, typically associated with poor-quality samples. All samples exhibited a MAPD score of 0.01 (+−0.01), irrespective of the size selection condition.

TAm-Seq

Tagged-Amplicon Deep Sequencing libraries were prepared as previously described (34), using primers designed to assess single nucleotide variants (SNV) and small indels across selected hotspots and the entire coding regions of TP53. Libraries were sequenced using MiSeq or HiSeq 4000 (Illumina).

Shallow Whole Genome Sequencing (sWGS)

Indexed sequencing libraries were prepared using commercially available kits (ThruPLEX-Plasma Seq and/or Tag-Seq, Rubicon Genomics). Libraries were pooled in equimolar amounts and sequenced to <0.4× depth of coverage on a HiSeq 4000 (Illumina) generating 150-bp paired-end reads. Sequence data were analyzed using an in-house pipeline. Paired end sequence reads were aligned to the human reference genome (GRCh37) using BWA-mem following the removal of contaminating adapter sequences (48). PCR and optical duplicates were marked using MarkDuplicates (Picard Tools) feature and these were excluded from downstream analysis along with reads of low mapping quality and supplementary alignments. When necessary, reads were down-sampled to 10 million in all samples for comparison purposes.

Somatic Copy Number Aberration Analysis

The analysis was performed in R using a software suite for shallow Whole Genome Sequencing copy number analysis named CNAclinic (github.com/sdchandra/CNAclinic) as well as the QDNAseq pipeline (49). Sequencing reads were randomly sampled to 10 million reads per dataset and allocated into equally sized (30 Kbp) non-overlapping bins throughout the length of the genome. Read counts in each bin were corrected to account for sequence GC content and mappability. Bins overlapping 'blacklisted' regions (derived from the ENCODE Project and the 1000 Genomes Project database) prone to artefacts were excluded from downstream analysis. Read counts in test samples were normalized by the counts from an identically processed healthy individual and log 2 transformed to obtained copy number ratio values per genomic bin. Read counts in healthy controls were normalized by their median genome-wide count. Bins were then segmented using both Circular Binary Segmentation and Hidden Markov Model algorithms. An averaged $\log_2$ R value per bin was calculated.

An in-house empirical blacklist of aberrant read count regions was constructed. Firstly, 65 sWGS datasets from healthy plasma were used to calculate median read counts per 30 Kbp genomic bin as a function of GC content and mappability. A 2D LOESS surface was then applied and the difference between the actual count and the LOESS fitted values were calculated. The median of these residual values across the 65 controls were calculated per genomic bin and regions with median residuals greater than 4 standard deviations were blacklisted. The averaged segmental $\log_2$ R values in each test sample that overlap this cfDNA blacklist were trimmed and the median absolute value was calculated. This score was defined as the trimmed median absolute deviation (t-MAD) from $\log_2$ R=0. The R code to reproduce this analysis is provided in github.com/sdchandra/tMAD (incorporated herein by reference in its entirety).

Whole Exome Sequencing (WES)

Indexed sequencing libraries were prepared as described above (see Methods, sWGS). Plasma DNA libraries from each sample were made and pooled together for exome capture (TruSeq Exome Enrichment Kit, Illumina). Pools were concentrated using a SpeedVac vacuum concentrator (Eppendorf). Exome enrichment was performed following the manufacturer's protocol. Enriched libraries were quantified using quantitative PCR (KAPA library quantification, KAPA Biosystems), and DNA fragments sizes observed by Bioanalyzer (2100 Bioanalyzer, Agilent Genomics) and pooled in equimolar ratios for paired-end next generation sequencing on a HiSeq4000 (Illumina). Sequencing reads were de-multiplexed allowing zero mismatches in barcodes. Paired-end alignment to the GRCh37 reference genome was performed using BWA-mem for all exome sequencing data (germline/plasma/tumor tissue DNA). PCR duplicates were marked using Picard. Base quality score recalibration and local realignment were performed using Genome Analysis Tool Kit (GATK).

Mutation Calling

Mutation allele fractions (MAFs) for each single-base locus were calculated with MuTect2 for all bases with PHRED quality ≥30. Filtering parameters were then applied so that a mutation was called if no mutant reads for an allele were observed in germline DNA at a locus that was covered at least 10×, and if at least 4 reads supporting the mutant were found in the plasma data with at least 1 read on each strand (forward and reverse). At loci with <10× coverage in normal DNA and no mutant reads, mutations were called in plasma if a prior plasma sample showed no evidence of a mutation and was covered adequately (10× or more). A method called Integrated Signal Amplification for Non-invasive Interrogation of Tumors was used to aggregate mutations called before and after size selection. This method combined different subsets of mutations called from the same plasma DNA sample using different processing approaches. The mutation aggregation as used in this study was formalized as follows: aggregated mutations=mutations detected without size selection U (mutations detected with in vitro size selection U mutations detected with in silico size selection).

In Silico Size Selection

Paired-end reads are generated by sequencing DNA from both ends of the fragments present in the library. The original length of the DNA can be inferred using the mapping locations of the read ends in the genome. Once alignment is complete, Samtools software is used to select paired reads that correspond to fragment lengths in a specific range. Mutect2 is used to call mutations from this in silico size selected data as described in the previous section.

Tumor-Guided Capture Sequencing

Matched tumor tissue DNA and plasma DNA samples of 19 patients collected from the RigsHospitalet (Copenhagen, Denmark) with advanced cancer were sequenced by WES. Variants were called from these samples by mutation calling (see above). Hybrid-based capture for longitudinal plasma samples analysis were designed to cover these variants for each patient using SureDesign (Agilent). A median of 160 variants were included per patient, and in addition, 41 common genes of interest for pan-cancer analysis were included in the tumor-guided sequencing panel. Indexed sequencing libraries were prepared as per sWGS (see above). Plasma DNA libraries from each sample were made and pooled together for tumor-guided capture sequencing (SureSelect, Agilent). Pools were concentrated using a SpeedVac vacuum concentrator (Eppendorf). Capture enrichment was performed following the manufacturer's protocol. Enriched libraries were quantified using quantitative PCR (KAPA library quantification, KAPA Biosystems), and DNA fragments sizes controlled by Bioanalyzer (2100 Bioanalyzer, Agilent Genomics) and pooled in equimolar ratio for paired-end next generation sequencing on a HiSeq4000 (Illumina). Sequencing reads were de-multiplexed allowing zero mismatches in barcodes. Paired-end alignment to the GRCh37 reference genome was performed using BWA-mem for all exome sequencing data including germline, plasma and tumor tissue DNA where generated. PCR duplicates were marked using Picard. Base quality score recalibration and local realignment were performed using Genome Analysis Tool Kit (GATK).

Classification Analysis

The preliminary analysis was carried out on 304 samples (182 high ctDNA cancer samples, 57 low ctDNA cancer samples and 65 healthy controls). For each sample the following features were calculated from sWGS data: t-MAD, amplitude_10 bp, P(20-150), P(160-180), P(20-150)/P(160-180), P(100-150), P(100-150)/P(163-169), P(180-220), P(250-320), P(20-150)/P(180-220) (see Table 2). The data was arranged in a matrix where the rows represent each sample and the columns held the aforementioned features with an extra "class" column with the binary labels of "cancer"/"healthy". The following analysis was carried out in R utilising RandomForest, caret, and pROC packages. The caret package is available and is described at the following URL: topepo.github.io/caret/index.html. Exemplary source code for the classification algorithms described in the Examples herein is shown below in the section headed "Code". The pairwise correlations between the features were calculated to assess multi-collinearity in the dataset. A single variable was selected for removal from pairs with Pearson correlation >0.75. Highly correlated fragmentation features that were composite of individual variables already in the dataset such as P(20-150)/P(180-220), were prioritized for removal. The features were also assessed for zero variance and linear dependencies but none were flagged. After this pre-processing the following 5 variables were selected for further analysis: t-MAD, amplitude_10 bp, P(160-180), P(180-220) and P(250-320) (see Table 2). All 57 low ctDNA samples were set aside for validation of the models. The data matrix for the remaining high ctDNA cancer samples and healthy controls (n=247) were randomly partitioned in a 60:40 split into 1 training and 1 validation dataset with the different cancer types and healthy samples represented in similar proportions. Hence, the training data contained 153 samples (cancer=114, healthy=39) while the first validation set of high ctDNA cancers contained 94 samples (cancer=68, healthy=26). This validation dataset was only utilized for final assessment of the classifiers.

Classification of samples as healthy or cancer was performed using one linear and one non-linear machine learning algorithm, namely logistic regression (LR), and random forest (RF). Each algorithm was paired with recursive feature selection in order to identify the best predictor variables. This analysis was carried out with caret within the framework of 5 repeats of 10-fold cross-validation on the training set. The algorithm was configured to explore all possible subsets of the features. The optimal model for each classifier was selected using ROC metric. Separately, a logistic regression model was trained only using t-MAD as a predictor in order to assess the difference in performance without the addition of fragmentation features. Finally, the 68 high ctDNA cancer samples, 57 low ctDNA cancer samples and 26 healthy controls set aside for validation were used to test the classifiers, utilizing area under the curve in a ROC analysis to quantify their performance.

A secondary analysis was carried out on the same training and validation cohorts with the only difference being the features used in the model. Here, we tested predictive ability of fragmentation features without the addition of information from SCNAs (i.e. t-MAD). Hence the features utilized were: amplitude_10 bp, P(160-180), P(180-220) and P(250-320).

Quantification of the 10 bp Periodic Oscillation

The amplitude of the 10 bp periodic oscillation observed in the size distribution of cfDNA samples was determined from the sWGS data as follows. Local maxima and minima in the range 75 bp to 150 bp were identified. The average of their positions across the samples was calculated (for minima: 84, 96, 106, 116, 126, 137, 148, and maxima: 81, 92, 102, 112, 122, 134, 144). To compute the amplitude of the oscillations with 10 bp periodicity observed below 150 bp, the sum of the minima were subtracted from the sum of the heights of the maxima. The larger this difference, the more distinct the peaks. The height of the x bp peak is defined as the number of fragments with length x divided by the total number of fragments. To define local maxima, y positions were selected such that y was the largest value in the interval [y−2, y+2]. The same rationale was used to pick minima.

Example 1: Surveying the Fragmentation Features of Tumour cfDNA

A catalogue of cfDNA fragmentation features was generated using 344 plasma samples from 200 patients with 18 different cancer types, and an additional 65 plasma samples from healthy controls (FIG. 1 and FIG. 2A). The size distribution of cfDNA fragments in cancer patients differed in the size ranges of 90-150 bp, 180-220 bp and 250-320 bp compared to healthy individuals (FIG. 2B and FIG. 3). cfDNA fragment sizes in plasma of healthy individuals, and in plasma of patients with late stage glioma, renal, pancreatic and bladder cancers, were significantly longer than in other late stage cancer types including breast, ovarian, lung, melanoma, colorectal and cholangiocarcinoma (p<0.001, Kruskal-Wallis; FIG. 2C). Sorting the 18 cancer types according to the proportion of cfDNA fragments in the size range 20-150 bp was very similar to ordering by Bettegowda et al. based on the concentrations of ctDNA measured by individual mutation assays (FIG. 2D) (6). In contrast to previous reports (6, 34), this sorting analysis was performed without any prior knowledge of the presence of mutations or somatic copy number alterations (SCNAs), yet allowed the investigation of ctDNA content in different cancers.

Example 2: Sizing Up Mutant ctDNA

Figure 4:
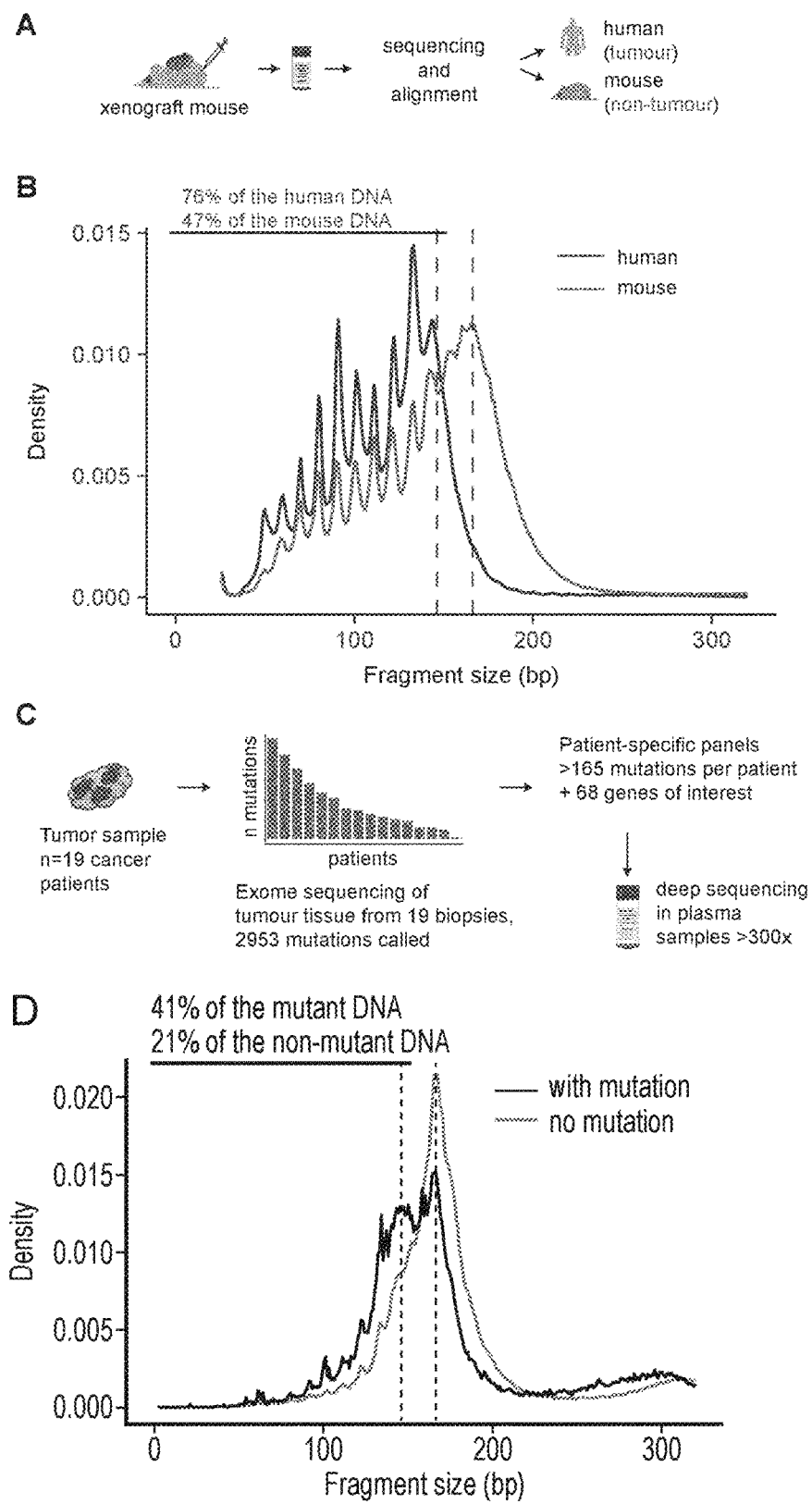
FIG. 4 depicts the determination of the size profile of mutant ctDNA with animal models and personalized capture sequencing. A, A mouse model with xenografted human tumor cells enabled the discrimination of DNA fragments released by cancer cells (reads aligning to the human genome) from the DNA released by healthy cells (reads aligning to the mouse genome), with the use of sWGS. B, Fragment size distribution, from the plasma extracted from a mouse xenografted with a human ovarian tumor, showing ctDNA originating from tumor cells and cfDNA from non-cancerous cells. Two vertical lines indicate 145 bp and 167 bp. The fraction of reads shorter than 150 bp is indicated. C, Design of personalized hybrid-capture sequencing panels developed to specifically determine the size profiles of mutant DNA and non-mutant DNA in plasma from 19 patients with late stage cancers. Capture panels included somatic mutations identified in tumor tissue by WES. A mean of 165 mutations per patient were then analyzed from matched plasma samples. Reads were aligned and separated into fragments that carry either the reference or the mutant sequence. Fragment sizes for paired-end reads were calculated. D, Size profiles of mutant DNA and non-mutant DNA in plasma from 19 patients with late stage cancers were determined by tumor-guided capture sequencing. The fraction of reads shorter than 150 bp is indicated.
Figure 5:
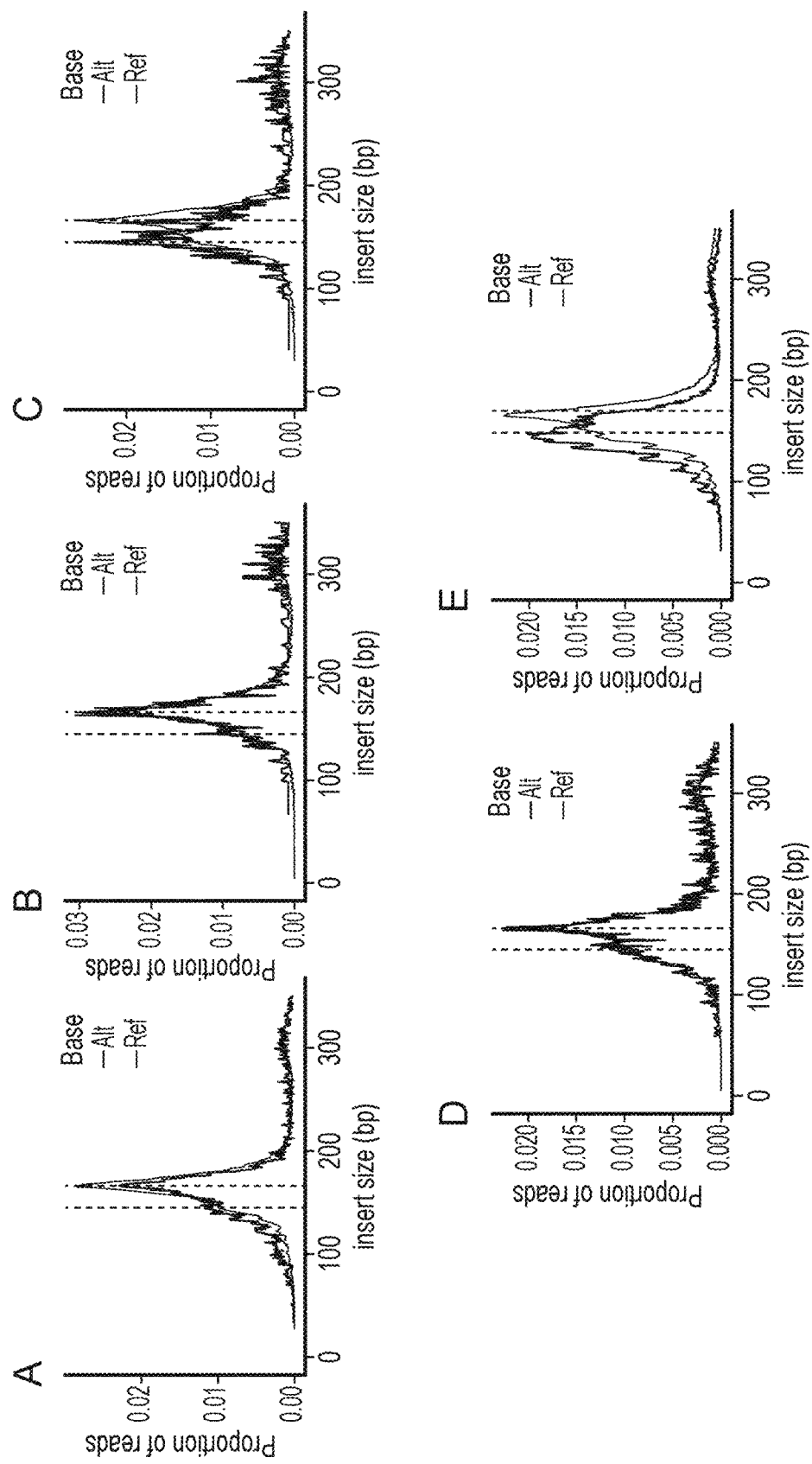
FIG. 5 shows the insert size distribution determined with hybrid-capture sequencing for 19 patients included in the mutant DNA size distribution analysis (A-S). The size distribution of mutant DNA fragments is shown in red and the distribution of non-tumour reference cfDNA from the same sample is shown in grey. The vertical dashed lines represent 145 bp and 167 bp. The insert sizes were determined by aggregating the insert sizes observed from mutant DNA and reference DNA of all samples for each patient.
Figure 5:
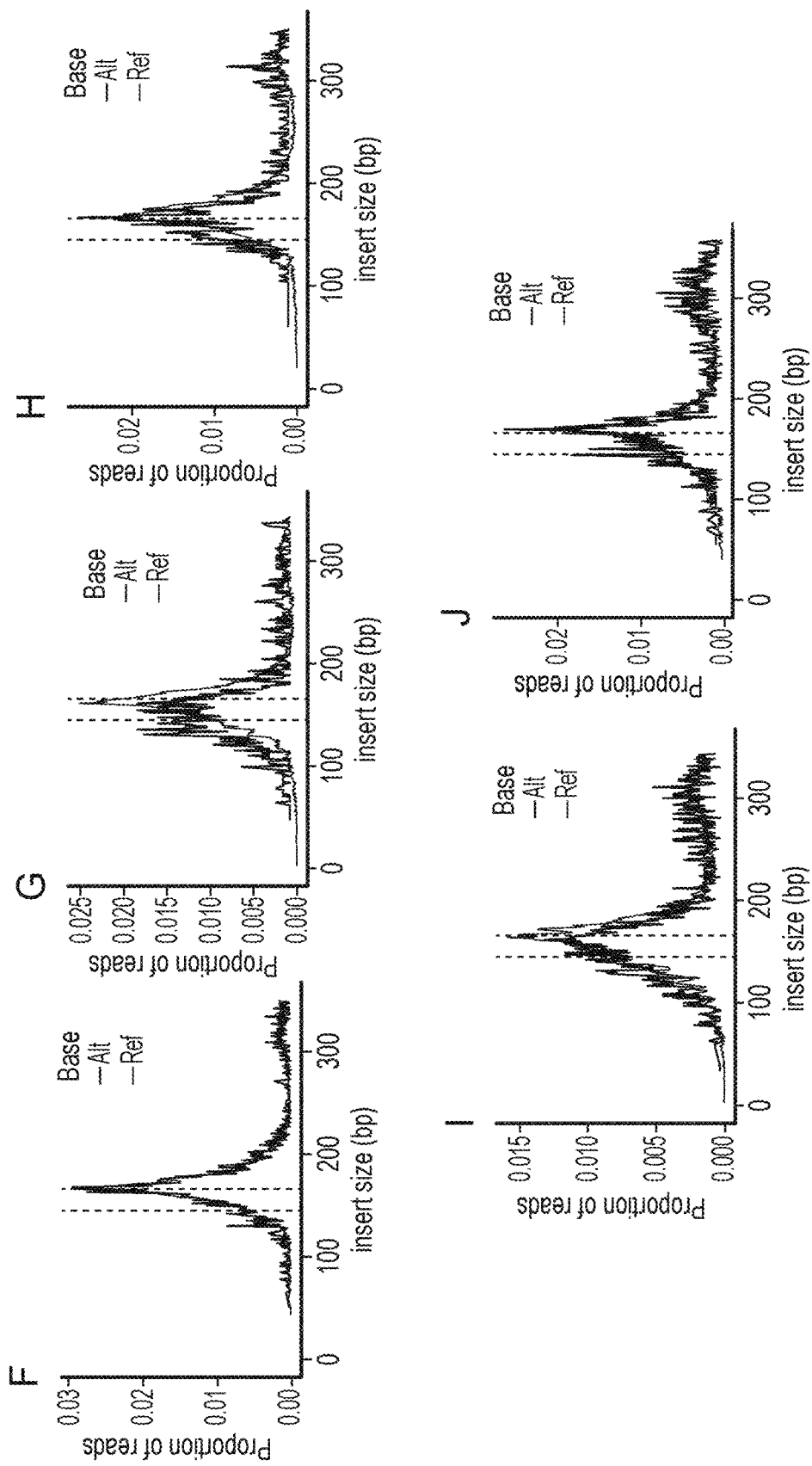
Figure 5:
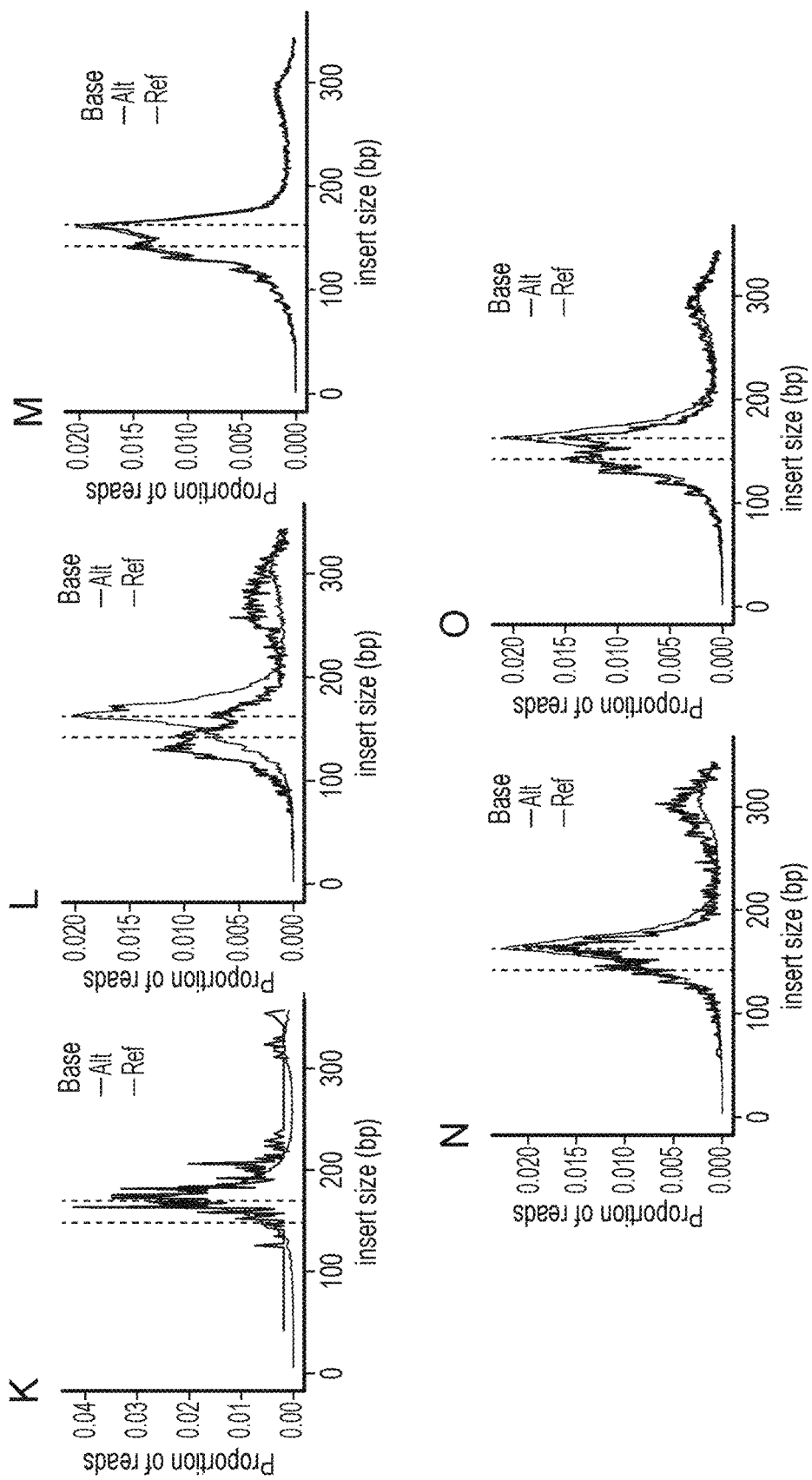
Figure 5:
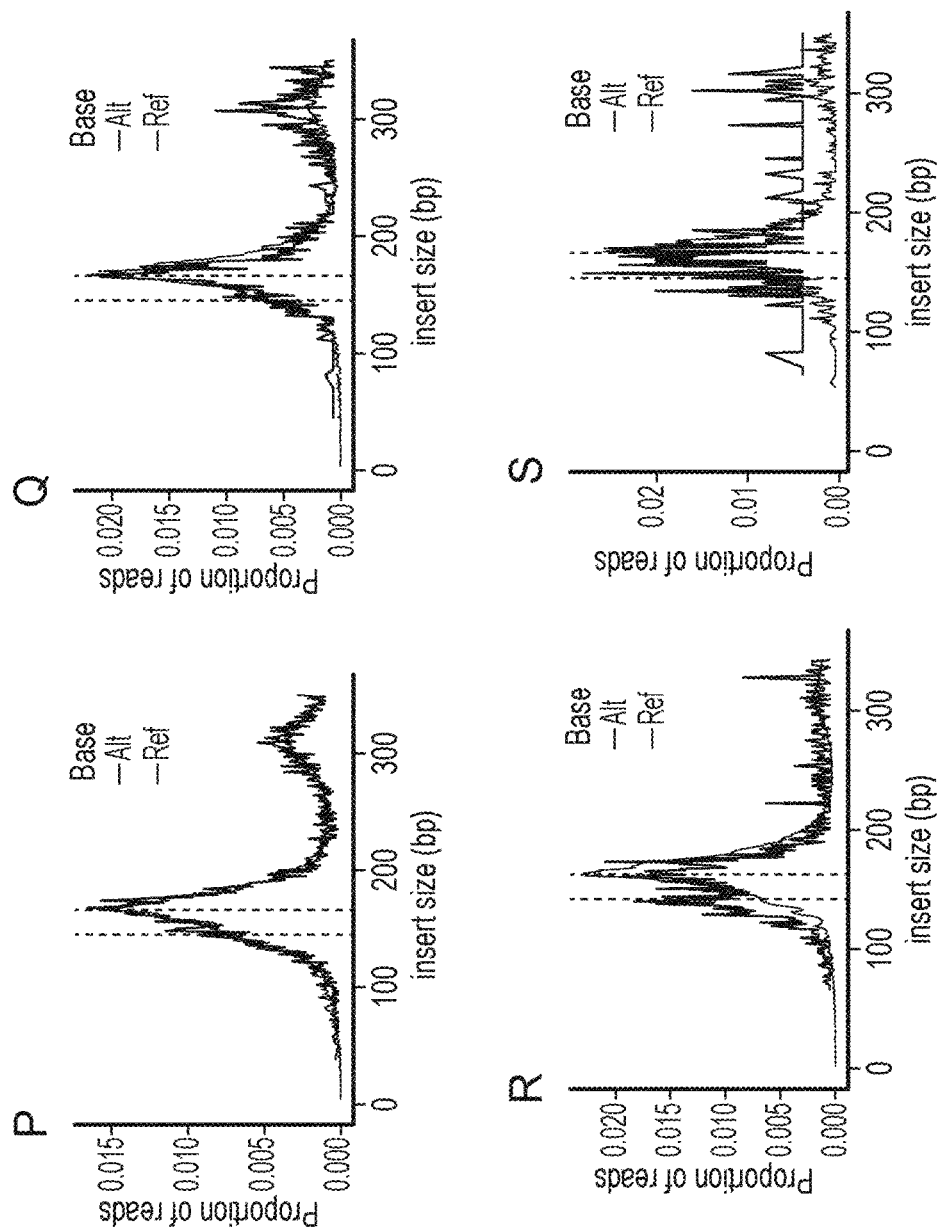

The size profile of mutant ctDNA in plasma was determined using two high specificity approaches. First, the specific size profile of ctDNA and non-tumor cfDNA was inferred with sWGS from the plasma of mice bearing human ovarian cancer xenografts (FIG. 4A). There was a shift in ctDNA fragment sizes to less than 167 bp (FIG. 4B). Second, the size profile of mutant ctDNA was determined in plasma from 19 cancer patients, using deep sequencing with patient-specific hybrid-capture panels developed from whole-exome profiling of matched tumor samples (FIG. 4C). By sequencing hundreds of mutations at a depth >300× in cfDNA, allele-specific reads from mutant and normal DNA were obtained. Enrichment of DNA fragments carrying tumor-mutated alleles was observed in fragments ~20-40 bp shorter than nucleosomal DNA sizes (multiples of 167 bp) (FIG. 4D). Mutant ctDNA was generally more fragmented than non-mutant cfDNA, with a maximum enrichment of ctDNA in fragments between 90 and 150 bp (FIG. 5), as well as enrichment in the size range 250-320 bp. These data also indicated that mutant DNA in plasma of patients with advanced cancer (pre-treatment) is consistently shorter than predicted mono-, and di-nucleosomal DNA fragment lengths (FIG. 4D).

Example 3: Selecting Tumour-Derived DNA Fragments

Figure 6:
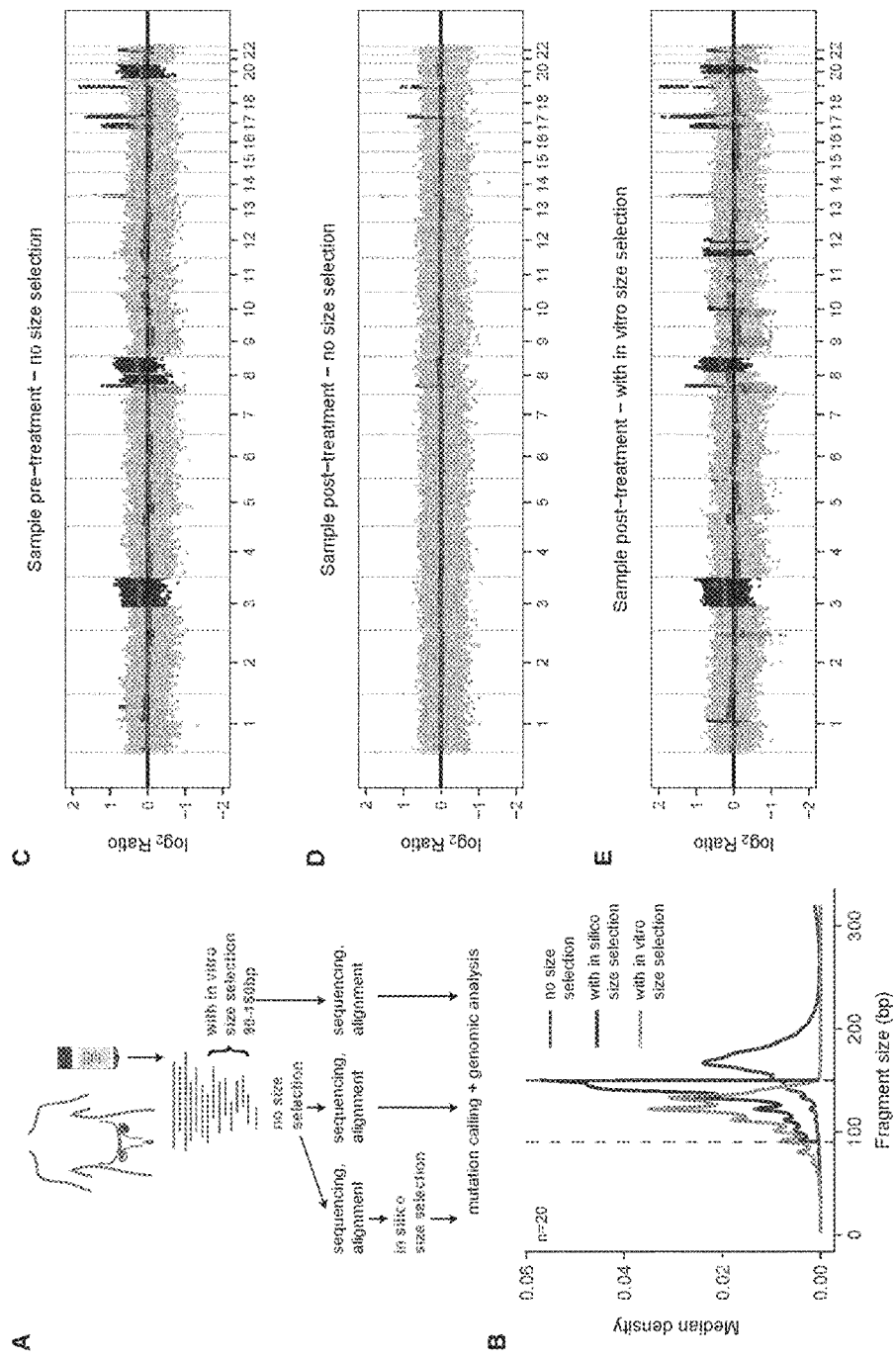
FIG. 6 shows the enhancement of the tumor fraction from plasma sequencing with size selection. A, Plasma samples collected from ovarian cancer patients were analyzed in parallel without size selection, or using either in silico and in vitro size selection. B, Accuracy of the in vitro and in silico size selection determined on a cohort of 20 healthy controls. Shows the size distribution before size selection, after in silico size selection (with sharp cutoff at 90 and 150 bp) and after in vitro size selection. C, SCNA analysis with sWGS from plasma DNA of an ovarian cancer patient collected before initiation of treatment, when ctDNA MAF was 0.271 for a TP53 mutation as determined by TAm-Seq. Shows inferred amplifications and deletions. Copy number neutral regions are in grey. D, SCNA analysis of a plasma sample from the same patient as panel C collected three weeks after treatment start. The MAF for the TP53 mutation was 0.068, and ctDNA was not detected at this time-point by sWGS (before size selection). E, Analysis of the same plasma sample as D after in vitro size selection of fragments between 90 bp and 150 bp in length. The MAF for the TP53 mutation increased to 0.402 after in vitro size selection, and SCNAs were clearly apparent by sWGS. More SCNAs are detected in comparison to C and D (e.g. in chr2, chr9, chr10).
Figure 7:
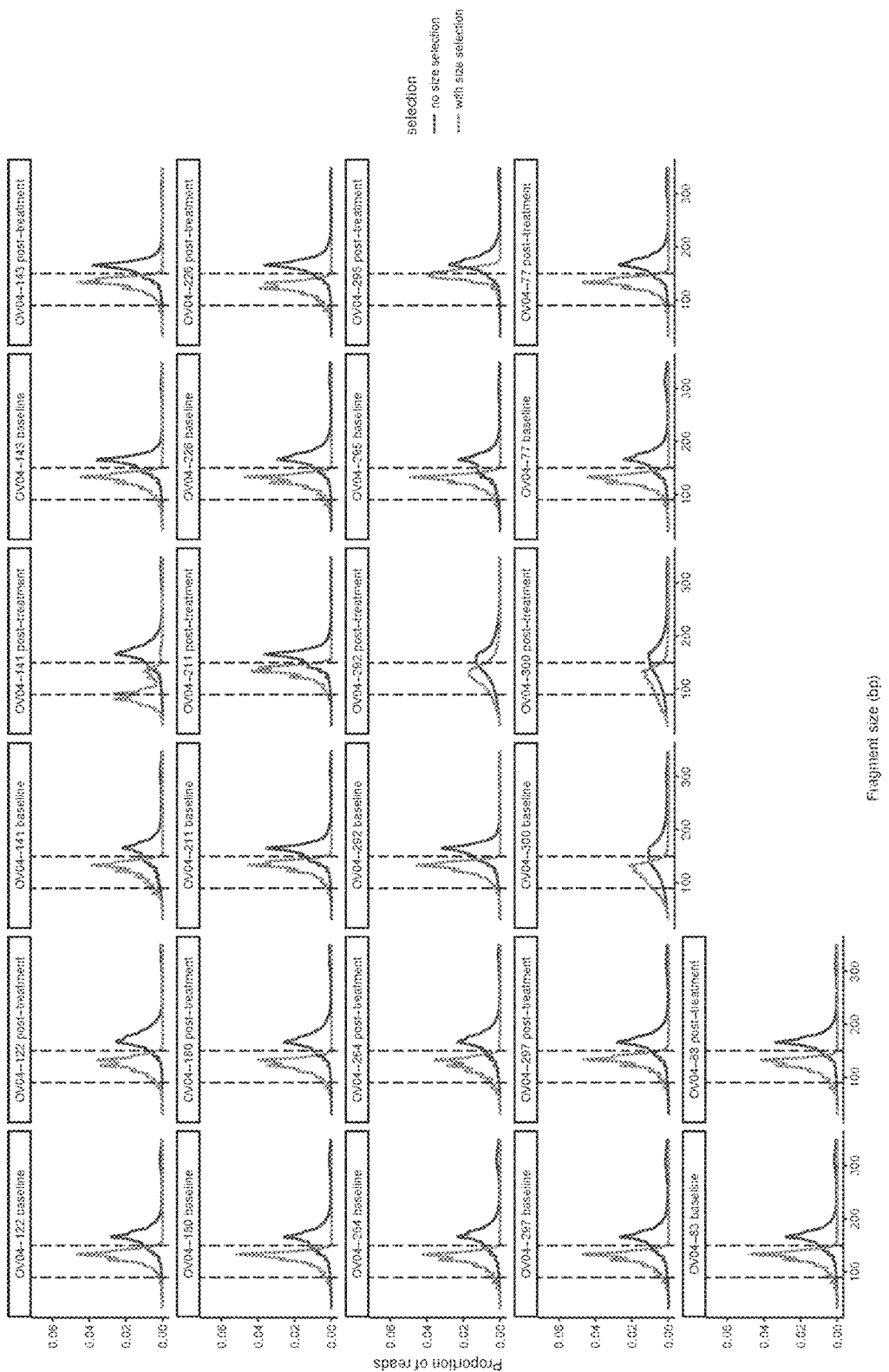
FIG. 7 shows the distribution of insert sizes determined with sWGS for each plasma sample from the 13 ovarian patients of the OV04 cohort, collected before and after treatment. The distribution of cell-free DNA (cfDNA) without size selection is shown and the distribution of the same cfDNA samples after size selection is shown. The vertical lines represent the range of fragments selected with the PippinHT cassettes, between 90 and 150 bp. To note that patient OV04-292 and OV04-300 exhibit an altered fragmentation profile indicating a possible issue with the preparation or pre-analytical preservation of the samples.
Figure 8:
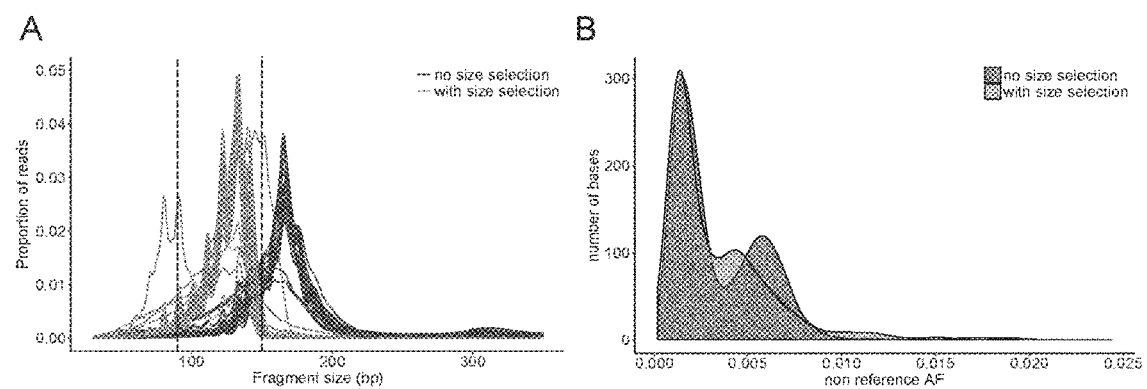
FIG. 8 shows the quality control assessment of the in vitro size selection, estimated with sWGS and targeted sequencing. A, Size distribution of DNA fragments from the plasma samples included in the size selection study, assessed by sWGS, before size-selection and after in vitro size-selection. The two dotted vertical lines indicate the size selection range between 90 bp and 150 bp. B, Proportion of non-reference allele fractions corresponding to the sequencing background noise as determined during targeted sequencing (TAm-Seq) of plasma DNA sample from ovarian cancer patients, with and without in vitro size selection.
Figure 9:
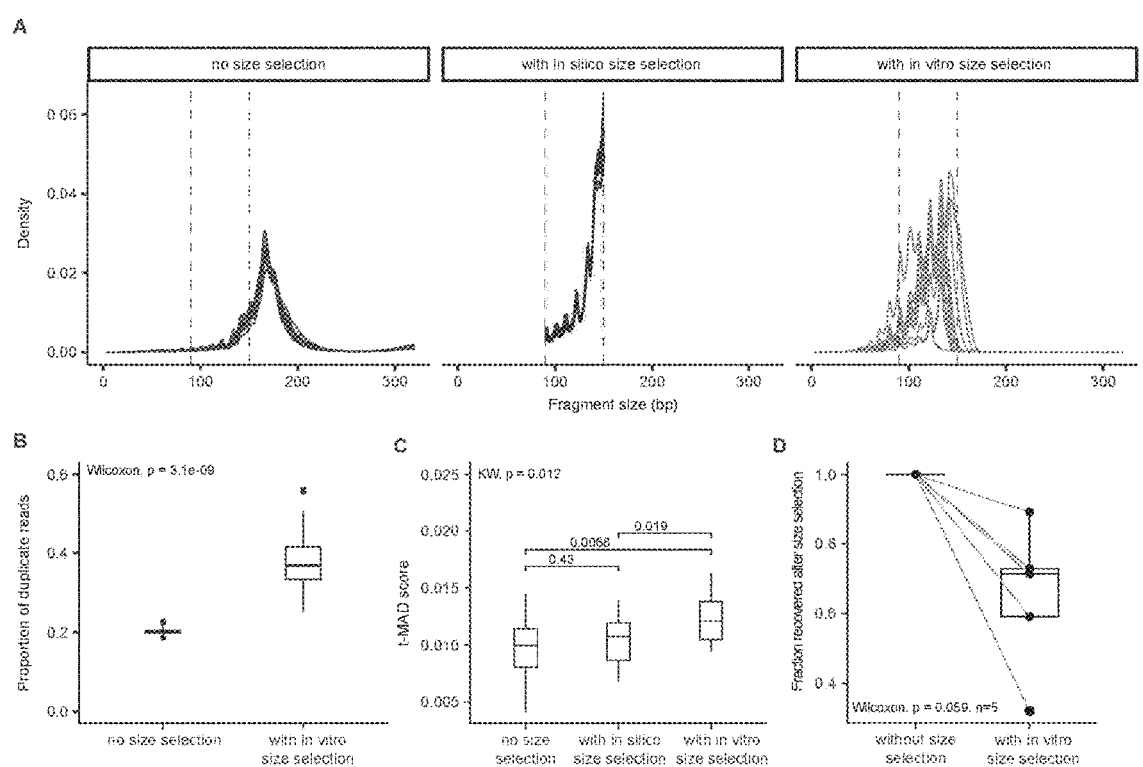
FIG. 9 shows the second quality control assessment of the in vitro and in silico size selection. 20 plasmas were selected from healthy controls, extracted DNA and performed sWGS without size selection, with in vitro and in silico size selection on these samples. A, The size profile determined for each samples and condition. B, There was an increase in the fraction of duplicated reads, and therefore these were removed for any downstream size selection analysis. In order to determine if the size selection could introduce more sequencing noise during the analysis, a QC metric called the median absolute pairwise difference (MAPD) algorithm was used to find the sequencing noise. MAPD measured the absolute difference between the log 2 CN ratios of every pair of neighboring bins and found the median across all bins. Higher MAPD scores reflected greater noise, typically associated with poor-quality samples. All samples exhibited a MAPD score of 0.01 (+−0.01), irrespective of the size selection condition. C, In addition to the noise estimation the ctDNA fraction between the 20 controls samples as estimated by the t-MAD score were compared. The t-MAD score from the samples without size selected was not significant different with the t-MAD determined after in silico size selection (t-test, p=0.43), but a significant difference with the samples after in vitro size selection (t-test, p=0.0068) was observed. Even if the t-MAD value was increased after in vitro size selection, the mean (0.011) and the maxima (0.016) detected were still constrained in the threshold limit determined empirically from the whole cohort of controls (n=65). D, The yield of DNA recovered after in vitro size selection was determined (as in silico size selection is not affected by this technical bias).

These data indicated that ctDNA is shorter than non-tumor cfDNA and suggested that biological differences in fragment lengths could be harnessed to improve ctDNA detection. The feasibility of selective sequencing of shorter fragments was determined using in vitro size selection with a bench-top microfluidic device followed by sWGS, in 48 plasma samples from 35 patients with high-grade serous ovarian cancer (HGSOC) (FIG. 6A, FIG. 7 and FIG. 8). The accuracy and quality of the size selection was assessed using the plasma from 20 healthy individuals (FIG. 6B and FIG. 9). The utility of in silico size selection of fragmented DNA was also explored using read-pair positioning from unprocessed sWGS data (FIG. 6A). In silico size selection was performed once reads were aligned to the genome reference, by selecting the paired-end reads that corresponded to the fragments lengths in a 90-150 bp size range. FIG. 6C, FIG. 6D and FIG. 6E illustrate the effect of in vitro size selection for one HGSOC case. SCNAs in plasma cfDNA before treatment were identified, when the concentration of ctDNA was high (FIG. 6C). Only a small number of focal SCNAs were observed in the subsequent plasma sample collected 3 weeks after initiation of chemotherapy (without size selection, FIG. 6D). In vitro size selection of the same post-treatment plasma sample showed a median increase of 6.4 times in the amplitude of detectable SCNAs without size selection. Selective sequencing of shorter fragments in this sample resulted in the detection of multiple other SCNAs that were not observed without size selection (FIG. 6E), and a genome-wide copy-number profile that was similar to that obtained before treatment when ctDNA levels were 4 times higher (FIG. 6C). It was concluded that selecting short DNA fragments in plasma can enrich tumor content on a genome-wide scale.

Example 4: Quantifying the Impact of Size Selection

Figure 10:
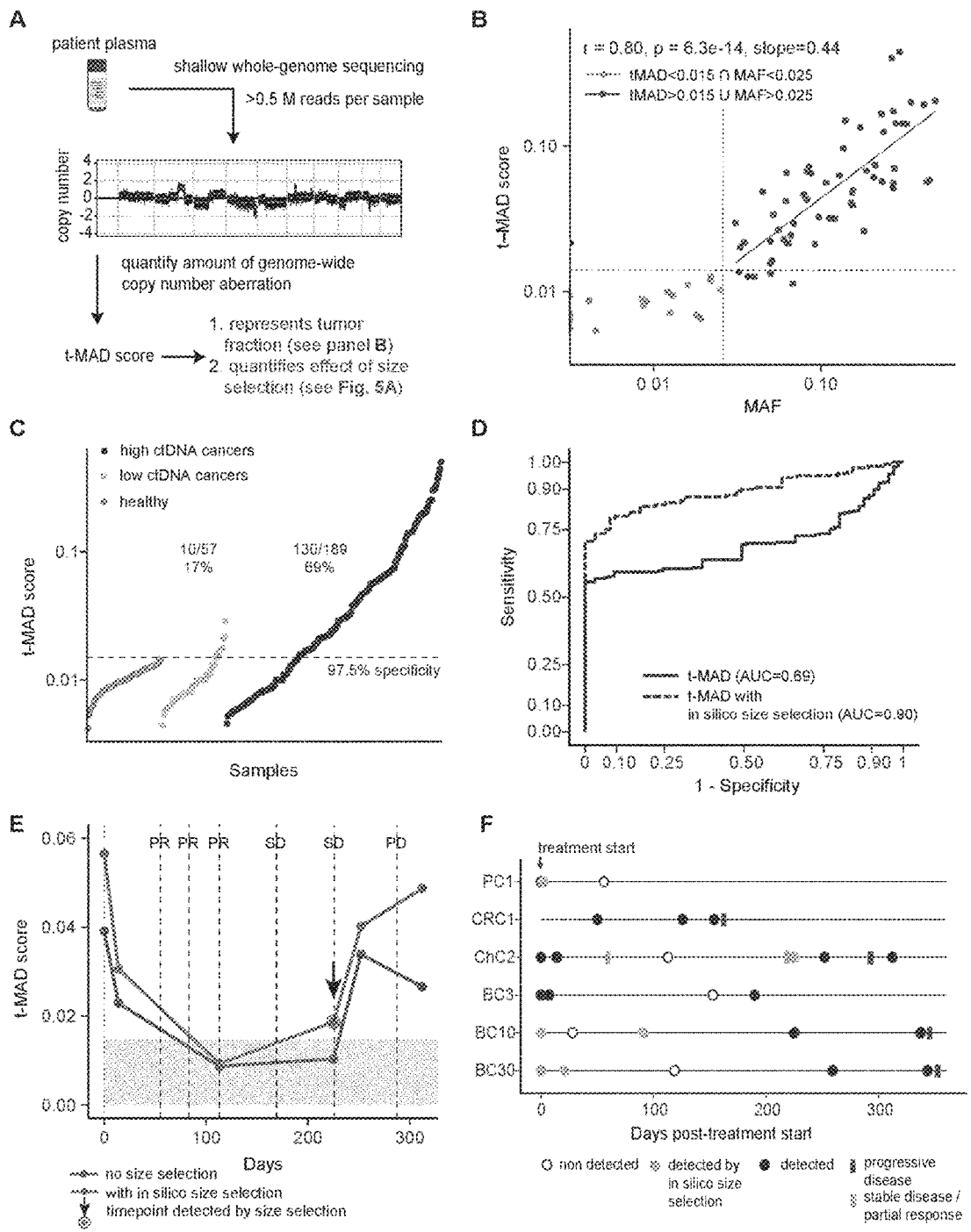
FIG. 10 shows the quantification of the ctDNA enrichment by sWGS with in silico size selection and t-MAD. A, Workflow to quantify tumor fraction from SCNA as a genome-wide score named t-MAD. B, Correlation between the MAF of SNVs determined by digital PCR or hybrid-capture sequencing and t-MAD score determined by sWGS. Data included 97 samples from cancer patients of multiples cancer types with matched MAF measurements and t-MAD scores. Pearson correlation (coefficient r) between MAF and t-MAD scores was calculated for all cases with MAF>0.025 and t-MAD>0.015. Linear regression indicated a fit with a slope of 0.44 (solid line). C, Comparison of t-MAD scores determined from sWGS between healthy samples, samples collected from patients with cancer types that exhibited low amounts of ctDNA in circulation and from patients with cancer types that exhibited high amounts of ctDNA in circulation. All samples for which t-MAD could be calculated have been included. D, ROC analysis comparing the classification of these plasma samples from high ctDNA cancer samples (n=189) and plasma samples from healthy controls (n=65) using t-MAD had an area under curve (AUC) of 0.69 without size selection (black solid curve). After applying in silico size selection to the samples from the cancer patients, we observed an AUC of 0.90 (black dashed curve). E, Determination of t-MAD from longitudinal plasma samples of a colorectal cancer patient. t-MAD was analyzed before and after in silico size selection of the DNA fragments 90-150 bp, and then compared to the RECIST status for this patient. F, Application of in silico size selection to 6 patients with long follow-up. t-MAD score was determined before and after in silico size selection of the short DNA fragments. Dark circles indicate samples in which ctDNA was detected both with and without in silico size selection. Light circles indicate samples where ctDNA was detected only after in silico size selection. Empty circles indicate samples where ctDNA was not detected by either analysis. Times when RECIST status was assessed are indicated by a bar for progression, or a bar for regression or stable disease.
Figure 11:
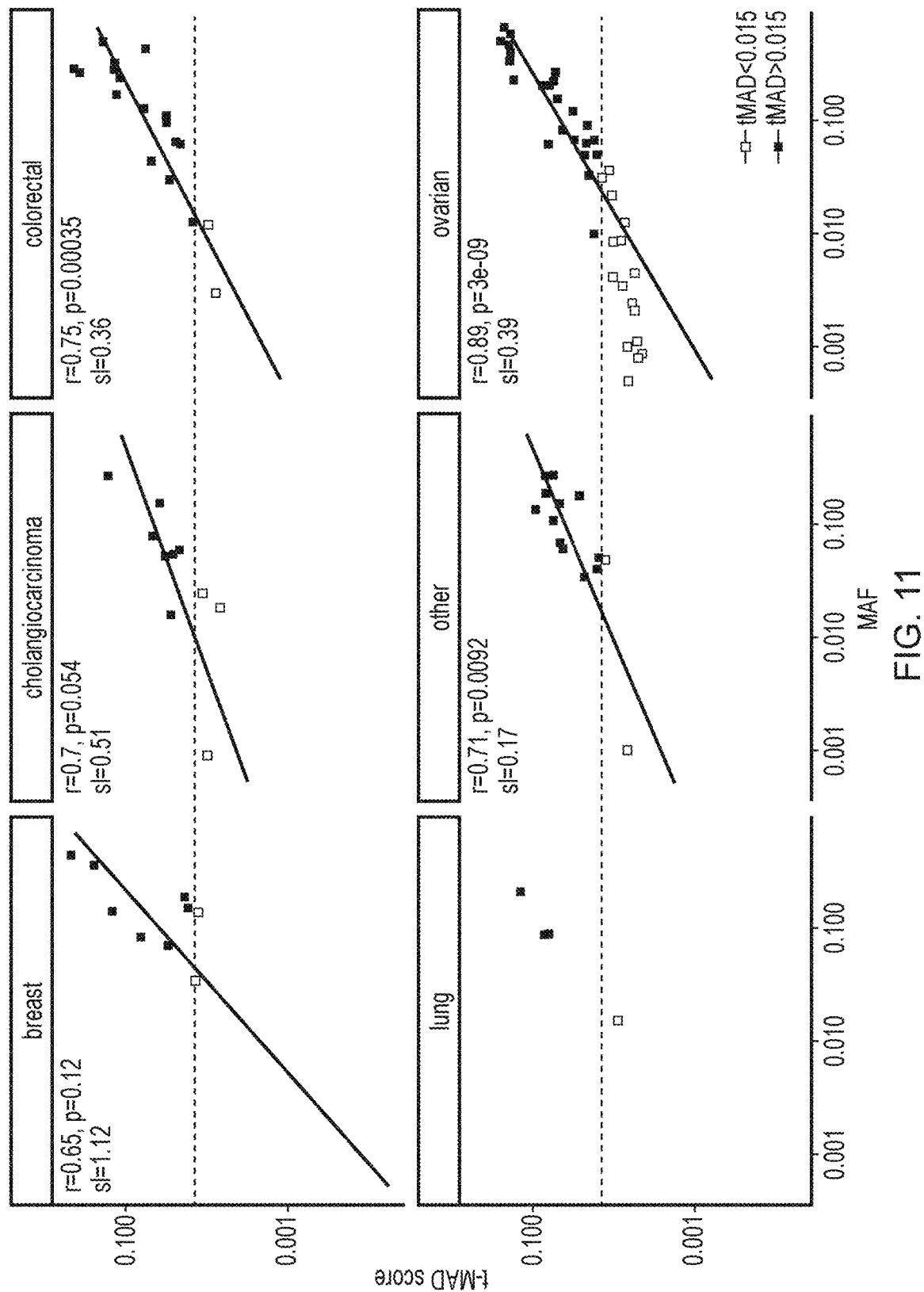
FIG. 11 shows a comparison of the MAF and t-MAD score depending on the cancer type for available matched data. Data from ovarian, breast, cholangiocarcinoma, colorectal and lung are detailed. Other cancer types are grouped in the category "other". Samples are labelled depending on their t-MAD score, with t-MAD<0.015, and t-MAD>0.015. Pearson correlations, p values and slopes are indicated when n>5 and t-MAD>0.015.
Figure 12:
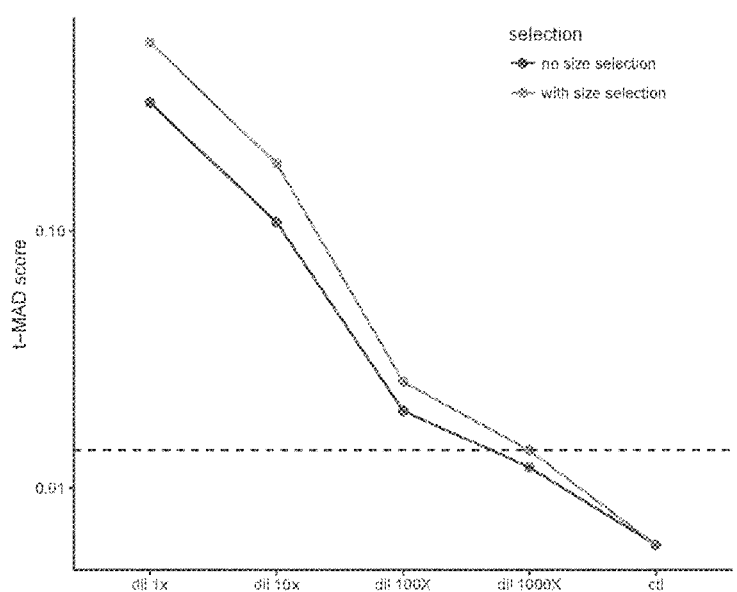
FIG. 12 shows plasma DNA from a breast cancer patient, which was spiked into pooled plasma DNA derived from healthy individual. This was serially diluted in steps of 10-, 100- and 1000-fold. A total of 10ng of DNA was used for the initial DNA library preparation. The allele fraction for a TP53 mutation of the neat sample was estimated by both WES and TAm-Seq to be ~45.6%, and was used as the reference for the dilution. In the dilution series data, the t-MAD score appears to detect SCNA with very low coverage and mutant AF (down to ~0.4% AF, or 100× diluted sample). In addition the sequencing data has been in silico size selected for the short fragments (90-150 bp), improving the t-MAD score for the lower AF.
Figure 13:
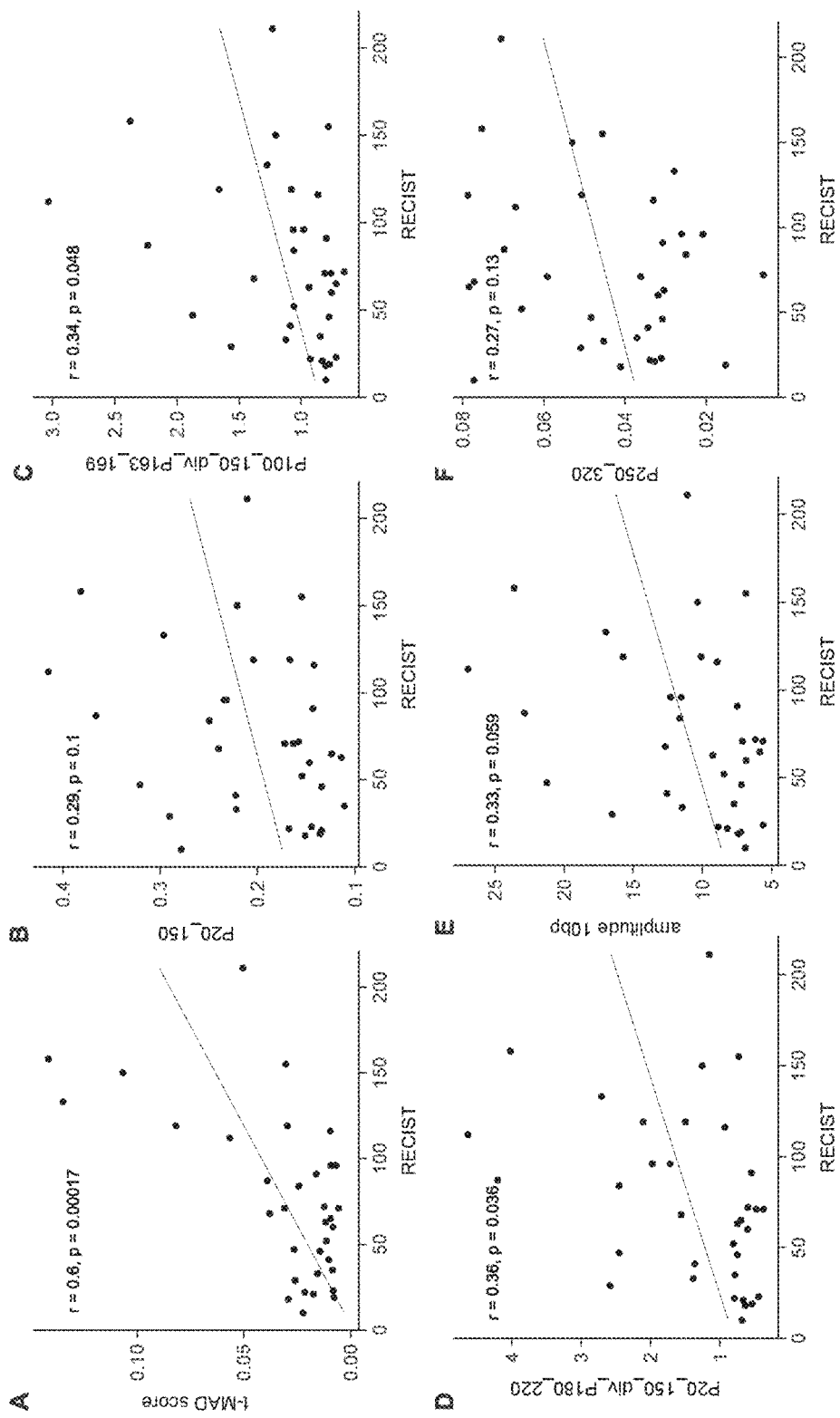
FIG. 13 shows a comparison of the available RECIST volume (in mm) determined by CT-scan to the tMAD score and fragmentation features. The RECIST volume was compared to the tMAD score (A), the proportion of fragments between 20 and 150 bp (B), the ratio of the proportion of fragments between 100-150 bp and the proportion of fragments between 163-169 bp (C), the ratio of the proportion of fragments between 20-150 bp and the proportion of fragments between 180-220 bp (D), the statistic amplitude of the 10 bp peaks and valleys (E), and the proportion of fragments between 250-350 bp (F). Correlation and p values are calculated for each comparison.

To quantitatively assess the enrichment after size selection on a genome-wide scale, a metric from sWGS data (<0.4× coverage) called t-MAD (trimmed Median Absolute Deviation from copy-number neutrality, see FIG. 10A) was developed. All sWGS data were downsampled to 10 million sequencing reads for comparison. To define the detection threshold, the t-MAD score for sWGS data from 65 plasma samples from 46 healthy individuals was measured and the maximal value found (median=0.01, range 0.004-0.015). On comparison of the t-MAD to the mutant allele fraction (MAF) in the high ctDNA cancer types assessed by digital PCR (dPCR) or WES in 97 samples, there was a high correlation (Pearson correlation, r=0.80) (FIG. 10B) between t-MAD and MAF, for samples with t-MAD greater than the detection threshold (0.015), or with MAF>0.025. FIG. 11 shows that the slope of t-MAD versus MAF fit lines differed between cancer types (range 0.17-1.12) reflecting likely differences in the extent of SCNAs. The sensitivity of t-MAD for detecting low ctDNA levels was estimated using a spike-in dilution of DNA from a patient with a TP53 mutation into DNA from a pool of 7 healthy individuals (FIG. 12) which confirmed that the t-MAD score was linear with ctDNA levels down to MAF of ~0.01. In addition, t-MAD scores greater than the detection threshold (0.015) for samples were present even in samples with a MAF as low as 0.004. t-MAD was also strongly correlated with tumor volume determined by RECIST1.1 (Pearson correlation, r=0.6, p<0.0001, n=35) (FIG. 13).

Using t-MAD ctDNA was detected from 69% (130/189) of the samples from cancer types where ctDNA levels have been shown to be high (FIG. 10C). From cancer types for which ctDNA levels are suspected to be low (glioma, renal, bladder, pancreatic), ctDNA was detected in 17% (10/57) of the cases (FIG. 10C). To improve the sensitivity for detecting t-MAD in silico size selection of the DNA fragments between 90-150 bp from the high ctDNA cancers (n=189) and healthy controls (n=65) was used (FIG. 10D). Receiver operating characteristic (ROC) analysis comparing the t-MAD score for the samples revealed an area under the curve (AUC) of 0.90 after in silico size selection, against an AUC of 0.69 without size selection (FIG. 10D).

To explore whether size selected sequencing could improve the detection of response or disease progression, sWGS of longitudinal plasma samples from six cancer patients (FIGS. 10E and F) and in silico size selection of the cfDNA fragments between 90-150 bp was used. In two patients, size selected samples indicated tumor progression 60 and 87 days before detection by imaging or unselected t-MAD analysis (FIGS. 10E and F). Other longitudinal samples exhibited improvements in the detection of ctDNA with t-MAD and size selection (FIG. 10F). Confirmation in large clinical studies will be necessary to determine the potential of selective sequencing of ctDNA for clinical applications.

Example 6: Identifying More Clinically Relevant Mutations with Size Selection

Figure 14:
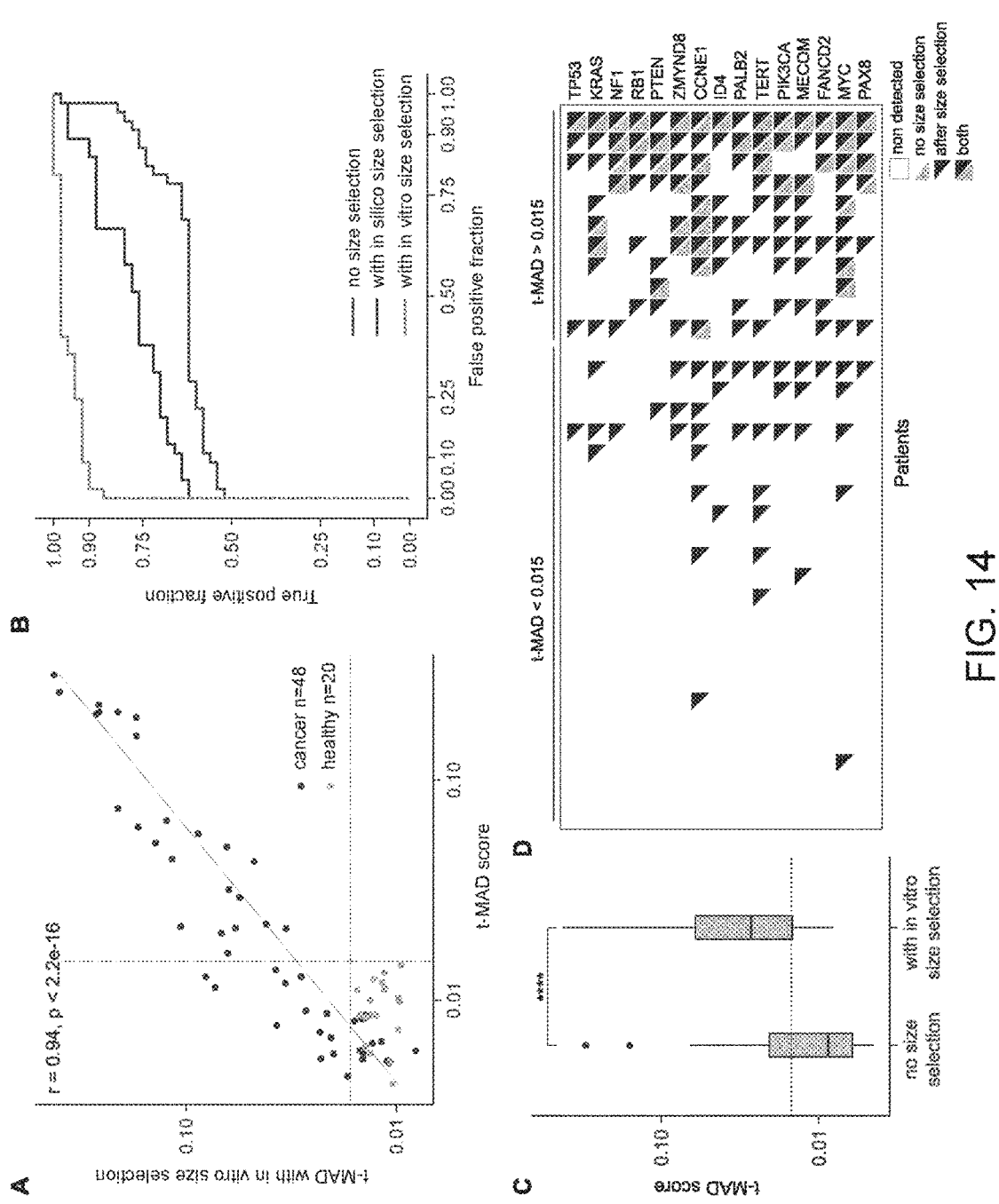
FIG. 14 shows the quantification of the ctDNA enrichment by sWGS with in vitro size selection. A, The effect of in vitro size selection on the t-MAD score. For each of 48 plasma samples collected from 35 patients, the t-MAD score was determined from the sWGS after in vitro size selection (y axis) and without size selection (x axis). In vitro size selection increased the t-MAD score for nearly all samples, with a median increase of 2.1-fold (range from 1.1 to 6.4 fold). t-MAD scores determined from sWGS for 46 samples from healthy individuals were all <0.015 both before and after in vitro size selection. B, ROC analysis comparing the classification of these plasma samples from cancer samples (n=48) and plasma samples from healthy controls (n=46) using t-MAD had an area under curve (AUC) of 0.64 without size selection. After applying in silico size selection to the samples from the cancerous and healthy patients, an AUC of 0.78 was observed, and after in vitro size selection, an AUC of 0.97. C, Comparison of t-MAD scores determined from sWGS between matched ovarian cancer samples with and without in vitro size selection. The t-test for the difference in means indicate a significant increase in tumor fraction (measured by t-MAD) with in vitro size selection (p<0.0001). D, Detection of SCNAs across 15 genes frequently mutated in recurrent ovarian cancer, measured in plasma samples collected during treatment for 35 patients. Patients were ranked from left to right by increasing tumor fraction as quantified by tMAD (before in vitro size selection). SCNAs are labelled as detected for a gene if the relative copy number in that region was greater than 0.05. Empty squares represent copy number neutral regions, bottom left triangles indicate that SCNAs were detected without size selection and top right triangles in represent SCNAs detected after in vitro size selection.
Figure 15:
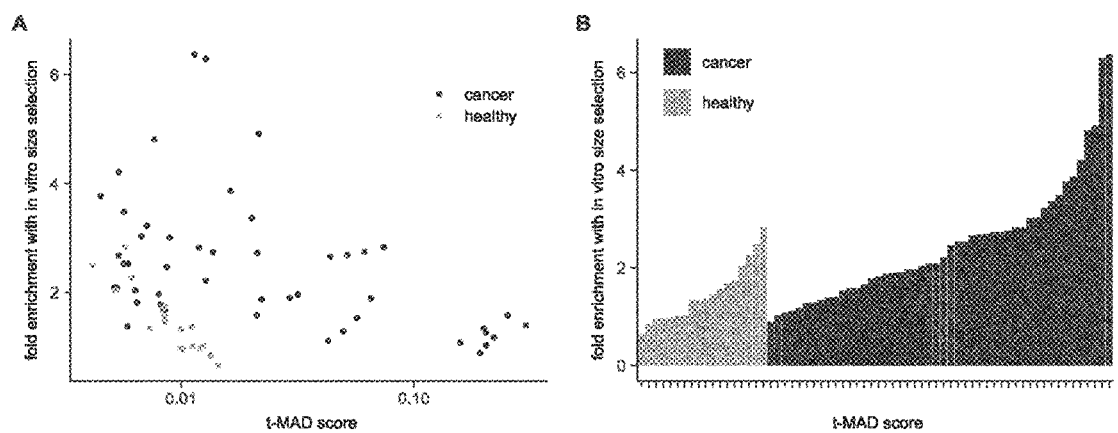
FIG. 15 shows the analysis of each of the 48 plasma samples collected from 35 ovarian patients with and without size selection. A, There is a negative correlation between the ctDNA fraction represented by the t-MAD score, and the level of enrichment (Pearson, −0.49, p<0.001. B, The t-MAD score determined from the sWGS with size selection was higher than without size selection for nearly all samples, with a median increase of 2.1-fold. The enrichment factor with size selection, determined by t-MAD, varied per sample but was higher for samples with low initial t-MAD score. Values from healthy individuals are added for comparison purposes.

The ability of size selection to increase the sensitivity for detecting new mutations in cfDNA was examined. To test effects on copy number aberrations, 35 patients with HGSOC were studied as this is the archetypal copy-number driven cancer (35). t-MAD was used to quantify the enrichment of ctDNA with in vitro size selection in 48 plasma samples, including samples collected before and after initiation of chemotherapy treatment. In vitro size selection resulted in an increase in the calculated t-MAD score from the sWGS data for 47/48 of the plasma samples (98%, t-test, p=0.06) with a mean 2.5 and median 2.1-fold increase (FIG. 14A). The t-MAD scores were then compared against those obtained by sWGS for the plasma samples from healthy individuals. 44 of the 48 size-selected HGSOC plasma samples (92%) had a t-MAD score greater than the highest t-MAD value determined in the in vitro size selected healthy plasma samples (FIG. 14A and FIG. 15), compared to only 24 out of 48 without size selection (50%). ROC analysis comparing the t-MAD score for the samples from the cancer patients (pre- and post-treatment initiation, n=48) and healthy controls (n=46) revealed an AUC of 0.97 after in vitro size selection, with maximal sensitivity and specificity of 90% and 98%, respectively. This was significantly superior to detection by sWGS without size selection (AUC=0.64) (FIG. 14B).

Figure 16:
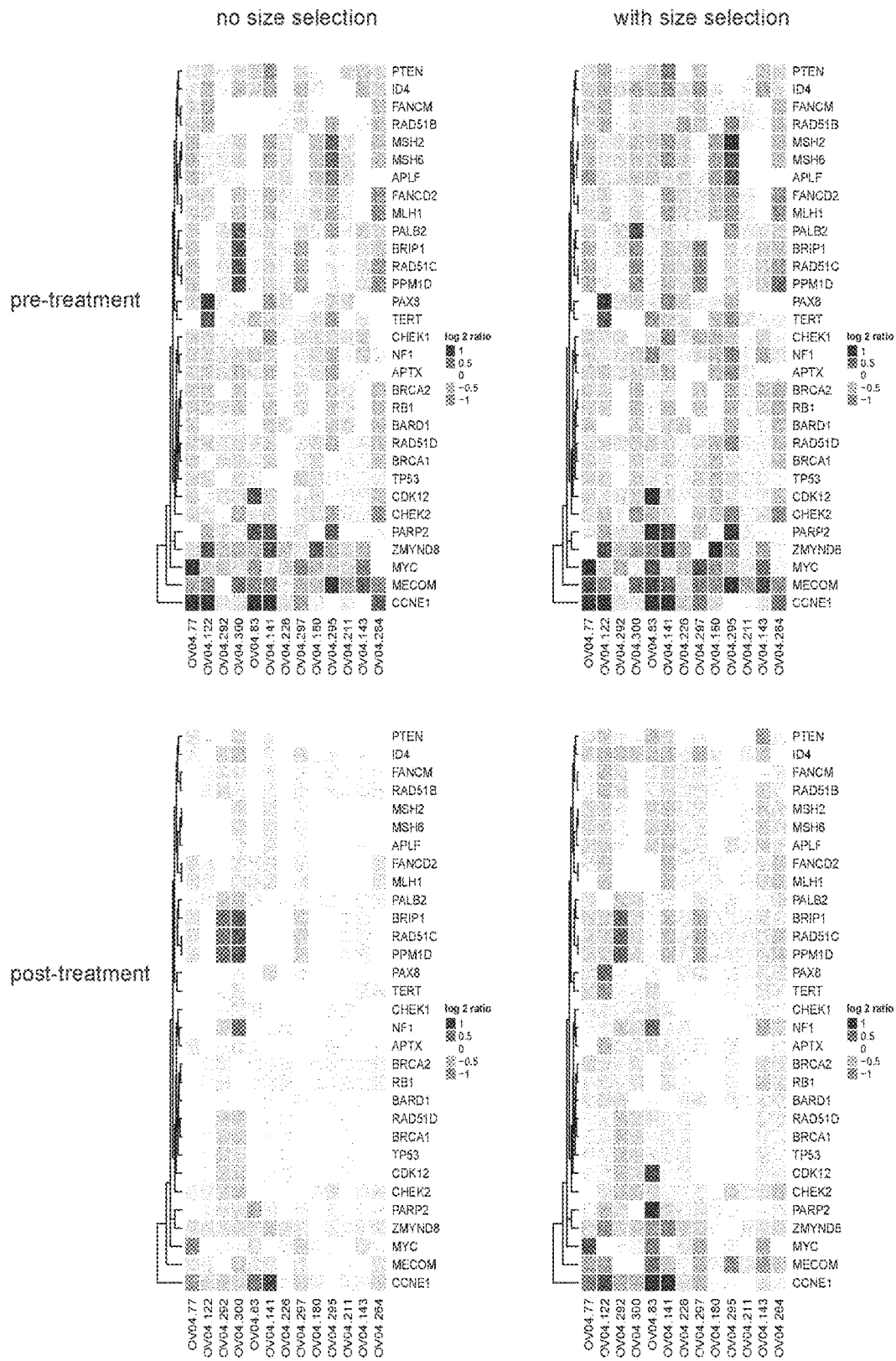
FIG. 16 shows the SCNA analysis of the segmental log 2 ratio determined after sWGS. This was performed using a list of 29 genes frequently mutated in recurrent ovarian cancer from the plasma samples collected at baseline and after treatment for 13 patients. The log 2 ratio are represented for the samples without size selection and with in vitro size selection of the shorter DNA.

This was then investigated to determine if improved sensitivity resulted in the detection of SCNAs with potential clinical value. Across the genome, t-MAD scores evaluating SCNAs were higher after size selection in 33/35 (94%) HGSOC patients, and the absolute level of the copy number (log 2 ratio) values significantly increased after in vitro size selection (t-test for the means, p=0.003) (FIG. 14C). The relative copy number values were then compared for 15 genes frequently altered in HGSOC (Table 3). Analysis of plasma cfDNA after size selection revealed a large number of SCNAs that were not observed in the same samples without size selection (FIG. 14D), including amplifications in key genes such as NF1, TERT, and MYC (FIG. 16).

Figure 2:
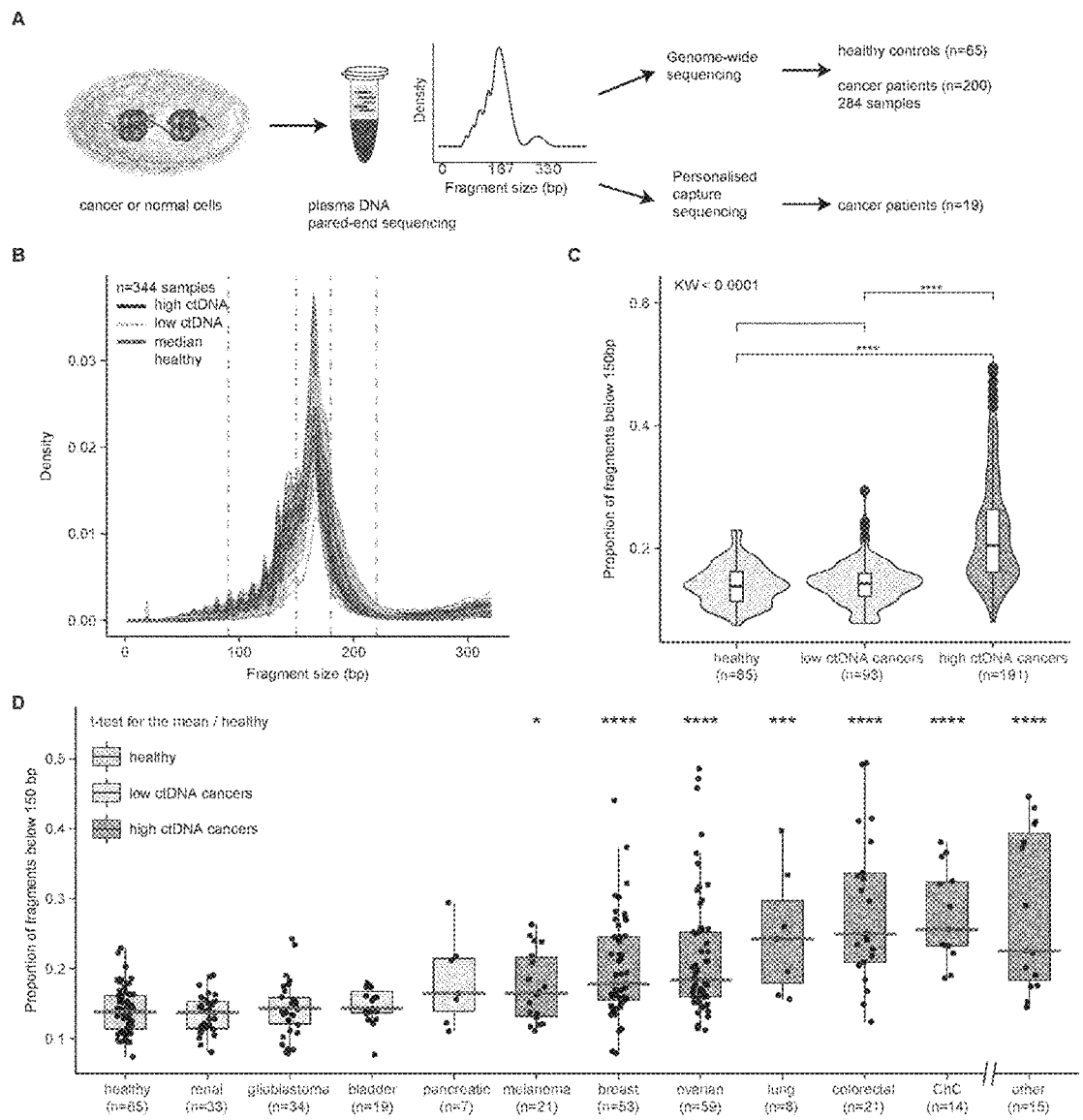
FIG. 2 shows a survey of plasma DNA fragmentation with genome-wide sequencing on a pan-cancer scale. A, The size profile of cfDNA can be determined from paired-end sequencing of plasma samples and reflects its organization around the nucleosome. cfDNA is released in the blood circulation by various means, each of which leaves a signature on the fragment sizes. The size profile of cfDNA was inferred by analyzing with sWGS (n=344 plasma samples from 65 healthy controls and 200 cancer patients), and the size profile of mutant ctDNA by personalized capture sequencing (n=18 plasma samples). B, Fragment size distributions of 344 plasma samples from 200 cancer patients. Patients are split into two groups based on previous literature (3), cancer samples previously observed to have low levels of ctDNA (renal, bladder, pancreatic, and glioma) and cancer samples observed to have higher ctDNA levels (breast, melanoma, ovarian, lung, colorectal, cholangiocarcinoma, and others, see Table 1). C, Proportion of cfDNA fragments below 150 bp by cancer grouping defined in B. The Kruskal-Wallis test for difference in size distributions indicated a significant difference between the group of cancer types releasing high amounts of ctDNA, and the group releasing low amounts as well as the group of healthy individuals (p<0.001). D, Proportion of cfDNA fragments below 150 bp by cancer type (all samples). Cancer types represented by fewer than 4 individuals are grouped in the "other" category. The line indicates the median proportion per cancer type.
Figure 3:
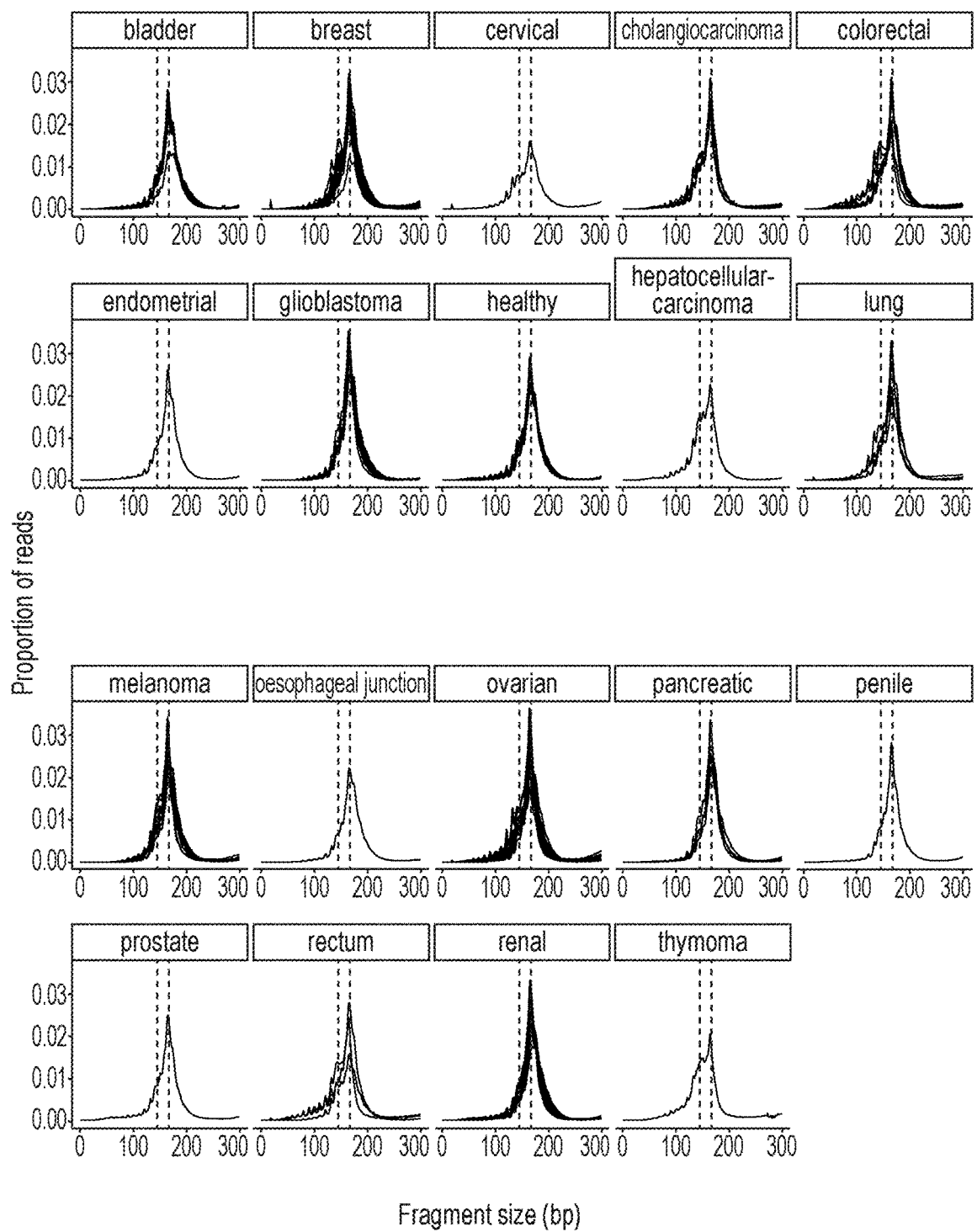
FIG. 3 shows the size distribution of cfDNA for all plasma samples of healthy individuals and cancer patients included in this study depending on their cancer type, determined by sWGS. The plasma samples showed here were collected from renal cancer (n=33), glioblastoma (n=11), bladder cancer (n=19), breast cancer (n=34), melanoma (n=21), pancreatic (n=7), ovarian (n=59), lung (n=8), colorectal (n=21), cholangiocarcinoma (n=14), cervical (n=1), penile (n=1), endometrial (n=1), thymoma (n=1), hepatocellular carcinoma (n=1). The size profile of cfDNA from healthy individuals (n=46) is also shown.
Figure 17:
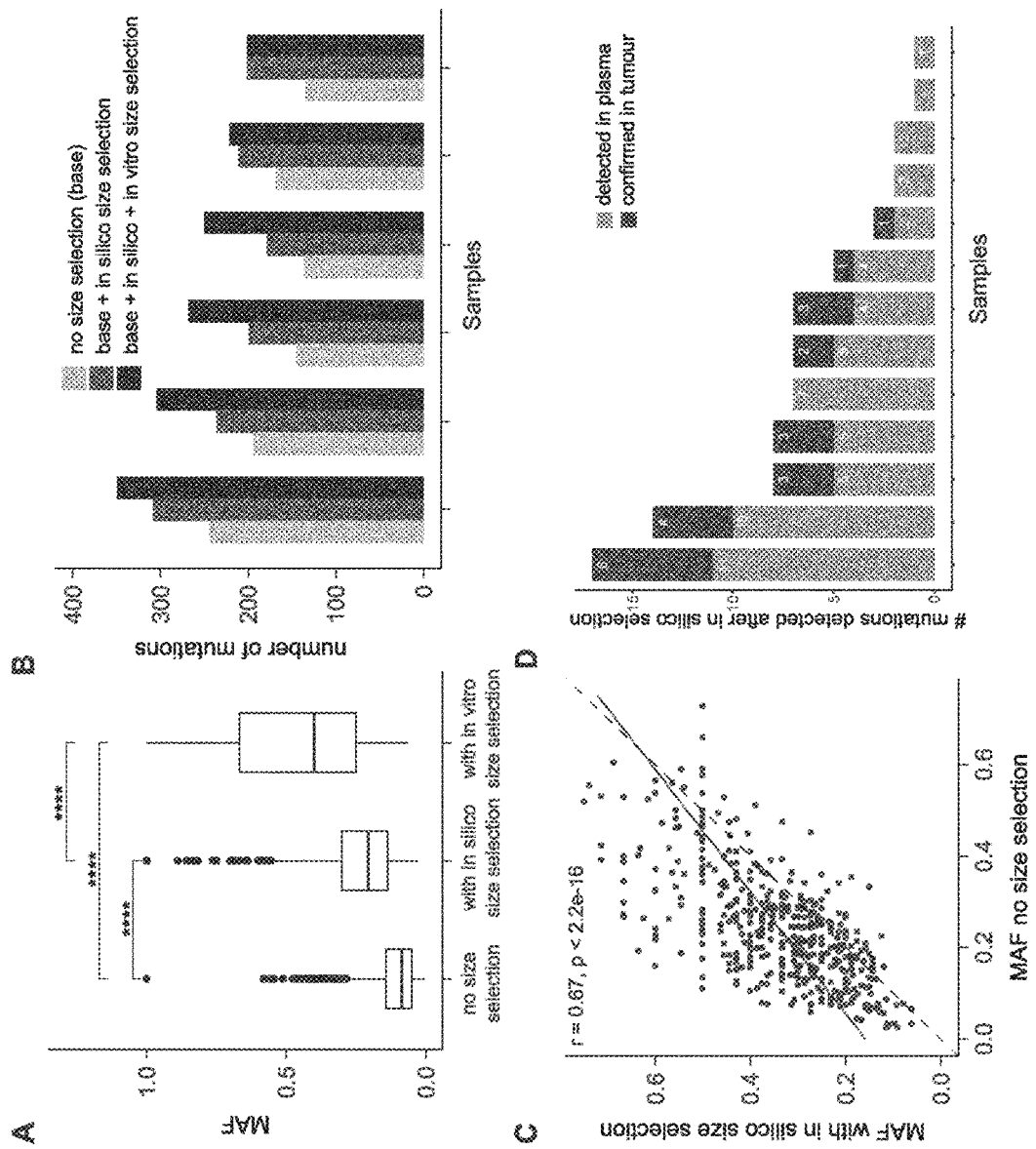
FIG. 17 shows the improvement in the detection of somatic alterations by WES in multiple cancer types with size selection. A, Analysis of the MAF of mutations detected by WES in 6 patients with HGSOC without size selection and with in vitro and in silico size selection. B, Comparison of size-selected WES data with non-selected WES data to assess the number of mutations detected in plasma samples from 6 patients with HGSOC. For each patient, the first bar shows the number of mutations called without size selection, the second bar quantifies the number of mutations called after the addition of those identified with in silico size selection, and the third bar shows the number of mutations called after addition of mutations called after in vitro size selection. C, Patients (n=16) were retrospectively selected from a cohort with different cancer types (colorectal, cholangiocarcinoma, pancreatic, prostate) enrolled in early phase clinical trials. Matched tumor tissue DNA was available for each plasma sample, and 2 patients also had a biopsy collected at relapse. WES was performed on tumor tissue DNA and plasma DNA samples, and in silico size selection was applied to the data. 2061/2133, 97% of the shared mutations detected by WES showed higher MAF after in silico size selection. D, Mutations detected only after in silico selection of WES data from 16 patients (as in C) compared to mutations called by WES of the matched tumor tissue. Three of 16 patients had no additional mutations identified after in silico size selection. Of the 82 mutations detected in plasma after in silico size selection, 23 (28%) had low signal levels in tumor WES data and were not initially identified in those samples.
Figure 18:
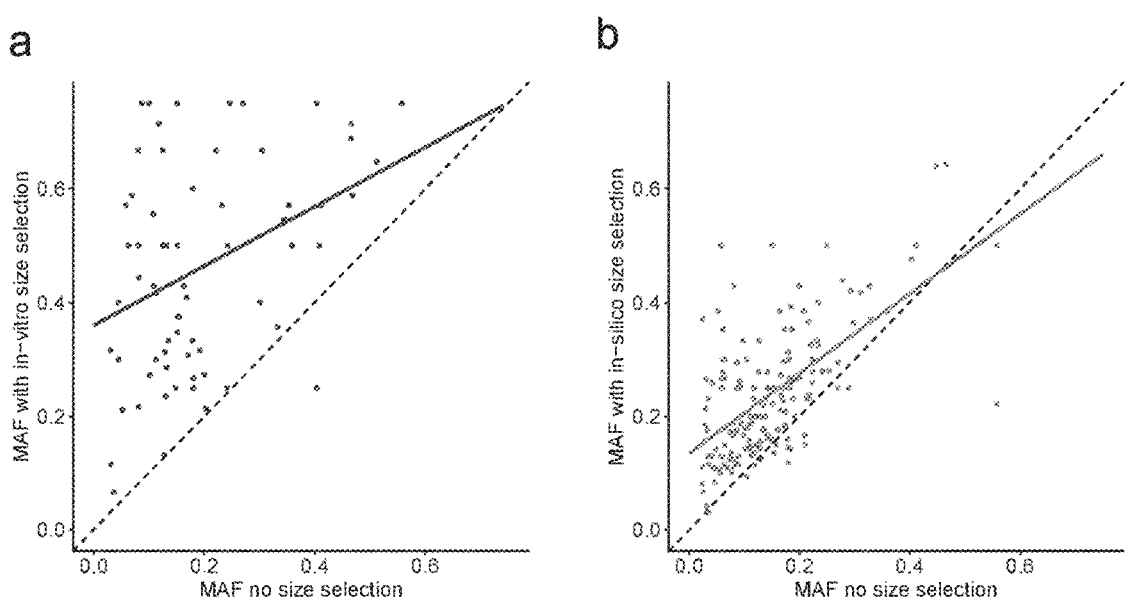
FIG. 18 shows the Mutant allelic fraction (MAF) for each single nucleotide variants (SNVs) called by WES on the OV04 samples without and with size-selection. A, The MAF determined by WES with in vitro size selection (vertical) was higher than without in vitro size selection (horizontal) for most of the mutations detected from the plasma samples of 6 HGSOC patients. B, Enrichment is also observed in the same samples after in silico size selection from WES data.
Figure 19:
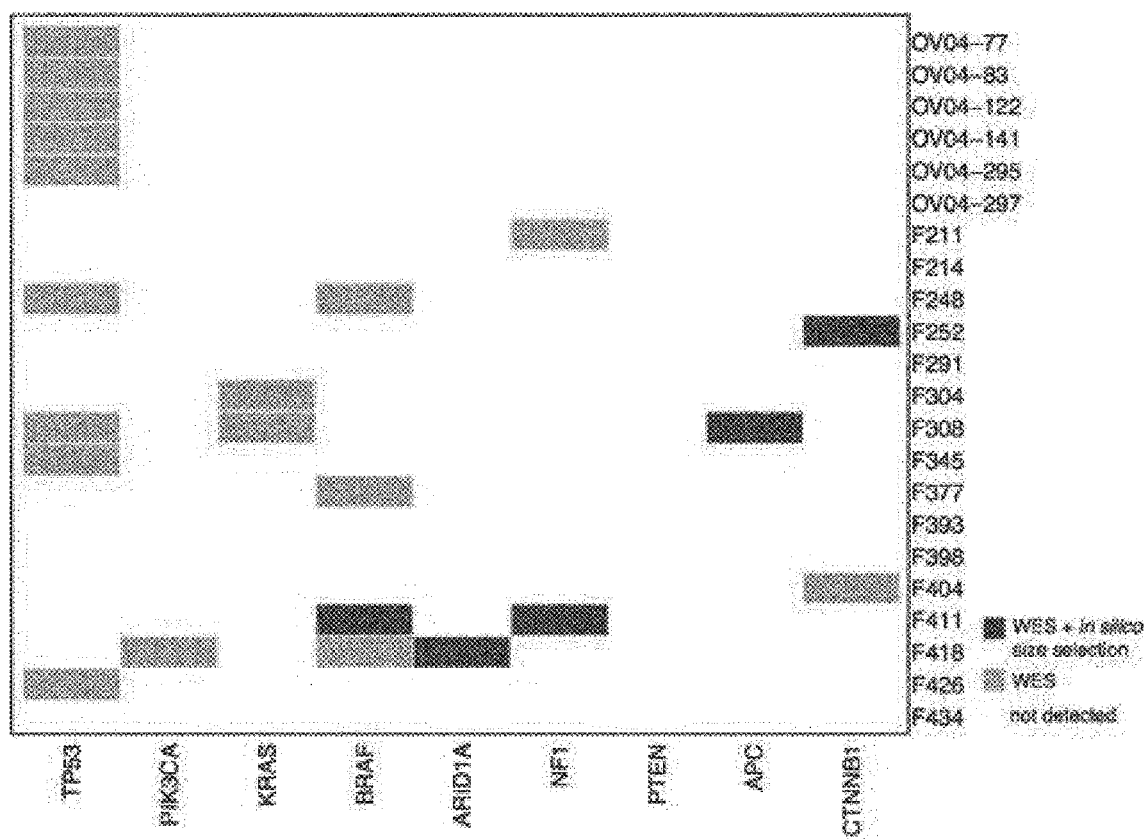
FIG. 19 depicts the mutations detected for 9 genes of clinical importance by WES with and without size selection of the short DNA fragments. All the plasma samples submitted to WES (6 ovarian cancer cases from OV04 study, and 16 cancers from the CoPPO study) were analysed. Mutations called by without size selection were integrated, and also the new mutations called by WES after in vitro and in-silico size selection.

To exclude the possibilty that size selection might only increase the sensitivity for sWGS analysis, it was examined if enrichment was seen for substitutions. Whole exome sequencing of plasma cfDNA from 23 patients with 7 cancer types was performed (FIG. 2). A comparison of the size distributions of fragments carrying mutant or non-mutant alleles (FIG. 17A) could be made using the WES data, and indicated whether size selection could identify additional mutations. 6 patients with HGSOC were selected and WES of plasma DNA with and without in vitro size selection in the 90-150 bp range was performed, analysing time-points before and after initiation of treatment (36). In addition, in silico size selection for the same range of fragment sizes was performed (FIG. 17A). Analysis of the MAF of SNVs revealed statistically significant enrichment of the tumor fraction with both in vitro size selection (mean 4.19-fold, median 4.27-fold increase, t-test, p<0.001) and in silico size selection (mean 2.20-fold, median 2.25-fold increase, t-test, p<0.001) (FIG. 17A and FIG. 18). Three weeks after initiation of treatment, ctDNA levels are often lower (36), and therefore post-treatment plasma samples were further analyzed using Tagged-Amplicon Deep Sequencing (TAm-Seq) (37). Enrichment of MAFs by in vitro size selection was observed to be between 0.9 and 118 times (mean 2.1 times, median 1.5 times) compared to the same samples without size selection (FIG. 19).

Figure 20:
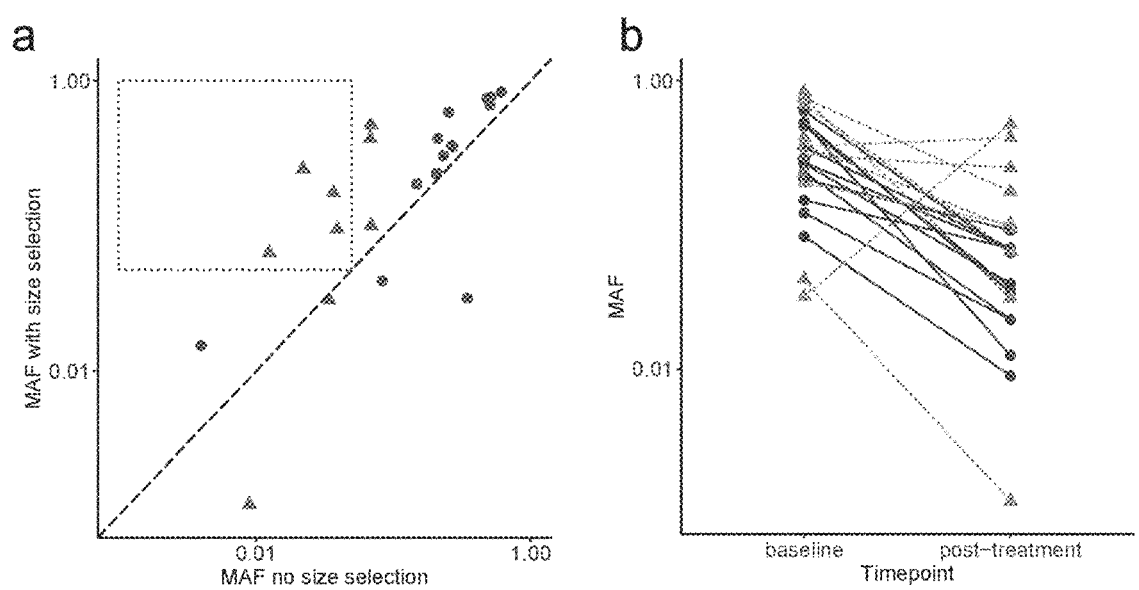
FIG. 20 shows A, The MAF for TP53 mutations determined by TAm-Seq with in vitro size selection was higher than without size selection for most samples, including samples collected at baseline (circles) and after initiation of treatment (triangles). Only the 26 samples collected from 13 patients with a sample collected before and after treatment are shown. The dotted area highlights samples which had initially low MAF (<5%), where methods such as whole-exome sequencing (at sequencing depth of ~100×) would not be effective, and where in vitro size selection enriched the MAF to >5% and therefore accessible for wide-scale analysis. B, Comparison of the MAF detected by TAm-Seq before treatment and after initiation of treatment with in vitro size selection (triangles) and without size selection (circles).

Size selection with both in vitro and in silico methods increased the number of mutations detected by WES by an average of 53% compared to no size selection (FIG. 17B). A total of 1023 mutations in the non-size-selected samples were identified. An additional 260 mutations were detected by in vitro size selection, and an additional 310 mutations were called after in silico size selection (FIG. 17B and Table 4). New mutations were also detectable in tumor specimens, which excludes the possibility that the improved sensitivity for mutation detection was a result of sequencing artefacts. In silico size selection was then used in an independent cohort of 16 patients, where matched tumor tissue DNA was available. In silico size selection enriched the MAF for nearly all mutations (2061/2133, 97%), with an average increase of MAF of ×1.7 (FIG. 17C). For 13 of 16 patients (81%) additional mutations in plasma after in silico size selection were identified. Of these 82 additional mutations, 23 (28%) were confirmed to be present in the matched tumor tissue DNA (FIG. 17D). Notably, this included mutations in key cancer genes including BRAF, ARID1A, and NF1 (FIG. 20).

Figure 21:
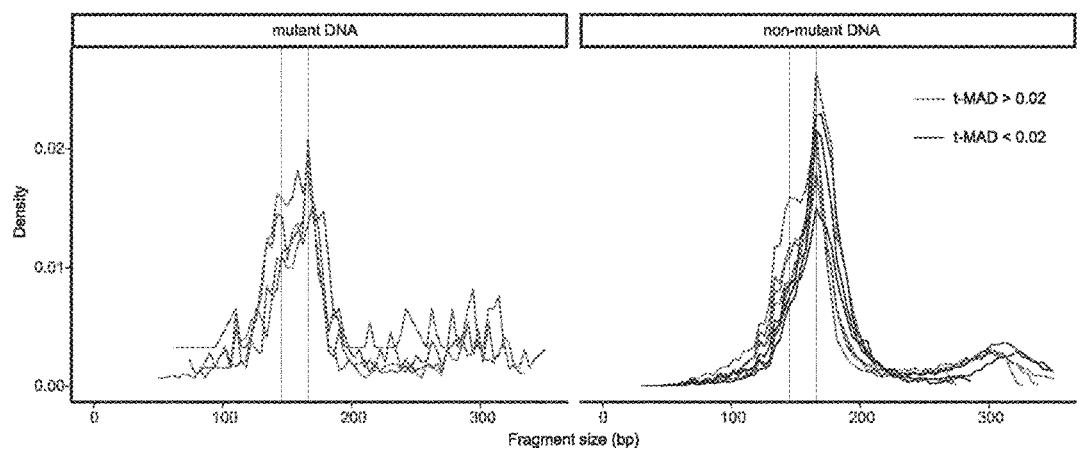
FIG. 21 shows the size distribution of mutant and non-mutant DNA obtained from the personalised sequencing. A fraction of 10 patients from this figure were sub-selected. The loci selected corresponded to clinically validated variants (based on the WES of the tumor tissue DNA). The left panel exhibit the size distribution of mutant DNA, and the right panel the size distribution of the corresponding non-mutant DNA. The mutant ctDNA confirm enrichment in the size range 90-150 bp (as previously described in the manuscript). The non-mutant exhibited a lower enrichment in the size range 90-150 bp, but with variations depending on the patient. The patient with the highest concentration of ctDNA as determined by t-MAD, had an enrichment in shorter non-mutant DNA, whereas the patients with a lower value of t-MAD, have less short fragments. This suggests that even in the non-mutant DNA, tumor signal (=non-mutant ctDNA) can be detected by analysing the size of the cfDNA fragments.

Example 7: Detecting Cancer by Supervised Machine Learning Combining cfDNA Fragmentation and Somatic Alteration Analysis It is important to note that although in vitro and in silico size selection increase the sensitivity of detection, they also result in a loss of cfDNA for analysis. Regions of the cancer genome which are not altered by mutation also excluded and cannot contribute to the analysis (FIG. 21). It was hypothesized that leveraging other biological properties of the cfDNA fragmentation profile could enhance the detection of ctDNA.

The sWGS data defined other cfDNA fragmentation features including (1) the proportion of fragments in multiple size ranges, (2) the ratios of proportions of fragments in different sizes and (3) the amplitude of oscillations in fragment-size density with 10 bp periodicity (FIG. 22A). These fragmentation features were compared between cancer patients and healthy individuals (FIG. 23) and the feature representing the proportion (P) of fragments between 20-150 bp exhibited the highest AUC (0.819). Principal component analysis (PCA) of the samples represented by t-MAD and fragmentation features showed a separation between healthy and cancerous samples and that fragment features clustered with t-MAD scores (FIG. 22B).

Figure 24:
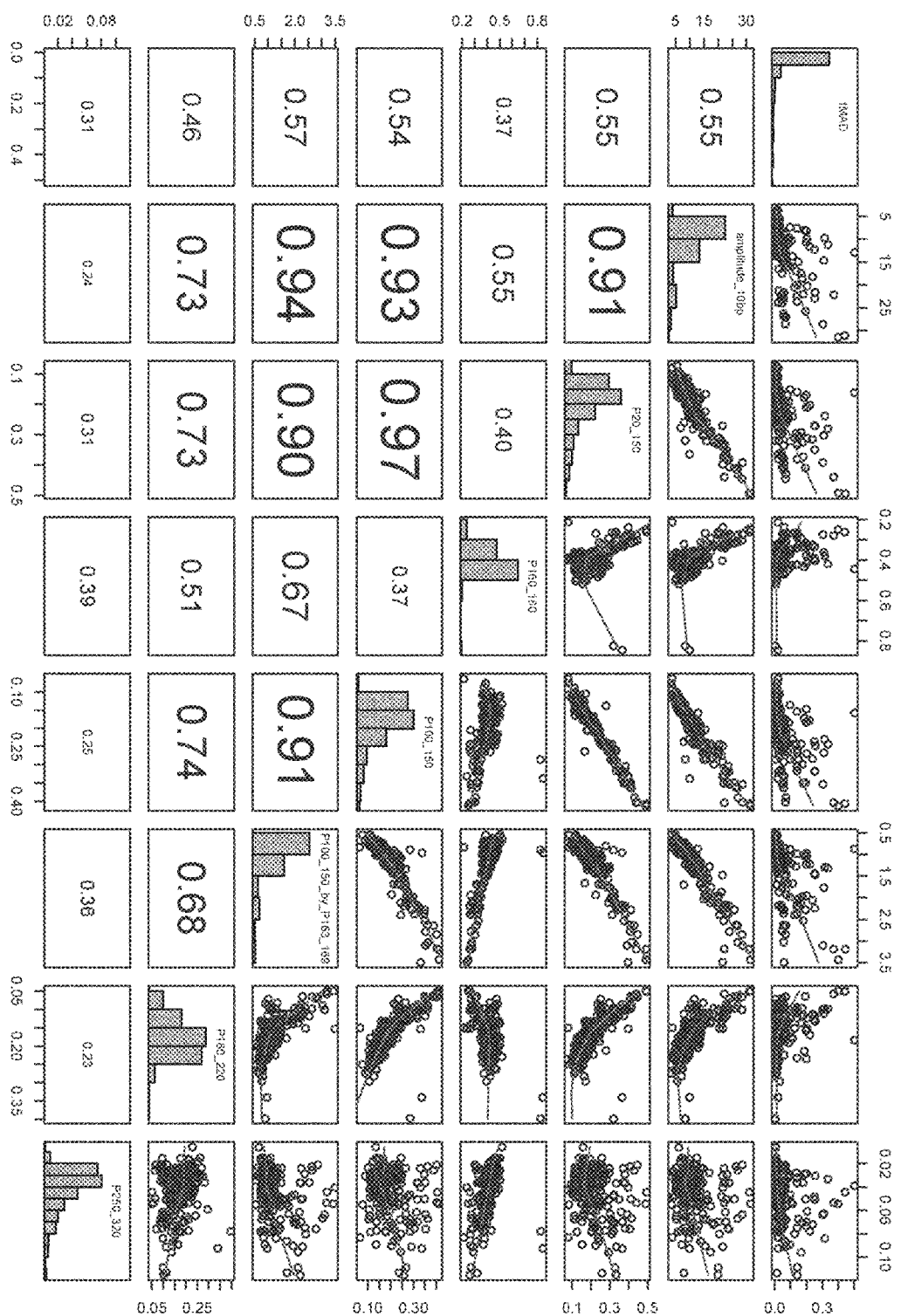
FIG. 24 shows a comparison of t-MAD score to the 9 fragmentation features determined by sWGS from the 147 plasma samples from cancer patients included in the training and validation dataset of the classifier models. The correlation score was estimated for each cross-comparison, and the value displayed on the bottom left side of the figure.

Furthermore, the potential of fragmentation features to enhance the detection of tumor DNA in plasma samples was explored. A predictive analysis was performed using the t-MAD score and 9 fragmentation features across 304 samples (239 from cancers patients and 65 from healthy controls) (FIG. 22C and FIG. 24 and Table 2). The 9 fragmentation features determined from sWGS included five features based on the proportion (P) of fragments in defined size ranges: P(20-150), P(100-150), P(160-180), P(180-220), P(250-320); three features based on ratios of those proportions: P(20-150)/P(160-180), P(100-150)/P(163-169), P(20-150)/P(180-220); and a further feature based on the amplitude of the oscillations having 10 bp periodicity observed below 150 bp.

Figure 25:
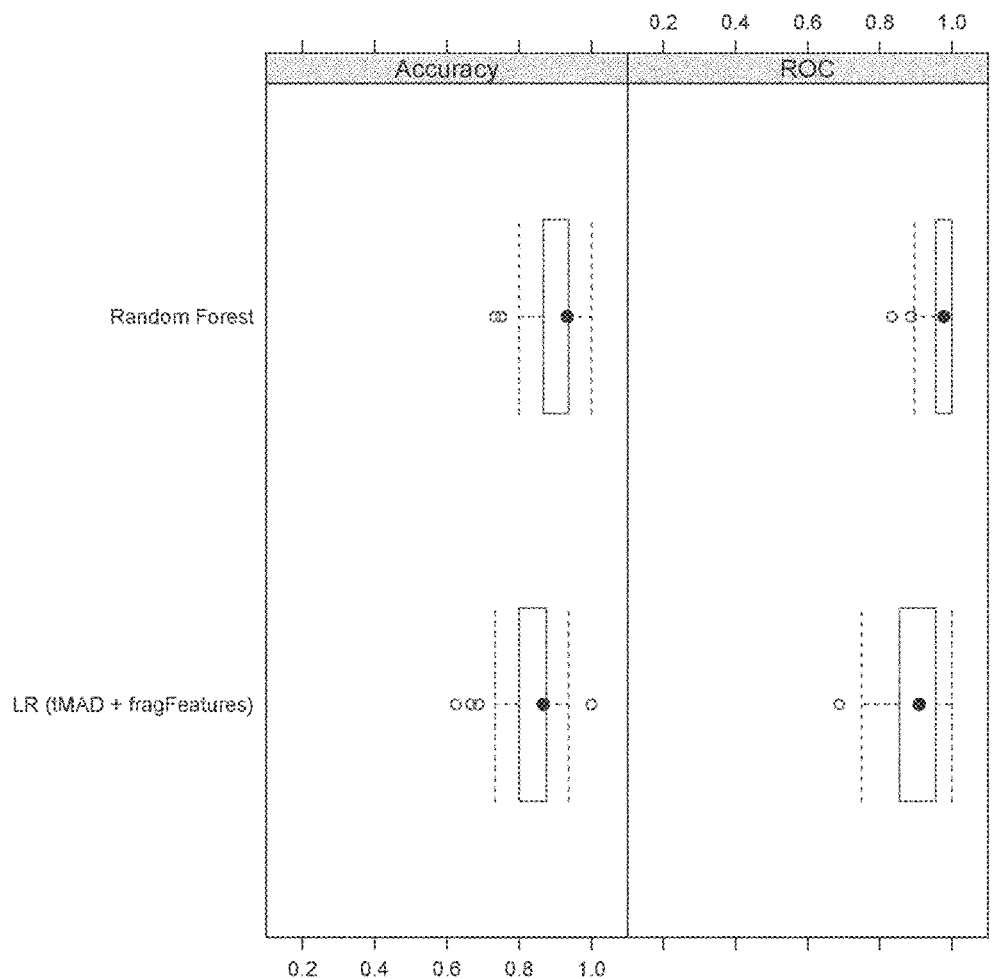
FIG. 25 shows the performance metrics for the different algorithms: logistic regression (on t-MAD score and the fragmentation features), and random forest (RF) on training set data from sWGS (n=153; 114 cancer samples, and 39 healthy controls). The median ROC score and accuracy values are displayed for each models, as well as the 0.95 confidence level.
Figure 26:
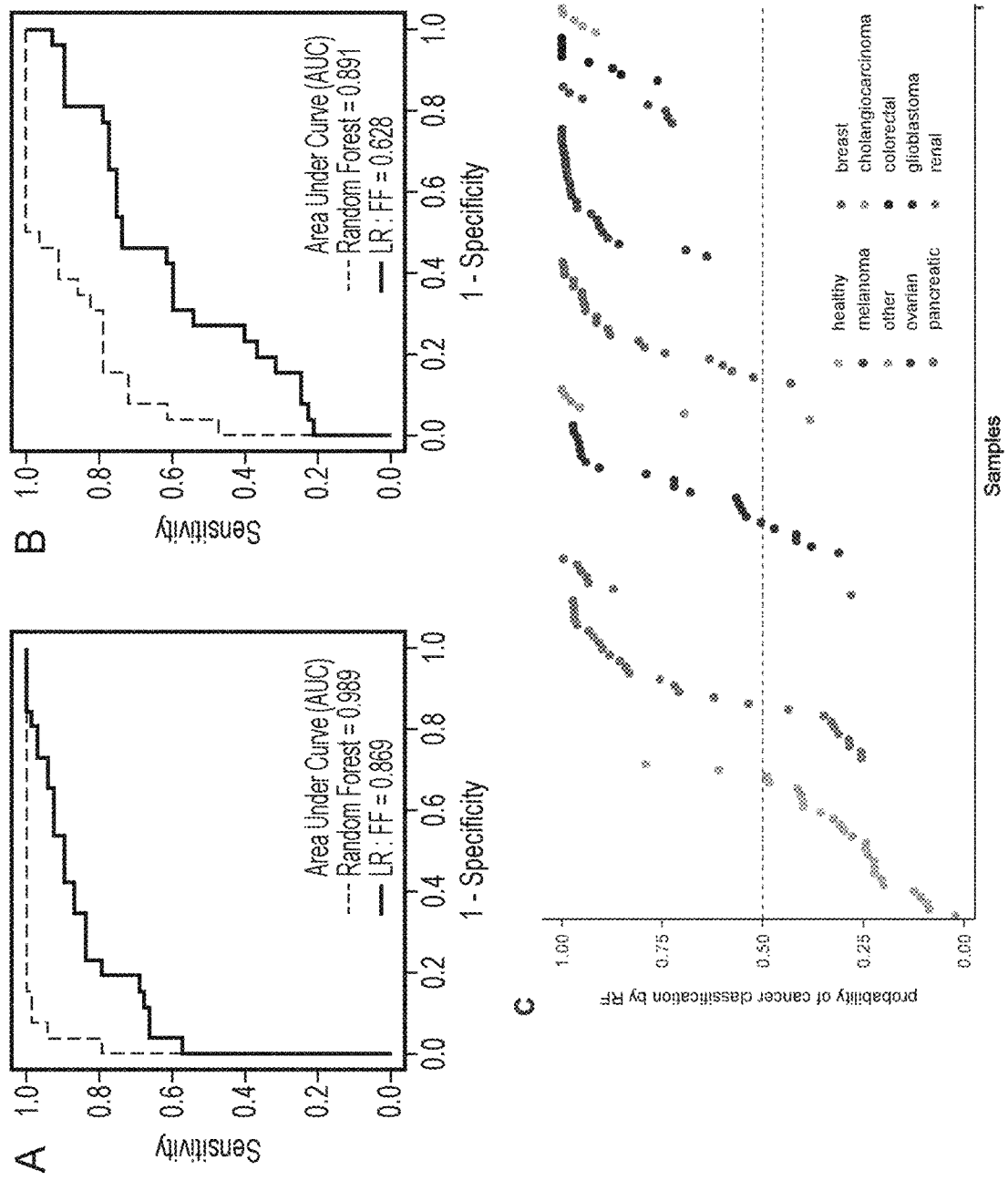
FIG. 26 shows LR and RF models, which detect cancer from healthy samples with the fragmentation features alone. A, ROC curves from the first validation sample set (cancer=68, healthy=26) for 2 classifiers built on the pan-cancer training cohort (cancer=114, healthy=39). The curve represents the ROC for a logistic regression model trained only with the fragmentation features without t-MAD and the dashed curve shows the result for a random forest classifier trained on the combination of the best 3 predictive fragmentation features (amplitude_10 bp, P(160-180), and P(250-320)). B, ROC curves from the second validation sample set (cancer=57, healthy=26) for 2 classifiers built on the same training set as A. The curve represents the logistic regression model trained only with the fragmentation features and the dashed curve shows the result for a random forest classifier trained on the combination of 3 predictive features (amplitude_10 bp, P(160-180), and P(250-320)). C, plot representing the probability of classification as cancer with the RF model for the second validation dataset (described in B). Samples are ranked by cancer-type and by probability of classification as cancer. The dashed horizontal line represents the 50% probability.

Variable selection and the classification of samples as "healthy" or "cancer" were performed using logistic regression (LR) and random forests (RF) trained on 153 samples, and validated on two datasets of 94 and 83 independent samples (FIG. 22C). The best feature set for the LR model included t-MAD, 10 bp amplitude, P(160-180), P(180-220) and P(250-320). The same five variables were independently identified using the RF model (with some differences in their ranking). FIG. 25 shows performance metrics for the different algorithms on training set data using cross-validation. The source code for the classification algorithms is shown below in the section headed "Code". Using t-MAD alone in the validation pan-cancer dataset (FIG. 22D and FIG. 24), cancer samples could be distinguished from healthy individuals with AUC=0.764. Using the LR model improved the classification of the samples to AUC=0.908. The RF model (trained on the 153-sample training set) could distinguish cancer from healthy individuals even more accurately in the validation data set (n=94) with AUC=0.994. On the second validation dataset containing low-ctDNA cancer samples (n=83) (FIG. 22E), t-MAD alone or the LR performed less well, with AUC values of 0.421 and 0.532 respectively. However, the RF model was still able to distinguish samples from low-ctDNA cancer samples from healthy controls with AUC=0.914. At a specificity of 95%, the RF model correctly classified as cancer 64/68 (94%) of the samples from high-ctDNA cancers (colorectal, cholangiocarcinoma, ovarian, breast, melanoma), and 37/57 (65%) of the samples from low-ctDNA cancers (pancreatic, renal, glioma) (FIG. 22F). In a second iteration of model training, t-MAD was omitted, using only the 4 fragmentation features (FIG. 26). The RF model could still distinguish cancer from healthy controls albeit with slightly reduced AUCs (0.989 for cancer types with high levels of ctDNA and 0.891 for cancer types with low levels of ctDNA), suggesting that the cfDNA fragmentation pattern is most important predictive component.

Example 8: Use of Random Forest (RF) Model to Predict Detection of ctDNA in Cancer Patient Fluid A random forest (RF) model in accordance with the present invention and as described in Example 7 was based on the density or proportion of plasma cell-free DNA fragments with length 20-150, 100-150, 160-180, 163-169, 180-220 and 250-320 bp, as well as the amplitude of the oscillations with 10 bp periodicity and can predict the probability that a given plasma sample has been collected from an individual with cancer.

In addition, our data indicates that the output of this same RF classification model might allow for the triage of cancer patient fluid samples into those with sufficiently high levels of ctDNA for detection by other methods (including those with greater sensitivity and/or that allow targeted analysis of specific somatic mutations), and those without.

Figure 27:
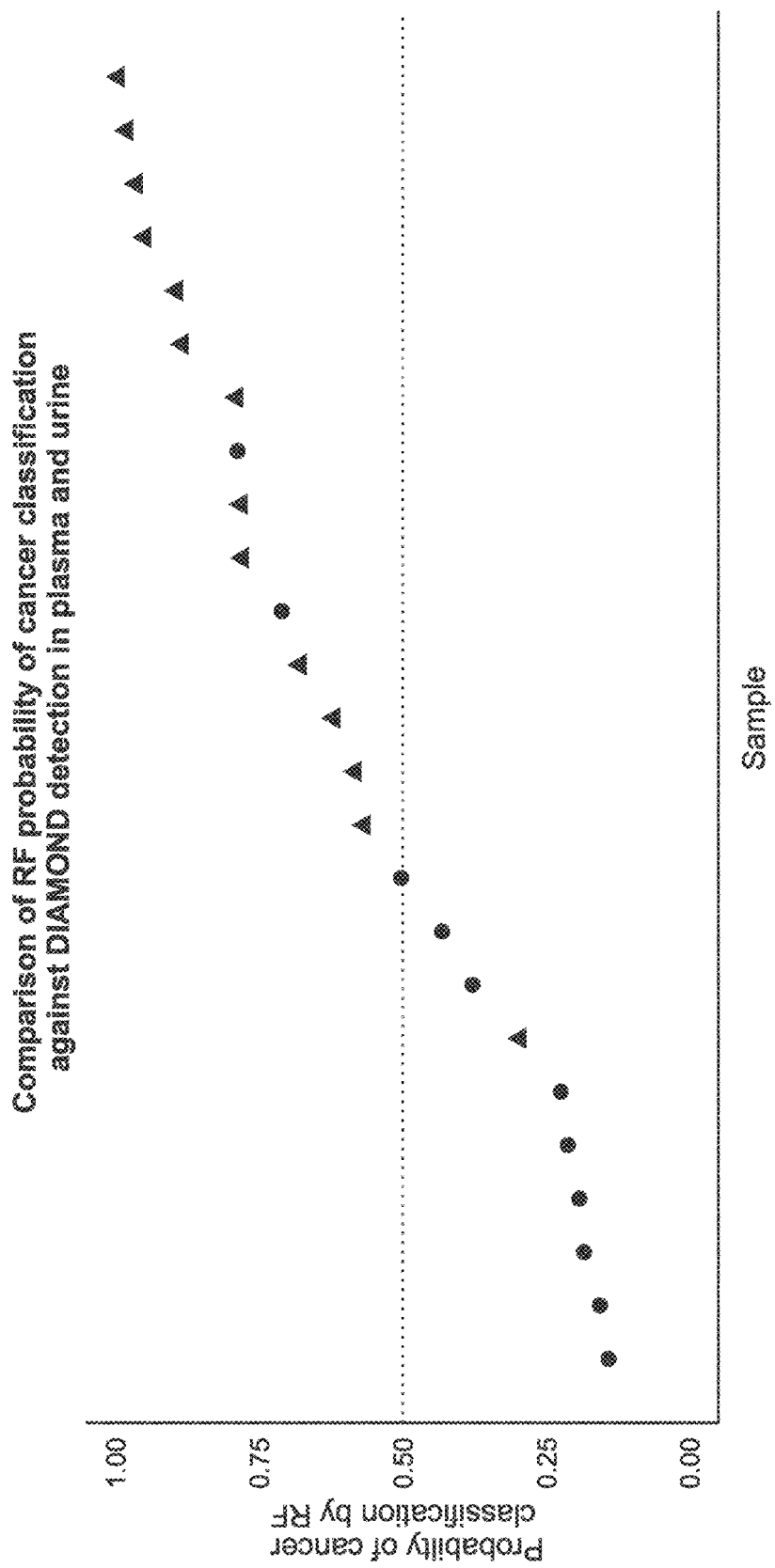
FIG. 27 shows the probability of cancer classification by the random forest (RF) model, for a given renal cell carcinoma (RCC) patient plasma sample, as indicated on the y-axis. Patient plasma samples are indicated on the x-axis. For each patient, this same plasma sample (and in some cases matched urine supernatant) were assessed for ctDNA content by INVAR-TAPAS and t-MAD analysis. Circles indicate patients in which ctDNA was not detected in either fluid by either approach. Triangles indicate patients in which ctDNA was detected in either fluid by either method.

After applying the RF model to plasma samples from patients with renal cell carcinoma (RCC), of those with >50% probability of cancer by the RF model:
  ~62% had detectable ctDNA in plasma by our INtegration of VAriant Reads of TAilor PAnel Sequencing (INVAR TAPAS) method (see co-pending patent application GB1803596.4 filed 6 Mar. 2018, the contents of which are incorporated herein by reference);
  ~63% had detectable ctDNA in plasma by INVAR and/or t-MAD (the latter of which is as described above);
  ~81% had detectable ctDNA in plasma and/or urine by INVAR and/or t-MAD. Conversely, only 11% of plasma samples with <50% probability of cancer by RF model, had detectable ctDNA. This is summarised in FIG. 27.

In summary, this analysis has the potential to highlight those cancer patients in which ctDNA analysis (by more sensitive or targeted methods such as INVAR-TAPAS) is more likely to yield informative output. In-turn these samples are more likely to prove clinically useful, potentially allowing, for example, prediction of response to therapy through identification of resistance mutations, disease prognostication, and assessment of clonal evolution through application of targeted methods. This may prove particularly relevant in those cancer types in which ctDNA detection is unreliable (such as renal cancer and glioblastoma), even at later stages of disease at which ctDNA detection would be expected to be reliable (based on equivalent data from other cancer types). Moreover, preliminary results (not shown) suggest that the above findings for RCC are corroborated in a glioblastoma cohort.

Tables

TABLE 1 summary table of the samples and patients included in the study

| index | patient | sample | SLX | barcode | cancer | cancer_type | timepoint | RECIST_volume |
|---|---|---|---|---|---|---|---|---|
| 1 | GB2 | GB2_1 | SLX-11868 | D710-D505 | glioblastoma | low_ctDNA_cancer | baseline | NA |
| 2 | GB3 | GB3_1 | SLX-11868 | D710-D506 | glioblastoma | low_ctDNA_cancer | baseline | NA |
| 3 | GB4 | GB4_1 | SLX-11868 | D710-D507 | glioblastoma | low_ctDNA_cancer | baseline | NA |
| 4 | GB5 | GB5_1 | SLX-11868 | D710-D508 | glioblastoma | low_ctDNA_cancer | baseline | NA |

TABLE 1-continued summary table of the samples and patients included in the study

| index | patient | sample | SLX | barcode | cancer | cancer_type | timepoint | RECIST_volume |
|---|---|---|---|---|---|---|---|---|
| 5 | GB6 | GB6_1 | SLX-11868 | D711-D505 | glioblastoma | low_ctDNA_cancer | baseline | NA |
| 6 | GB7 | GB7_1 | SLX-11868 | D711-D506 | glioblastoma | low_ctDNA_cancer | baseline | NA |
| 7 | GB8 | GB8_1 | SLX-11868 | D711-D507 | glioblastoma | low_ctDNA_cancer | baseline | NA |
| 8 | GB9 | GB9_1 | SLX-11868 | D711-D508 | glioblastoma | low_ctDNA_cancer | baseline | NA |
| 9 | GB10 | GB10_1 | SLX-11868 | D712-D505 | glioblastoma | low_ctDNA_cancer | baseline | NA |
| 10 | GB11 | GB11_1 | SLX-11868 | D712-D506 | glioblastoma | low_ctDNA_cancer | baseline | NA |
| 11 | GB12 | GB12_1 | SLX-11868 | D712-D507 | glioblastoma | low_ctDNA_cancer | baseline | NA |
| 12 | GB13 | GB13_1 | SLX-11868 | D712-D508 | glioblastoma | low_ctDNA_cancer | baseline | NA |
| 13 | Os1 | Os1_1 | SLX-11870 | D707-D505 | esophageal junction | low_ctDNA_cancer | baseline | NA |
| 14 | B1 | B1_1 | SLX-11034 | A019 | breast | high_ctDNA_cancer | baseline | NA |
| 15 | L1 | L1_1 | SLX-11870 | D711-D504 | lung | high_ctDNA_cancer | baseline | NA |
| 16 | Ov1 | Ov1_1 | SLX-11870 | D712-D502 | ovarian | high_ctDNA_cancer | baseline | NA |
| 17 | Ov2 | Ov2_1 | SLX-11870 | D708-D505 | ovarian | high_ctDNA_cancer | baseline | NA |
| 18 | Ren1 | Ren1_1 | SLX-11870 | D708-D507 | renal | low_ctDNA_cancer | baseline | NA |
| 19 | B2 | B2_1 | SLX-11870 | D710-D501 | breast | high_ctDNA_cancer | baseline | NA |
| 20 | L2 | L2_1 | SLX-11870 | D712-D504 | lung | high_ctDNA_cancer | baseline | NA |
| 21 | L3 | L3_1 | SLX-11870 | D712-D503 | lung | high_ctDNA_cancer | baseline | NA |
| 22 | T1 | T1_1 | SLX-11870 | D709-D506 | thymoma | high_ctDNA_cancer | baseline | NA |
| 23 | R1 | R1_1 | SLX-11870 | D710-D504 | rectum | high_ctDNA_cancer | baseline | NA |
| 24 | B3 | B3_1 | SLX-11870 | D711-D502 | breast | high_ctDNA_cancer | baseline | NA |
| 25 | L4 | L4_1 | SLX-13710 | D708-D508 | lung | high_ctDNA_cancer | baseline | NA |
| 26 | R2 | R2_1 | SLX-13710 | D707-D502 | rectum | high_ctDNA_cancer | baseline | NA |
| 27 | B4 | B4_1 | SLX-13710 | D706-D503 | breast | high_ctDNA_cancer | baseline | NA |
| 28 | P1 | P1_1 | SLX-13710 | D705-D504 | pancreatic | low_ctDNA_cancer | baseline | NA |
| 29 | Ov3 | Ov3_1 | SLX-13710 | D704-D505 | ovarian | high_ctDNA_cancer | baseline | NA |
| 30 | B5 | B5_1 | SLX-13710 | D702-D507 | breast | high_ctDNA_cancer | baseline | NA |
| 31 | B6 | B6_1 | SLX-13710 | D701-D508 | breast | high_ctDNA_cancer | baseline | NA |
| 32 | L5 | L5_1 | SLX-12841 | D701-D501 | lung | high_ctDNA_cancer | baseline | NA |
| 33 | ChC1 | ChC1_1 | SLX-12841 | D701-D502 | cholangio-carcinoma | high_ctDNA_cancer | baseline | 96 |
| 34 | B7 | B7_1 | SLX-12841 | D701-D503 | breast | high_ctDNA_cancer | baseline | NA |
| 35 | C1 | C1_1 | SLX-12841 | D701-D504 | colorectal | high_ctDNA_cancer | baseline | NA |
| 36 | ChC2 | ChC2_1 | SLX-12841 | D702-D501 | cholangio-carcinoma | high_ctDNA_cancer | baseline | 87 |
| 37 | HCC1 | HCC1_1 | SLX-12841 | D702-D502 | hepatocellular | high_ctDNA_cancer | baseline | NA |
| 38 | C2 | C2_1 | SLX-12841 | D702-D503 | colorectal | high_ctDNA_cancer | baseline | NA |
| 39 | P2 | P2_1 | SLX-12841 | D702-D504 | pancreatic | low_ctDNA_cancer | baseline | NA |
| 40 | ChC3 | ChC3_1 | SLX-12841 | D703-D505 | cholangio-carcinoma | high_ctDNA_cancer | baseline | NA |
| 41 | P3 | P3_1 | SLX-12841 | D703-D506 | pancreatic | low_ctDNA_cancer | baseline | NA |
| 42 | R3 | R3_1 | SLX-12841 | D703-D507 | rectum | high_ctDNA_cancer | baseline | NA |
| 43 | ChC4 | ChC4_1 | SLX-12841 | D703-D508 | cholangio-carcinoma | high_ctDNA_cancer | baseline | NA |
| 44 | ChC5 | ChC5_1 | SLX-12841 | D704-D505 | cholangio-carcinoma | high_ctDNA_cancer | baseline | NA |
| 45 | P4 | P4_1 | SLX-12841 | D704-D506 | pancreatic | low_ctDNA_cancer | baseline | NA |
| 46 | C3 | C3_1 | SLX-12841 | D704-D507 | colorectal | high_ctDNA_cancer | baseline | 158 |
| 47 | Ov4 | Ov4_1 | SLX-12841 | D704-D508 | ovarian | high_ctDNA_cancer | baseline | NA |
| 48 | Ov5 | Ov5_1 | SLX-12841 | D705-D501 | ovarian | high_ctDNA_cancer | baseline | NA |
| 49 | B8 | B8_1 | SLX-12841 | D705-D502 | breast | high_ctDNA_cancer | baseline | NA |
| 50 | L6 | L6_1 | SLX-12841 | D705-D503 | lung | high_ctDNA_cancer | baseline | NA |
| 51 | C4 | C4_1 | SLX-12841 | D705-D504 | colorectal | high_ctDNA_cancer | baseline | NA |
| 52 | Pe1 | Pe1_1 | SLX-12841 | D706-D501 | penile | high_ctDNA_cancer | baseline | NA |
| 53 | Pr1 | Pr1_1 | SLX-12841 | D706-D502 | prostate | high_ctDNA_cancer | baseline | 33 |
| 54 | Ce1 | Ce1_1 | SLX-12841 | D706-D503 | cervical | high_ctDNA_cancer | baseline | NA |
| 55 | C5 | C5_1 | SLX-12841 | D706-D504 | colorectal | high_ctDNA_cancer | baseline | 112 |
| 56 | Ov6 | Ov6_1 | SLX-12841 | D707-D505 | ovarian | high_ctDNA_cancer | baseline | NA |
| 57 | En1 | En1_1 | SLX-12841 | D707-D506 | endometrial | high_ctDNA_cancer | baseline | NA |
| 58 | C6 | C6_1 | SLX-12841 | D707-D507 | colorectal | high_ctDNA_cancer | baseline | 22 |
| 59 | C7 | C7_1 | SLX-12841 | D707-D508 | colorectal | high_ctDNA_cancer | baseline | NA |
| 60 | OV04-77 | JBLAB_5688 | SLX-13223 | D701-D501 | ovarian | high_ctDNA_cancer | baseline | NA |
| 61 | OV04-77 | JBLAB_5689 | SLX-13223 | D701-D502 | ovarian | high_ctDNA_cancer | post-treatment | NA |
| 62 | OV04-83 | JBLAB_5203 | SLX-13223 | D703-D501 | ovarian | high_ctDNA_cancer | baseline | NA |
| 63 | OV04-83 | JBLAB_5205 | SLX-13223 | D703-D502 | ovarian | high_ctDNA_cancer | post-treatment | NA |
| 64 | OV04-122 | JBLAB_5712 | SLX-13223 | D701-D503 | ovarian | high_ctDNA_cancer | baseline | NA |
| 65 | OV04-122 | JBLAB_5713 | SLX-13223 | D701-D504 | ovarian | high_ctDNA_cancer | post-treatment | NA |
| 66 | OV04-141 | JBLAB_5392 | SLX-13223 | D703-D503 | ovarian | high_ctDNA_cancer | baseline | NA |
| 67 | OV04-141 | JBLAB_5393 | SLX-13223 | D703-D504 | ovarian | high_ctDNA_cancer | post-treatment | NA |
| 68 | OV04-143 | JBLAB_5587 | SLX-11873 | D707-D501 | ovarian | high_ctDNA_cancer | baseline | NA |
| 69 | OV04-143 | JBLAB_5588 | SLX-11873 | D707-D502 | ovarian | high_ctDNA_cancer | post-treatment | NA |

TABLE 1-continued summary table of the samples and patients included in the study

| index | patient | sample | SLX | barcode | cancer | cancer_type | timepoint | RECIST_volume |
|---|---|---|---|---|---|---|---|---|
| 70 | OV04-180 | JBLAB_5432 | SLX-13223 | D705-D505 | ovarian | high_ctDNA_cancer | baseline | NA |
| 71 | OV04-180 | JBLAB_5433 | SLX-13223 | D705-D506 | ovarian | high_ctDNA_cancer | post-treatment | NA |
| 72 | OV04-211 | JBLAB_5471 | SLX-13223 | D706-D505 | ovarian | high_ctDNA_cancer | baseline | NA |
| 73 | OV04-211 | JBLAB_5472 | SLX-13223 | D706-D506 | ovarian | high_ctDNA_cancer | post-treatment | NA |
| 74 | OV04-226 | JBLAB_5507 | SLX-13223 | D704-D505 | ovarian | high_ctDNA_cancer | baseline | NA |
| 75 | OV04-226 | JBLAB_5508 | SLX-13223 | D704-D506 | ovarian | high_ctDNA_cancer | post-treatment | NA |
| 76 | OV04-264 | JBLAB_5622 | SLX-11873 | D707-D503 | ovarian | high_ctDNA_cancer | baseline | NA |
| 77 | OV04-264 | JBLAB_5623 | SLX-11873 | D707-D504 | ovarian | high_ctDNA_cancer | post-treatment | NA |
| 78 | OV04-292 | JBLAB_5742 | SLX-13223 | D702-D501 | ovarian | high_ctDNA_cancer | baseline | NA |
| 79 | OV04-292 | JBLAB_5743 | SLX-13223 | D702-D502 | ovarian | high_ctDNA_cancer | post-treatment | NA |
| 80 | OV04-295 | JBLAB_5420 | SLX-13223 | D705-D507 | ovarian | high_ctDNA_cancer | baseline | NA |
| 81 | OV04-295 | JBLAB_5422 | SLX-13223 | D705-D508 | ovarian | high_ctDNA_cancer | post-treatment | NA |
| 82 | OV04-297 | JBLAB_5288 | SLX-13223 | D704-D507 | ovarian | high_ctDNA_cancer | baseline | NA |
| 83 | OV04-297 | JBLAB_5289 | SLX-13223 | D704-D508 | ovarian | high_ctDNA_cancer | post-treatment | NA |
| 84 | OV04-300 | JBLAB_5754 | SLX-13223 | D702-D503 | ovarian | high_ctDNA_cancer | baseline | NA |
| 85 | OV04-300 | JBLAB_5755 | SLX-13223 | D702-D504 | ovarian | high_ctDNA_cancer | post-treatment | NA |
| 86 | X76 | X76_T1_pre | SLX-13621 | D701-D501 | ovarian | high_ctDNA_cancer | baseline | NA |
| 87 | X75_2 | X75_T13_pre | SLX-13621 | D702-D501 | ovarian | high_ctDNA_cancer | baseline | NA |
| 88 | X52 | X52_T1_pre | SLX-13621 | D703-D501 | ovarian | high_ctDNA_cancer | baseline | NA |
| 89 | X150 | X150_T1_pre | SLX-13621 | D704-D501 | ovarian | high_ctDNA_cancer | baseline | NA |
| 90 | X129 | X129_T8_pre | SLX-13621 | D705-D501 | ovarian | high_ctDNA_cancer | baseline | NA |
| 91 | X57 | X57_T1_pre | SLX-13621 | D706-D501 | ovarian | high_ctDNA_cancer | baseline | NA |
| 92 | X73 | X73_T3B_pre | SLX-13621 | D707-D501 | ovarian | high_ctDNA_cancer | baseline | NA |
| 93 | JG090 | JG090_T6_12_pre | SLX-13621 | D708-D501 | ovarian | high_ctDNA_cancer | baseline | NA |
| 94 | X145 | X145_T8_pre | SLX-13621 | D709-D501 | ovarian | high_ctDNA_cancer | baseline | NA |
| 95 | X112 | X112_T1_pre | SLX-13621 | D710-D501 | ovarian | high_ctDNA_cancer | baseline | NA |
| 96 | X75_1 | X75_T1_pre | SLX-13621 | D711-D501 | ovarian | high_ctDNA_cancer | baseline | NA |
| 97 | X72 | X72_T1_pre | SLX-13621 | D712-D501 | ovarian | high_ctDNA_cancer | baseline | NA |
| 98 | X74 | X74_T1_pre | SLX-13621 | D701-D502 | ovarian | high_ctDNA_cancer | baseline | NA |
| 99 | X127 | X127_T1_pre | SLX-13621 | D702-D502 | ovarian | high_ctDNA_cancer | baseline | NA |
| 100 | X30 | X30_T1_pre | SLX-13621 | D703-D502 | ovarian | high_ctDNA_cancer | baseline | NA |
| 101 | JBLAB_5180 | JBLAB.5180_pre | SLX-13621 | D704-D502 | ovarian | high_ctDNA_cancer | baseline | NA |
| 102 | JBLAB_5027 | JBLAB.5027_pre | SLX-13621 | D705-D502 | ovarian | high_ctDNA_cancer | baseline | NA |
| 103 | JBLAB_5595 | JBLAB.5595_pre | SLX-13621 | D706-D502 | ovarian | high_ctDNA_cancer | baseline | NA |
| 104 | JBLAB_5599 | JBLAB.5599_pre | SLX-13621 | D707-D502 | ovarian | high_ctDNA_cancer | baseline | NA |
| 105 | JBLAB_5611 | JBLAB.5611_pre | SLX-13621 | D708-D502 | ovarian | high_ctDNA_cancer | baseline | NA |
| 106 | JBLAB_5477 | JBLAB.5477_pre | SLX-13621 | D709-D502 | ovarian | high_ctDNA_cancer | baseline | NA |
| 107 | JBLAB_5632 | JBLAB.5632_pre | SLX-13621 | D710-D502 | ovarian | high_ctDNA_cancer | baseline | NA |
| 108 | B9 | B9_1 | SLX-11043 | D705-D506 | breast | high_ctDNA_cancer | baseline | 119 |
| 109 | B10 | B10_1 | SLX-11043 | D702-D501 | breast | high_ctDNA_cancer | baseline | 46 |
| 110 | B11 | B11_1 | SLX-11043 | D701-D501 | breast | high_ctDNA_cancer | baseline | 52 |
| 111 | B12 | B12_1 | SLX-11043 | D705-D508 | breast | high_ctDNA_cancer | baseline | 23 |
| 112 | B13 | B13_1 | SLX-11043 | D704-D508 | breast | high_ctDNA_cancer | baseline | 35 |
| 113 | B14 | B14_1 | SLX-11043 | D704-D505 | breast | high_ctDNA_cancer | baseline | 60 |
| 114 | B15 | B15_1 | SLX-11043 | D703-D503 | breast | high_ctDNA_cancer | baseline | 116 |
| 115 | B16 | B16_1 | SLX-11042 | D703-D508 | breast | high_ctDNA_cancer | baseline | 10 |
| 116 | B17 | B17_1 | SLX-11042 | D704-D504 | breast | high_ctDNA_cancer | baseline | 71 |
| 117 | B18 | B18_1 | SLX-11042 | D704-D502 | breast | high_ctDNA_cancer | baseline | 19 |
| 118 | B19 | B19_1 | SLX-11042 | D705-D502 | breast | high_ctDNA_cancer | baseline | 63 |
| 119 | B20 | B20_1 | SLX-11042 | D705-D504 | breast | high_ctDNA_cancer | baseline | 72 |
| 120 | B21 | B21_1 | SLX-11042 | D701-D505 | breast | high_ctDNA_cancer | baseline | 21 |
| 121 | B22 | B22_1 | SLX-11042 | D701-D507 | breast | high_ctDNA_cancer | baseline | 71 |
| 122 | B23 | B23_1 | SLX-11042 | D702-D506 | breast | high_ctDNA_cancer | baseline | 68 |
| 123 | B24 | B24_1 | SLX-11042 | D702-D508 | breast | high_ctDNA_cancer | baseline | 18 |
| 124 | B25 | B25_1 | SLX-11042 | D703-D506 | breast | high_ctDNA_cancer | baseline | 150 |
| 125 | B26 | B26_1 | SLX-11042 | D706-D502 | breast | high_ctDNA_cancer | baseline | 211 |
| 126 | B27 | B27_1 | SLX-11042 | D706-D503 | breast | high_ctDNA_cancer | baseline | 91 |
| 127 | B28 | B28_1 | SLX-11042 | D706-D504 | breast | high_ctDNA_cancer | baseline | 155 |
| 128 | B29 | B29_1 | SLX-11043 | D703-D502 | breast | high_ctDNA_cancer | baseline | NA |
| 129 | B30 | B30_1 | SLX-11043 | D701-D504 | breast | high_ctDNA_cancer | post-treatment | NA |
| 130 | B31 | B31_1 | SLX-11043 | D704-D507 | breast | high_ctDNA_cancer | post-treatment | NA |
| 131 | B32 | B32_1 | SLX-11042 | D703-D507 | breast | high_ctDNA_cancer | post-treatment | NA |
| 132 | B11 | B11_1 | SLX-10991 | | bladder | low_ctDNA_cancer | baseline | NA |
| 133 | B12 | B12_1 | SLX-10991 | | bladder | low_ctDNA_cancer | baseline | NA |
| 134 | B13 | B13_1 | SLX-11094 | D708-D501 | bladder | low_ctDNA_cancer | baseline | NA |

TABLE 1-continued summary table of the samples and patients included in the study

| index | patient | sample | SLX | barcode | cancer | cancer_type | timepoint | RECIST_volume |
|---|---|---|---|---|---|---|---|---|
| 135 | B14 | B14_1 | SLX-10575 | iPCRtagT014 | bladder | low_ctDNA_cancer | baseline | NA |
| 136 | B15 | B15_1 | SLX-11904 | D709-D507 | bladder | low_ctDNA_cancer | baseline | NA |
| 137 | B16 | B16_1 | SLX-10572 | D704-D505 | bladder | low_ctDNA_cancer | baseline | NA |
| 138 | B17 | B17_1 | SLX-10572 | D708-D507 | bladder | low_ctDNA_cancer | baseline | NA |
| 139 | B18 | B18_1 | SLX-11896 | D708-D504 | bladder | low_ctDNA_cancer | baseline | NA |
| 140 | B19 | B19_1 | SLX-11896 | D707-D507 | bladder | low_ctDNA_cancer | baseline | NA |
| 141 | B110 | B110_1 | SLX-11896 | D707-D508 | bladder | low_ctDNA_cancer | baseline | NA |
| 142 | B111 | B111_1 | SLX-11904 | D709-D506 | bladder | low_ctDNA_cancer | baseline | NA |
| 143 | B112 | B112_1 | SLX-11904 | D708-D504 | bladder | low_ctDNA_cancer | baseline | NA |
| 144 | B113 | B113_1 | SLX-11904 | D709-D501 | bladder | low_ctDNA_cancer | baseline | NA |
| 145 | B114 | B114_1 | SLX-11986 | D709-D504 | bladder | low_ctDNA_cancer | baseline | NA |
| 146 | B115 | B115_1 | SLX-10572 | D708-D508 | bladder | low_ctDNA_cancer | baseline | NA |
| 147 | B116 | B116_1 | SLX-11896 | D707-D502 | bladder | low_ctDNA_cancer | baseline | NA |
| 148 | B117 | B117_1 | SLX-10572 | D708-D505 | bladder | low_ctDNA_cancer | baseline | NA |
| 149 | B118 | B118_1 | SLX-11896 | D709-D503 | bladder | low_ctDNA_cancer | baseline | NA |
| 150 | B119 | B119_1 | SLX-11896 | D708-D503 | bladder | low_ctDNA_cancer | baseline | NA |
| 151 | Ren2 | Ren2_1 | SLX-13900 | D707-D501 | renal | low_ctDNA_cancer | baseline | NA |
| 152 | Ren3 | Ren3_1 | SLX-13900 | D707-D502 | renal | low_ctDNA_cancer | baseline | NA |
| 153 | Ren4 | Ren4_1 | SLX-13900 | D707-D503 | renal | low_ctDNA_cancer | baseline | NA |
| 154 | Ren5 | Ren5_1 | SLX-13900 | D707-D504 | renal | low_ctDNA_cancer | baseline | NA |
| 155 | Ren6 | Ren6_1 | SLX-13900 | D708-D501 | renal | low_ctDNA_cancer | baseline | NA |
| 156 | Ren7 | Ren7_1 | SLX-13900 | D708-D502 | renal | low_ctDNA_cancer | baseline | NA |
| 157 | Ren8 | Ren8_1 | SLX-13900 | D708-D503 | renal | low_ctDNA_cancer | baseline | NA |
| 158 | Ren9 | Ren9_1 | SLX-13900 | D708-D504 | renal | low_ctDNA_cancer | baseline | NA |
| 159 | Ren10 | Ren10_1 | SLX-13900 | D708-D505 | renal | low_ctDNA_cancer | baseline | NA |
| 160 | Ren11 | Ren11_1 | SLX-13900 | D708-D506 | renal | low_ctDNA_cancer | baseline | NA |
| 161 | Ren12 | Ren12_1 | SLX-13900 | D708-D507 | renal | low_ctDNA_cancer | baseline | NA |
| 162 | Ren13 | Ren13_1 | SLX-13900 | D708-D508 | renal | low_ctDNA_cancer | baseline | NA |
| 163 | Ren14 | Ren14_1 | SLX-13900 | D709-D501 | renal | low_ctDNA_cancer | baseline | NA |
| 164 | Ren15 | Ren15_1 | SLX-13900 | D709-D502 | renal | low_ctDNA_cancer | baseline | NA |
| 165 | Ren16 | Ren16_1 | SLX-13900 | D709-D503 | renal | low_ctDNA_cancer | baseline | NA |
| 166 | Ren17 | Ren17_1 | SLX-13900 | D709-D504 | renal | low_ctDNA_cancer | baseline | NA |
| 167 | Ren18 | Ren18_1 | SLX-13900 | D709-D505 | renal | low_ctDNA_cancer | baseline | NA |
| 168 | Ren19 | Ren19_1 | SLX-13900 | D709-D506 | renal | low_ctDNA_cancer | baseline | NA |
| 169 | Ren20 | Ren20_1 | SLX-13900 | D710-D501 | renal | low_ctDNA_cancer | baseline | NA |
| 170 | Ren21 | Ren21_1 | SLX-13900 | D710-D502 | renal | low_ctDNA_cancer | baseline | NA |
| 171 | Ren22 | Ren22_1 | SLX-13900 | D710-D503 | renal | low_ctDNA_cancer | baseline | NA |
| 172 | Ren23 | Ren23_1 | SLX-13900 | D710-D504 | renal | low_ctDNA_cancer | baseline | NA |
| 173 | Ren24 | Ren24_1 | SLX-13900 | D710-D505 | renal | low_ctDNA_cancer | baseline | NA |
| 174 | Ren25 | Ren25_1 | SLX-13900 | D710-D506 | renal | low_ctDNA_cancer | baseline | NA |
| 175 | Ren26 | Ren26_1 | SLX-13900 | D710-D507 | renal | low_ctDNA_cancer | baseline | NA |
| 176 | Ren27 | Ren27_1 | SLX-13900 | D710-D508 | renal | low_ctDNA_cancer | baseline | NA |
| 177 | Ren28 | Ren28_1 | SLX-13900 | D711-D501 | renal | low_ctDNA_cancer | baseline | NA |
| 178 | Ren29 | Ren29_1 | SLX-13900 | D711-D502 | renal | low_ctDNA_cancer | baseline | NA |
| 179 | Ren30 | Ren30_1 | SLX-13900 | D711-D503 | renal | low_ctDNA_cancer | baseline | NA |
| 180 | Ren31 | Ren31_1 | SLX-13900 | D711-D504 | renal | low_ctDNA_cancer | baseline | NA |
| 181 | Ren32 | Ren32_1 | SLX-13900 | D711-D505 | renal | low_ctDNA_cancer | baseline | NA |
| 182 | Ren33 | Ren33_1 | SLX-13900 | D711-D506 | renal | low_ctDNA_cancer | baseline | NA |
| 183 | HIP_1 | HIP_1 | SLX-12531 | D703-D501 | healthy | healthy | baseline | NA |
| 184 | HIP_10 | HIP_10 | SLX-12531 | D705-D507 | healthy | healthy | baseline | NA |
| 185 | HIP_11 | HIP_11 | SLX-12531 | D705-D507 | healthy | healthy | baseline | NA |
| 186 | HIP_12 | HIP_12 | SLX-12531 | D705-D508 | healthy | healthy | baseline | NA |
| 187 | HIP_13 | HIP_13 | SLX-12531 | D706-D505 | healthy | healthy | baseline | NA |
| 188 | HIP_14 | HIP_14 | SLX-12531 | D706-D506 | healthy | healthy | baseline | NA |
| 189 | HIP_15 | HIP_15 | SLX-12531 | D706-D507 | healthy | healthy | baseline | NA |
| 190 | HIP_16 | HIP_16 | SLX-12531 | D706-D508 | healthy | healthy | baseline | NA |
| 191 | HIP_17 | HIP_17 | SLX-12531 | D707-D501 | healthy | healthy | baseline | NA |
| 192 | HIP_18 | HIP_18 | SLX-12531 | D707-D502 | healthy | healthy | baseline | NA |
| 193 | HIP_19 | HIP_19 | SLX-12531 | D707-D503 | healthy | healthy | baseline | NA |
| 194 | HIP_2 | HIP_2 | SLX-12531 | D703-D502 | healthy | healthy | baseline | NA |
| 195 | HIP_20 | HIP_20 | SLX-12531 | D707-D504 | healthy | healthy | baseline | NA |
| 196 | HIP_21 | HIP_21 | SLX-12531 | D708-D501 | healthy | healthy | baseline | NA |
| 197 | HIP_22 | HIP_22 | SLX-12531 | D708-D502 | healthy | healthy | baseline | NA |
| 198 | HIP_23 | HIP_23 | SLX-12531 | D708-D503 | healthy | healthy | baseline | NA |
| 199 | HIP_24 | HIP_24 | SLX-12531 | D708-D504 | healthy | healthy | baseline | NA |
| 200 | HIP_27 | HIP_27 | SLX-12534 | D707-D502 | healthy | healthy | baseline | NA |
| 201 | HIP_28 | HIP_28 | SLX-12534 | D707-D503 | healthy | healthy | baseline | NA |
| 202 | HIP_29 | HIP_29 | SLX-12534 | D707-D504 | healthy | healthy | baseline | NA |
| 203 | HIP_3 | HIP_3 | SLX-12531 | D703-D503 | healthy | healthy | baseline | NA |
| 204 | HIP_30 | HIP_30 | SLX-12534 | D708-D501 | healthy | healthy | baseline | NA |
| 205 | HIP_31 | HIP_31 | SLX-12534 | D708-D502 | healthy | healthy | baseline | NA |
| 206 | HIP_32 | HIP_32 | SLX-12534 | D708-D503 | healthy | healthy | baseline | NA |
| 207 | HIP_33 | HIP_33 | SLX-12534 | D708-D504 | healthy | healthy | baseline | NA |
| 208 | HIP_34 | HIP_34 | SLX-12534 | D709-D501 | healthy | healthy | baseline | NA |
| 209 | HIP_35 | HIP_35 | SLX-12534 | D709-D503 | healthy | healthy | baseline | NA |
| 210 | HIP_36 | HIP_36 | SLX-12534 | D709-D504 | healthy | healthy | baseline | NA |

TABLE 1-continued summary table of the samples and patients included in the study

| index | patient | sample | SLX | barcode | cancer | cancer_type | timepoint | RECIST_volume |
|---|---|---|---|---|---|---|---|---|
| 211 | HIP_37 | HIP_37 | SLX-12534 | D710-D501 | healthy | healthy | baseline | NA |
| 212 | HIP_38 | HIP_38 | SLX-12534 | D710-D502 | healthy | healthy | baseline | NA |
| 213 | HIP_39 | HIP_39 | SLX-12534 | D710-D503 | healthy | healthy | baseline | NA |
| 214 | HIP_4 | HIP_4 | SLX-12531 | D703-D504 | healthy | healthy | baseline | NA |
| 215 | HIP_40 | HIP_40 | SLX-12534 | D710-D504 | healthy | healthy | baseline | NA |
| 216 | HIP_41 | HIP_41 | SLX-12534 | D711-D505 | healthy | healthy | baseline | NA |
| 217 | HIP_42 | HIP_42 | SLX-12534 | D711-D506 | healthy | healthy | baseline | NA |
| 218 | HIP_43 | HIP_43 | SLX-12534 | D711-D507 | healthy | healthy | baseline | NA |
| 219 | HIP_44 | HIP_44 | SLX-12534 | D711-D508 | healthy | healthy | baseline | NA |
| 220 | HIP_45 | HIP_45 | SLX-12534 | D712-D505 | healthy | healthy | baseline | NA |
| 221 | HIP_46 | HIP_46 | SLX-12534 | D712-D506 | healthy | healthy | baseline | NA |
| 222 | HIP_47 | HIP_47 | SLX-12534 | D712-D507 | healthy | healthy | baseline | NA |
| 223 | HIP_48 | HIP_48 | SLX-12534 | D712-D508 | healthy | healthy | baseline | NA |
| 224 | HIP_5 | HIP_5 | SLX-12531 | D704-D501 | healthy | healthy | baseline | NA |
| 225 | HIP_6 | HIP_6 | SLX-12531 | D704-D502 | healthy | healthy | baseline | NA |
| 226 | HIP_7 | HIP_7 | SLX-12531 | D704-D503 | healthy | healthy | baseline | NA |
| 227 | HIP_8 | HIP_8 | SLX-12531 | D704-D504 | healthy | healthy | baseline | NA |
| 228 | HIP_9 | HIP_9 | SLX-12531 | D705-D505 | healthy | healthy | baseline | NA |
| 229 | M1 | M1_1 | SLX-11379 | D701-D502 | melanoma | high_ctDNA_cancer | baseline | 23.8895 |
| 230 | M1 | M1_2 | SLX-11379 | D701-D501 | melanoma | high_ctDNA_cancer | post-treatment | 11.3665 |
| 231 | M4 | M4_1 | SLX-11379 | D702-D501 | melanoma | high_ctDNA_cancer | baseline | 4.61105 |
| 232 | M4 | M4_2 | SLX-12758 | D704-D501 | melanoma | high_ctDNA_cancer | post-treatment | 1.02111 |
| 233 | M4 | M4_3 | SLX-12759 | D708-D501 | melanoma | high_ctDNA_cancer | post-treatment | 1.29681 |
| 234 | M4 | M4_4 | SLX-12758 | D709-D502 | melanoma | high_ctDNA_cancer | post-treatment | 5.49329 |
| 235 | M4 | M4_5 | SLX-12758 | D702-D501 | melanoma | high_ctDNA_cancer | post-treatment | 28.2798 |
| 236 | M4 | M4_6 | SLX-11383 | D701-D506 | melanoma | high_ctDNA_cancer | post-treatment | 157.486 |
| 237 | M4 | M4_7 | SLX-11379 | D701-D503 | melanoma | high_ctDNA_cancer | post-treatment | 307.577 |
| 238 | M12 | M12_1 | SLX-11379 | D703-D502 | melanoma | high_ctDNA_cancer | baseline | 991.038 |
| 239 | M12 | M12_2 | SLX-11847 | D704-D502 | melanoma | high_ctDNA_cancer | post-treatment | 135.874 |
| 240 | M12 | M12_3 | SLX-11847 | D704-D503 | melanoma | high_ctDNA_cancer | post-treatment | 186.259 |
| 241 | M12 | M12_4 | SLX-11847 | D707-D507 | melanoma | high_ctDNA_cancer | post-treatment | 499.186 |
| 242 | M14 | M14_1 | SLX-11383 | D708-D503 | melanoma | high_ctDNA_cancer | baseline | 0.95626 |
| 243 | M14 | M14_2 | SLX-12758 | D706-D506 | melanoma | high_ctDNA_cancer | post-treatment | 0.46476 |
| 244 | M22 | M22_1 | SLX-11379 | D704-D507 | melanoma | high_ctDNA_cancer | baseline | 34.9164 |
| 245 | M22 | M22_2 | SLX-12758 | D706-D507 | melanoma | high_ctDNA_cancer | post-treatment | 19.8097 |
| 246 | M22 | M22_3 | SLX-11379 | D704-D508 | melanoma | high_ctDNA_cancer | post-treatment | 21.37 |
| 247 | M22 | M22_4 | SLX-12758 | D704-D508 | melanoma | high_ctDNA_cancer | post-treatment | 46.8143 |
| 248 | M32 | M32_1 | SLX-11379 | D705-D506 | melanoma | high_ctDNA_cancer | baseline | 70.2068 |
| 249 | M32 | M32_2 | SLX-11847 | D705-D503 | melanoma | high_ctDNA_cancer | baseline | 123.343 |
| 250 | C8 | C8_T1 | SLX-12832 | D709-D501 | colorectal | high_ctDNA_cancer | post-treatment | 133 |
| 251 | C8 | C8_T2 | SLX-12832 | D709-D502 | colorectal | high_ctDNA_cancer | post-treatment | 84 |
| 252 | L5 | L5_T2 | SLX-12832 | D709-D503 | lung | high_ctDNA_cancer | post-treatment | NA |
| 253 | ChC1 | ChC1_3 | SLX-12832 | D709-D504 | cholangio-carcinoma | high_ctDNA_cancer | post-treatment | 96 |
| 254 | ChC1 | ChC1_4 | SLX-12832 | D710-D501 | cholangio-carcinoma | high_ctDNA_cancer | post-treatment | NA |
| 255 | ChC2 | ChC2_2 | SLX-12832 | D710-D502 | cholangio-carcinoma | high_ctDNA_cancer | post-treatment | NA |
| 256 | ChC2 | ChC2_3 | SLX-12832 | D710-D503 | cholangio-carcinoma | high_ctDNA_cancer | post-treatment | NA |
| 257 | HCC1 | HCC1_2 | SLX-12832 | D710-D504 | hepatocellular | high_ctDNA_cancer | post-treatment | NA |
| 258 | HCC1 | HCC1_3 | SLX-12832 | D711-D505 | hepatocellular | high_ctDNA_cancer | post-treatment | NA |
| 259 | HCC1 | HCC1_4 | SLX-12832 | D711-D506 | hepatocellular | high_ctDNA_cancer | post-treatment | NA |
| 260 | HCC1 | HCC1_5 | SLX-12832 | D711-D507 | hepatocellular | high_ctDNA_cancer | post-treatment | NA |

TABLE 1-continued summary table of the samples and patients included in the study

| index | patient | sample | SLX | barcode | cancer | cancer_type | timepoint | RECIST_volume |
|---|---|---|---|---|---|---|---|---|
| 261 | P2 | P2_2 | SLX-12832 | D711-D508 | pancreatic | low_ctDNA_cancer | post-treatment | NA |
| 262 | P4 | P4_2 | SLX-12832 | D712-D505 | pancreatic | low_ctDNA_cancer | post-treatment | NA |
| 263 | C4 | C4_2 | SLX-12832 | D712-D506 | colorectal | high_ctDNA_cancer | post-treatment | NA |
| 264 | Pr1 | Pr1_4 | SLX-12832 | D712-D507 | prostate | high_ctDNA_cancer | post-treatment | 29 |
| 265 | Ov6 | Ov6_2 | SLX-12832 | D712-D508 | ovarian | high_ctDNA_cancer | post-treatment | NA |
| 266 | ChC2 | ChC2_6 | SLX-12838 | D701-D505 | cholangio-carcinoma | high_ctDNA_cancer | post-treatment | 47 |
| 267 | ChC3 | ChC3_2 | SLX-12838 | D701-D506 | cholangio-carcinoma | high_ctDNA_cancer | post-treatment | NA |
| 268 | C3 | C3_5 | SLX-12838 | D701-D507 | colorectal | high_ctDNA_cancer | post-treatment | NA |
| 269 | L6 | L6_2 | SLX-12838 | D701-D508 | lung | high_ctDNA_cancer | post-treatment | NA |
| 270 | Pr1 | Pr1_3 | SLX-12838 | D702-D505 | prostate | high_ctDNA_cancer | post-treatment | NA |
| 271 | B7 | B7_2 | SLX-12838 | D702-D506 | breast | high_ctDNA_cancer | post-treatment | NA |
| 272 | C1 | C1_2 | SLX-12838 | D702-D507 | colorectal | high_ctDNA_cancer | post-treatment | NA |
| 273 | ChC2 | ChC2_4 | SLX-12838 | D702-D508 | cholangio-carcinoma | high_ctDNA_cancer | post-treatment | 41 |
| 274 | ChC2 | ChC2_5 | SLX-12838 | D703-D501 | cholangio-carcinoma | high_ctDNA_cancer | post-treatment | NA |
| 275 | P4 | P4_3 | SLX-12838 | D703-D502 | pancreatic | low_ctDNA_cancer | post-treatment | NA |
| 276 | C3 | C3_4 | SLX-12838 | D703-D503 | colorectal | high_ctDNA_cancer | post-treatment | 119 |
| 277 | Ov4 | Ov4_2 | SLX-12838 | D703-D504 | ovarian | high_ctDNA_cancer | post-treatment | NA |
| 278 | Ov5 | Ov5_2 | SLX-12838 | D704-D501 | ovarian | high_ctDNA_cancer | post-treatment | NA |
| 279 | B8 | B8_2 | SLX-12838 | D704-D502 | breast | high_ctDNA_cancer | post-treatment | NA |
| 280 | C5 | C5_3 | SLX-12838 | D704-D503 | colorectal | high_ctDNA_cancer | post-treatment | 65 |
| 281 | En1 | En1_2 | SLX-12838 | D704-D504 | endometrial | high_ctDNA_cancer | post-treatment | NA |
| 282 | C6 | C6_2 | SLX-12838 | D705-D505 | colorectal | high_ctDNA_cancer | post-treatment | NA |
| 283 | ChC1 | ChC1_2 | SLX-12838 | D705-D506 | cholangio-carcinoma | high_ctDNA_cancer | post-treatment | NA |
| 284 | C3 | C3_2 | SLX-12838 | D705-D507 | colorectal | high_ctDNA_cancer | post-treatment | NA |
| 285 | C3 | C3_3 | SLX-12838 | D705-D508 | colorectal | high_ctDNA_cancer | post-treatment | NA |
| 286 | Ov4 | Ov4_3 | SLX-12838 | D706-D505 | ovarian | high_ctDNA_cancer | post-treatment | NA |
| 287 | Ov5 | Ov5_3 | SLX-12838 | D706-D506 | ovarian | high_ctDNA_cancer | post-treatment | NA |
| 288 | Pr1 | Pr1_2 | SLX-12838 | D706-D507 | prostate | high_ctDNA_cancer | post-treatment | NA |
| 289 | C5 | C5_2 | SLX-12838 | D706-D508 | colorectal | high_ctDNA_cancer | post-treatment | NA |
| 290 | B33 | B33_1 | SLX-15332 | D707-D505 | breast | high_ctDNA_cancer | baseline | NA |
| 291 | B34 | B34_1 | SLX-15332 | D707-D506 | breast | high_ctDNA_cancer | baseline | NA |
| 292 | B35 | B35_1 | SLX-15332 | D707-D508 | breast | high_ctDNA_cancer | baseline | NA |
| 293 | B36 | B36_1 | SLX-15332 | D708-D505 | breast | high_ctDNA_cancer | baseline | NA |
| 294 | B37 | B37_1 | SLX-15332 | D708-D506 | breast | high_ctDNA_cancer | baseline | NA |
| 295 | B38 | B38_1 | SLX-15332 | D708-D507 | breast | high_ctDNA_cancer | baseline | NA |
| 296 | B39 | B39_1 | SLX-15332 | D709-D502 | breast | high_ctDNA_cancer | baseline | NA |
| 297 | B40 | B40_1 | SLX-15332 | D708-D508 | breast | high_ctDNA_cancer | baseline | NA |
| 298 | B41 | B41_1 | SLX-15332 | D709-D501 | breast | high_ctDNA_cancer | baseline | NA |
| 299 | B42 | B42_1 | SLX-15332 | D709-D503 | breast | high_ctDNA_cancer | baseline | NA |
| 300 | B43 | B43_1 | SLX-15332 | D709-D504 | breast | high_ctDNA_cancer | baseline | NA |
| 301 | B44 | B44_1 | SLX-13227 | D704-D506 | breast | high_ctDNA_cancer | baseline | NA |
| 302 | B45 | B45_1 | SLX-13227 | D704-D508 | breast | high_ctDNA_cancer | baseline | NA |
| 303 | B46 | B46_1 | SLX-13227 | D705-D506 | breast | high_ctDNA_cancer | baseline | NA |
| 304 | B47 | B47_1 | SLX-13227 | D701-D502 | breast | high_ctDNA_cancer | baseline | NA |
| 305 | B48 | B48_1 | SLX-13227 | D701-D504 | breast | high_ctDNA_cancer | baseline | NA |
| 306 | B49 | B49_1 | SLX-13227 | D702-D502 | breast | high_ctDNA_cancer | baseline | NA |
| 307 | B50 | B50_1 | SLX-13227 | D702-D504 | breast | high_ctDNA_cancer | baseline | NA |

TABLE 1-continued summary table of the samples and patients included in the study

| index | patient | sample | SLX | barcode | cancer | cancer_type | timepoint | RECIST_volume |
|---|---|---|---|---|---|---|---|---|
| 308 | B51 | B51_1 | SLX-13227 | D703-D502 | breast | high_ctDNA_cancer | baseline | NA |
| 309 | GB14 | GB14_1 | SLX-12839 | D701-D501 | glioblastoma | low_ctDNA_cancer | baseline | NA |
| 310 | GB15 | GB15_1 | SLX-12839 | D701-D502 | glioblastoma | low_ctDNA_cancer | baseline | NA |
| 311 | GB16 | GB16_1 | SLX-12839 | D701-D503 | glioblastoma | low_ctDNA_cancer | baseline | NA |
| 312 | GB17 | GB17_1 | SLX-12839 | D701-D504 | glioblastoma | low_ctDNA_cancer | baseline | NA |
| 313 | GB18 | GB18_1 | SLX-12839 | D702-D501 | glioblastoma | low_ctDNA_cancer | baseline | NA |
| 314 | GB19 | GB19_1 | SLX-12839 | D702-D502 | glioblastoma | low_ctDNA_cancer | baseline | NA |
| 315 | GB20 | GB20_1 | SLX-12839 | D702-D503 | glioblastoma | low_ctDNA_cancer | baseline | NA |
| 316 | GB21 | GB21_1 | SLX-12839 | D702-D504 | glioblastoma | low_ctDNA_cancer | baseline | NA |
| 317 | GB22 | GB22_1 | SLX-12839 | D703-D505 | glioblastoma | low_ctDNA_cancer | baseline | NA |
| 318 | GB23 | GB23_1 | SLX-12839 | D703-D506 | glioblastoma | low_ctDNA_cancer | baseline | NA |
| 319 | GB24 | GB24_1 | SLX-12839 | D704-D505 | glioblastoma | low_ctDNA_cancer | baseline | NA |
| 320 | GB25 | GB25_1 | SLX-12839 | D704-D506 | glioblastoma | low_ctDNA_cancer | baseline | NA |
| 321 | GB26 | GB26_1 | SLX-12839 | D703-D507 | glioblastoma | low_ctDNA_cancer | baseline | NA |
| 322 | GB27 | GB27_1 | SLX-12839 | D703-D508 | glioblastoma | low_ctDNA_cancer | baseline | NA |
| 323 | GB28 | GB28_1 | SLX-12839 | D704-D507 | glioblastoma | low_ctDNA_cancer | baseline | NA |
| 324 | GB29 | GB29_1 | SLX-12839 | D704-D508 | glioblastoma | low_ctDNA_cancer | baseline | NA |
| 325 | GB30 | GB30_1 | SLX-12839 | D705-D501 | glioblastoma | low_ctDNA_cancer | baseline | NA |
| 326 | GB31 | GB31_1 | SLX-12839 | D705-D502 | glioblastoma | low_ctDNA_cancer | baseline | NA |
| 327 | GB32 | GB32_1 | SLX-12839 | D705-D503 | glioblastoma | low_ctDNA_cancer | baseline | NA |
| 328 | GB33 | GB33_1 | SLX-12839 | D706-D501 | glioblastoma | low_ctDNA_cancer | baseline | NA |
| 329 | GB34 | GB34_1 | SLX-12839 | D706-D502 | glioblastoma | low_ctDNA_cancer | baseline | NA |
| 330 | GB35 | GB35_1 | SLX-12839 | D706-D503 | glioblastoma | low_ctDNA_cancer | baseline | NA |
| 331 | batch2_ctl1 | batch2_ctl1 | SLX-13222 | D701-D501 | healthy | healthy | baseline | NA |
| 332 | batch2_ctl2 | batch2_ctl2 | SLX-13222 | D701-D502 | healthy | healthy | baseline | NA |
| 333 | batch2_ctl3 | batch2_ctl3 | SLX-13222 | D701-D503 | healthy | healthy | baseline | NA |
| 334 | batch2_ctl4 | batch2_ctl4 | SLX-13222 | D701-D504 | healthy | healthy | baseline | NA |
| 335 | batch2_ctl5 | batch2_ctl5 | SLX-13222 | D702-D501 | healthy | healthy | baseline | NA |
| 336 | batch2_ctl6 | batch2_ctl6 | SLX-13222 | D702-D502 | healthy | healthy | baseline | NA |
| 337 | batch2_ctl7 | batch2_ctl7 | SLX-13222 | D702-D503 | healthy | healthy | baseline | NA |
| 338 | batch2_ctl8 | batch2_ctl8 | SLX-13222 | D702-D504 | healthy | healthy | baseline | NA |
| 339 | batch2_ctl9 | batch2_ctl9 | SLX-13222 | D703-D501 | healthy | healthy | baseline | NA |
| 340 | batch2_ctl10 | batch2_ctl10 | SLX-13222 | D703-D502 | healthy | healthy | baseline | NA |
| 341 | batch2_ctl11 | batch2_ctl11 | SLX-13222 | D703-D503 | healthy | healthy | baseline | NA |
| 342 | batch2_ctl12 | batch2_ctl12 | SLX-13222 | D703-D504 | healthy | healthy | baseline | NA |
| 343 | batch2_ctl13 | batch2_ctl13 | SLX-13222 | D704-D505 | healthy | healthy | baseline | NA |
| 344 | batch2_ctl14 | batch2_ctl14 | SLX-13222 | D704-D506 | healthy | healthy | baseline | NA |
| 345 | batch2_ctl15 | batch2_ctl15 | SLX-13222 | D704-D507 | healthy | healthy | baseline | NA |
| 346 | batch2_ctl16 | batch2_ctl16 | SLX-13222 | D704-D508 | healthy | healthy | baseline | NA |
| 347 | batch2_ctl17 | batch2_ctl17 | SLX-13222 | D705-D505 | healthy | healthy | baseline | NA |
| 348 | batch2_ctl18 | batch2_ctl18 | SLX-13222 | D705-D506 | healthy | healthy | baseline | NA |
| 349 | batch2_ctl19 | batch2_ctl19 | SLX-13222 | D705-D507 | healthy | healthy | baseline | NA |
| 350 | batch2_ctl20 | batch2_ctl20 | SLX-13222 | D705-D508 | healthy | healthy | baseline | NA |
| 351 | batch2_ctl21 | batch2_ctl21 | SLX-13222 | D706-D505 | healthy | healthy | baseline | NA |
| 352 | batch2_ctl22 | batch2_ctl22 | SLX-13222 | D706-D506 | healthy | healthy | baseline | NA |
| 353 | batch2_ctl23 | batch2_ctl23 | SLX-13222 | D706-D507 | healthy | healthy | baseline | NA |
| 354 | batch2_ctl24 | batch2_ctl24 | SLX-13222 | D706-D508 | healthy | healthy | baseline | NA |

TABLE 2 values for 9 fragmentation features determined from shallow Whole Genome Sequencing (sWGS) data for the samples included in the study.

| index | patient | sample | SLX | barcode | cancer | tMAD | MAF | amplitude_10 bp |
|---|---|---|---|---|---|---|---|---|
| 1 | GB2 | GB2_1 | SLX-11868 | D710-D505 | glioblastoma | NA | NA | 8.288894 |
| 2 | GB3 | GB3_1 | SLX-11868 | D710-D506 | glioblastoma | NA | NA | 7.066083 |
| 3 | GB4 | GB4_1 | SLX-11868 | D710-D507 | glioblastoma | NA | NA | 11.734284 |
| 4 | GB5 | GB5_1 | SLX-11868 | D710-D508 | glioblastoma | NA | NA | 7.039499 |
| 5 | GB6 | GB6_1 | SLX-11868 | D711-D505 | glioblastoma | NA | NA | 11.29576 |
| 6 | GB7 | GB7_1 | SLX-11868 | D711-D506 | glioblastoma | NA | NA | 8.584404 |
| 7 | GB8 | GB8_1 | SLX-11868 | D711-D507 | glioblastoma | NA | NA | 6.550569 |
| 8 | GB9 | GB9_1 | SLX-11868 | D711-D508 | glioblastoma | NA | NA | 6.966088 |
| 9 | GB10 | GB10_1 | SLX-11868 | D712-D505 | glioblastoma | NA | NA | 8.034286 |
| 10 | GB11 | GB11_1 | SLX-11868 | D712-D506 | glioblastoma | NA | NA | 6.35459 |
| 11 | GB12 | GB12_1 | SLX-11868 | D712-D507 | glioblastoma | NA | NA | 9.182074 |
| 12 | GB13 | GB13_1 | SLX-11868 | D712-D508 | glioblastoma | NA | NA | 5.20761 |
| 13 | Other1 | Os1_1 | SLX-11870 | D707-D505 | esophageal junction | 0.00662352 | 0.001 | 7.951253 |
| 14 | B1 | B1_1 | SLX-11034 | A019 | breast | 0.25477547 | 0.355 | 21.5673 |
| 15 | L1 | L1_1 | SLX-11870 | D711-D504 | lung | 0.14086039 | 0.21 | 22.320015 |
| 16 | Ov1 | Ov1_1 | SLX-11870 | D712-D502 | ovarian | 0.01414883 | 0 | 8.014098 |

TABLE 2-continued values for 9 fragmentation features determined from shallow Whole Genome
Sequencing (sWGS) data for the samples included in the study.

| | | | | | | | | |
|---|---|---|---|---|---|---|---|---|
| 17 | Ov2 | Ov2_1 | SLX-11870 | D708-D505 | ovarian | 0.0069475 | 0 | 8.096442 |
| 18 | Ren1 | Ren1_1 | SLX-11870 | D708-D507 | renal | 0.01326047 | 0 | 7.85597 |
| 19 | B2 | B2_1 | SLX-11870 | D710-D501 | breast | 0.00749228 | 0 | 8.054861 |
| 20 | L2 | L2_1 | SLX-11870 | D712-D504 | lung | 0.00857841 | 0 | 8.572217 |
| 21 | L3 | L3_1 | SLX-11870 | D712-D503 | lung | 0.10416469 | NA | NA |
| 22 | T1 | T1_1 | SLX-11870 | D709-D506 | thymoma | 0.04634427 | 0.07 | 23.961321 |
| 23 | R1 | R1_1 | SLX-11870 | D710-D504 | rectum | 0.19414737 | 0.51 | 25.748101 |
| 24 | B3 | B3_1 | SLX-11870 | D711-D502 | breast | 0.50279607 | 0.44 | 12.878295 |
| 25 | L4 | L4_1 | SLX-13710 | D708-D508 | lung | 0.009 | 0.015 | 8.106984 |
| 26 | R2 | R2_1 | SLX-13710 | D707-D502 | rectum | 0.00763274 | 0.003 | 9.901117 |
| 27 | B4 | B4_1 | SLX-13710 | D706-D503 | breast | 0.18705825 | NA | 8.006449 |
| 28 | P1 | P1_1 | SLX-13710 | D705-D504 | pancreatic | 0.00595467 | 0.35 | 10.773805 |
| 29 | Ov3 | Ov3_1 | SLX-13710 | D704-D505 | ovarian | 0.01732876 | 0.01 | 9.946289 |
| 30 | B5 | B5_1 | SLX-13710 | D702-D507 | breast | 0.17913012 | NA | 22.000805 |
| 31 | B6 | B6_1 | SLX-13710 | D701-D508 | breast | 0.08931304 | NA | 9.669002 |
| 32 | L5 | L5_1 | SLX-12841 | D701-D501 | lung | 0.06389893 | NA | 8.526598 |
| 33 | ChC1 | ChC1_1 | SLX-12841 | D701-D502 | cholangio-carcinoma | 0.00692924 | 0.018 | 12.278605 |
| 34 | B7 | B7_1 | SLX-12841 | D701-D503 | breast | 0.06720376 | 0.08287293 | 11.908794 |
| 35 | C1 | C1_1 | SLX-12841 | D701-D504 | colorectal | 0.04858582 | 0.04494382 | 12.522493 |
| 36 | ChC2 | ChC2_1 | SLX-12841 | D702-D501 | cholangio-carcinoma | 0.03907079 | 0.1541502 | 22.848699 |
| 37 | HCC1 | HCC1_1 | SLX-12841 | D702-D502 | hepatocellular | 0.04818769 | 0.15384615 | 22.112355 |
| 38 | C2 | C2_1 | SLX-12841 | D702-D503 | colorectal | 0.00692044 | 0 | 10.343191 |
| 39 | P2 | P2_1 | SLX-12841 | D702-D504 | pancreatic | 0.0070876 | 0 | 7.825945 |
| 40 | ChC3 | ChC3_1 | SLX-12841 | D703-D505 | cholangio-carcinoma | 0.04646124 | 0.07926829 | 17.505159 |
| 41 | P3 | P3_1 | SLX-12841 | D703-D506 | pancreatic | 0.02184309 | 0.03488372 | 4.892972 |
| 42 | R3 | R3_1 | SLX-12841 | D703-D507 | rectum | 0.12517655 | 0.23728814 | 20.528309 |
| 43 | ChC4 | ChC4_1 | SLX-12841 | D703-D508 | cholangio-carcinoma | NA | NA | 14.256425 |
| 44 | ChC5 | ChC5_1 | SLX-12841 | D704-D505 | cholangio-carcinoma | 0.17356419 | 0.27091634 | 18.516276 |
| 45 | P4 | P4_1 | SLX-12841 | D704-D506 | pancreatic | 0.01773972 | NA | 7.91764 |
| 46 | C3 | C3_1 | SLX-12841 | D704-D507 | colorectal | 0.14143417 | 0.32478633 | 23.59296 |
| 47 | Ov4 | Ov4_1 | SLX-12841 | D704-D508 | ovarian | 0.017 | 0 | 9.236843 |
| 48 | Ov5 | Ov5_1 | SLX-12841 | D705-D501 | ovarian | 0.03797909 | NA | 7.842298 |
| 49 | B8 | B8_1 | SLX-12841 | D705-D502 | breast | 0.0223823 | 0 | 3.839284 |
| 50 | L6 | L6_1 | SLX-12841 | D705-D503 | lung | 0.06512785 | 0.08759124 | 13.906832 |
| 51 | C4 | C4_1 | SLX-12841 | D705-D504 | colorectal | 0.40146873 | 0.265 | 31.447239 |
| 52 | Pe1 | Pe1_1 | SLX-12841 | D706-D501 | penile | 0.0242622 | NA | 8.477035 |
| 53 | Pr1 | Pr1_1 | SLX-12841 | D706-D502 | prostate | 0.01561834 | 0.05 | 11.439743 |
| 54 | Ce1 | Ce1_1 | SLX-12841 | D706-D503 | cervical | 0.07434257 | NA | 15.444474 |
| 55 | C5 | C5_1 | SLX-12841 | D706-D504 | colorectal | 0.05664277 | 0.42857143 | 26.925413 |
| 56 | Ov6 | Ov6_1 | SLX-12841 | D707-D505 | ovarian | 0.16596734 | 0.23046875 | 17.404671 |
| 57 | En1 | En1_1 | SLX-12841 | D707-D506 | endometrial | 0.0418592 | 0.0619469 | 10.411982 |
| 58 | C6 | C6_1 | SLX-12841 | D707-D507 | colorectal | 0.02161484 | 0.063 | 8.831578 |
| 59 | C7 | C7_1 | SLX-12841 | D707-D508 | colorectal | 0.03247175 | 0.097 | 13.613727 |
| 60 | OV04-77 | JBLAB_5688 | SLX-13223 | D701-D501 | ovarian | 0.19930844 | 0.346385 | 10.676947 |
| 61 | OV04-77 | JBLAB_5689 | SLX-13223 | D701-D502 | ovarian | 0.02929487 | 0.068603 | 7.963182 |
| 62 | OV04-83 | JBLAB_5203 | SLX-13223 | D703-D501 | ovarian | 0.05179566 | 0.271 | 10.330216 |
| 63 | OV04-83 | JBLAB_5205 | SLX-13223 | D703-D502 | ovarian | 0.017 | 0.068 | 7.807751 |
| 64 | OV04-122 | JBLAB_5712 | SLX-13223 | D701-D503 | ovarian | 0.20397411 | 0.483385 | 9.899396 |
| 65 | OV04-122 | JBLAB_5713 | SLX-13223 | D701-D504 | ovarian | 0.011 | 0.036652 | 5.144907 |
| 66 | OV04-141 | JBLAB_5392 | SLX-13223 | D703-D503 | ovarian | 0.2039022 | 0.615 | 20.206744 |
| 67 | OV04-141 | JBLAB_5393 | SLX-13223 | D703-D504 | ovarian | 0.02154792 | 0.064 | 9.725611 |
| 68 | OV04-143 | JBLAB_5587 | SLX-11873 | D707-D501 | ovarian | 0.05706915 | 0.232 | 11.863282 |
| 69 | OV04-143 | JBLAB_5588 | SLX-11873 | D707-D502 | ovarian | 0.01 | 0.022 | 10.518337 |
| 70 | OV04-180 | JBLAB_5432 | SLX-13223 | D705-D505 | ovarian | 0.07421503 | 0.211 | 14.773896 |
| 71 | OV04-180 | JBLAB_5433 | SLX-13223 | D705-D506 | ovarian | 0.00647481 | 5.00E-04 | 8.364709 |
| 72 | OV04-211 | JBLAB_5471 | SLX-13223 | D706-D505 | ovarian | 0.04274618 | 0.083 | 12.104319 |
| 73 | OV04-211 | JBLAB_5472 | SLX-13223 | D706-D506 | ovarian | 0.00853438 | 0.00899 | 12.612275 |
| 74 | OV04-226 | JBLAB_5507 | SLX-13223 | D704-D505 | ovarian | 0.03174241 | 0.121 | 8.218534 |
| 75 | OV04-226 | JBLAB_5508 | SLX-13223 | D704-D506 | ovarian | 0.011 | 0.022 | 8.056518 |
| 76 | OV04-264 | JBLAB_5622 | SLX-11873 | D707-D503 | ovarian | 0.22037788 | 0.515 | 11.585238 |
| 77 | OV04-264 | JBLAB_5623 | SLX-11873 | D707-D504 | ovarian | 0.02013793 | 0.033 | 12.866111 |
| 78 | OV04-292 | JBLAB_5742 | SLX-13223 | D702-D501 | ovarian | 0.04971341 | 0.15521975 | 14.84172 |
| 79 | OV04-292 | JBLAB_5743 | SLX-13223 | D702-D502 | ovarian | 0.06534916 | 0.0622645 | 26.770428 |
| 80 | OV04-295 | JBLAB_5420 | SLX-13223 | D705-D507 | ovarian | 0.25240821 | 0.5065815 | 23.020453 |
| 81 | OV04-295 | JBLAB_5422 | SLX-13223 | D705-D508 | ovarian | 0.00713784 | 0.0124825 | 5.92881 |
| 82 | OV04-297 | JBLAB_5288 | SLX-13223 | D704-D507 | ovarian | 0.06130302 | 0.207 | 13.04636 |
| 83 | OV04-297 | JBLAB_5289 | SLX-13223 | D704-D508 | ovarian | 0.0212589 | 0.092 | 9.992376 |
| 84 | OV04-300 | JBLAB_5754 | SLX-13223 | D702-D503 | ovarian | 0.19251179 | 0.413839 | 26.927287 |
| 85 | OV04-300 | JBLAB_5755 | SLX-13223 | D702-D504 | ovarian | 0.15867713 | 0.003498 | 24.640525 |
| 86 | X76 | X76_T1_pre | SLX-13621 | D701-D501 | ovarian | 0.02212855 | 0.05 | 8.202772 |
| 87 | X75_2 | X75_T13_pre | SLX-13621 | D702-D501 | ovarian | 0.00516137 | 8.00E-04 | 8.364272 |
| 88 | X52 | X52_T1_pre | SLX-13621 | D703-D501 | ovarian | 0.00569295 | 0.0023 | 10.387042 |

TABLE 2-continued values for 9 fragmentation features determined from shallow Whole Genome
Sequencing (sWGS) data for the samples included in the study.

| | | | | | | | | |
|---|---|---|---|---|---|---|---|---|
| 89 | X150 | X150_T1_pre | SLX-13621 | D704-D501 | ovarian | 0.00567981 | 0 | 10.834321 |
| 90 | X129 | X129_T8_pre | SLX-13621 | D705-D501 | ovarian | 0.00801224 | 0.0087 | 8.14525 |
| 91 | X57 | X57_T1_pre | SLX-13621 | D706-D501 | ovarian | 0.00538757 | 0.0045 | 8.245349 |
| 92 | X73 | X73_T3B_pre | SLX-13621 | D707-D501 | ovarian | 0.00590527 | 0.0026 | 8.39421 |
| 93 | JG090 | JG090_T6_12_pre | SLX-13621 | D708-D501 | ovarian | 0.30281177 | 0.0035 | 28.590867 |
| 94 | X145 | X145_T8_pre | SLX-13621 | D709-D501 | ovarian | 0.04365296 | 0.0815 | 12.781026 |
| 95 | X112 | X112_T1_pre | SLX-13621 | D710-D501 | ovarian | 0.00530119 | 0.0011 | 7.404288 |
| 96 | X75_1 | X75_T1_pre | SLX-13621 | D711-D501 | ovarian | 0.01 | 0.0041 | 8.398895 |
| 97 | X72 | X72_T1_pre | SLX-13621 | D712-D501 | ovarian | 0.00541364 | 0.0021 | 6.959961 |
| 98 | X74 | X74_T1_pre | SLX-13621 | D701-D502 | ovarian | 0.01631991 | 0.051 | 8.243635 |
| 99 | X127 | X127_T1_pre | SLX-13621 | D702-D502 | ovarian | 0.01 | 0.0085 | 13.720821 |
| 100 | X30 | X30_T1_pre | SLX-13621 | D703-D502 | ovarian | 0.01369393 | 0.0325 | 9.152518 |
| 101 | JBLAB_5180 | JBLAB_5180_pre | SLX-13621 | D704-D502 | ovarian | 0.00451049 | 0.000868 | 8.458671 |
| 102 | JBLAB_5027 | JBLAB_5027_pre | SLX-13621 | D705-D502 | ovarian | 0.00636608 | 0 | 7.752972 |
| 103 | JBLAB_5595 | JBLAB_5595_pre | SLX-13621 | D706-D502 | ovarian | 0.00674627 | 0.001 | 8.053664 |
| 104 | JBLAB_5599 | JBLAB_5599_pre | SLX-13621 | D707-D502 | ovarian | 0.00587396 | 0.00015 | 8.060789 |
| 105 | JBLAB_5611 | JBLAB_5611_pre | SLX-13621 | D708-D502 | ovarian | 0.02116335 | NA | 10.693227 |
| 106 | JBLAB_5477 | JBLAB_5477_pre | SLX-13621 | D709-D502 | ovarian | 0.00767838 | 0.0035 | 6.907113 |
| 107 | JBLAB_5632 | JBLAB_5632_pre | SLX-13621 | D710-D502 | ovarian | 0.00817832 | NA | 11.709422 |
| 108 | B9 | B9_1 | SLX-11043 | D705-D506 | breast | 0.08182814 | 0 | 15.709117 |
| 109 | B10 | B10_1 | SLX-11043 | D702-D501 | breast | 0.0144354 | 0.0336 | 7.157944 |
| 110 | B11 | B11_1 | SLX-11043 | D701-D501 | breast | 0.013 | 0.14 | 8.434353 |
| 111 | B12 | B12_1 | SLX-11043 | D705-D508 | breast | 0.00826536 | NA | 5.589763 |
| 112 | B13 | B13_1 | SLX-11043 | D704-D508 | breast | 0.00851616 | NA | 7.701709 |
| 113 | B14 | B14_1 | SLX-11043 | D704-D505 | breast | 0.0083561 | NA | 6.830037 |
| 114 | B15 | B15_1 | SLX-11043 | D703-D503 | breast | 0.016 | NA | 8.918855 |
| 115 | B16 | B16_1 | SLX-11042 | D703-D508 | breast | 0.02232398 | NA | 6.883056 |
| 116 | B17 | B17_1 | SLX-11042 | D704-D504 | breast | 0.03101881 | NA | 5.61573 |
| 117 | B18 | B18_1 | SLX-11042 | D704-D502 | breast | 0.00787396 | NA | 7.21719 |
| 118 | B19 | B19_1 | SLX-11042 | D705-D502 | breast | 0.011 | NA | 9.233775 |
| 119 | B20 | B20_1 | SLX-11042 | D705-D504 | breast | 0.008 | NA | 6.159054 |
| 120 | B21 | B21_1 | SLX-11042 | D701-D505 | breast | 0.01747348 | NA | 8.186593 |
| 121 | B22 | B22_1 | SLX-11042 | D701-D507 | breast | 0.00567912 | 0 | 7.10042 |
| 122 | B23 | B23_1 | SLX-11042 | D702-D506 | breast | 0.03790757 | NA | 12.647919 |
| 123 | B24 | B24_1 | SLX-11042 | D702-D508 | breast | 0.02927472 | NA | 7.413094 |
| 124 | B25 | B25_1 | SLX-11042 | D703-D506 | breast | 0.10663707 | NA | 10.325842 |
| 125 | B26 | B26_1 | SLX-11042 | D706-D502 | breast | 0.05045255 | NA | 11.078386 |
| 126 | B27 | B27_1 | SLX-11042 | D706-D503 | breast | 0.01616385 | NA | 7.472691 |
| 127 | B28 | B28_1 | SLX-11042 | D706-D504 | breast | 0.03047302 | NA | 6.84986 |
| 128 | B29 | B29_1 | SLX-11043 | D703-D502 | breast | 0.01713247 | 0.15 | 13.732903 |
| 129 | B30 | B30_1 | SLX-11043 | D701-D504 | breast | 0.01909028 | 0.187 | 11.377318 |
| 130 | B31 | B31_1 | SLX-11043 | D704-D507 | breast | 0.021 | NA | 8.34953 |
| 131 | B32 | B32_1 | SLX-11042 | D703-D507 | breast | 0.03009715 | 0.069 | 9.774719 |
| 132 | B11 | B11_1 | SLX-10991 | | bladder | NA | NA | 9.623104 |
| 133 | B12 | B12_1 | SLX-10991 | | bladder | NA | NA | 10.97826 |
| 134 | B13 | B13_1 | SLX-11094 | D708-D501 | bladder | NA | NA | 8.160181 |
| 135 | B14 | B14_1 | SLX-10575 | iPCRtagT014 | bladder | NA | NA | 8.833716 |
| 136 | B15 | B15_1 | SLX-11904 | D709-D507 | bladder | NA | NA | 10.470188 |
| 137 | B16 | B16_1 | SLX-10572 | D704-D505 | bladder | NA | NA | 6.389604 |
| 138 | B17 | B17_1 | SLX-10572 | D708-D507 | bladder | NA | NA | 6.944738 |
| 139 | B18 | B18_1 | SLX-11896 | D708-D504 | bladder | NA | NA | 6.260227 |
| 140 | B19 | B19_1 | SLX-11896 | D707-D507 | bladder | NA | NA | 9.249265 |
| 141 | B110 | B110_1 | SLX-11896 | D707-D508 | bladder | NA | NA | 7.690463 |
| 142 | B111 | B111_1 | SLX-11896 | D709-D506 | bladder | NA | NA | 6.911543 |
| 143 | B112 | B112_1 | SLX-11904 | D708-D504 | bladder | NA | NA | 6.175549 |
| 144 | B113 | B113_1 | SLX-11904 | D709-D501 | bladder | NA | NA | 8.109819 |
| 145 | B114 | B114_1 | SLX-11986 | D709-D504 | bladder | NA | NA | 7.198525 |
| 146 | B115 | B115_1 | SLX-10572 | D708-D508 | bladder | NA | NA | 7.008704 |
| 147 | B116 | B116_1 | SLX-11896 | D707-D502 | bladder | NA | NA | 7.624244 |
| 148 | B117 | B117_1 | SLX-10572 | D708-D505 | bladder | NA | NA | 3.485591 |
| 149 | B118 | B118_1 | SLX-11896 | D709-D503 | bladder | NA | NA | 7.159521 |
| 150 | B119 | B119_1 | SLX-11896 | D708-D503 | bladder | NA | NA | 6.175549 |
| 151 | Ren2 | Ren2_1 | SLX-13900 | D707-D501 | renal | 0.009 | NA | 8.015464 |
| 152 | Ren3 | Ren3_1 | SLX-13900 | D707-D502 | renal | 0.01 | NA | 6.723075 |
| 153 | Ren4 | Ren4_1 | SLX-13900 | D707-D503 | renal | NA | NA | 7.36545 |
| 154 | Ren5 | Ren5_1 | SLX-13900 | D707-D504 | renal | 0.016 | NA | 7.647632 |
| 155 | Ren6 | Ren6_1 | SLX-13900 | D708-D501 | renal | 0.011 | NA | 8.659006 |
| 156 | Ren7 | Ren7_1 | SLX-13900 | D708-D502 | renal | 0.013 | NA | 10.431801 |
| 157 | Ren8 | Ren8_1 | SLX-13900 | D708-D503 | renal | 0.011 | NA | 8.256359 |
| 158 | Ren9 | Ren9_1 | SLX-13900 | D708-D504 | renal | 0.016 | NA | 9.455503 |
| 159 | Ren10 | Ren10_1 | SLX-13900 | D708-D505 | renal | 0.021 | NA | 8.747445 |
| 160 | Ren11 | Ren11_1 | SLX-13900 | D708-D506 | renal | 0.008 | NA | 7.754859 |
| 161 | Ren12 | Ren12_1 | SLX-13900 | D708-D507 | renal | 0.015 | NA | 6.455444 |
| 162 | Ren13 | Ren13_1 | SLX-13900 | D708-D508 | renal | 0.01 | NA | 6.676499 |
| 163 | Ren14 | Ren14_1 | SLX-13900 | D709-D501 | renal | 0.017 | NA | 6.44203 |
| 164 | Ren15 | Ren15_1 | SLX-13900 | D709-D502 | renal | NA | NA | 6.350268 |
| 165 | Ren16 | Ren16_1 | SLX-13900 | D709-D503 | renal | NA | NA | 5.155092 |

TABLE 2-continued values for 9 fragmentation features determined from shallow Whole Genome Sequencing (sWGS) data for the samples included in the study.

| | | | | | | | | |
|---|---|---|---|---|---|---|---|---|
| 166 | Ren17 | Ren17_1 | SLX-13900 | D709-D504 | renal | 0.01 | NA | 5.96514 |
| 167 | Ren18 | Ren18_1 | SLX-13900 | D709-D505 | renal | NA | NA | 6.973824 |
| 168 | Ren19 | Ren19_1 | SLX-13900 | D709-D506 | renal | NA | NA | 5.656564 |
| 169 | Ren20 | Ren20_1 | SLX-13900 | D710-D501 | renal | 0.01 | NA | 5.302966 |
| 170 | Ren21 | Ren21_1 | SLX-13900 | D710-D502 | renal | 0.013 | NA | 8.643075 |
| 171 | Ren22 | Ren22_1 | SLX-13900 | D710-D503 | renal | 0.011 | NA | 7.52024 |
| 172 | Ren23 | Ren23_1 | SLX-13900 | D710-D504 | renal | 0.011 | NA | 7.240543 |
| 173 | Ren24 | Ren24_1 | SLX-13900 | D710-D505 | renal | 0.009 | NA | 9.334261 |
| 174 | Ren25 | Ren25_1 | SLX-13900 | D710-D506 | renal | 0.009 | NA | 7.926276 |
| 175 | Ren26 | Ren26_1 | SLX-13900 | D710-D507 | renal | 0.01 | NA | 6.722133 |
| 176 | Ren27 | Ren27_1 | SLX-13900 | D710-D508 | renal | 0.017 | NA | 8.249813 |
| 177 | Ren28 | Ren28_1 | SLX-13900 | D711-D501 | renal | 0.012 | NA | 7.25222 |
| 178 | Ren29 | Ren29_1 | SLX-13900 | D711-D502 | renal | NA | NA | 4.414937 |
| 179 | Ren30 | Ren30_1 | SLX-13900 | D711-D503 | renal | 0.008 | NA | 8.771539 |
| 180 | Ren31 | Ren31_1 | SLX-13900 | D711-D504 | renal | 0.01 | NA | 7.213912 |
| 181 | Ren32 | Ren32_1 | SLX-13900 | D711-D505 | renal | 0.029 | NA | 12.043137 |
| 182 | Ren33 | Ren33_1 | SLX-13900 | D711-D506 | renal | 0.01 | NA | 6.888756 |
| 183 | HIP_1 | HIP_1 | SLX-12531 | D703-D501 | healthy | 0.01365609 | 0 | 13.501879 |
| 184 | HIP_10 | HIP_10 | SLX-12531 | D705-D506 | healthy | 0.00999028 | 0 | 6.935871 |
| 185 | HIP_11 | HIP_11 | SLX-12531 | D705-D507 | healthy | 0.01083427 | 0 | 7.631476 |
| 186 | HIP_12 | HIP_12 | SLX-12531 | D705-D508 | healthy | 0.01109017 | 0 | 7.216118 |
| 187 | HIP_13 | HIP_13 | SLX-12531 | D706-D505 | healthy | 0.01131455 | 0 | 11.239094 |
| 188 | HIP_14 | HIP_14 | SLX-12531 | D706-D506 | healthy | 0.00870144 | 0 | 10.114669 |
| 189 | HIP_15 | HIP_15 | SLX-12531 | D706-D507 | healthy | 0.00967468 | 0 | 11.822457 |
| 190 | HIP_16 | HIP_16 | SLX-12531 | D706-D508 | healthy | 0.00967468 | 0 | 10.495134 |
| 191 | HIP_17 | HIP_17 | SLX-12531 | D707-D501 | healthy | 0.01094406 | 0 | 8.925692 |
| 192 | HIP_18 | HIP_18 | SLX-12531 | D707-D502 | healthy | 0.00912639 | 0 | 8.826753 |
| 193 | HIP_19 | HIP_19 | SLX-12531 | D707-D503 | healthy | 0.01262082 | 0 | 8.844247 |
| 194 | HIP_2 | HIP_2 | SLX-12531 | D703-D502 | healthy | 0.00692027 | 0 | 8.965581 |
| 195 | HIP_20 | HIP_20 | SLX-12531 | D707-D504 | healthy | 0.01190763 | 0 | 8.817493 |
| 196 | HIP_21 | HIP_21 | SLX-12531 | D708-D501 | healthy | 0.01254617 | 0 | 6.088202 |
| 197 | HIP_22 | HIP_22 | SLX-12531 | D708-D502 | healthy | 0.01158689 | 0 | 5.580461 |
| 198 | HIP_23 | HIP_23 | SLX-12531 | D708-D503 | healthy | 0.0100046 | 0 | 6.269189 |
| 199 | HIP_24 | HIP_24 | SLX-12531 | D708-D504 | healthy | 0.00925125 | 0 | 6.397577 |
| 200 | HIP_27 | HIP_27 | SLX-12534 | D707-D502 | healthy | 0.01217069 | 0 | 10.192695 |
| 201 | HIP_28 | HIP_28 | SLX-12534 | D707-D503 | healthy | 0.00878362 | 0 | 8.708552 |
| 202 | HIP_29 | HIP_29 | SLX-12534 | D707-D504 | healthy | 0.01030374 | 0 | 8.964653 |
| 203 | HIP_3 | HIP_3 | SLX-12531 | D703-D503 | healthy | 0.01246399 | 0 | 13.230074 |
| 204 | HIP_30 | HIP_30 | SLX-12534 | D708-D501 | healthy | 0.00751474 | 0 | 9.209964 |
| 205 | HIP_31 | HIP_31 | SLX-12534 | D708-D502 | healthy | 0.0105142 | 0 | 12.926568 |
| 206 | HIP_32 | HIP_32 | SLX-12534 | D708-D503 | healthy | 0.00923109 | 0 | 12.841358 |
| 207 | HIP_33 | HIP_33 | SLX-12534 | D708-D504 | healthy | 0.00824142 | 0 | 12.632627 |
| 208 | HIP_34 | HIP_34 | SLX-12534 | D709-D501 | healthy | 0.00603306 | 0 | 10.537875 |
| 209 | HIP_35 | HIP_35 | SLX-12534 | D709-D503 | healthy | 0.00704468 | 0 | 8.31893 |
| 210 | HIP_36 | HIP_36 | SLX-12534 | D709-D504 | healthy | 0.01441797 | 0 | 13.65382 |
| 211 | HIP_37 | HIP_37 | SLX-12534 | D710-D501 | healthy | 0.00760246 | 0 | 7.728377 |
| 212 | HIP_38 | HIP_38 | SLX-12534 | D710-D502 | healthy | 0.00764811 | 0 | 7.876856 |
| 213 | HIP_39 | HIP_39 | SLX-12534 | D710-D503 | healthy | 0.01278262 | 0 | 8.859789 |
| 214 | HIP_4 | HIP_4 | SLX-12531 | D703-D504 | healthy | 0.00885683 | 0 | 10.26619 |
| 215 | HIP_40 | HIP_40 | SLX-12534 | D710-D504 | healthy | 0.0126438 | 0 | 8.609954 |
| 216 | HIP_41 | HIP_41 | SLX-12534 | D711-D505 | healthy | 0.00779714 | 0 | 11.232596 |
| 217 | HIP_42 | HIP_42 | SLX-12534 | D711-D506 | healthy | 0.01226728 | 0 | 11.377068 |
| 218 | HIP_43 | HIP_43 | SLX-12534 | D711-D507 | healthy | 0.00886215 | 0 | 6.246131 |
| 219 | HIP_44 | HIP_44 | SLX-12534 | D711-D508 | healthy | 0.01102103 | 0 | 6.132778 |
| 220 | HIP_45 | HIP_45 | SLX-12534 | D712-D505 | healthy | 0.01151546 | 0 | 9.07452 |
| 221 | HIP_46 | HIP_46 | SLX-12534 | D712-D506 | healthy | 0.01069675 | 0 | 9.130738 |
| 222 | HIP_47 | HIP_47 | SLX-12534 | D712-D507 | healthy | 0.01326822 | 0 | 7.09071 |
| 223 | HIP_48 | HIP_48 | SLX-12534 | D712-D508 | healthy | 0.01307578 | 0 | 7.300919 |
| 224 | HIP_5 | HIP_5 | SLX-12531 | D704-D501 | healthy | 0.00640521 | 0 | 10.374444 |
| 225 | HIP_6 | HIP_6 | SLX-12531 | D704-D502 | healthy | 0.00943859 | 0 | 10.338882 |
| 226 | HIP_7 | HIP_7 | SLX-12531 | D704-D503 | healthy | 0.01017749 | 0 | 6.260851 |
| 227 | HIP_8 | HIP_8 | SLX-12531 | D704-D504 | healthy | 0.0097156 | 0 | 6.251434 |
| 228 | HIP_9 | HIP_9 | SLX-12531 | D705-D505 | healthy | 0.00951729 | 0 | 7.246416 |
| 229 | M1 | M1_1 | SLX-11379 | D701-D502 | melanoma | 0.31468668 | NA | 9.697099 |
| 230 | M1 | M1_2 | SLX-11379 | D701-D501 | melanoma | 0.086146 | NA | 10.911943 |
| 231 | M4 | M4_1 | SLX-11379 | D702-D501 | melanoma | 0.009 | NA | 6.333177 |
| 232 | M4 | M4_2 | SLX-12758 | D704-D501 | melanoma | 0.00607225 | NA | 5.256442 |
| 233 | M4 | M4_3 | SLX-12759 | D708-D501 | melanoma | 0.01 | NA | NA |
| 234 | M4 | M4_4 | SLX-12758 | D709-D502 | melanoma | 0.0059634 | NA | 6.364361 |
| 235 | M4 | M4_5 | SLX-12758 | D702-D501 | melanoma | 0.009 | NA | 5.814897 |
| 236 | M4 | M4_6 | SLX-11383 | D701-D506 | melanoma | 0.00622659 | NA | 6.624192 |
| 237 | M4 | M4_7 | SLX-11379 | D701-D503 | melanoma | 0.008 | NA | 7.809595 |
| 238 | M12 | M12_1 | SLX-11379 | D703-D502 | melanoma | 0.06257905 | NA | 14.629729 |
| 239 | M12 | M12_2 | SLX-11847 | D704-D502 | melanoma | 0.00825359 | NA | NA |
| 240 | M12 | M12_3 | SLX-11847 | D704-D503 | melanoma | 0.02188627 | NA | 5.297918 |
| 241 | M12 | M12_4 | SLX-11847 | D707-D507 | melanoma | 0.02521355 | NA | 12.502367 |
| 242 | M14 | M14_1 | SLX-11383 | D708-D503 | melanoma | 0.01 | NA | 5.840336 |

TABLE 2-continued values for 9 fragmentation features determined from shallow Whole Genome Sequencing (sWGS) data for the samples included in the study.

| | | | | | | | | |
|---|---|---|---|---|---|---|---|---|
| 243 | M14 | M14_2 | SLX-12758 | D706-D506 | melanoma | 0.03887853 | NA | 9.645063 |
| 244 | M22 | M22_1 | SLX-11379 | D704-D507 | melanoma | 0.05850595 | NA | 9.814777 |
| 245 | M22 | M22_2 | SLX-12758 | D706-D507 | melanoma | 0.00659093 | NA | 9.526423 |
| 246 | M22 | M22_3 | SLX-11379 | D704-D508 | melanoma | 0.1123879 | NA | 13.690301 |
| 247 | M22 | M22_4 | SLX-12758 | D706-D508 | melanoma | 0.11091958 | NA | NA |
| 248 | M32 | M32_1 | SLX-11379 | D705-D506 | melanoma | 0.01892249 | NA | 12.693561 |
| 249 | M32 | M32_2 | SLX-11847 | D705-D503 | melanoma | 0.013 | NA | 5.940992 |
| 250 | C8 | C8_T1 | SLX-12832 | D709-D501 | colorectal | 0.13461166 | 0.172 | 16.962419 |
| 251 | C8 | C8_T2 | SLX-12832 | D709-D502 | colorectal | 0.02433155 | 0.066 | 11.609216 |
| 252 | L5 | L5_T2 | SLX-12832 | D709-D503 | lung | 0.05910309 | NA | 21.626269 |
| 253 | ChC1 | ChC1_3 | SLX-12832 | D709-D504 | cholangio-carcinoma | 0.01 | 9.00E-04 | 11.508524 |
| 254 | ChC1 | ChC1_4 | SLX-12832 | D710-D501 | cholangio-carcinoma | 0.029 | 0.016 | 12.450543 |
| 255 | ChC2 | ChC2_2 | SLX-12832 | D710-D502 | cholangio-carcinoma | 0.04069151 | 0.151 | 22.573541 |
| 256 | ChC2 | ChC2_3 | SLX-12832 | D710-D503 | cholangio-carcinoma | 0.02290481 | 0.06 | 23.862973 |
| 257 | HCC1 | HCC1_2 | SLX-12832 | D710-D504 | hepatocellular | 0.05593432 | 0.27118644 | 26.256276 |
| 258 | HCC1 | HCC1_3 | SLX-12832 | D711-D505 | hepatocellular | 0.05623691 | 0.10752688 | 23.117649 |
| 259 | HCC1 | HCC1_4 | SLX-12832 | D711-D506 | hepatocellular | 0.07020201 | 0.27419355 | 26.963935 |
| 260 | HCC1 | HCC1_5 | SLX-12832 | D711-D507 | hepatocellular | 0.06769479 | 0.18627451 | 28.550948 |
| 261 | P2 | P2_2 | SLX-12832 | D711-D508 | pancreatic | 0.00737544 | NA | 14.787661 |
| 262 | P4 | P4_2 | SLX-12832 | D712-D505 | pancreatic | 0.00845528 | NA | 10.00907 |
| 263 | C4 | C4_2 | SLX-12832 | D712-D506 | colorectal | 0.44317612 | 0.29581 | 31.032157 |
| 264 | Pr1 | Pr1_4 | SLX-12832 | D712-D507 | prostate | 0.02602964 | 0.18 | 16.496767 |
| 265 | Ov6 | Ov6_2 | SLX-12832 | D712-D508 | ovarian | 0.23784565 | 0.68421053 | 18.167153 |
| 266 | ChC2 | ChC2_6 | SLX-12838 | D701-D505 | cholangio-carcinoma | 0.02660187 | 0.056 | 21.228646 |
| 267 | ChC3 | ChC3_2 | SLX-12838 | D701-D506 | cholangio-carcinoma | 0.01405692 | NA | 8.910375 |
| 268 | C3 | C3_5 | SLX-12838 | D701-D507 | colorectal | 0.03204027 | 0.1126 | 12.617733 |
| 269 | L6 | L6_2 | SLX-12838 | D701-D508 | lung | 0.07217697 | 0.08536585 | 15.980205 |
| 270 | Pr1 | Pr1_3 | SLX-12838 | D702-D505 | prostate | 0.01337188 | 0.05 | 9.977327 |
| 271 | B7 | B7_2 | SLX-12838 | D702-D506 | breast | 0.14971349 | 0.14012739 | 14.947559 |
| 272 | C1 | C1_2 | SLX-12838 | D702-D507 | colorectal | 0.06302754 | 0.12903226 | 13.778461 |
| 273 | ChC2 | ChC2_4 | SLX-12838 | D702-D508 | cholangio-carcinoma | 0.012 | 0.025 | 12.537779 |
| 274 | ChC2 | ChC2_5 | SLX-12838 | D703-D501 | cholangio-carcinoma | 0.03388701 | 0.052 | 13.979455 |
| 275 | P4 | P4_3 | SLX-12838 | D703-D502 | pancreatic | 0.01492043 | NA | 5.27804 |
| 276 | C3 | C3_4 | SLX-12838 | D703-D503 | colorectal | 0.02969907 | 0.031 | 10.068633 |
| 277 | Ov4 | Ov4_2 | SLX-12838 | D703-D504 | ovarian | 0.01768853 | NA | 6.630927 |
| 278 | Ov5 | Ov5_2 | SLX-12838 | D704-D501 | ovarian | 0.03000071 | NA | 7.998805 |
| 279 | B8 | B8_2 | SLX-12838 | D704-D502 | breast | 0.01711789 | NA | 3.530712 |
| 280 | C5 | C5_3 | SLX-12838 | D704-D503 | colorectal | 0.015 | 0.013 | 5.842702 |
| 281 | En1 | En1_2 | SLX-12838 | D704-D504 | endometrial | 0.09648123 | 0.13636364 | 7.334034 |
| 282 | C6 | C6_2 | SLX-12838 | D705-D505 | colorectal | 0.01 | 0.01208459 | 7.172645 |
| 283 | ChC1 | ChC1_2 | SLX-12838 | D705-D506 | cholangio-carcinoma | 0.00657679 | 0.019 | 9.598663 |
| 284 | C3 | C3_2 | SLX-12838 | D705-D507 | colorectal | 0.14260432 | 0.306 | 19.957145 |
| 285 | C3 | C3_3 | SLX-12838 | D705-D508 | colorectal | 0.14314493 | 0.279 | 20.082879 |
| 286 | Ov4 | Ov4_3 | SLX-12838 | D706-D505 | ovarian | 0.00620281 | NA | 4.993292 |
| 287 | Ov5 | Ov5_3 | SLX-12838 | D706-D506 | ovarian | 0.02161473 | NA | 5.251961 |
| 288 | Pr1 | Pr1_2 | SLX-12838 | D706-D507 | prostate | 0.016 | 0.04 | 8.320772 |
| 289 | C5 | C5_2 | SLX-12838 | D706-D508 | colorectal | 0.05837149 | 0.442 | 21.62809 |
| 290 | B33 | B33_1 | SLX-15332 | D707-D505 | breast | 0.00834566 | NA | 9.791907 |
| 291 | B34 | B34_1 | SLX-15332 | D707-D506 | breast | 0.01937858 | NA | 6.730765 |
| 292 | B35 | B35_1 | SLX-15332 | D707-D508 | breast | 0.3099655 | NA | 14.597755 |
| 293 | B36 | B36_1 | SLX-15332 | D708-D505 | breast | 0.2510418 | NA | 12.289165 |
| 294 | B37 | B37_1 | SLX-15332 | D708-D506 | breast | 0.37214783 | NA | 22.172124 |
| 295 | B38 | B38_1 | SLX-15332 | D708-D507 | breast | 0.0073204 | NA | 7.164991 |
| 296 | B39 | B39_1 | SLX-15332 | D709-D502 | breast | 0.01750562 | NA | 13.298013 |
| 297 | B40 | B40_1 | SLX-15332 | D708-D508 | breast | 0.04741394 | NA | 10.688568 |
| 298 | B41 | B41_1 | SLX-15332 | D709-D501 | breast | 0.02476021 | NA | 9.688568 |
| 299 | B42 | B42_1 | SLX-15332 | D709-D503 | breast | 0.33542756 | NA | 11.255362 |
| 300 | B43 | B43_1 | SLX-15332 | D709-D504 | breast | 0.09644121 | NA | 15.910215 |
| 301 | B44 | B44_1 | SLX-13227 | D704-D506 | breast | 0.14065498 | NA | 7.600141 |
| 302 | B45 | B45_1 | SLX-13227 | D704-D508 | breast | 0.00602283 | NA | 10.007613 |
| 303 | B46 | B46_1 | SLX-13227 | D705-D506 | breast | 0.06773296 | NA | 9.009748 |
| 304 | B47 | B47_1 | SLX-13227 | D701-D502 | breast | 0.06050266 | NA | 13.950487 |
| 305 | B48 | B48_1 | SLX-13227 | D701-D504 | breast | 0.01216587 | NA | 11.799779 |
| 306 | B49 | B49_1 | SLX-13227 | D702-D502 | breast | 0.0714198 | NA | 13.12547 |
| 307 | B50 | B50_1 | SLX-13227 | D702-D504 | breast | 0.19923403 | NA | 8.242535 |
| 308 | B51 | B51_1 | SLX-13227 | D703-D502 | breast | 0.01111396 | NA | 8.697999 |
| 309 | GB14 | GB14_1 | SLX-12839 | D701-D501 | glioblastoma | 0.00722063 | NA | 7.080957 |
| 310 | GB15 | GB15_1 | SLX-12839 | D701-D502 | glioblastoma | 0.00999163 | NA | 14.661355 |

TABLE 2-continued values for 9 fragmentation features determined from shallow Whole Genome Sequencing (sWGS) data for the samples included in the study.

| | | | | | | | | |
|---|---|---|---|---|---|---|---|---|
| 311 | GB16 | GB16_1 | SLX-12839 | D701-D503 | glioblastoma | 0.00721647 | NA | 5.489901 |
| 312 | GB17 | GB17_1 | SLX-12839 | D701-D504 | glioblastoma | 0.00439372 | NA | 6.653279 |
| 313 | GB18 | GB18_1 | SLX-12839 | D702-D501 | glioblastoma | 0.00439372 | NA | 5.622385 |
| 314 | GB19 | GB19_1 | SLX-12839 | D702-D502 | glioblastoma | 0.00638382 | NA | 8.614033 |
| 315 | GB20 | GB20_1 | SLX-12839 | D702-D503 | glioblastoma | 0.0080133 | NA | 7.875018 |
| 316 | GB21 | GB21_1 | SLX-12839 | D702-D504 | glioblastoma | 0.00624728 | NA | 7.793591 |
| 317 | GB22 | GB22_1 | SLX-12839 | D703-D505 | glioblastoma | 0.00798411 | NA | 6.866106 |
| 318 | GB23 | GB23_1 | SLX-12839 | D703-D506 | glioblastoma | 0.00728569 | NA | 7.021117 |
| 319 | GB24 | GB24_1 | SLX-12839 | D704-D505 | glioblastoma | 0.00533865 | NA | 6.255948 |
| 320 | GB25 | GB25_1 | SLX-12839 | D704-D506 | glioblastoma | 0.00624778 | NA | 6.436536 |
| 321 | GB26 | GB26_1 | SLX-12839 | D703-D507 | glioblastoma | 0.00716135 | NA | 6.559556 |
| 322 | GB27 | GB27_1 | SLX-12839 | D703-D508 | glioblastoma | 0.0080133 | NA | 4.092081 |
| 323 | GB28 | GB28_1 | SLX-12839 | D704-D507 | glioblastoma | 0.00748374 | NA | 3.369344 |
| 324 | GB29 | GB29_1 | SLX-12839 | D704-D508 | glioblastoma | 0.00575898 | NA | 3.147369 |
| 325 | GB30 | GB30_1 | SLX-12839 | D705-D501 | glioblastoma | 0.00716136 | NA | 4.833878 |
| 326 | GB31 | GB31_1 | SLX-12839 | D705-D502 | glioblastoma | 0.008039 | NA | 6.508036 |
| 327 | GB32 | GB32_1 | SLX-12839 | D705-D503 | glioblastoma | 0.00784711 | NA | 3.701836 |
| 328 | GB33 | GB33_1 | SLX-12839 | D706-D501 | glioblastoma | 0.00589295 | NA | 3.437975 |
| 329 | GB34 | GB34_1 | SLX-12839 | D706-D502 | glioblastoma | 0.00753282 | NA | 4.445443 |
| 330 | GB35 | GB35_1 | SLX-12839 | D706-D503 | glioblastoma | 0.0094776 | NA | 5.014607 |
| 331 | batch2_ctl1 | batch2_ctl1 | SLX-13222 | D701-D501 | healthy | 0.0052298 | NA | 3.951958833 |
| 332 | batch2_ctl2 | batch2_ctl2 | SLX-13222 | D701-D502 | healthy | 0.00999545 | NA | 4.727964376 |
| 333 | batch2_ctl3 | batch2_ctl3 | SLX-13222 | D701-D503 | healthy | 0.0098635 | NA | 4.938835262 |
| 334 | batch2_ctl4 | batch2_ctl4 | SLX-13222 | D701-D504 | healthy | 0.00854238 | NA | 5.246187382 |
| 335 | batch2_ctl5 | batch2_ctl5 | SLX-13222 | D702-D501 | healthy | 0.01278923 | NA | 5.614708486 |
| 336 | batch2_ctl6 | batch2_ctl6 | SLX-13222 | D702-D502 | healthy | 0.01022994 | NA | 6.18756695 |
| 337 | batch2_ctl7 | batch2_ctl7 | SLX-13222 | D702-D503 | healthy | 0.00852297 | NA | 5.890944354 |
| 338 | batch2_ctl8 | batch2_ctl8 | SLX-13222 | D702-D504 | healthy | 0.01441504 | NA | 6.420205184 |
| 339 | batch2_ctl9 | batch2_ctl9 | SLX-13222 | D703-D501 | healthy | 0.01112863 | NA | 5.311079311 |
| 340 | batch2_ctl10 | batch2_ctl10 | SLX-13222 | D703-D502 | healthy | 0.01338507 | NA | 5.201380596 |
| 341 | batch2_ctl11 | batch2_ctl11 | SLX-13222 | D703-D503 | healthy | 0.00614274 | NA | 8.477556672 |
| 342 | batch2_ctl12 | batch2_ctl12 | SLX-13222 | D703-D504 | healthy | 0.00826772 | NA | 8.689480759 |
| 343 | batch2_ctl13 | batch2_ctl13 | SLX-13222 | D704-D505 | healthy | 0.01203538 | NA | 4.368212002 |
| 344 | batch2_ctl14 | batch2_ctl14 | SLX-13222 | D704-D506 | healthy | 0.00573838 | NA | 4.262652277 |
| 345 | batch2_ctl15 | batch2_ctl15 | SLX-13222 | D704-D507 | healthy | 0.00830256 | NA | 4.178525131 |
| 346 | batch2_ctl16 | batch2_ctl16 | SLX-13222 | D704-D508 | healthy | 0.00415128 | NA | 6.211221242 |
| 347 | batch2_ctl17 | batch2_ctl17 | SLX-13222 | D705-D505 | healthy | 0.00852753 | NA | 6.224810739 |
| 348 | batch2_ctl18 | batch2_ctl18 | SLX-13222 | D705-D506 | healthy | 0.00813013 | NA | 7.844697188 |
| 349 | batch2_ctl19 | batch2_ctl19 | SLX-13222 | D705-D507 | healthy | 0.00770952 | NA | 4.230016234 |
| 350 | batch2_ctl20 | batch2_ctl20 | SLX-13222 | D705-D508 | healthy | 0.01082298 | NA | 7.472602686 |
| 351 | batch2_ctl21 | batch2_ctl21 | SLX-13222 | D706-D505 | healthy | 0.01246369 | NA | 3.721390103 |
| 352 | batch2_ctl22 | batch2_ctl22 | SLX-13222 | D706-D506 | healthy | 0.00731629 | NA | 9.490694405 |
| 353 | batch2_ctl23 | batch2_ctl23 | SLX-13222 | D706-D507 | healthy | 0.01123012 | NA | 9.211483447 |
| 354 | batch2_ctl24 | batch2_ctl24 | SLX-13222 | D706-D508 | healthy | 0.00948864 | NA | 8.60534524 |

| index | P(20_150) | P(160_180) | P(20_150)/ P(160_180) | P(100_150) | P(100_150)/ P(163_169) | P(180_220) | P(250_320) | P(20_150)/ P(180_220) |
|---|---|---|---|---|---|---|---|---|
| 1 | 0.15593628 | 0.474759905 | 0.328452926 | 0.150467716 | 0.797230669 | 0.242257259 | 0.01344566 | 0.643680527 |
| 2 | 0.153305045 | 0.517651152 | 0.296155132 | 0.151170814 | 0.716017076 | 0.210272306 | 0.003406292 | 0.729078633 |
| 3 | 0.190293559 | 0.42569701 | 0.447016433 | 0.17607343 | 1.097693843 | 0.242204427 | 0.031265598 | 0.785673333 |
| 4 | 0.153458877 | 0.532513429 | 0.288178417 | 0.151180028 | 0.676444354 | 0.191137675 | 0.0031301 | 0.802870897 |
| 5 | 0.234162421 | 0.481611843 | 0.486205695 | 0.228334925 | 1.022916892 | 0.123317396 | 0.003111174 | 1.898859598 |
| 6 | 0.182383923 | 0.500662425 | 0.364285222 | 0.178274903 | 0.797659738 | 0.170358622 | 0.004612955 | 1.070588159 |
| 7 | 0.125970767 | 0.435908671 | 0.288984311 | 0.119404664 | 0.735520087 | 0.300845212 | 0.026021089 | 0.418722857 |
| 8 | 0.150216458 | 0.506601991 | 0.296517702 | 0.146539351 | 0.685757089 | 0.211474161 | 0.004645669 | 0.710330082 |
| 9 | 0.150859409 | 0.445272059 | 0.338802775 | 0.143907267 | 0.829470351 | 0.268316043 | 0.021243303 | 0.562245205 |
| 10 | 0.134771126 | 0.507443882 | 0.265588237 | 0.132198502 | 0.669215178 | 0.239142669 | 0.007797143 | 0.563559513 |
| 11 | 0.168015932 | 0.470466497 | 0.357126242 | 0.16075196 | 0.871359965 | 0.235433337 | 0.012234413 | 0.713645461 |
| 12 | 0.119421664 | 0.516409351 | 0.231253876 | 0.117728563 | 0.590052228 | 0.255304555 | 0.004916546 | 0.467761588 |
| 13 | 0.144461769 | 0.384670633 | 0.375546654 | 0.13414291 | 0.931861214 | 0.227571414 | 0.039721361 | 0.63479752 |
| 14 | 0.270943962 | 0.403405095 | 0.671642389 | 0.24852795 | 1.472004778 | 0.132617318 | 0.030309159 | 2.043051131 |
| 15 | 0.333745777 | 0.341029821 | 0.978641035 | 0.316934675 | 2.213760282 | 0.124345996 | 0.036590701 | 2.684009046 |
| 16 | 0.258242277 | 0.321164069 | 0.804082093 | 0.237227487 | 1.700196737 | 0.112764896 | 0.113684512 | 2.290094577 |
| 17 | 0.161376514 | 0.472136335 | 0.341800667 | 0.157467767 | 0.80410171 | 0.180049905 | 0.024531581 | 0.896287691 |
| 18 | 0.155759138 | 0.432486714 | 0.360147798 | 0.150598877 | 0.853785668 | 0.186174631 | 0.040511621 | 0.836629232 |
| 19 | 0.159149606 | 0.457356112 | 0.347977433 | 0.155320273 | 0.83295436 | 0.18830049 | 0.028989014 | 0.845189548 |
| 20 | 0.161875577 | 0.441582658 | 0.366580467 | 0.156550382 | 0.880657715 | 0.203818787 | 0.027965978 | 0.79421323 |
| 21 | NA | NA | NA | NA | NA | NA | NA | NA |
| 22 | 0.406794901 | 0.271498664 | 1.498331135 | 0.353708315 | 2.778961716 | 0.07056407 | 0.076066888 | 5.764901312 |
| 23 | 0.410998565 | 0.31613605 | 1.300068642 | 0.348798067 | 2.281498855 | 0.064663009 | 0.050209365 | 6.356007447 |
| 24 | 0.161643441 | 0.443226021 | 0.364697543 | 0.157566047 | 0.868614807 | 0.184260953 | 0.038850541 | 0.877252821 |
| 25 | 0.156543642 | 0.484951752 | 0.322802508 | 0.149583553 | 0.778941478 | 0.215896693 | 0.016460595 | 0.725085873 |
| 26 | 0.183928705 | 0.453968867 | 0.405157089 | 0.176759494 | 0.97390446 | 0.195448459 | 0.022055332 | 0.941059886 |
| 27 | 0.178035293 | 0.432936842 | 0.411226941 | 0.171816011 | 1.030458873 | 0.214017304 | 0.029019478 | 0.831873358 |
| 28 | 0.211253249 | 0.485403371 | 0.435211747 | 0.203936205 | 0.952144517 | 0.137147125 | 0.017063151 | 1.540340336 |
| 29 | 0.183987884 | 0.444977085 | 0.413477211 | 0.17537584 | 0.990412234 | 0.208852123 | 0.022703094 | 0.880948117 |

TABLE 2-continued values for 9 fragmentation features determined from shallow Whole Genome Sequencing (sWGS) data for the samples included in the study.

| | | | | | | | | |
|---|---|---|---|---|---|---|---|---|
| 30 | 0.373651123 | 0.330317782 | 1.131186825 | 0.351126228 | 2.535757483 | 0.117785898 | 0.036146948 | 3.172290831 |
| 31 | 0.192042383 | 0.440323373 | 0.436139426 | 0.184151466 | 1.033220425 | 0.190902129 | 0.029367931 | 1.005972978 |
| 32 | 0.195634501 | 0.470283418 | 0.415992769 | 0.179655422 | 0.855911241 | 0.132722224 | 0.0342264 | 1.474014639 |
| 33 | 0.234285284 | 0.443711618 | 0.528012508 | 0.209863532 | 1.064884228 | 0.136684496 | 0.025990906 | 1.714058954 |
| 34 | 0.246402964 | 0.419197496 | 0.587796841 | 0.223178899 | 1.217363539 | 0.127859241 | 0.039894758 | 1.927142396 |
| 35 | 0.218133185 | 0.416633278 | 0.523561599 | 0.188209718 | 1.107617829 | 0.1803737 | 0.030131069 | 1.209340299 |
| 36 | 0.365963849 | 0.310301799 | 1.179380364 | 0.319366002 | 2.233561733 | 0.086990576 | 0.069801698 | 4.206936711 |
| 37 | 0.37234333 | 0.334068814 | 1.114570755 | 0.328863789 | 2.244572418 | 0.102276814 | 0.023961362 | 3.640544858 |
| 38 | 0.208979406 | 0.441172944 | 0.47369044 | 0.174640318 | 0.892459838 | 0.159919909 | 0.029363935 | 1.306775413 |
| 39 | 0.155553467 | 0.494238737 | 0.314733458 | 0.14137831 | 0.710571482 | 0.190505787 | 0.018445822 | 0.816528828 |
| 40 | 0.288496965 | 0.355753466 | 0.810946322 | 0.261935758 | 1.761053787 | 0.132752439 | 0.056370821 | 2.173195214 |
| 41 | 0.110732423 | 0.388888117 | 0.284741082 | 0.103419258 | 0.705912562 | 0.249477774 | 0.044903715 | 0.443856869 |
| 42 | 0.311464417 | 0.265496866 | 1.173137828 | 0.244366095 | 2.394471916 | 0.151694859 | 0.080430915 | 2.05322987 |
| 43 | 0.255958363 | 0.38695262 | 0.661472102 | 0.219256999 | 1.329090513 | 0.146195262 | 0.0465542 | 1.750797938 |
| 44 | 0.32512436 | 0.333788232 | 0.974043806 | 0.298621802 | 1.976699433 | 0.096767777 | 0.070787047 | 3.359841155 |
| 45 | 0.164441165 | 0.402483662 | 0.408566062 | 0.15348016 | 0.921795727 | 0.177039399 | 0.057287586 | 0.928839381 |
| 46 | 0.381782679 | 0.284988491 | 1.339642445 | 0.304093638 | 2.373800524 | 0.094895414 | 0.075328562 | 4.02319418 |
| 47 | 0.192920981 | 0.473558402 | 0.407385827 | 0.164906046 | 0.803434646 | 0.138879879 | 0.028034919 | 1.389121177 |
| 48 | 0.160627048 | 0.419643921 | 0.382769868 | 0.150576832 | 0.905687757 | 0.176063841 | 0.062752074 | 0.912322755 |
| 49 | 0.079086104 | 0.213333612 | 0.370715628 | 0.064024278 | 0.829166341 | 0.150084266 | 0.083225368 | 0.526944671 |
| 50 | 0.242407441 | 0.313131707 | 0.774138917 | 0.213558003 | 1.686641693 | 0.144280061 | 0.086569629 | 1.680117402 |
| 51 | 0.492169778 | 0.249011727 | 1.976492372 | 0.412314316 | 3.435046089 | 0.049609219 | 0.054388342 | 9.920933831 |
| 52 | 0.174789703 | 0.41729972 | 0.418858903 | 0.160196374 | 0.900671719 | 0.167363434 | 0.054417692 | 1.044372115 |
| 53 | 0.221824022 | 0.391836765 | 0.566113345 | 0.181085397 | 1.1240962 | 0.16057811 | 0.045186068 | 1.381408845 |
| 54 | 0.225281622 | 0.267689347 | 0.841578584 | 0.203761552 | 1.930091537 | 0.140103214 | 0.090344407 | 1.607968985 |
| 55 | 0.414771135 | 0.2747978 | 1.509368471 | 0.363272115 | 3.031676253 | 0.089505852 | 0.067049133 | 4.634011348 |
| 56 | 0.293308692 | 0.291000072 | 1.007933398 | 0.243748213 | 2.113962168 | 0.13724112 | 0.09592302 | 2.137177921 |
| 57 | 0.190447908 | 0.416434178 | 0.457330157 | 0.170760995 | 1.018636509 | 0.183060541 | 0.045326628 | 1.040354776 |
| 58 | 0.167834816 | 0.427769909 | 0.392348345 | 0.155894317 | 0.925631929 | 0.212147344 | 0.033749912 | 0.791123817 |
| 59 | 0.241403377 | 0.406674156 | 0.593603929 | 0.213651862 | 1.212571751 | 0.138508494 | 0.049172312 | 1.742877782 |
| 60 | 0.209942844 | 0.373901389 | 0.561492549 | 0.183134512 | 1.224460712 | 0.157982681 | 0.073075452 | 1.328897846 |
| 61 | 0.170534613 | 0.4327878 | 0.394037478 | 0.153672697 | 0.899259351 | 0.187885022 | 0.037175775 | 0.907654111 |
| 62 | 0.198152745 | 0.415482823 | 0.476921629 | 0.182876855 | 1.041758285 | 0.14711832 | 0.065140484 | 1.346893739 |
| 63 | 0.167020438 | 0.470359819 | 0.355090787 | 0.15372062 | 0.745276536 | 0.157545076 | 0.039898514 | 1.060143815 |
| 64 | 0.210448513 | 0.41124538 | 0.511734655 | 0.181899732 | 1.036175861 | 0.152058836 | 0.060875519 | 1.383993979 |
| 65 | 0.114585257 | 0.430595794 | 0.26610863 | 0.100212575 | 0.627859658 | 0.268849631 | 0.023391561 | 0.426205746 |
| 66 | 0.312045324 | 0.327531931 | 0.952717261 | 0.269724373 | 1.955386949 | 0.123527324 | 0.069931645 | 2.52612389 |
| 67 | 0.179497931 | 0.407743288 | 0.440222895 | 0.166693276 | 1.016741973 | 0.197377192 | 0.034564026 | 0.909415765 |
| 68 | 0.249831622 | 0.460833887 | 0.542129451 | 0.224564376 | 1.005150323 | 0.088788005 | 0.034901025 | 2.813799237 |
| 69 | 0.2358918 | 0.483953069 | 0.487427016 | 0.21490821 | 0.904629619 | 0.084814548 | 0.023637568 | 2.78126577 |
| 70 | 0.256271996 | 0.375256286 | 0.682925258 | 0.237793454 | 1.463278506 | 0.137751803 | 0.055404157 | 1.860389413 |
| 71 | 0.162974631 | 0.401695067 | 0.405717283 | 0.153990624 | 0.953199717 | 0.198324542 | 0.034884124 | 0.821757256 |
| 72 | 0.252258541 | 0.442786705 | 0.569706675 | 0.241444826 | 1.112506999 | 0.094505801 | 0.029761744 | 2.669238692 |
| 73 | 0.256678238 | 0.462784706 | 0.554638549 | 0.245740959 | 1.086974631 | 0.095810434 | 0.015204963 | 2.679021769 |
| 74 | 0.159102438 | 0.45384074 | 0.350568876 | 0.149415026 | 0.810936667 | 0.18386854 | 0.035410568 | 0.865305388 |
| 75 | 0.175935056 | 0.500623889 | 0.351431604 | 0.16731153 | 0.735747804 | 0.137725931 | 0.025527302 | 1.277428695 |
| 76 | 0.203551414 | 0.363594584 | 0.559830709 | 0.177492681 | 1.220186161 | 0.169919557 | 0.077960442 | 1.197928114 |
| 77 | 0.204525264 | 0.387519789 | 0.52778018 | 0.180306116 | 1.207034277 | 0.204559659 | 0.036280509 | 0.999831858 |
| 78 | 0.297671057 | 0.423516893 | 0.702855215 | 0.265577046 | 1.33470103 | 0.08173969 | 0.023931715 | 3.641695471 |
| 79 | 0.485854018 | 0.208719424 | 2.327785355 | 0.390507206 | 4.685248615 | 0.130596759 | 0.02419897 | 3.720260927 |
| 80 | 0.350313731 | 0.332732151 | 1.052840039 | 0.318223881 | 2.235742157 | 0.116346386 | 0.050561748 | 3.010954989 |
| 81 | 0.131521416 | 0.445875848 | 0.294973178 | 0.125331767 | 0.711455474 | 0.217575886 | 0.029099053 | 0.604485261 |
| 82 | 0.224237379 | 0.378695998 | 0.592130311 | 0.207986858 | 1.285211569 | 0.139332811 | 0.073041588 | 1.60936521 |
| 83 | 0.364910312 | 0.845720084 | 0.43147883 | 0.337663675 | 0.961250622 | 0.340142216 | 0.092718998 | 1.072816882 |
| 84 | 0.471544747 | 0.1840065 | 2.562648681 | 0.368628602 | 5.182417747 | 0.12342867 | 0.061690527 | 3.820376685 |
| 85 | 0.458234472 | 0.187039916 | 2.449928774 | 0.339190518 | 4.766713956 | 0.13171405 | 0.051089419 | 3.47900982 |
| 86 | 0.15699058 | 0.413114544 | 0.380017074 | 0.145701161 | 0.887288569 | 0.192594761 | 0.040096908 | 0.815134219 |
| 87 | 0.146804885 | 0.358438892 | 0.4095674 | 0.134000855 | 1.008039667 | 0.225017444 | 0.036997483 | 0.652415574 |
| 88 | 0.177299915 | 0.421352618 | 0.420787501 | 0.162414174 | 0.972389496 | 0.185352058 | 0.034150708 | 0.956557575 |
| 89 | 0.185868674 | 0.384467583 | 0.483444332 | 0.168767637 | 1.054973607 | 0.156097764 | 0.052384631 | 1.190719642 |
| 90 | 0.165487688 | 0.413170828 | 0.40053091 | 0.147137418 | 0.872256091 | 0.176033328 | 0.049239008 | 0.940092935 |
| 91 | 0.149268675 | 0.383692757 | 0.389031777 | 0.135166048 | 0.935511685 | 0.213579194 | 0.034986546 | 0.698891462 |
| 92 | 0.165840691 | 0.42224989 | 0.392754847 | 0.154772183 | 0.887110037 | 0.168928955 | 0.050768714 | 0.981718562 |
| 93 | 0.391926212 | 0.274058463 | 1.430082503 | 0.353280088 | 3.101741864 | 0.100876782 | 0.063729856 | 3.885197388 |
| 94 | 0.224282438 | 0.412662857 | 0.543500425 | 0.202773307 | 1.167788345 | 0.149415023 | 0.04140024 | 1.501070199 |
| 95 | 0.139204647 | 0.425434693 | 0.327205678 | 0.129793796 | 0.785884276 | 0.216346282 | 0.029182383 | 0.643434433 |
| 96 | 0.151524919 | 0.39329787 | 0.385267581 | 0.13989207 | 0.947337852 | 0.214843109 | 0.040945596 | 0.705281725 |
| 97 | 0.144399427 | 0.44072744 | 0.327638839 | 0.135867119 | 0.765927407 | 0.187545689 | 0.038482862 | 0.769942663 |
| 98 | 0.171509302 | 0.492866532 | 0.347983258 | 0.158406056 | 0.721919355 | 0.131754951 | 0.041705983 | 1.301729461 |
| 99 | 0.250644804 | 0.419186758 | 0.597931112 | 0.237451824 | 1.247844727 | 0.114156014 | 0.043484171 | 2.195633812 |
| 100 | 0.179387063 | 0.435691279 | 0.411729754 | 0.17015 | 0.909160167 | 0.145449743 | 0.054977677 | 1.233326783 |
| 101 | 0.319751591 | 0.825370715 | 0.387403606 | 0.285657761 | 0.895151845 | 0.397802484 | 0.07801792 | 0.803794858 |
| 102 | 0.151665816 | 0.36698396 | 0.413276418 | 0.13818925 | 1.010127569 | 0.194234558 | 0.069660432 | 0.780838478 |
| 103 | 0.174958987 | 0.457130715 | 0.38273295 | 0.161440649 | 0.811954 | 0.144274859 | 0.037386306 | 1.212678279 |
| 104 | 0.160117686 | 0.423975245 | 0.3776581 | 0.136849665 | 0.827673931 | 0.207899793 | 0.032569221 | 0.770167607 |
| 105 | 0.202305485 | 0.359111292 | 0.563350386 | 0.168053397 | 1.20653922 | 0.188623811 | 0.054564343 | 1.07253418 |
| 106 | 0.136785869 | 0.434117548 | 0.315089472 | 0.128520055 | 0.737799407 | 0.199822575 | 0.039336563 | 0.684536615 |

TABLE 2-continued values for 9 fragmentation features determined from shallow Whole Genome
Sequencing (sWGS) data for the samples included in the study.

| | | | | | | | | |
|---|---|---|---|---|---|---|---|---|
| 107 | 0.251586376 | 0.472963587 | 0.531936036 | 0.23374244 | 0.995584861 | 0.071815615 | 0.020815367 | 3.503226627 |
| 108 | 0.166915813 | 0.373534746 | 0.446854851 | 0.264090675 | 1.659065781 | 0.132430417 | 0.050651894 | 2.102380295 |
| 109 | 0.134098385 | 0.460240443 | 0.291365931 | 0.143474481 | 0.775497549 | 0.196918533 | 0.030734885 | 0.745293201 |
| 110 | 0.154426352 | 0.377765086 | 0.408789371 | 0.15523863 | 1.059221675 | 0.202696396 | 0.065536332 | 0.805538392 |
| 111 | 0.144515182 | 0.40407801 | 0.357641788 | 0.109650746 | 0.718876451 | 0.257021736 | 0.030988029 | 0.443672849 |
| 112 | 0.110933743 | 0.446425392 | 0.248493354 | 0.150148338 | 0.847512299 | 0.197599382 | 0.037014493 | 0.781512321 |
| 113 | 0.146762044 | 0.440845558 | 0.332910339 | 0.129928998 | 0.756772127 | 0.223193853 | 0.031795433 | 0.60081576 |
| 114 | 0.142147792 | 0.455344894 | 0.312176097 | 0.161895976 | 0.865416046 | 0.179876175 | 0.032981696 | 0.927948422 |
| 115 | 0.278419099 | 0.432806361 | 0.643287908 | 0.137696966 | 0.802732788 | 0.21216938 | 0.077273671 | 0.681131188 |
| 116 | 0.172031969 | 0.395808685 | 0.434634144 | 0.105044112 | 0.759593054 | 0.295969205 | 0.059184743 | 0.374815155 |
| 117 | 0.135980829 | 0.47262159 | 0.287716075 | 0.137554147 | 0.771294253 | 0.263411719 | 0.015144429 | 0.53964111 |
| 118 | 0.114033566 | 0.453228633 | 0.25160274 | 0.164748849 | 0.93572563 | 0.230802589 | 0.030361609 | 0.745364121 |
| 119 | 0.157730849 | 0.519098322 | 0.30385544 | 0.134017288 | 0.653814872 | 0.228535828 | 0.005898812 | 0.595008802 |
| 120 | 0.133976264 | 0.460589967 | 0.290879684 | 0.150251296 | 0.830905324 | 0.238247785 | 0.032684414 | 0.662045396 |
| 121 | 0.163279729 | 0.42238088 | 0.386569887 | 0.126458821 | 0.810783402 | 0.282116547 | 0.036065064 | 0.474896864 |
| 122 | 0.240025328 | 0.377378128 | 0.63603402 | 0.219182256 | 1.381020221 | 0.154104093 | 0.07720812 | 1.557553233 |
| 123 | 0.151195588 | 0.457915638 | 0.33018219 | 0.144636993 | 0.804120376 | 0.238183498 | 0.041028861 | 0.634786159 |
| 124 | 0.220844112 | 0.426407826 | 0.517917586 | 0.212237611 | 1.204025152 | 0.175938628 | 0.052989149 | 1.255233794 |
| 125 | 0.210739529 | 0.398324391 | 0.529065088 | 0.200213913 | 1.230956989 | 0.182841461 | 0.070556964 | 1.15258065 |
| 126 | 0.143097819 | 0.460652155 | 0.310641809 | 0.136206275 | 0.799652587 | 0.261977417 | 0.030677916 | 0.546221963 |
| 127 | 0.154837338 | 0.46878037 | 0.330298255 | 0.148754542 | 0.781467471 | 0.212338809 | 0.045513974 | 0.72919943 |
| 128 | 0.242644984 | 0.393074804 | 0.617299765 | 0.217877813 | 1.320387692 | 0.151851708 | 0.048457436 | 1.597907503 |
| 129 | 0.220341779 | 0.354058424 | 0.622331695 | 0.209080371 | 1.436801203 | 0.158020314 | 0.075238966 | 1.394388949 |
| 130 | 0.156387338 | 0.396041211 | 0.394876427 | 0.148042531 | 0.966600487 | 0.222609627 | 0.034938441 | 0.702518307 |
| 131 | 0.191638069 | 0.469464414 | 0.408205741 | 0.18471631 | 0.945150432 | 0.187623715 | 0.027096543 | 1.021395772 |
| 132 | 0.173735933 | 0.407813395 | 0.426018211 | 0.160661535 | 1.031168062 | 0.217414361 | 0.030294635 | 0.799100539 |
| 133 | 0.179674699 | 0.405004689 | 0.443636096 | 0.163084809 | 1.07385385 | 0.234830039 | 0.023370359 | 0.765126557 |
| 134 | 0.138289733 | 0.365110242 | 0.378761583 | 0.128498898 | 0.96963611 | 0.264541865 | 0.033597861 | 0.522751789 |
| 135 | 0.15865778 | 0.450048025 | 0.352535221 | 0.152592037 | 0.854624442 | 0.218062102 | 0.021116693 | 0.727580713 |
| 136 | 0.176786827 | 0.405921011 | 0.435520267 | 0.16409909 | 1.02780899 | 0.224718389 | 0.026500812 | 0.786703874 |
| 137 | 0.12762252 | 0.423974765 | 0.301014425 | 0.117014958 | 0.734626951 | 0.2427356 | 0.032428748 | 0.525767628 |
| 138 | 0.14297929 | 0.437827082 | 0.32656566 | 0.127819968 | 0.744528052 | 0.212391697 | 0.038279407 | 0.673186815 |
| 139 | 0.121496202 | 0.393307566 | 0.308908885 | 0.111117689 | 0.747878077 | 0.236063828 | 0.043231489 | 0.514675218 |
| 140 | 0.173554913 | 0.424613101 | 0.408736595 | 0.146550169 | 0.889132178 | 0.211541557 | 0.02856987 | 0.820429402 |
| 141 | 0.142555072 | 0.38874445 | 0.366706385 | 0.125033669 | 0.852840677 | 0.24210563 | 0.034015226 | 0.588813535 |
| 142 | 0.135400676 | 0.403118898 | 0.33588273 | 0.118810449 | 0.786422965 | 0.249003252 | 0.031924015 | 0.543770714 |
| 143 | 0.173584847 | 0.428429264 | 0.40516571 | 0.163747928 | 0.972210719 | 0.206591418 | 0.033938831 | 0.840232615 |
| 144 | 0.160847046 | 0.4420072 | 0.363901416 | 0.15283327 | 0.844975699 | 0.190609596 | 0.036493661 | 0.84385597 |
| 145 | 0.137916293 | 0.420457473 | 0.328014846 | 0.127003906 | 0.786253289 | 0.227901117 | 0.033920391 | 0.605158478 |
| 146 | 0.139330392 | 0.425283135 | 0.327617957 | 0.129122385 | 0.785374026 | 0.22540984 | 0.031208884 | 0.618120275 |
| 147 | 0.15783898 | 0.424377898 | 0.371930255 | 0.144344954 | 0.856952959 | 0.204234602 | 0.038677044 | 0.772831727 |
| 148 | 0.077188219 | 0.253762355 | 0.264768267 | 0.060702415 | 0.69699619 | 0.25430252 | 0.049614678 | 0.264205872 |
| 149 | 0.154031747 | 0.441304009 | 0.349037724 | 0.141516733 | 0.778852063 | 0.194156774 | 0.036306691 | 0.793336975 |
| 150 | 0.126661829 | 0.402062305 | 0.315030351 | 0.11384707 | 0.73102704 | 0.224247616 | 0.039617073 | 0.564830216 |
| 151 | 0.127869432 | 0.413907617 | 0.3089323 | 0.133954898 | 0.893492871 | 0.238350545 | 0.027294558 | 0.656068257 |
| 152 | 0.108812647 | 0.416416314 | 0.261307359 | 0.116382928 | 0.753107087 | 0.243995939 | 0.028995885 | 0.553428684 |
| 153 | 0.121353613 | 0.363636809 | 0.333722027 | 0.12567048 | 0.950891087 | 0.231189053 | 0.041857439 | 0.639199211 |
| 154 | 0.165155724 | 0.461551597 | 0.357827218 | 0.150918426 | 0.827992121 | 0.185371478 | 0.028634328 | 0.890944636 |
| 155 | 0.17649294 | 0.417526042 | 0.422711213 | 0.145129688 | 0.896305276 | 0.206316268 | 0.033881771 | 0.855448493 |
| 156 | 0.190443038 | 0.401948334 | 0.473799794 | 0.156948152 | 1.04400375 | 0.218427279 | 0.027303223 | 0.87188303 |
| 157 | 0.136832452 | 0.43700844 | 0.313111692 | 0.143548008 | 0.862025572 | 0.212590595 | 0.025848333 | 0.791759139 |
| 158 | 0.150765546 | 0.39054486 | 0.386038997 | 0.137730351 | 0.969926244 | 0.24206138 | 0.026972008 | 0.730747084 |
| 159 | 0.141309597 | 0.419107617 | 0.337167809 | 0.144732846 | 0.918771073 | 0.220458538 | 0.028708106 | 0.779323281 |
| 160 | 0.139293803 | 0.32444719 | 0.429326582 | 0.109359931 | 1.043112809 | 0.292157195 | 0.028673267 | 0.476776903 |
| 161 | 0.112748587 | 0.409899124 | 0.27506423 | 0.11927306 | 0.780454236 | 0.238285131 | 0.030819834 | 0.588416827 |
| 162 | 0.11406393 | 0.433653471 | 0.263030133 | 0.120520538 | 0.758186671 | 0.241711247 | 0.029300708 | 0.585197401 |
| 163 | 0.137166722 | 0.414628062 | 0.330818714 | 0.117167604 | 0.776877292 | 0.238986811 | 0.032871664 | 0.57395101 |
| 164 | 0.10906998 | 0.444149355 | 0.245570502 | 0.114347779 | 0.695793205 | 0.224074388 | 0.036120476 | 0.603653385 |
| 165 | 0.090840547 | 0.412419639 | 0.220262418 | 0.098081174 | 0.679495596 | 0.269957192 | 0.033457224 | 0.423774723 |
| 166 | 0.104532866 | 0.435164303 | 0.240214708 | 0.115613733 | 0.700101333 | 0.221857384 | 0.033741618 | 0.597177486 |
| 167 | 0.144657748 | 0.421663927 | 0.343064082 | 0.117767047 | 0.768008931 | 0.238268333 | 0.031831992 | 0.607121167 |
| 168 | 0.11820181 | 0.364140014 | 0.324605387 | 0.098506062 | 0.772035853 | 0.261092657 | 0.034664687 | 0.452719779 |
| 169 | 0.101000277 | 0.456167048 | 0.221410726 | 0.110203693 | 0.637793899 | 0.222958492 | 0.027325709 | 0.574805259 |
| 170 | 0.148281373 | 0.489932199 | 0.302656926 | 0.159876373 | 0.794107306 | 0.155292774 | 0.02345978 | 1.185648003 |
| 171 | 0.153195604 | 0.393626339 | 0.389190429 | 0.126329184 | 0.869536037 | 0.23700974 | 0.030274623 | 0.646368387 |
| 172 | 0.119156061 | 0.414959681 | 0.287150936 | 0.125400011 | 0.809815449 | 0.22676638 | 0.030353319 | 0.648461877 |
| 173 | 0.151085588 | 0.429754957 | 0.351562176 | 0.164873603 | 0.965569967 | 0.192047298 | 0.027684698 | 0.97075211 |
| 174 | 0.159147467 | 0.388403377 | 0.409747897 | 0.133050583 | 0.919911613 | 0.227114913 | 0.028700644 | 0.700735435 |
| 175 | 0.114173244 | 0.434549618 | 0.262739258 | 0.127198667 | 0.756327517 | 0.206693952 | 0.036480477 | 0.694707149 |
| 176 | 0.147111178 | 0.430180645 | 0.341975353 | 0.155229524 | 0.876828748 | 0.159460373 | 0.053744379 | 1.135810241 |
| 177 | 0.128579056 | 0.456721543 | 0.281526146 | 0.136035245 | 0.763114024 | 0.212178064 | 0.026665283 | 0.753343701 |
| 178 | 0.080581755 | 0.3932327 | 0.204921297 | 0.081556298 | 0.599782601 | 0.310150458 | 0.022968567 | 0.322334107 |
| 179 | 0.162703217 | 0.486994855 | 0.334096378 | 0.174181463 | 0.823442554 | 0.144207543 | 0.020291146 | 1.407863584 |
| 180 | 0.127703041 | 0.457080008 | 0.279388814 | 0.14198401 | 0.79395246 | 0.201688597 | 0.028945798 | 0.79647378 |
| 181 | 0.188253011 | 0.388127485 | 0.485028807 | 0.186649251 | 1.26335737 | 0.18856276 | 0.038425191 | 1.17941429 |
| 182 | 0.153441115 | 0.458848968 | 0.334404402 | 0.136187553 | 0.758136507 | 0.197273599 | 0.035619542 | 0.777808667 |
| 183 | 0.180776017 | 0.386068836 | 0.468248147 | 0.20406178 | 1.350219159 | 0.194362076 | 0.031104149 | 1.128134664 |

TABLE 2-continued values for 9 fragmentation features determined from shallow Whole Genome
Sequencing (sWGS) data for the samples included in the study.

| | | | | | | | | |
|---|---|---|---|---|---|---|---|---|
| 184 | 0.103391318 | 0.384187388 | 0.269116898 | 0.121811495 | 0.844423195 | 0.22918591 | 0.046272707 | 0.571224935 |
| 185 | 0.111773903 | 0.386361043 | 0.289299103 | 0.129638881 | 0.892063917 | 0.225817972 | 0.043831887 | 0.621135377 |
| 186 | 0.1074418 | 0.388338027 | 0.276670819 | 0.126023328 | 0.863792396 | 0.229043506 | 0.044197508 | 0.592354257 |
| 187 | 0.160558232 | 0.403156222 | 0.398253141 | 0.175229306 | 1.120822566 | 0.201941167 | 0.029956186 | 0.968296456 |
| 188 | 0.147158047 | 0.40743339 | 0.361183081 | 0.164414693 | 1.044625836 | 0.208086152 | 0.031633636 | 0.870837788 |
| 189 | 0.168356529 | 0.400864027 | 0.419984129 | 0.18005573 | 1.155951519 | 0.198753135 | 0.029231525 | 1.024388444 |
| 190 | 0.152056399 | 0.404624665 | 0.375796169 | 0.167820624 | 1.073842965 | 0.205143577 | 0.031311123 | 0.908532825 |
| 191 | 0.138105454 | 0.44741857 | 0.308671707 | 0.16005989 | 0.864011038 | 0.173569773 | 0.032537859 | 1.002760831 |
| 192 | 0.136400227 | 0.447462996 | 0.304830183 | 0.158103392 | 0.854240147 | 0.174231613 | 0.032945877 | 0.987224685 |
| 193 | 0.137137789 | 0.447704739 | 0.306313016 | 0.159143385 | 0.858162836 | 0.173576414 | 0.032805632 | 0.996336342 |
| 194 | 0.129322651 | 0.435753885 | 0.296779112 | 0.14940478 | 0.888293499 | 0.227716173 | 0.023025908 | 0.710039418 |
| 195 | 0.136506055 | 0.448915645 | 0.304079522 | 0.158074764 | 0.853078869 | 0.175787123 | 0.032396022 | 0.979404407 |
| 196 | 0.095398289 | 0.401312845 | 0.237715514 | 0.115202837 | 0.766479218 | 0.233240006 | 0.040753214 | 0.525125326 |
| 197 | 0.073898347 | 0.399622288 | 0.222455928 | 0.108344709 | 0.726723395 | 0.236210357 | 0.042373968 | 0.48597889 |
| 198 | 0.095796512 | 0.385264369 | 0.248651367 | 0.112484034 | 0.781440847 | 0.237436406 | 0.042540718 | 0.512940463 |
| 199 | 0.097828838 | 0.383711448 | 0.254954181 | 0.113779698 | 0.792973657 | 0.234870569 | 0.042706344 | 0.52745769 |
| 200 | 0.153027896 | 0.454161276 | 0.336946156 | 0.174751419 | 0.923980984 | 0.167246611 | 0.026221411 | 1.142575807 |
| 201 | 0.12532337 | 0.426513853 | 0.293831887 | 0.148227265 | 0.904895765 | 0.222070634 | 0.027369446 | 0.710286688 |
| 202 | 0.128712994 | 0.42174217 | 0.30519356 | 0.149267286 | 0.921664258 | 0.220512006 | 0.02800619 | 0.729692749 |
| 203 | 0.17843971 | 0.410185691 | 0.435021781 | 0.203048295 | 1.26567091 | 0.183953796 | 0.032725244 | 1.186195356 |
| 204 | 0.130727911 | 0.425438242 | 0.307278232 | 0.152009644 | 0.928389515 | 0.21882491 | 0.026428899 | 0.746833209 |
| 205 | 0.18561624 | 0.397957207 | 0.466422612 | 0.188997366 | 1.216066833 | 0.191795002 | 0.026212141 | 1.154993291 |
| 206 | 0.184055242 | 0.397955929 | 0.462501571 | 0.188107342 | 1.210994881 | 0.192259582 | 0.026389616 | 1.143434177 |
| 207 | 0.185224177 | 0.395469321 | 0.468365476 | 0.184433935 | 1.197251283 | 0.191562109 | 0.027103473 | 1.150991768 |
| 208 | 0.14586037 | 0.43033054 | 0.338949613 | 0.164714617 | 0.970784164 | 0.201611325 | 0.025674222 | 0.890983553 |
| 209 | 0.120720237 | 0.441428954 | 0.273476028 | 0.144170431 | 0.844182628 | 0.229885064 | 0.022951243 | 0.665084353 |
| 210 | 0.183925288 | 0.40758976 | 0.451251003 | 0.207490834 | 1.296486488 | 0.180009167 | 0.032138544 | 1.245447485 |
| 211 | 0.111591861 | 0.411957603 | 0.270881907 | 0.130776464 | 0.829643748 | 0.236736575 | 0.027711101 | 0.594942712 |
| 212 | 0.113387864 | 0.414209039 | 0.273745509 | 0.133315789 | 0.839507255 | 0.234605466 | 0.026765433 | 0.609731756 |
| 213 | 0.125093198 | 0.412924801 | 0.30294426 | 0.146491489 | 0.937801933 | 0.235273444 | 0.026862149 | 0.662329143 |
| 214 | 0.142602516 | 0.431314747 | 0.330622862 | 0.161794407 | 0.953645817 | 0.204160282 | 0.026245478 | 0.862190525 |
| 215 | 0.122162042 | 0.413416206 | 0.295494081 | 0.143777095 | 0.919216506 | 0.237367299 | 0.02735997 | 0.643235685 |
| 216 | 0.161334709 | 0.408139379 | 0.39529317 | 0.177017386 | 1.117002198 | 0.2011959 | 0.027811151 | 0.978321962 |
| 217 | 0.162816682 | 0.410016983 | 0.39709741 | 0.178566729 | 1.11986344 | 0.201285601 | 0.02679188 | 0.986581677 |
| 218 | 0.096231745 | 0.399666929 | 0.240779854 | 0.114929533 | 0.770746142 | 0.243065379 | 0.037246845 | 0.506119129 |
| 219 | 0.094680432 | 0.40046724 | 0.236424912 | 0.113557032 | 0.759184804 | 0.244241478 | 0.037360852 | 0.496878898 |
| 220 | 0.139785038 | 0.452221044 | 0.309107769 | 0.162373048 | 0.86832697 | 0.173897801 | 0.03025472 | 1.01329711 |
| 221 | 0.140965128 | 0.452610471 | 0.311449109 | 0.162951486 | 0.869785651 | 0.173314119 | 0.029846734 | 1.02346582 |
| 222 | 0.106468624 | 0.389627553 | 0.273257431 | 0.125457122 | 0.858062654 | 0.228304524 | 0.042826076 | 0.589918215 |
| 223 | 0.108852516 | 0.385939255 | 0.282045723 | 0.126922099 | 0.874053685 | 0.225111454 | 0.043659332 | 0.60903341 |
| 224 | 0.143254727 | 0.432390721 | 0.331308513 | 0.162677663 | 0.955757501 | 0.204536462 | 0.025833343 | 0.863959155 |
| 225 | 0.143014366 | 0.432398229 | 0.330746882 | 0.162621711 | 0.95525956 | 0.204619152 | 0.025788302 | 0.862388784 |
| 226 | 0.095202262 | 0.386234434 | 0.246488282 | 0.112171058 | 0.775874833 | 0.238528831 | 0.042923825 | 0.507498568 |
| 227 | 0.095515852 | 0.384434918 | 0.248457795 | 0.112030467 | 0.780096678 | 0.236702653 | 0.043502291 | 0.512066183 |
| 228 | 0.106908303 | 0.383696307 | 0.278627397 | 0.124997848 | 0.866968889 | 0.2274441 | 0.045703912 | 0.59266263 |
| 229 | 0.238325802 | 0.378729443 | 0.629277197 | 0.230230012 | 1.295364577 | 0.098183184 | 0.083988137 | 2.427358646 |
| 230 | 0.247603211 | 0.445755255 | 0.555468966 | 0.240122126 | 1.150971734 | 0.100732727 | 0.031661914 | 2.458021532 |
| 231 | 0.135781777 | 0.46491816 | 0.292055223 | 0.13148883 | 0.716589727 | 0.215028832 | 0.030041604 | 0.631458466 |
| 232 | 0.120838065 | 0.491448742 | 0.245881319 | 0.117279721 | 0.595036706 | 0.201799798 | 0.030528529 | 0.598801712 |
| 233 | NA | NA | NA | NA | NA | NA | NA | NA |
| 234 | 0.137267436 | 0.455133491 | 0.301598188 | 0.131961096 | 0.711802185 | 0.213117501 | 0.029879545 | 0.644092742 |
| 235 | 0.119256126 | 0.435755139 | 0.273676924 | 0.114558961 | 0.683996532 | 0.239618633 | 0.030645425 | 0.49769137 |
| 236 | 0.150694465 | 0.483592426 | 0.311614609 | 0.147026232 | 0.687218901 | 0.174956425 | 0.028534464 | 0.8613257 |
| 237 | 0.167241544 | 0.453164686 | 0.369052464 | 0.162850829 | 0.827955994 | 0.176392746 | 0.032113766 | 0.948120301 |
| 238 | 0.26323029 | 0.406019539 | 0.648319268 | 0.247582419 | 1.478561926 | 0.145320535 | 0.036349682 | 1.811377104 |
| 239 | NA | NA | NA | NA | NA | NA | NA | NA |
| 240 | 0.110918656 | 0.362377898 | 0.306085599 | 0.107899641 | 0.805112779 | 0.243286649 | 0.064719543 | 0.455917564 |
| 241 | 0.208974579 | 0.37776163 | 0.553191649 | 0.197637298 | 1.329949951 | 0.18841799 | 0.051379853 | 1.109100987 |
| 242 | 0.117303182 | 0.450908069 | 0.260148776 | 0.112521284 | 0.66520017 | 0.24203587 | 0.029290151 | 0.484652057 |
| 243 | 0.173656682 | 0.42739194 | 0.406317164 | 0.166333017 | 0.979098958 | 0.186303432 | 0.036302358 | 0.932117458 |
| 244 | 0.184759937 | 0.367483292 | 0.502770985 | 0.174482236 | 1.255993305 | 0.224636285 | 0.046337539 | 0.822484831 |
| 245 | 0.162418039 | 0.395862079 | 0.410289461 | 0.15202915 | 1.009169668 | 0.224525245 | 0.02888924 | 0.723384307 |
| 246 | 0.239834546 | 0.34727023 | 0.690628004 | 0.229769694 | 1.677026589 | 0.178528566 | 0.054277453 | 1.343395918 |
| 247 | NA | NA | NA | NA | NA | NA | NA | NA |
| 248 | 0.218536379 | 0.397883861 | 0.549246653 | 0.206359002 | 1.299512734 | 0.183588458 | 0.035357494 | 1.190360122 |
| 249 | 0.130236319 | 0.44257172 | 0.29427167 | 0.128402163 | 0.719043199 | 0.211297719 | 0.04409814 | 0.616364057 |
| 250 | 0.296333759 | 0.42298309 | 0.700580628 | 0.244242208 | 1.274965515 | 0.10954067 | 0.027854902 | 2.705239603 |
| 251 | 0.249511646 | 0.455540738 | 0.547726307 | 0.227587432 | 1.059143344 | 0.101792078 | 0.024935887 | 2.451189241 |
| 252 | 0.397185364 | 0.237889582 | 1.669620676 | 0.331280471 | 3.491379606 | 0.153121367 | 0.040445845 | 2.593925151 |
| 253 | 0.231945197 | 0.466368633 | 0.497343047 | 0.212830228 | 0.97987261 | 0.117702183 | 0.02075739 | 1.970610841 |
| 254 | 0.255937954 | 0.460905262 | 0.55529406 | 0.234815146 | 1.052175729 | 0.094620989 | 0.020832646 | 2.70487506 |
| 255 | 0.360287615 | 0.319394694 | 1.12803256 | 0.314280635 | 2.166812881 | 0.096305961 | 0.061391805 | 3.741072844 |
| 256 | 0.381211908 | 0.32107735 | 1.187289942 | 0.319910374 | 2.187291061 | 0.100891528 | 0.036447214 | 3.778433272 |
| 257 | 0.410540571 | 0.315504803 | 1.301218133 | 0.36216227 | 2.630991448 | 0.097417174 | 0.022478004 | 4.2142525 |
| 258 | 0.379798271 | 0.325642061 | 1.166305941 | 0.347647229 | 2.36013303 | 0.093714181 | 0.028925862 | 4.052729981 |
| 259 | 0.429897664 | 0.31126637 | 1.381124675 | 0.389912921 | 2.642278285 | 0.065607478 | 0.02560373 | 6.552571076 |
| 260 | 0.446133281 | 0.301626326 | 1.479092647 | 0.402113506 | 2.849930974 | 0.0662419 | 0.021014652 | 6.734910727 |

TABLE 2-continued values for 9 fragmentation features determined from shallow Whole Genome
Sequencing (sWGS) data for the samples included in the study.

| | | | | | | | | |
|---|---|---|---|---|---|---|---|---|
| 261 | 0.294207264 | 0.436012273 | 0.674768309 | 0.262645486 | 1.198481458 | 0.085647731 | 0.011857701 | 3.435085325 |
| 262 | 0.21771416 | 0.449475044 | 0.484374301 | 0.201075882 | 1.0016554 | 0.132803948 | 0.033684878 | 1.639365114 |
| 263 | 0.494610689 | 0.261346697 | 1.892546163 | 0.405776456 | 3.189559891 | 0.050829578 | 0.044351355 | 9.730765226 |
| 264 | 0.290181549 | 0.383847984 | 0.755980392 | 0.261055881 | 1.562164601 | 0.112517193 | 0.050868602 | 2.578997405 |
| 265 | 0.31672744 | 0.324716963 | 0.975395426 | 0.282923038 | 2.05699947 | 0.112945144 | 0.072074905 | 2.804259035 |
| 266 | 0.320835307 | 0.335583023 | 0.956053451 | 0.274503601 | 1.872423465 | 0.130948432 | 0.048297807 | 2.450088954 |
| 267 | 0.190312076 | 0.436818606 | 0.435677586 | 0.179893797 | 0.930122351 | 0.141624128 | 0.043908168 | 1.343782865 |
| 268 | 0.227927831 | 0.37136491 | 0.613757049 | 0.196195758 | 1.186246921 | 0.15163898 | 0.060360923 | 1.503095253 |
| 269 | 0.259855925 | 0.373714798 | 0.695332179 | 0.240402497 | 1.458351661 | 0.127487048 | 0.06787375 | 2.038292736 |
| 270 | 0.20084982 | 0.439443222 | 0.457055224 | 0.178353866 | 0.95918104 | 0.148779857 | 0.039707143 | 1.349979925 |
| 271 | 0.304478058 | 0.324181415 | 0.9392212 | 0.286077246 | 2.025426271 | 0.109094229 | 0.067354536 | 2.790963944 |
| 272 | 0.233829166 | 0.396952931 | 0.589060183 | 0.191357841 | 1.180659652 | 0.169393843 | 0.036974593 | 1.380387636 |
| 273 | 0.222293018 | 0.417998758 | 0.531803058 | 0.195475374 | 1.088229546 | 0.163016011 | 0.034313989 | 1.363626906 |
| 274 | 0.232940344 | 0.360937878 | 0.645375169 | 0.209024855 | 1.410903656 | 0.164910589 | 0.053208246 | 1.412525086 |
| 275 | 0.12250988 | 0.37923633 | 0.323043628 | 0.115257486 | 0.745305302 | 0.181574481 | 0.075733316 | 0.674708685 |
| 276 | 0.204290719 | 0.375792916 | 0.543625785 | 0.179361302 | 1.080140426 | 0.136647855 | 0.078732056 | 1.495015922 |
| 277 | 0.144421259 | 0.461160496 | 0.31316919 | 0.138049955 | 0.733952461 | 0.172900155 | 0.040040861 | 0.835287044 |
| 278 | 0.151698799 | 0.382931036 | 0.396151747 | 0.141063184 | 0.962679329 | 0.210666934 | 0.053627918 | 0.72008832 |
| 279 | 0.081864537 | 0.387486254 | 0.211270816 | 0.076499627 | 0.546388046 | 0.250190849 | 0.055123295 | 0.32720836 |
| 280 | 0.124028833 | 0.376987135 | 0.329000174 | 0.111022078 | 0.7201616 | 0.178330572 | 0.078476212 | 0.695499554 |
| 281 | 0.152455274 | 0.368058473 | 0.414214819 | 0.134828269 | 0.878375274 | 0.164807301 | 0.089289393 | 0.925051701 |
| 282 | 0.14881089 | 0.423466603 | 0.35141116 | 0.139293344 | 0.785866832 | 0.184812287 | 0.054098311 | 0.805200196 |
| 283 | 0.186278188 | 0.406019125 | 0.458791659 | 0.167835108 | 0.958814019 | 0.156738821 | 0.047904777 | 1.188462349 |
| 284 | 0.33263218 | 0.261717156 | 1.270960548 | 0.259581263 | 2.194915705 | 0.102075095 | 0.115412262 | 3.258700652 |
| 285 | 0.328326019 | 0.273864795 | 1.198861722 | 0.267229915 | 2.113471632 | 0.100017803 | 0.108968891 | 3.282675768 |
| 286 | 0.118545301 | 0.5026349 | 0.235847732 | 0.110156511 | 0.538003412 | 0.193625084 | 0.034160461 | 0.612241445 |
| 287 | 0.111687114 | 0.368619799 | 0.30298729 | 0.103060454 | 0.75373772 | 0.21323298 | 0.067546309 | 0.523779738 |
| 288 | 0.175408731 | 0.415231651 | 0.42243584 | 0.152683765 | 0.883233764 | 0.15385457 | 0.057658663 | 1.140094382 |
| 289 | 0.336553636 | 0.291314112 | 1.155294654 | 0.29207276 | 2.281307043 | 0.112877566 | 0.091278704 | 2.981581276 |
| 290 | 0.213284963 | 0.410371336 | 0.519736502 | 0.166800252 | 1.090694483 | 0.222513864 | 0.019850794 | 0.958524378 |
| 291 | 0.157935967 | 0.42880046 | 0.368320423 | 0.121457335 | 0.762833029 | 0.253485147 | 0.018124934 | 0.623058072 |
| 292 | 0.302416603 | 0.361841148 | 0.835771732 | 0.267082414 | 1.767500879 | 0.111794262 | 0.062969151 | 2.705117395 |
| 293 | 0.2695563 | 0.390837186 | 0.689689491 | 0.237245883 | 1.439194827 | 0.127184591 | 0.048369538 | 2.119410046 |
| 294 | 0.440352362 | 0.277962144 | 1.584217028 | 0.403762929 | 3.184480202 | 0.057559153 | 0.053462573 | 7.650431638 |
| 295 | 0.168584563 | 0.501951925 | 0.335857986 | 0.145511085 | 0.716112652 | 0.176527978 | 0.015393813 | 0.955001949 |
| 296 | 0.272907335 | 0.427429645 | 0.638484809 | 0.237092075 | 1.289255384 | 0.116001467 | 0.028750217 | 2.352619698 |
| 297 | 0.245452727 | 0.395474288 | 0.620654072 | 0.204549058 | 1.369398211 | 0.18792353 | 0.052352444 | 1.306130887 |
| 298 | 0.219819546 | 0.430729411 | 0.51034255 | 0.184465317 | 1.064076392 | 0.171550203 | 0.023421872 | 1.281371531 |
| 299 | 0.281588618 | 0.417724131 | 0.674101871 | 0.243890023 | 1.309396641 | 0.099299983 | 0.033303349 | 2.835736832 |
| 300 | 0.322051575 | 0.351128603 | 0.917189803 | 0.284365929 | 1.977348231 | 0.124186654 | 0.046676436 | 2.593286502 |
| 301 | 0.16072668 | 0.422743181 | 0.380199344 | 0.153108737 | 0.980730729 | 0.233015698 | 0.032051388 | 0.689767604 |
| 302 | 0.193838295 | 0.451067608 | 0.429732244 | 0.166551555 | 0.975085536 | 0.210190414 | 0.016129348 | 0.922203308 |
| 303 | 0.189588042 | 0.425749283 | 0.445304431 | 0.174767381 | 1.045839188 | 0.184492733 | 0.039180038 | 1.027617939 |
| 304 | 0.26193088 | 0.39856909 | 0.657178107 | 0.236979697 | 1.499244799 | 0.153952541 | 0.023654221 | 1.70137419 |
| 305 | 0.239150862 | 0.440941029 | 0.542364731 | 0.218629297 | 1.163654095 | 0.133126871 | 0.03118334 | 1.79641316 |
| 306 | 0.245509887 | 0.384222223 | 0.638978882 | 0.216522735 | 1.449964298 | 0.168665704 | 0.056352444 | 1.455600518 |
| 307 | 0.169350479 | 0.41618809 | 0.406908518 | 0.147607814 | 0.969281781 | 0.235335039 | 0.028487217 | 0.719614383 |
| 308 | 0.169137762 | 0.439189893 | 0.385113057 | 0.152472686 | 0.929697921 | 0.223485838 | 0.021850779 | 0.756816466 |
| 309 | 0.150711196 | 0.437803816 | 0.344243677 | 0.128389461 | 0.776660903 | 0.241156626 | 0.023140789 | 0.624951501 |
| 310 | 0.242614257 | 0.381833299 | 0.635393137 | 0.193665716 | 1.390561815 | 0.215822171 | 0.018853832 | 1.124139638 |
| 311 | 0.136534027 | 0.485941266 | 0.280968168 | 0.121705469 | 0.624819378 | 0.212192808 | 0.018961657 | 0.643443238 |
| 312 | 0.138614772 | 0.419540262 | 0.330396828 | 0.123864918 | 0.792754868 | 0.265148962 | 0.020828615 | 0.522780743 |
| 313 | 0.132576105 | 0.471176489 | 0.281372496 | 0.115368624 | 0.661923616 | 0.238281528 | 0.021597059 | 0.556384316 |
| 314 | 0.17471474 | 0.431188982 | 0.40519296 | 0.146511338 | 0.903989096 | 0.224683055 | 0.020820903 | 0.777605323 |
| 315 | 0.178177176 | 0.475491161 | 0.374722373 | 0.152890496 | 0.78008563 | 0.182235038 | 0.016212709 | 0.977732811 |
| 316 | 0.174805305 | 0.47629855 | 0.367007847 | 0.151975126 | 0.775143419 | 0.182585139 | 0.016808803 | 0.957390652 |
| 317 | 0.15582976 | 0.486426931 | 0.320355947 | 0.142613397 | 0.721503681 | 0.196265803 | 0.016881639 | 0.79397306 |
| 318 | 0.159072104 | 0.482958672 | 0.329370013 | 0.144709073 | 0.734623925 | 0.19213924 | 0.017970077 | 0.827900141 |
| 319 | 0.141366379 | 0.484371193 | 0.291855464 | 0.130992064 | 0.691150208 | 0.220441825 | 0.015900618 | 0.641286559 |
| 320 | 0.144021353 | 0.479848392 | 0.300139285 | 0.13258503 | 0.705634937 | 0.219097363 | 0.016228602 | 0.657339512 |
| 321 | 0.133601158 | 0.414027623 | 0.322686581 | 0.120029387 | 0.790623041 | 0.26821663 | 0.023377257 | 0.498109152 |
| 322 | 0.101808581 | 0.43815792 | 0.232355908 | 0.088641719 | 0.566270829 | 0.283529499 | 0.02500423 | 0.359075799 |
| 323 | 0.078815102 | 0.369919405 | 0.213060198 | 0.070853755 | 0.554182408 | 0.290948696 | 0.046186279 | 0.270890033 |
| 324 | 0.084700472 | 0.47280812 | 0.179143439 | 0.079311782 | 0.467187404 | 0.278455114 | 0.023502635 | 0.304179985 |
| 325 | 0.108054039 | 0.433233706 | 0.249412818 | 0.096443778 | 0.626482251 | 0.278293607 | 0.026006606 | 0.388273522 |
| 326 | 0.139308825 | 0.426111366 | 0.326930554 | 0.130121943 | 0.82878481 | 0.24589481 | 0.026978293 | 0.566538288 |
| 327 | 0.083793223 | 0.370302853 | 0.226282953 | 0.076949021 | 0.637249797 | 0.330562292 | 0.028318595 | 0.253486938 |
| 328 | 0.079844454 | 0.409231385 | 0.195083898 | 0.071804143 | 0.51584626 | 0.327978143 | 0.020652772 | 0.243413945 |
| 329 | 0.0911902 | 0.367962253 | 0.247824876 | 0.080090913 | 0.665086464 | 0.339104787 | 0.023537401 | 0.268914516 |
| 330 | 0.111265048 | 0.439048915 | 0.253422898 | 0.10413692 | 0.634132441 | 0.259909413 | 0.025541049 | 0.428091645 |
| 331 | 0.11863192 | 0.4051442 | 0.292814066 | 0.109337003 | 0.7226509 | 0.224746414 | 0.048725847 | 0.527847889 |
| 332 | 0.134014268 | 0.403382081 | 0.332226628 | 0.121981511 | 0.802604918 | 0.212998906 | 0.047637727 | 0.629178201 |
| 333 | 0.142303796 | 0.426193737 | 0.333894621 | 0.128717088 | 0.796302132 | 0.218865257 | 0.036176049 | 0.650189063 |
| 334 | 0.146207376 | 0.41084307 | 0.355871589 | 0.131448029 | 0.842789226 | 0.209249832 | 0.041058174 | 0.698721596 |
| 335 | 0.158986703 | 0.391360686 | 0.406240864 | 0.143509079 | 0.948683233 | 0.200990697 | 0.040414618 | 0.791015234 |
| 336 | 0.173374262 | 0.399868389 | 0.433578313 | 0.154579432 | 0.992908344 | 0.197404337 | 0.035306087 | 0.878269768 |
| 337 | 0.165920439 | 0.397005752 | 0.417929559 | 0.149322862 | 0.96994409 | 0.1986964 | 0.036772799 | 0.835045019 |

TABLE 2-continued values for 9 fragmentation features determined from shallow Whole Genome
Sequencing (sWGS) data for the samples included in the study.

| | | | | | | | | |
|---|---|---|---|---|---|---|---|---|
| 338 | 0.179043752 | 0.40279764 | 0.4445005 | 0.156516401 | 0.995156689 | 0.195795219 | 0.032222904 | 0.914443945 |
| 339 | 0.153789879 | 0.384579996 | 0.399890481 | 0.139614476 | 0.939119253 | 0.197631967 | 0.043190347 | 0.778162973 |
| 340 | 0.151687512 | 0.390862158 | 0.388084415 | 0.138701569 | 0.917641434 | 0.198408563 | 0.042495211 | 0.764520995 |
| 341 | 0.202828454 | 0.38526313 | 0.526467337 | 0.183556194 | 1.223146834 | 0.19508449 | 0.031409195 | 1.039695435 |
| 342 | 0.214794205 | 0.376699468 | 0.570200447 | 0.181221462 | 1.238168985 | 0.185805333 | 0.031992862 | 1.156017439 |
| 343 | 0.137307321 | 0.429936632 | 0.319366415 | 0.119809959 | 0.738055807 | 0.231063427 | 0.02681307 | 0.594240823 |
| 344 | 0.133695268 | 0.428157382 | 0.312257299 | 0.117586519 | 0.727508555 | 0.231158515 | 0.027550362 | 0.578370509 |
| 345 | 0.132021502 | 0.432975105 | 0.304917073 | 0.117675672 | 0.72313081 | 0.235034549 | 0.026771733 | 0.561711042 |
| 346 | 0.163394787 | 0.402317221 | 0.406134209 | 0.151179887 | 0.978981206 | 0.210723204 | 0.034161649 | 0.775400067 |
| 347 | 0.163034832 | 0.396959389 | 0.410709098 | 0.15057059 | 0.986908486 | 0.207057515 | 0.035907789 | 0.78738911 |
| 348 | 0.215344642 | 0.446933098 | 0.481827467 | 0.186152356 | 0.992390381 | 0.152964257 | 0.023425551 | 1.407810211 |
| 349 | 0.134232226 | 0.429097862 | 0.312824271 | 0.119169742 | 0.737495251 | 0.232784327 | 0.027005169 | 0.576637731 |
| 350 | 0.209426922 | 0.446487965 | 0.469053902 | 0.181170839 | 0.967777005 | 0.155600599 | 0.025020308 | 1.345926195 |
| 351 | 0.110719663 | 0.374297401 | 0.295806657 | 0.088920222 | 0.672869906 | 0.274581447 | 0.030802323 | 0.403230676 |
| 352 | 0.229414294 | 0.424955266 | 0.539855161 | 0.20464533 | 1.16131228 | 0.160407165 | 0.028328176 | 1.430199789 |
| 353 | 0.222260906 | 0.41089728 | 0.540915982 | 0.196935416 | 1.179464903 | 0.170880962 | 0.028556532 | 1.300676818 |
| 354 | 0.224566246 | 0.454347959 | 0.494260492 | 0.202018713 | 1.027491671 | 0.139032167 | 0.025108809 | 1.615210712 |

TABLE 3 t-MAD score for the 48 plasma samples of the OV04 cohort before and after in vitro size selection.

| index | SLXID | binSize | control | Sample Names | median TP53 MAF | median_tMAD_ no_size_selection | selection | treatment | patient | median_ tMAD_with_ size_selection | fold_ enrichment |
|---|---|---|---|---|---|---|---|---|---|---|---|
| 1 | SLX-11873 | 30 | K5042 310_1 | R146 | 0.232 | 0.057069147 | no | before | OV04-143 | 0.087364547 | 1.530854264 |
| 2 | SLX-11873 | 30 | K5042 310_1 | R147 | 0.022 | 0.012773248 | no | post | OV04-143 | 0.028316869 | 2.216888688 |
| 3 | SLX-11873 | 30 | K5042 310_1 | R148 | 0.514 | 0.220377876 | no | before | OV04-264 | 0.258905932 | 1.174827241 |
| 4 | SLX-11873 | 30 | K5042 310_1 | R149 | 0.034 | 0.020137929 | no | post | OV04-264 | 0.067751424 | 3.364368997 |
| 7 | SLX-13223 | 30 | K5042 310_1 | JBLAB_5688 | 0.346385 | 0.199308443 | no | before | OV04-77 | 0.266627416 | 1.337762776 |
| 8 | SLX-13223 | 30 | K5042 310_1 | JBLAB_5689 | 0.068603 | 0.029294865 | no | post | OV04-77 | 0.055629976 | 1.898966798 |
| 9 | SLX-13223 | 30 | K5042 310_1 | JBLAB_5712 | 0.483385 | 0.203974112 | no | before | OV04-122 | 0.210309045 | 1.031057534 |
| 10 | SLX-13223 | 30 | K5042 310_1 | JBLAB_5713 | 0.036652 | 0.012782907 | no | post | OV04-122 | 0.080429849 | 6.29198421 |
| 11 | SLX-13223 | 30 | K5042 310_1 | JBLAB_5742 | 0.14797 | 0.049713406 | no | before | OV04-292 | 0.063867761 | 1.284719076 |
| 12 | SLX-13223 | 30 | K5042 310_1 | JBLAB_5743 | 0.069141 | 0.065349155 | no | post | OV04-292 | 0.123748162 | 1.893645939 |
| 13 | SLX-13223 | 30 | K5042 310_1 | JBLAB_5754 | 0.266115 | 0.192511793 | no | before | OV04-300 | 0.171876244 | 0.89280891 |
| 14 | SLX-13223 | 30 | K5042 310_1 | JBLAB_5755 | 0.03915 | 0.15867713 | no | post | OV04-300 | 0.171629671 | 1.081628279 |
| 15 | SLX-13223 | 30 | K5042 310_1 | JBLAB_5203 | 0.2712105 | 0.05179566 | no | before | OV04-83 | 0.139343378 | 2.690252002 |
| 16 | SLX-13223 | 30 | K5042 310_1 | JBLAB_5205 | 0.0687565 | 0.011382743 | no | post | OV04-83 | 0.072524334 | 6.371428574 |
| 17 | SLX-13223 | 30 | K5042 310_1 | JBLAB_5342 | 0.610217 | 0.203902197 | no | before | OV04-141 | 0.259249767 | 1.271441754 |
| 18 | SLX-13223 | 30 | K5042 310_1 | JBLAB_5343 | 0.064836 | 0.021547924 | no | post | OV04-141 | 0.105868625 | 4.913170522 |
| 19 | SLX-13223 | 30 | K5042 310_1 | JBLAB_5507 | 0.123199135 | 0.031742405 | no | before | OV04-226 | 0.062392469 | 1.965587327 |
| 20 | SLX-13223 | 30 | K5042 310_1 | JBLAB_5508 | 0.022327219 | 0.011923695 | no | post | OV04-226 | 0.033677313 | 2.824402419 |
| 21 | SLX-13223 | 30 | K5042 310_1 | JBLAB_5288 | 0.20705 | 0.061303019 | no | before | OV04-297 | 0.168597772 | 2.750236036 |
| 22 | SLX-13223 | 30 | K5042 310_1 | JBLAB_5289 | 0.092029 | 0.0212589 | no | post | OV04-297 | 0.05805594 | 2.73090047 |
| 23 | SLX-13223 | 30 | K5042 310_1 | JBLAB_5432 | 0.212771398 | 0.074215033 | no | before | OV04-180 | 0.210353293 | 2.834375793 |
| 24 | SLX-13223 | 30 | K5042 310_1 | JBLAB_5433 | 0.001046472 | 0.006474814 | no | post | OV04-180 | 0.011753831 | 1.815315621 |
| 25 | SLX-13223 | 30 | K5042 310_1 | JBLAB_5420 | 0.5065815 | 0.252408213 | no | before | OV04-295 | 0.399111409 | 1.581214035 |
| 26 | SLX-13223 | 30 | K5042 310_1 | JBLAB_5422 | 0.0124825 | 0.007137838 | no | post | OV04-295 | 0.023034569 | 3.227107284 |

TABLE 3-continued t-MAD score for the 48 plasma samples of the OV04 cohort before and after in vitro size selection.

| index | SLXID | binSize | control | Sample Names | median TP53 MAF | median_tMAD_ no_size_selection | selection | treatment | patient | median_ tMAD_with_ size_selection | fold_ enrichment |
|---|---|---|---|---|---|---|---|---|---|---|---|
| 27 | SLX-13223 | 30 | K5042 310_1 | JBLAB_5471 | 0.082816831 | 0.04274618 | no | before | OV04-211 | 0.047433825 | 1.109662314 |
| 28 | SLX-13223 | 30 | K5042 310_1 | JBLAB_5472 | 0.008998983 | 0.008534381 | no | post | OV04-211 | 0.014143088 | 1.657189666 |
| 29 | SLX-13621 | 30 | K5042 310_1 | X76_T1_pre | 0 | 0.022128547 | no | | OV04-76 | 0.041468333 | 1.873974509 |
| 30 | SLX-13621 | 30 | K5042 310_1 | X75_T13_pre | 0.0007705 | 0.005161371 | no | | OV04-75 | 0.01079341 | 2.0911905 |
| 31 | SLX-13621 | 30 | K5042 310_1 | X52_T1_pre | 0.0024735 | 0.005692945 | no | | OV04-52 | 0.019834069 | 3.483973409 |
| 32 | SLX-13621 | 30 | K5042 310_1 | X150_T1_pre | 0 | 0.005679811 | no | | OV04-150 | 0.014364408 | 2.529029223 |
| 33 | SLX-13621 | 30 | K5042 310_1 | X129_T8pre | 0.00119 | 0.008012243 | no | | OV04-129 | 0.015789503 | 1.970672008 |
| 34 | SLX-13621 | 30 | K5042 310_1 | X57_T1_pre | 0.00119 | 0.005387574 | no | | OV04-57 | 0.014437579 | 2.67979224 |
| 35 | SLX-13621 | 30 | K5042 310_1 | X73_T3B_pre | 0.0021 | 0.005905265 | no | | OV04-73 | 0.014933244 | 2.528801671 |
| 36 | SLX-13621 | 30 | K5042 310_1 | JG090_T612_pre | 0.003092 | 0.302811769 | no | | JG090 | 0.423426811 | 1.39831689 |
| 37 | SLX-13621 | 30 | K5042 310_1 | X145_T8_pre | 0 | 0.043652958 | no | | OV04-145 | 0.116005436 | 2.657447314 |
| 38 | SLX-13621 | 30 | K5042 310_1 | X112_T1_pre | 0 | 0.005301188 | no | | OV04-112 | 0.011067067 | 2.087657899 |
| 39 | SLX-13621 | 30 | K5042 310_1 | X75_T1_pre | 0.0041885 | 0.008682287 | no | | OV04-75 | 0.021401469 | 2.464957562 |
| 40 | SLX-13621 | 30 | K5042 310_1 | X72_T1_pre | 0 | 0.005413644 | no | | OV04-72 | 0.022785962 | 4.208987883 |
| 41 | SLX-13621 | 30 | K5042 310_1 | X74_T1_pre | 0.001392 | 0.016319911 | no | | OV04-74 | 0.063135101 | 3.868593462 |
| 42 | SLX-13621 | 30 | K5042 310_1 | X127_T1_pre | 0.0022355 | 0.008930611 | no | | OV04-127 | 0.026903941 | 3.012553228 |
| 43 | SLX-13621 | 30 | K5042 310_1 | X30_T1_pre | 0.032437 | 0.013693931 | no | | OV04-30 | 0.037435405 | 2.733722333 |
| 44 | SLX-13621 | 30 | K5042 310_1 | JBLAB.5180_pre | 0 | 0.004510492 | no | | JBLAB.5180 | 0.017007543 | 3.770662491 |
| 45 | SLX-13621 | 30 | K5042 310_1 | JBLAB.5027_pre | 0 | 0.006366084 | no | | JBLAB.5027 | 0.012995165 | 2.04131221 |
| 46 | SLX-13621 | 30 | K5042 310_1 | JBLAB.5595_pre | 0 | 0.006746273 | no | | JBLAB.5595 | 0.020444819 | 3.030535379 |
| 47 | SLX-13621 | 30 | K5042 310_1 | JBLAB.5599_pre | 0 | 0.005873961 | no | | JBLAB.5599 | 0.00810866 | 1.380441579 |
| 48 | SLX-13621 | 30 | K5042 310_1 | JBLAB.5611_pre | 0.045 | 0.021163354 | no | | JBLAB.5611 | 0.033449519 | 1.580539597 |
| 49 | SLX-13621 | 30 | K5042 310_1 | JBLAB.5477_pre | 0 | 0.007678384 | no | | JBLAB.5477 | 0.036978881 | 4.815971824 |
| 50 | SLX-13621 | 30 | K5042 310_1 | JBLAB.5632_pre | 0 | 0.008178321 | no | | JBLAB.5632 | 0.014573466 | 1.78196307 |

TABLE 4 log2 of the signal ratio observed by sWGS of the plasma samples from the OV04 cohort.

| Sample | OV04-143 | OV04-264 | OV04-77 | OV04-73 | OV04-122 | OV04-292 | OV04-145 | OV04-112 | OV04-300 | OV04-75_2 | OV04-83 | OV04-72 | OV04-141 | OV04-74 | OV04-226 | OV04-127 | OV04-297 | OV04-30 | OV04-180 | OV04-295 | OV04-211 | OV04-76 | OV04-75 | OV04-52 | OV04-150 | OV04-129 |
|---|---|---|---|---|---|---|---|---|---|---|---|---|---|---|---|---|---|---|---|---|---|---|---|---|---|---|
| NRAS | 0.008 | -0.002 | 0.001 | -0.008 | 0.004 | -0.037 | 0.006 | 0.001 | -0.092 | -0.008 | -0.004 | 0 | 0.011 | 0 | 0.008 | -0.006 | 0.005 | 0.008 | 0.003 | -0.002 | -0.005 | -0.004 | 0.002 | -0.009 | 0.001 | -0.009 |
| MSH2 | 0.001 | 0.014 | -0.002 | 0.006 | 0.007 | 0.015 | 0.06 | 0.006 | -0.021 | -0.001 | 0.009 | 0.013 | 0.046 | 0.015 | 0.014 | 0.013 | 0.016 | 0.004 | 0.016 | 0.007 | 0.004 | 0.025 | 0.008 | 0.001 | 0.012 | 0.006 |
| MSH6 | 0.001 | 0.014 | -0.002 | 0.006 | 0.007 | 0.015 | 0.06 | 0.006 | -0.021 | -0.001 | 0.009 | 0.013 | 0.046 | 0.015 | 0.014 | 0.013 | 0.016 | 0.004 | 0.016 | 0.007 | 0.004 | 0.025 | 0.008 | 0.001 | 0.012 | 0.006 |
| APLF | 0.001 | 0.014 | -0.002 | 0.006 | 0.007 | -0.069 | 0.06 | 0.006 | -0.078 | -0.001 | 0.009 | 0.013 | 0.046 | 0.015 | 0.014 | 0.013 | 0.016 | 0.004 | 0.016 | 0.007 | 0.004 | 0.025 | 0.007 | 0 | 0.012 | 0.006 |
| PAX8 | 0 | 0.002 | -0.02 | -0.02 | 0.009 | -0.024 | | | -0.099 | | 0.001 | | 0.107 | | | -0.006 | 0.006 | | 0.013 | 0.002 | 0.004 | 0.012 | 0.007 | -0.002 | 0.01 | 0.005 |
| BARD1 | 0 | 0.002 | -0.02 | -0.02 | 0.009 | -0.083 | | | -0.085 | | 0.001 | | 0.019 | | | -0.006 | 0.006 | | 0.013 | 0.002 | 0 | 0.012 | 0.003 | 0 | 0.01 | 0.005 |
| FANCD2 | -0.003 | 0.039 | 0.006 | 0.006 | 0.013 | -0.12 | | | -0.192 | | 0.016 | | 0.037 | | 0.004 | 0.016 | 0.005 | | 0.002 | 0.001 | 0.001 | 0 | 0.003 | -0.002 | -0.002 | 0.003 |
| MLH1 | -0.003 | 0.039 | 0.006 | 0.006 | 0.013 | -0.076 | | | -0.221 | | 0.016 | | 0.037 | | 0.004 | 0.016 | 0.005 | | 0.002 | 0.001 | 0.001 | 0 | 0.003 | -0.002 | -0.002 | 0.003 |
| CTNB1 | -0.003 | 0.039 | 0.006 | 0.006 | 0.013 | -0.076 | | | -0.221 | | 0.016 | | 0.037 | | 0.004 | 0.016 | 0.005 | | 0.002 | 0.001 | 0.001 | 0 | 0.003 | -0.002 | -0.002 | 0.003 |
| MECOM | 0.009 | 0.046 | 0.03 | | 0.023 | -0.024 | | | -0.001 | | 0.016 | | 0.045 | | 0.009 | 0.012 | 0.008 | | 0.002 | 0.002 | 0.01 | 0.01 | 0.003 | 0.002 | 0.002 | 0.003 |
| PIK3CA | 0.009 | 0.046 | 0.03 | | 0.023 | -0.024 | | | 0.051 | | 0.016 | | 0.045 | | 0.009 | 0.012 | 0.008 | | 0.008 | 0.002 | 0.01 | 0.01 | 0.003 | 0.002 | 0.002 | 0.003 |
| TERT | -0.025 | -0.014 | -0.011 | | 0.02 | -0.223 | | | -0.298 | | 0.015 | | 0.002 | | -0.004 | -0.01 | -0.004 | | 0.004 | 0.013 | -0.005 | 0.019 | 0.008 | 0.01 | -0.003 | -0.001 |
| ID4 | 0.013 | 0.019 | 0.014 | | 0.02 | -0.11 | | | 0.015 | | -0.011 | | 0.019 | | 0.005 | 0.026 | -0.006 | | 0.004 | -0.006 | -0.006 | 0.015 | -0.008 | -0.004 | 0.016 | -0.002 |
| PMS2 | -0.013 | 0.005 | 0.014 | | 0.005 | -0.018 | | | -0.079 | | -0.011 | | 0.017 | | -0.005 | -0.009 | -0.006 | | 0.006 | -0.006 | 0.006 | 0.015 | 0.002 | -0.004 | -0.004 | -0.003 |
| EGFR | -0.013 | 0.005 | 0.014 | | 0.005 | -0.062 | | | -0.235 | | -0.004 | | 0.017 | | -0.014 | -0.053 | -0.006 | | 0.006 | -0.006 | 0.006 | -0.015 | 0.002 | -0.004 | -0.004 | -0.003 |
| BRAF | -0.016 | 0.005 | 0.014 | | 0.001 | 0.147 | | | -0.014 | | -0.004 | | 0.006 | | -0.008 | -0.009 | 0.002 | | 0.002 | -0.009 | 0.008 | 0.01 | 0.003 | -0.001 | -0.005 | -0.007 |
| MYC | 0.037 | -0.006 | 0.145 | | -0.023 | -0.068 | | | -0.109 | | 0.045 | | -0.001 | | -0.004 | -0.014 | 0.082 | | 0.005 | 0.004 | 0.006 | 0.017 | 0 | 0.012 | -0.005 | 0.006 |
| APTX | -0.008 | 0.026 | -0.002 | | -0.002 | 0.008 | | | -0.143 | | -0.014 | | -0.012 | | -0.009 | -0.019 | -0.019 | | 0.012 | 0.003 | 0.004 | -0.052 | -0.001 | -0.008 | -0.001 | -0.004 |
| PTEN | 0.002 | -0.011 | 0.015 | | 0.005 | -0.085 | | | -0.157 | | 0.007 | | 0.018 | | -0.008 | 0.012 | 0.006 | | 0.001 | 0.004 | 0.002 | 0.015 | 0.001 | 0 | -0.006 | 0.007 |
| CHEK1 | -0.003 | -0.007 | -0.033 | | -0.019 | -0.046 | | | -0.086 | | 0.004 | | -0.015 | | -0.006 | -0.008 | 0.002 | | -0.004 | 0.001 | -0.004 | -0.04 | -0.004 | -0.007 | 0 | -0.005 |
| KRAS | 0.013 | 0.003 | 0.011 | | 0.036 | -0.034 | | | -0.041 | | 0.024 | | 0.051 | | -0.005 | -0.038 | 0.001 | | 0.001 | 0.018 | 0.018 | 0.265 | 0.002 | -0.007 | 0.008 | -0.001 |
| BRAC2 | -0.017 | -0.036 | -0.022 | | -0.01 | -0.04 | | | -0.111 | | -0.004 | | -0.016 | | -0.014 | -0.001 | -0.002 | | -0.001 | -0.12 | -0.01 | -0.011 | 0.006 | -0.004 | -0.001 | -0.012 |
| RB1 | -0.017 | -0.036 | -0.022 | | -0.01 | -0.04 | | | -0.111 | | -0.004 | | -0.016 | | -0.014 | -0.001 | -0.002 | | -0.001 | -0.012 | -0.01 | -0.011 | 0.003 | -0.004 | -0.001 | -0.012 |
| PARP2 | -0.009 | -0.021 | -0.023 | | 0.011 | -0.103 | | | -0.153 | | 0.181 | | 0.018 | | 0.012 | -0.053 | 0.016 | | -0.005 | 0.018 | -0.006 | -0.013 | 0.008 | -0.002 | 0.004 | -0.001 |
| FANCM | -0.009 | -0.021 | -0.023 | | 0.011 | -0.026 | | | 0.453 | | 0.008 | | 0.018 | | 0.012 | -0.053 | 0.046 | | -0.005 | 0.018 | -0.014 | -0.013 | 0.003 | -0.002 | 0.004 | -0.012 |
| RAD51B | -0.009 | -0.023 | -0.023 | | 0.011 | 0.005 | | | -0.023 | | 0.008 | | 0.018 | | 0.012 | -0.053 | 0.046 | | -0.005 | 0.018 | -0.006 | -0.013 | 0.003 | -0.002 | 0.004 | -0.012 |
| PALB2 | -0.023 | -0.026 | -0.045 | | -0.005 | 0.119 | | | 0.159 | | -0.008 | | -0.026 | | -0.001 | -0.024 | -0.011 | | -0.005 | 0.012 | -0.006 | -0.042 | 0.003 | 0.011 | -0.023 | -0.004 |
| TP53 | -0.001 | 0.01 | -0.021 | | -0.013 | 0.048 | | | 0.034 | | -0.015 | | 0.009 | | -0.006 | -0.007 | -0.004 | | -0.04 | 0 | -0.005 | -0.005 | -0.011 | -0.004 | -0.004 | -0.008 |
| NF1 | 0.003 | -0.017 | -0.019 | | -0.01 | 0.091 | | | 0.222 | | -0.003 | | -0.003 | | -0.013 | 0.01 | 0.01 | | -0.007 | -0.001 | -0.014 | -0.004 | -0.012 | -0.008 | 0.007 | -0.013 |
| RAD51D | 0.003 | -0.017 | -0.019 | | -0.01 | -0.054 | | | 0.058 | | -0.003 | | -0.003 | | -0.013 | 0.01 | 0.01 | | 0 | -0.001 | -0.014 | -0.004 | -0.012 | -0.008 | 0.007 | -0.013 |
| CDK12 | 0.003 | -0.017 | -0.019 | | -0.01 | 0.132 | | | 0.153 | | -0.003 | | -0.003 | | -0.013 | 0.01 | 0.01 | | 0 | -0.001 | -0.014 | -0.011 | -0.012 | -0.008 | 0.007 | -0.013 |
| BRCA1 | 0.003 | -0.017 | -0.019 | | -0.01 | 0.125 | | | 0.121 | | -0.003 | | -0.003 | | -0.013 | 0.01 | 0.01 | | -0.005 | -0.004 | -0.017 | -0.013 | -0.012 | -0.008 | 0.007 | -0.013 |
| RAD51C | 0.005 | -0.006 | -0.002 | | -0.008 | 0.204 | | | 0.354 | | -0.018 | | -0.008 | | -0.006 | 0.046 | 0.046 | | -0.005 | -0.004 | -0.014 | -0.014 | -0.015 | -0.015 | 0.001 | -0.005 |
| PPM1D | -0.009 | -0.006 | -0.002 | | -0.008 | 0.204 | | | 0.354 | | -0.018 | | -0.008 | | -0.006 | 0.046 | 0.046 | | 0 | -0.004 | -0.014 | -0.014 | -0.015 | -0.015 | 0.001 | -0.005 |
| BRIP1 | 0.005 | -0.006 | -0.002 | | -0.008 | 0.204 | | | 0.354 | | -0.018 | | -0.008 | | -0.006 | 0.046 | 0.046 | | 0 | -0.004 | -0.017 | -0.014 | -0.015 | -0.015 | 0.001 | -0.005 |
| CCNE1 | -0.015 | 0.014 | 0.162 | | -0.013 | 0.093 | | | 0.028 | | 0.434 | | 0.723 | | 0.012 | 0.104 | -0.04 | | -0.007 | 0.004 | -0.024 | 0.097 | -0.019 | 0.002 | -0.027 | 0.002 |
| ZMYND8 | 0.01 | 0.018 | 0.016 | | 0.042 | 0.086 | | | -0.004 | | 0.04 | | 0.092 | | 0.035 | 0.014 | -0.007 | | 0.011 | 0.034 | -0.004 | 0.061 | -0.006 | -0.011 | -0.011 | 0.008 |
| CHEK2 | 0.002 | -0.004 | -0.024 | | -0.003 | 0.021 | | | 0.184 | | -0.035 | | -0.029 | | -0.015 | -0.025 | -0.015 | | 0.034 | -0.013 | -0.041 | 0.005 | -0.011 | -0.001 | 0.006 |

| Sample | OV04-57 | JG090 | JBLAB.5180 | JBLAB.5027 | JBLAB.5595 | JBLAB.5599 | JBLAB.5611 | JBLAB.5477 | JBLAB.5632 |
|---|---|---|---|---|---|---|---|---|---|
| NRAS | -0.006 | -0.086 | -0.001 | -0.016 | -0.003 | -0.001 | -0.014 | -0.006 | -0.003 |
| MSH2 | 0.003 | 0.355 | 0.001 | 0.005 | 0.008 | -0.003 | -0.004 | 0.004 | 0.008 |
| MSH6 | 0.003 | 0.355 | 0.001 | 0.005 | 0.008 | -0.003 | -0.004 | 0.004 | 0.008 |
| APLF | 0.003 | 0.286 | 0.001 | 0.005 | 0.008 | -0.003 | -0.004 | 0.004 | 0.008 |

TABLE 4-continued log2 of the signal ratio observed by sWGS of the plasma samples from the OV04 cohort.

| Gene | | | | | | | | | | | | | | | | | |
|---|---|---|---|---|---|---|---|---|---|---|---|---|---|---|---|---|---|
| PAX8 | 0.002 | 0.004 | -0.386 | 0.404 | 0.004 | -0.001 | 0.011 | 0.013 | 0.004 | 0.002 | 0.002 | 0.004 | 0.007 | -0.003 | -0.007 | 0.002 | 0.007 |
| BARD1 | 0.002 | 0.004 | 0.155 | 0.013 | 0.004 | -0.001 | 0.011 | 0.013 | 0.004 | 0.002 | 0.002 | 0.004 | 0.007 | -0.003 | -0.007 | 0.002 | 0.007 |
| FANCD2 | 0.001 | 0.002 | -0.263 | -0.004 | -0.001 | -0.004 | -0.002 | 0.002 | 0 | -0.003 | -0.001 | 0 | 0.002 | -0.004 | -0.005 | -0.005 | -0.005 |
| MLH1 | 0.001 | 0.002 | -0.263 | -0.004 | -0.001 | -0.004 | -0.002 | 0.002 | 0 | -0.001 | -0.003 | -0.001 | 0.002 | -0.004 | -0.005 | -0.005 | -0.005 |
| CTNB1 | 0.001 | 0.006 | -0.263 | -0.004 | -0.001 | -0.004 | -0.002 | 0.002 | 0.013 | -0.003 | -0.001 | -0.001 | 0.005 | -0.004 | -0.005 | -0.005 | -0.006 |
| MECOM | 0.001 | 0.006 | 0.325 | 0.079 | 0.001 | 0.002 | 0.002 | 0.009 | 0.013 | 0.003 | -0.001 | -0.003 | 0.005 | -0.003 | -0.006 | -0.005 | -0.006 |
| PIK3CA | 0.001 | 0.006 | 0.325 | 0.079 | 0.001 | 0.002 | 0.002 | 0.009 | 0.013 | 0.003 | -0.001 | -0.001 | 0.005 | -0.003 | -0.006 | -0.005 | -0.006 |
| TERT | 0.004 | 0.001 | 0.416 | -0.016 | -0.002 | 0 | -0.001 | 0.007 | 0.006 | 0.012 | 0.005 | -0.008 | 0.003 | -0.007 | -0.01 | 0 | -0.005 |
| ID4 | -0.004 | -0.004 | 0.106 | -0.031 | -0.009 | -0.007 | 0.017 | -0.005 | -0.008 | -0.001 | -0.001 | 0.002 | 0 | 0.008 | -0.15 | -0.005 | -0.003 |
| PMS2 | -0.003 | 0.002 | 0.142 | 0.019 | 0 | 0.008 | -0.003 | -0.001 | 0.002 | 0.004 | -0.003 | 0.004 | -0.003 | 0 | -0.015 | -0.007 | -0.004 |
| EGFR | -0.003 | 0.002 | 0.132 | 0.019 | 0 | 0.008 | -0.003 | 0.003 | 0.004 | 0.004 | -0.003 | 0.004 | 0 | 0 | -0.015 | -0.007 | -0.004 |
| BRAF | -0.005 | 0.002 | 0.13 | 0.021 | -0.007 | 0.007 | -0.004 | 0.003 | 0.002 | 0.003 | -0.005 | 0.002 | -0.002 | -0.007 | -0.014 | -0.005 | -0.005 |
| MYC | -0.004 | -0.002 | 0.213 | 0.048 | -0.002 | -0.01 | -0.003 | 0.016 | -0.01 | -0.003 | 0.006 | -0.018 | 0.008 | -0.002 | 0.327 | 0.008 | -0.008 |
| APTX | 0.004 | 0 | -0.463 | -0.057 | -0.004 | 0.001 | 0.001 | 0.005 | 0.008 | -0.003 | 0.006 | -0.002 | -0.004 | -0.007 | -0.008 | -0.002 | -0.005 |
| PTEN | -0.004 | 0.001 | 0.036 | -0.029 | 0.01 | 0.002 | 0.008 | -0.007 | -0.002 | 0.005 | -0.003 | -0.004 | 0.003 | -0.002 | 0.121 | -0.011 | 0.011 |
| CHEK1 | -0.001 | -0.009 | -0.241 | -0.009 | -0.009 | -0.005 | -0.004 | 0.024 | 0.004 | -0.003 | -0.003 | -0.002 | -0.01 | 0.003 | -0.013 | 0 | -0.008 |
| KRAS | -0.016 | -0.006 | 2.363 | 0.021 | 0.007 | 0.007 | 0.005 | 0.034 | 0.003 | -0.005 | -0.001 | -0.004 | -0.004 | -0.011 | -0.016 | 0 | 0.003 |
| BRAC2 | -0.008 | -0.001 | 0.077 | -0.018 | -0.008 | -0.011 | 0.002 | -0.004 | -0.001 | -0.008 | -0.007 | -0.006 | -0.008 | -0.004 | -0.016 | -0.005 | -0.005 |
| RB1 | -0.008 | -0.001 | 0.077 | 0.015 | -0.008 | -0.011 | 0.002 | -0.004 | -0.01 | -0.007 | -0.007 | -0.006 | -0.008 | -0.004 | -0.016 | -0.005 | -0.005 |
| PARP2 | -0.004 | 0.004 | -0.08 | -0.041 | 0.003 | -0.011 | -0.017 | -0.008 | 0.049 | -0.004 | 0.002 | -0.016 | 0.001 | 0.002 | -0.013 | 0.009 | 0 |
| FANCM | 0.004 | 0.004 | -0.08 | -0.041 | 0.003 | -0.004 | -0.02 | -0.008 | -0.02 | -0.004 | 0.002 | -0.016 | 0.001 | 0.004 | -0.013 | 0.009 | 0 |
| RAD51B | 0.004 | 0.004 | -0.08 | -0.041 | 0.003 | -0.004 | -0.02 | -0.008 | -0.02 | -0.004 | 0.002 | -0.016 | 0.001 | 0.004 | -0.013 | 0.009 | 0 |
| PALB2 | -0.005 | 0.002 | -0.034 | -0.017 | 0.009 | -0.002 | -0.01 | -0.004 | -0.009 | 0.01 | 0.011 | -0.011 | -0.006 | 0.019 | -0.003 | 0.02 | -0.008 |
| TP53 | -0.002 | -0.005 | -0.223 | -0.035 | 0.011 | -0.019 | 0.003 | -0.043 | -0.006 | -0.006 | -0.004 | -0.005 | -0.009 | -0.01 | -0.015 | 0.01 | 0.011 |
| NF1 | -0.005 | -0.007 | -0.085 | -0.07 | 0.007 | -0.019 | 0.004 | -0.045 | -0.024 | -0.004 | -0.004 | -0.006 | -0.009 | -0.013 | -0.017 | 0.004 | 0.007 |
| RAD51D | -0.005 | -0.007 | -0.085 | -0.07 | 0.007 | -0.019 | 0.004 | -0.045 | -0.024 | -0.004 | -0.004 | -0.006 | -0.009 | -0.013 | -0.017 | 0.004 | 0.007 |
| CDK12 | -0.005 | -0.007 | -0.085 | -0.07 | 0.007 | -0.019 | 0.004 | -0.045 | -0.024 | -0.004 | -0.004 | -0.006 | -0.009 | -0.013 | -0.017 | 0.004 | 0.007 |
| BRCA1 | -0.005 | -0.007 | -0.42 | -0.098 | 0.006 | -0.02 | -0.001 | -0.04 | -0.007 | -0.007 | -0.004 | -0.01 | -0.017 | -0.013 | -0.018 | 0.004 | 0.001 |
| RAD51C | -0.015 | -0.014 | -0.42 | -0.098 | 0.006 | -0.02 | -0.001 | -0.019 | -0.007 | -0.007 | -0.009 | -0.01 | -0.017 | -0.013 | -0.018 | 0.004 | 0.001 |
| PPM1D | -0.015 | -0.014 | -0.42 | -0.098 | 0.006 | -0.02 | -0.001 | -0.019 | -0.007 | -0.009 | -0.009 | -0.01 | -0.017 | -0.013 | -0.018 | 0.004 | 0.001 |
| BRIP1 | -0.013 | 0.002 | -0.158 | 0.026 | -0.01 | 0.006 | -0.03 | 0.318 | 0.022 | -0.014 | -0.014 | -0.016 | -0.029 | -0.005 | -0.004 | 0.012 | -0.017 |
| CCNE1 | -0.006 | 0.008 | 0.527 | 0.064 | 0.003 | 0.004 | 0.007 | 0.037 | 0.016 | 0.002 | 0.002 | 0.016 | -0.001 | -0.001 | -0.014 | -0.003 | -0.004 |
| ZMYND8 | -0.011 | -0.003 | 0.205 | -0.053 | 0.001 | -0.006 | 0.007 | -0.039 | -0.008 | -0.028 | -0.013 | -0.008 | 0.005 | -0.003 | -0.008 | 0.009 | 0.012 |

DISCUSSION

Our results indicate that exploiting fundamental properties of cfDNA with fragment specific analyses can provide more sensitive analysis of ctDNA. We based the selection criteria on a biological observation that ctDNA fragment size distribution is shifted from normal cfDNA. Our work builds on a comprehensive survey of plasma cfDNA fragmentation patterns across 200 patients with multiple cancer types and 65 healthy individuals. We identified features that could determine the presence and amount of ctDNA in plasma samples, without a priori knowledge of somatic aberrations. Although this catalogue is the first of its kind, we note that it employed double-stranded DNA from plasma samples, and is subject to potential biases incurred by the DNA extraction and sequencing methods we used. Additional biological effects could contribute to further selective analysis of cfDNA. Other bodily fluids (urine, cerebrospinal fluid, saliva), different nucleic acids and structures, altered mechanisms of release into circulation, or sample processing methods could exhibit varying fragment size signatures and could offer additional exploitable biological patterns for selective sequencing.

Previous work has reported the size distributions of mutant ctDNA, but only considered limited genomic loci, cancer types, or cases (30, 32, 33). We identified the size differences between mutant and non-mutant DNA on a genome-wide and pan-cancer scale. We developed a method to size mutant ctDNA without using high-depth WGS. By sequencing >150 mutations per patient at high depth we obtained large numbers of reads that could be unequivocally identified as tumor-derived, and thus determined the size distribution of mutant ctDNA and non-mutant cfDNA in cancer patients. A potential limitation of our approach is that capture-based sequencing is biased by probe capture efficiency and therefore our data may not accurately reflect ctDNA fragments <100 bp or >300 bp.

Our work provides strong evidence that the modal size of ctDNA for many cancer types is less than 167 bp, which is the length of DNA wrapped around the chromatosome. In addition, our work also shows that there is a high level of enrichment of mutant DNA fragments at sizes greater than 167 bp, notably in the range 250-320 bp. These longer fragments may explain previous observations that longer ctDNA can be detected in the plasma of cancer patients (29, 32). The origin of these long fragments is still unknown, and their observation could be linked to technical factors. However, it is likely that mechanisms of compaction and release of cfDNA into circulation, which may differ depending on its origin, will be reflected by different fragment sizes (38). Improving the characterization of these fragments will be important, especially for future work combining ctDNA analysis with other entities in blood such as microvesicles and tumor-educated platelets (39, 40). Fragment specific analyses not only increase the sensitivity for detection of rare mutations, but could be used to track modifications in the size distribution of ctDNA. Future work should address whether this approach could be used to elucidate mechanistic effects of treatment on tumor cells, for example by distinguishing between necrosis and apoptosis based on fragment size (41).

Genome-wide and exome sequencing of plasma DNA at multiple time-points during cancer treatment have been proposed as non-invasive means to study cancer evolution and for the identification of possible resistance mechanisms to treatment (3). However, WGS and WES approaches are costly and have thus far been applicable only in samples for which the tumor DNA fraction was >5-10% (3-5, 42). We demonstrated that we could exploit the differences in fragment lengths using in vitro and in silico size selection to enrich for tumor content in plasma samples which improved mutation and SCNA detection in sWGS and WES data. We demonstrated that size selection improved the detection of mutations that are present in plasma at low allelic fractions, while maintaining low sequencing depth by sWGS and WES. Size selection can be achieved with simple means and at low cost, and is compatible with a wide range of downstream genome-wide and targeted genomic analyses, greatly increasing the potential value and utility of liquid biopsies.

Figure 22:
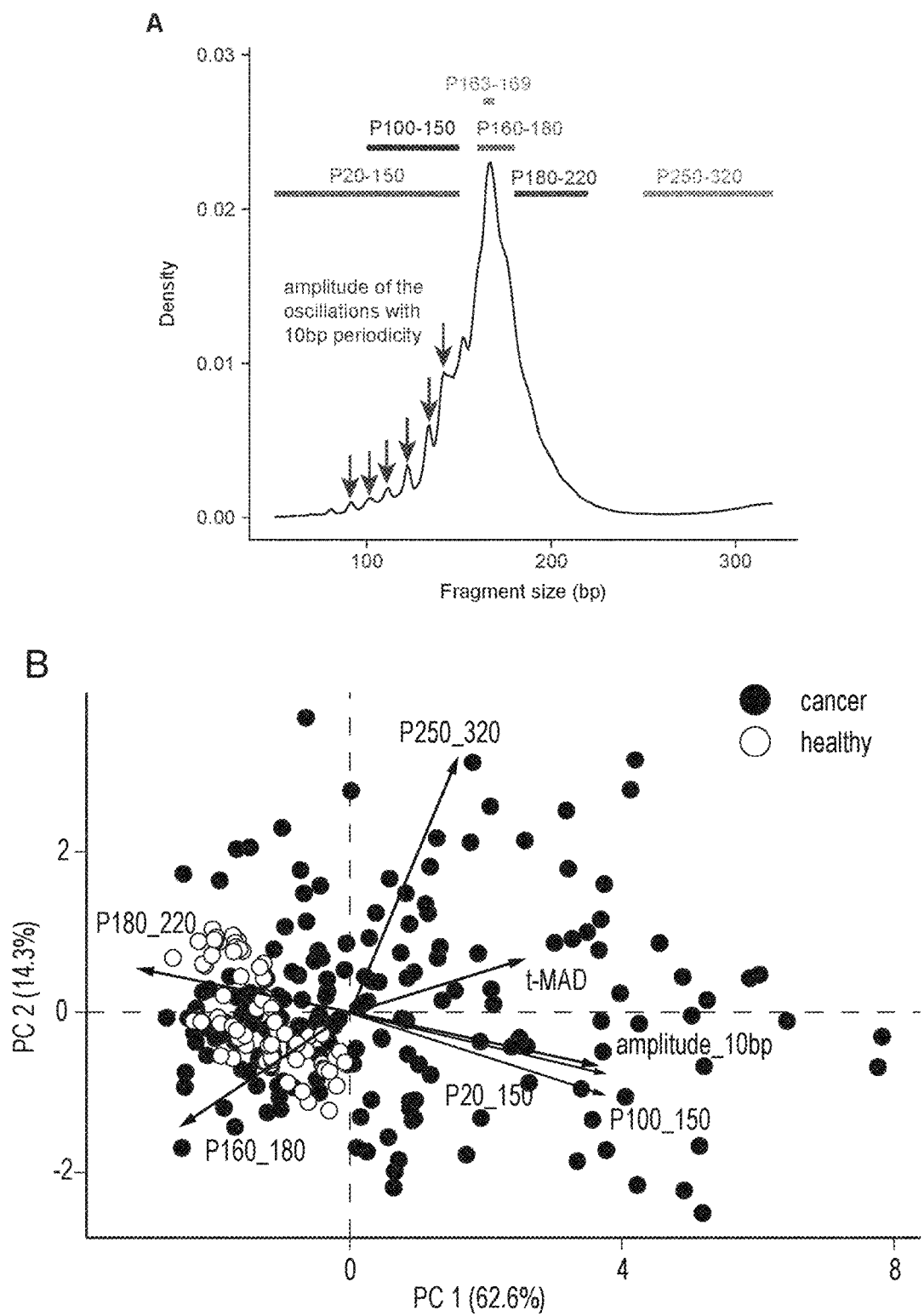
FIG. 22 depicts enhancing the potential for ctDNA detection by combining SCNAs and fragment-size features. A, Schematic illustrating the selection of different size ranges and features in the distribution of fragment sizes. For each sample, fragmentation features included the proportion (P) of fragments in specific size ranges, the ratio between certain ranges and a quantification of the amplitude of the 10 bp oscillations in the 90-145 size bp range calculated from the periodic "peaks" and "valleys". B, Principal Component Analysis (PCA) comparing cancer and healthy samples using data from t-MAD scores and the fragmentation features. Fragmentation features shown in grey are not included in the following steps. C, Workflow for the predictive analysis combining SCNAs and fragment size features. Plasma DNA sWGS data from healthy controls was split into a training set (60% of samples) and a validation set (used in both Validation data 1 and Validation set 2). sWGS data from plasma samples from a pan-cancer cohort of 182 samples from patients with cancer types with high levels of ctDNA (colorectal, cholangiocarcinoma, lung, ovarian, breast) was split into a training set (60% of samples) and a validation set (Validation data 1, together with the healthy individual validation set). A further dataset of sWGS from 57 samples from cancer types exhibiting low levels of ctDNA (glioma, renal, pancreatic) was used as Validation data 2, together with the healthy individual validation set. D, ROC curves for Validation data 1 (samples from cancer patients with high ctDNA levels=68, healthy=26) for 3 predictive models built on the pan-cancer training cohort (cancer=114, healthy=39). The curve represents the ROC curve for classification with t-MAD only, the long dashed line represents the logistic regression model combining the top 5 features based on recursive feature elimination (t-MAD score, 10 bp amplitude, P(160-180), P(180-220) and P(250-320)), and the dashed line shows the result for a random forest classifier trained on the combination of the same 5 features, independently chosen for the best RF predictive model. E, ROC curves for Validation data 2 (samples from cancer patients with low ctDNA levels=57, healthy=26) for the same 3 classifiers as D. The curve represents the model using t-MAD only, the long-dashed represents the logistic regression model combining the top 5 features (t-MAD score, 10 bp amplitude, P(160-180), P(180-220), and P(250-320)), and the dashed shows the result for a random forest classifier trained on the combination of same 5 predictive features. F, Plot representing the probability of classification as cancer with the RF model for all samples in both validation datasets. Samples are separated by cancer type and sorted within each by the RF probability of classification as cancer. The dashed horizontal line indicates 50% probability and the light long-dashed line indicates 33% probability.
Figure 22:
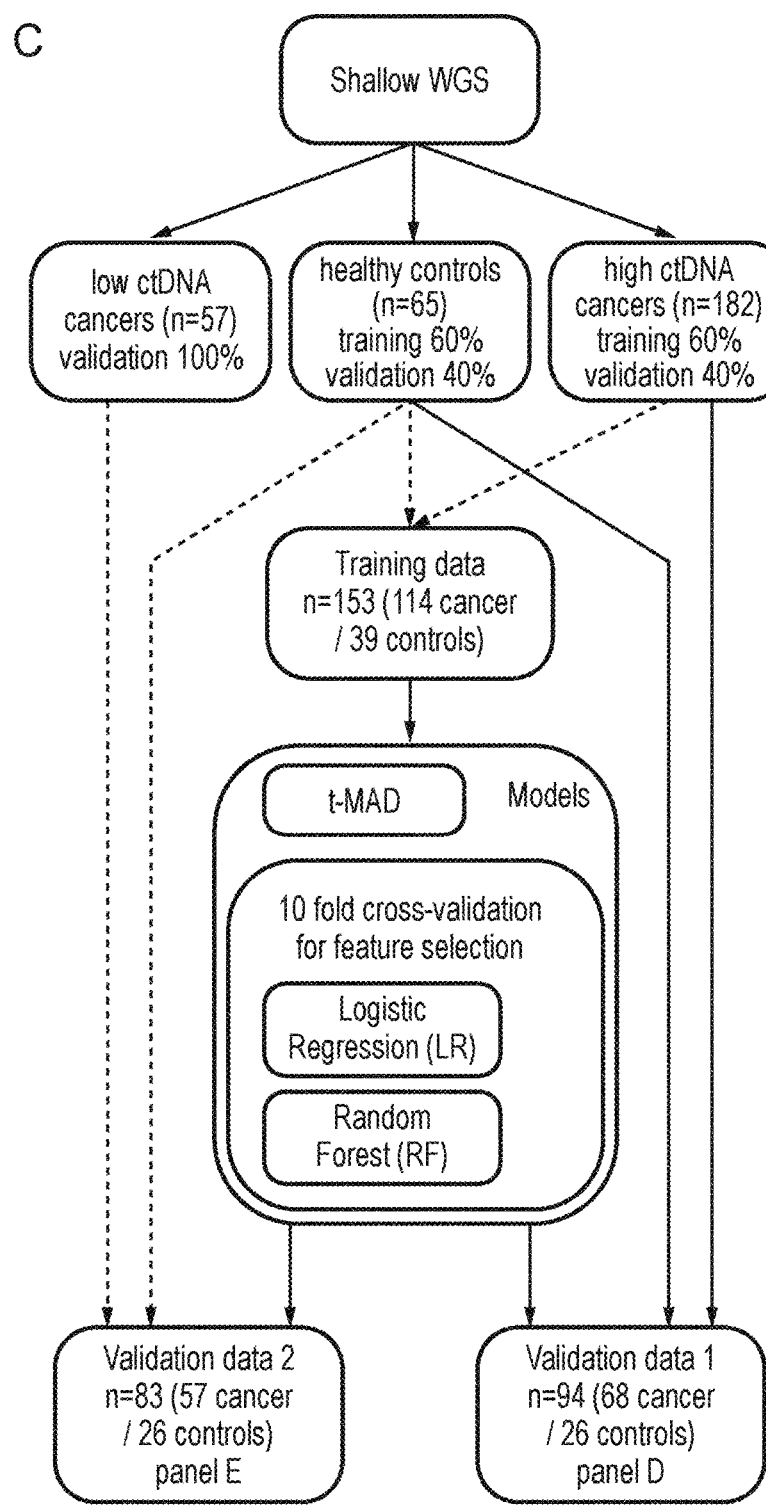
Figure 22:
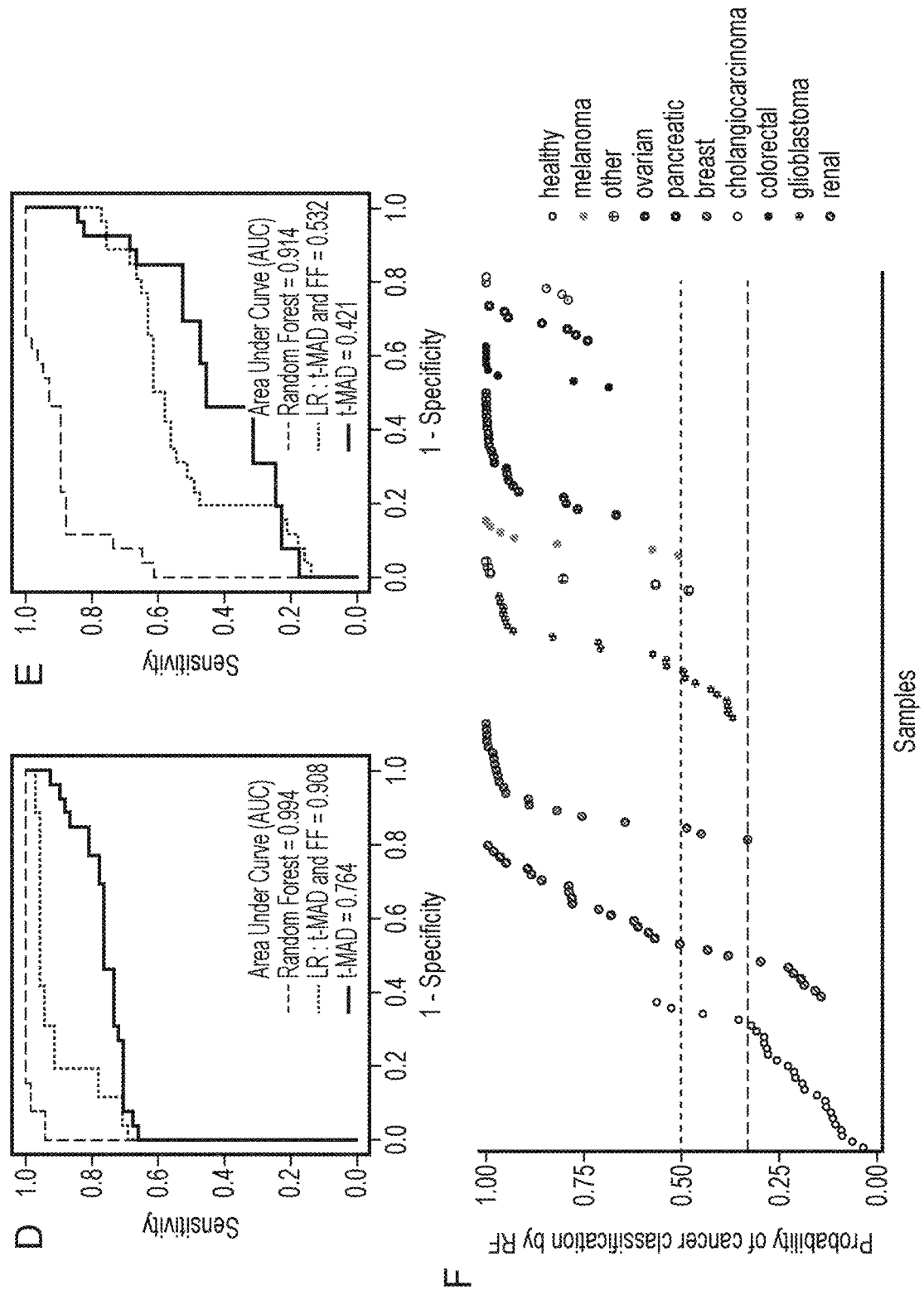
Figure 23:
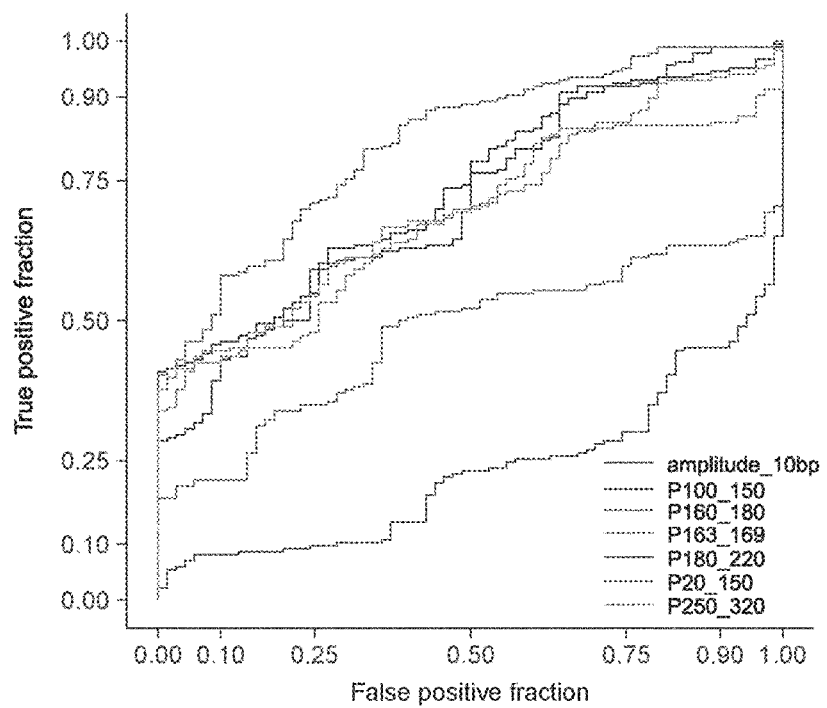
FIG. 23 shows the ROC analysis of the cfDNA fragmentation features between healthy samples and samples from patients with high ctDNA cancers.

Size selection can be applied in silico, which incurs no added costs, or in vitro, which adds a simple and low-cost intermediate step that can be applied to either the extracted DNA or the libraries created from it. This approach, applied prospectively to new studies, could boost the clinical utility of ctDNA detection and analysis, and creates an opportunity for re-analysis of large volumes of existing data (4, 34, 43). The limitation of this technique is a potential loss of material and information, since some of the informative fragments may be found in size ranges that are filtered out or de-prioritized in the analysis. This may be particularly problematic if only a few copies of the fragments of interest are present in plasma. Despite potential loss of material, we demonstrated that classification algorithms can learn from cfDNA fragmentation features and SCNAs analysis and improve the detection of ctDNA with a cheap sequencing approach (FIG. 22). Moreover, the cfDNA fragmentation features alone can be leveraged to classify cancer and healthy samples with a high accuracy (AUC=0.989 for high ctDNA cancers, and AUC=0.891 for low ctDNA cancers) (FIG. 26).

Analysis of fragment sizes could provide improvements in other applications. Introducing fragment size information on each read could enhance mutation-calling algorithms from high depth sequencing, to identify tumor-derived mutations from other sources such as somatic variants or background sequencing noise. In addition, cfDNA analysis in patients with CHIP is likely to be structurally different from ctDNA released during tumor cell proliferation (18, 19). Thus, fragmentation analysis or selective sequencing strategies could be applied to distinguish clinically relevant tumor mutations from those present in clonal expansions of normal cells. This will be critical for the development of cfDNA-based methods for identification of patients with early stage cancer.

Size selection could also have an impact on the detection of other types of DNA in body fluids or to enrich signals for circulating bacterial or pathogen DNA and mitochondrial DNA. These DNA fragments are not associated with nucleosomes and are often highly fragmented below 100 bp. Filtering such fragments may prove to be important in light of the recently established link between the microbiome and treatment efficiency (17, 44). Moreover, recent work highlights a stronger correlation between ctDNA detection and cellular proliferation, rather than cell-death (45). We hypothesize that the mode of the distribution of ctDNA fragment sizes at 145 bp could reflect cfDNA released during cell proliferation, and the fragments at 167 bp may reflect cfDNA released by apoptosis or maturation/turnover of blood cells. The effect of other cancer hallmarks (46) on ctDNA biology, structure, concentration and release is yet unknown.

In summary, ctDNA fragment size analysis, via size selection and machine learning approaches, boosts non-invasive genomic analysis of tumor DNA. Size selection of shorter plasma DNA fragments enriches ctDNA, and leads to the identification of a greater number of genomic alterations with both targeted and untargeted sequencing at a minimal additional cost. Combining cfDNA fragment size analysis and the detection of SCNAs with a non-linear classification algorithm improved the discrimination between samples from cancer patients and healthy individuals. As the analysis of fragment sizes is based on the structural property of ctDNA, size selection could be used with any downstream sequencing applications. Our work could help overcome current limitations of sensitivity for liquid biopsy, supporting expanded clinical and research applications. Our results indicate that exploiting the endogenous biological properties of cfDNA provides an alternative paradigm to deeper sequencing of ctDNA.

Code

The following exemplary analysis code for the classification algorithms described in the Examples above is in the R programming environment (see www.r-project.org/about.html). The features may be taken from Table 2, wherein the samples are separated into group A cancers ("high ctDNA cancers") and group B ("low ctDNA cancer"), and wherein healthy controls are used in each (i.e. a copy in each of the files).

```
---
title: "PAN-CANCER classifier"
author: "Dineika Chandrananda"
date: "20 November 2017"
output: html_document
---
Data pre-processing
* Separating out cancer types into Group A
* containing "healthy", "breast", "melanoma", "ovarian", "lung",
"colorectal", "cholangiocarcinoma"
* and Group B the low ctDNA cancers
* Only plasma
* No size selection
* Timepoints mixed (baseline and post-treatment)
* Remove degraded DNA
Run feature selection and model the training data
``` {r feature selection}
library(caret)
library(pROC)
MY_SEED <- 666
filename_NO_SZ <- "./2018_Group_A_cancers_noSZ.csv"
full_data_ NO SZ<- read.csv(filename_NO_SZ, header=TRUE,
                   stringsAsFactors=FALSE)
stopifnot(!anyNA(full_data_NO_SZ))
breast            cervical          cholangiocarcinoma    colorectal
53                1                 13                    18
endometrial       healthy           hepatocellular
lung
2                 65                5                     7
melanoma          ovarian           penile                prostate
18                56                1                     4
rectum            thymoma
3                 1
partition data so that the cancerTypes + healthy are evenly
separated
Use a 60:40 split in all cancer + healthy categories
full_data_NO_SZ$cancer <- factor(full_data_NO_SZ$cancer)
set.seed(MY_SEED)
intrain <- createDataPartition(y=full_data_NO_SZ$cancer, p=0.6,
           list = FALSE)

Convertmultiple cancer classes into cancer/healthy

full_data_NO_SZ$cancer <- as.character(full_data_NO_SZ$cancer)
full_data_NO_SZ$cancer[full_data_NO_SZ$cancer != "healthy"] <-
"cancer"
full_data_NO_SZ$cancer <-factor(full_data_NO_SZ$cancer,
           levels=c("healthy", "cancer"))

names (full_data_NO_SZ) [names(full_data_NO_SZ) == "cancer"] <-
"Class"
Split the test/train data sets
neat_train <- full_data_NO_SZ[intrain,]
neat_test <- full_data_NO_SZ[-intrain,]
table (neat_train$Class)

healthy           cancer
39                114
table (neat_test$Class)

healthy           cancer
26                68
The baseline set of predictors,
b1 <- c("tMAD",
    "amplitude_10bp",
```

```
    "P160_180",
    "P180_220",
    "P250_320")
training <- neat_train[, c("sample", "Class", b1)]
testing <- neat_test [, c("sample", "Class", b1)]
saveRDS(training, "training")
saveRDS(testing, "testing")
predVars <- names(training) [!(names(training) %in%
              c("sample", "Class"))
saveRDS(predVars, "predVars")
This summary function is used to evaluate the models.
fiveStats <- function(. . .) c(twoClassSummary(. . .),
              defaultSummary(. . .))
We create the cross-validation data as a list to use with
different
functions
index <- createMultiFolds(training$Class, times = 5)
The candidate set of the number of predictors to evaluate
varSeq <- seq(1, length(predVars) -1)
We can also use parallel processing to run each resampled RFE
iteration
library(doMC)
registerDoMC(20)
set.seed(MY_SEED)
ctrl <- rfeControl(method = "repeatedcv", repeats = 5,
          saveDetails = TRUE,
          index = index,
          returnResamp = "final")
set.seed(MY_SEED)
fullCtrl = <- trainControl (method - "repeatedcv",
          repeats = 5,
          summaryFunction = fiveStats,
          classProbs = TRUE,
          index = index)
######
Fit the RFE models
######
ctrl$functions <- rfFuncs
ctrl$functions$summary<- fiveStats
set.seed(MY_SEED)
rfRFE <- rfe(training[, predVars],
      training$Class,
      sizes = varSeq,
      metric = "ROC",
      ntree = 1000,
      rfeControl = ctrl
      ) # keep.forest=TRUE
rfRFE
saveRDS(rfRFE, file="rfRFE")
ctrl$functions <- lrFuncs
ctrl$functions$summary <- fiveStats
set.seed(MY_SEED)
lrRFE <- rfe(training[, predVars],
      training$Class,
      sizes = varSeq,
      metric = "ROC",
      rfeControl = ctrl)
lrRFE
saveRDS(lrRFE, file="lrRFE")
### Plotting ROC curves for test set (high ctDNA)
library(caret)
library(pROC)
library(ggplot2)
library(randomForest)
MY_SEED <- 666
testing <- training <- lrRFE <- rfRFE <- NULL
testing <- readRDS("testing")
training <- readRDS("training")
lrRFE <- readRDS("lrRFE")
rfRFE <- readRDS("rfRFE")
predVars <- c( "tMAD",
        "amplitude_10bp",
        "P160_180",
        "P180_220",
        "P250_320")
Get ROC curves for the different models
1) Only t-MAD
training_binary <- training
testing_binary <- testing
```

```
training_binary$Class <- as.character(training_binary$Class)
testing_binary$Class <- as.character(testing_binary$Class)
training_binary$Class[training_binary$Class == "healthy"] <- 0
training_binary$Class[training_binary$Class !="0"] <- 1
training_binary$Class <-factor(as.numeric(training_binary$Class))
testing_binary$Class[testing_binary$Class == "healthy"] <- 0
testing_binary$Class[testing_binary$Class != "0"] <- 1
testing_binary$Class <-factor(as.numeric(testing_binary$Class))
lr_tMAD <- glm(Class ~ tMAD,
               data = training_binary,
               family = binomial)
saveRDS(lr_tMAD , file="lr_tMAD")
prob <- predict(lr_tMAD, newdata=testing_binary, type="response")
pred <- ROCR::prediction(prob, testing_binary$Class)
perf <- ROCR::performance(pred, measure = "tpr", x.measure = "fpr")
tMAD_AUC <- ROCR::performance(pred, measure = "auc")@y.values[[1]]
df_tMAD <- data.frame(Specificity=perf@y.values[[1]],
             Sensitivity=perf@y.values[[1]])
Logistic regression, recursive feature elimination
ROC_lrRFE <- roc(testing$Class,
         predict(lrRFE, testing[,predVars])$cancer)
df_lrRFE <- data.frame(Sensitivity=ROC_lrRFE$sensitivities,
                Specificity=1-ROC_lrRFE$specificities)
Random Forest RFE
library(randomForest)
ROC_rfRFE <- roc(testing$Class,
         predict(rfRFE, testing[,predVars])$cancer,
levels=c("healthy", "cancer"))
ROC_rfRFE
df_rfRFE <- data.frame(Sensitivity=ROC_rfRFE$sensitivities,
                Specificity=1-ROC_rfRFE$specificities)
Plotting ROC curves
pdf("Model_Comparison_on_TestData_high_ctDNA.pdf")
plot(x=df_rfRFE$Specificity,
     y=df_rfRFE$Sensitivity,
     xlab="1 – Specificity",
     ylab="Sensitivity", type="l",
     col="blue")
points(x=df_lrRFE$Specificity,
     y=df_lrRFE$Sensitivity,
     type="l",
     col="red")
points(x=df_tMAD$Specificity,
     y=df_tMAD$Sensitivity,
     type="l",
     col="black")
AUC_values <- c(
     paste0("RF (", paste(rfRFE$optVariables, collapse=","), ") = ",
          round(ROC_rfRFE$auc, 3)),
     paste0("cancer ~ ",
          paste(lrRFE$optVariables, collapse="+"), " = ",
          round(ROC_lrRFE$auc, 3)),
     paste0("cancer ~ tMAD = ", round(tMAD_AUC, 3)))
legend(0.08, 0.3, title=" Area Under Curve (AUC) ", title.adj=0.1,
       legend = AUC_values,
       col=c("blue", "red", "black"),
       text.col=c("blue", "red", "black"),
       title.col="black",
       cex=0.8, bty="n")
dev.off( )
Get the resampling results for all the models in the training
data
rfeResamples <- resamples(list("Random Forest" = rfRFE,
       "LR (tMAD + fragFeatures)" = lrRFE))
saveRDS(rfeResamples, "rfeResamples")
pdf("Supplementary_Model_Comparison_on_trainingData_crossValidation.
pdf")
   print(bwplot(rfeResamples, metric=c("ROC", "Accuracy"),
       xlim=c(0.1, 1.1)))
dev.off( )
summary(rfeResamples)
```
Predict low-ctDNA cancers with test control cohort (n = 26)
```{r}
##########################################################
######### Plotting for training & test
library(ggplot2)
library(dplyr)
library (caret)
```

```
library(pROC)
library(ggplot2)
library(randomForest)
MY_SEED <- 666
groupB <- read.csv(file="./2018_Group_B_cancers_noSZ.csv",
             header=T,
             stringsAsFactors = F)
Convertmultiple cancer classes into cancer/healthy
groupB$cancer <- as.character(groupB$cancer)
groupB$cancer[groupB$cancer != "healthy"] <- "cancer"
groupB$cancer <-factor(groupB$cancer,
             levels=c("healthy", "cancer"))
names(groupB)[names(groupB) == "cancer"] <- "Class"
testing <- training <- lrRFE <- rfRFE <- NULL
testing <- readRDS("testing")
training <- readRDS("training")
lrRFE <- readRDS("lrRFE")
rfRFE <- readRDS("rfRFE")
predVars <- c("tMAD", "amplitude_10bp",
             "P160_180",
             "P180_220",
             "P250_320")
lowctDNA cancer data combined with healthy samples from test cohort
testing <- rbind(testing[testing$Class == "healthy", ],
             groupB[groupB$Class == "cancer", c("sample",
"Class", predVars)])
testing$Class <- factor(testing$Class, levels = c("healthy",
"cancer"))
Get ROC curves for the different models
1) Only t-MAD
training_binary <- training
testing_binary <- testing
training_binary$Class <- as.character(training_binary$Class)
testing_binary$Class <- as.character(testing_binary$Class)
training_binary$Class[training_binary$Class == "healthy"] <- 0
training_binary$Class[training_binary$Class != "0"] <- 1
training_binary$Class <-factor(as.numeric(training_binary$Class))
testing_binary$Class[testing_binary$Class == "healthy"] <- 0
testing_binary$Class[testing_binary$Class != "0"] <- 1
testing_binary$Class <-factor(as.numeric(testing_binary$Class))
lr_tMAD <- glm(Class ~ tMAD,
             data = training_binary,
             family = binomial)
saveRDS(lr_tMAD , file="lr_tMAD_groupB_26Controls")
prob <- predict(lr_tMAD, newdata=testing_binary, type="response")
pred <- ROCR::prediction(prob, testing_binary$Class)
perf <- ROCR::performance(pred, measure = "tpr", x.measure = "fpr")
tMAD_AUC <- ROCR::performance(pred, measure = "auc")@y.values[[1]]
df_tMAD <- data.frame(Specificity=perf@x.values[[1]],
             Sensitivity=perf@y.values[[1]])
Logistic regression, recursive feature elimination
ROC_lrRFE <- roc(testing$Class,
             predict(lrRFE, testing[,predVars])$cancer)
ROC_lrRFE
df_lrRFE <- data.frame(Sensitivity=ROC_lrRFE$sensitivities,
             Specificity=1-ROC_lrRFE$specificities)
Random Forest RFE
library(randomForest)
ROC_rfRFE <- roc(testing$Class,
             predict(rfRFE, testing[,predVars])$cancer,
levels=c("healthy", "cancer"))
ROC_rfRFE
df_rfRFE <- data.frame(Sensitivity=ROC _rfRFE$sensitivities,
             Specificity=1-ROC_rfRFE$specificities)
Plotting ROC curves
pdf("Model_Comparison_on_GroupB_26Controls.pdf")
plot(x=df_rfRFE$Specificity,
     y=df_rfRFE$Sensitivity,
     xlab="1 – Specificity",
     ylab="Sensitivity", type="l",
     col="red4")
points(x=df_lrRFE$Specificity,
     y=df_lrRFE$Sensitivity,
     type="l",
     col="orange3")
points(x=df_tMAD$Specificity,
     y=df_tMAD$Sensitivity,
     type="l",
```

```
    col="black")
AUC_values <- c(
    paste0("RF (", paste(rfRFE$optVariables, collapse=","), ") = ",
        round(ROC_rfRFE$auc, 3)),
    paste0("cancer ~ ",
        paste(lrRFE$optVariables, collapse="+"), " = ",
        round(ROC_lrRFE$auc, 3)),
    paste0("cancer ~ tMAD = ", round(tMAD_AUC, 3)))
legend(0.08, 0.3, title=" Area Under Curve (AUC) ", title.adj=0.1,
    legend = AUC_values,
    col=c("red4", "orange3", "black"),
    text.col=c("red4", "orange3", "black"),
    title.col="black",
    cex=0.8, bty="n")
dev.off( )
############
```
***

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

1. G. Siravegna, S. Marsoni, S. Siena, A. Bardelli, Integrating liquid biopsies into the management of cancer, *Nat. Rev. Clin. Oncol.* (2017), doi:10.1038/nrclinonc.2017.14.
2. J. C. M. Wan, C. Massie, J. Garcia-Corbacho, F. Mouliere, J. D. Brenton, C. Caldas, S. Pacey, R. Baird, N. Rosenfeld, Liquid biopsies come of age: towards implementation of circulating tumour DNA, *Nat. Rev. Cancer* 17, 223-238 (2017).
3. M. Murtaza, S.-J. Dawson, D. W. Y. Tsui, D. Gale, T. Forshew, A. M. Piskorz, C. Parkinson, S.-F. Chin, Z. Kingsbury, A. S. C. Wong, F. Marass, S. Humphray, J. Hadfield, D. Bentley, T. M. Chin, J. D. Brenton, C. Caldas, N. Rosenfeld, Non-invasive analysis of acquired resistance to cancer therapy by sequencing of plasma DNA, *Nature* 497, 108-112 (2013).
4. V. A. Adalsteinsson, G. Ha, S. S. Freeman, A. D. Choudhury, D. G. Stover, H. A. Parsons, G. Gydush, S. C. Reed, D. Rotem, J. Rhoades, D. Loginov, D. Livitz, D. Rosebrock, I. Leshchiner, J. Kim, C. Stewart, M. Rosenberg, J. M. Francis, C.-Z. Zhang, O. Cohen, C. Oh, H. Ding, P. Polak, M. Lloyd, S. Mahmud, K. Helvie, M. S. Merrill, R. A. Santiago, E. P. O'Connor, S. H. Jeong, R. Leeson, R. M. Barry, J. F. Kramkowski, Z. Zhang, L. Polacek, J. G. Lohr, M. Schleicher, E. Lipscomb, A. Saltzman, N. M. Oliver, L. Marini, A. G. Waks, L. C. Harshman, S. M. Tolaney, E. M. Van Allen, E. P. Winer, N. U. Lin, M. Nakabayashi, M.-E. Taplin, C. M. Johannessen, L. A. Garraway, T. R. Golub, J. S. Boehm, N. Wagle, G. Getz, J. C. Love, M. Meyerson, Scalable whole-exome sequencing of cell-free DNA reveals high concordance with metastatic tumors, *Nat. Commun.* 8, 1324 (2017).
5. E. Heitzer, P. Ulz, J. Belic, S. Gutschi, F. Quehenberger, K. Fischereder, T. Benezeder, M. Auer, C. Pischler, S. Mannweiler, M. Pichler, F. Eisner, M. Haeusler, S. Riethdorf, K. Pantel, H. Samonigg, G. Hoefler, H. Augustin, J. B. Geigl, M. R. Speicher, Tumor-associated copy number changes in the circulation of patients with prostate cancer identified through whole-genome sequencing, *Genome Med.* 5, 30 (2013).
6. C. Bettegowda, M. Sausen, R. J. Leary, I. Kinde, Y. Wang, N. Agrawal, B. R. Bartlett, H. Wang, B. Luber, R. M. Alani, E. S. Antonarakis, N. S. Azad, A. Bardelli, H. Brem, J. L. Cameron, C. C. Lee, L. A. Fecher, G. L. Gallia, P. Gibbs, D. Le, R. L. Giuntoli, M. Goggins, M. D. Hogarty, M. Holdhoff, S.-M. Hong, Y. Jiao, H. H. Juhl, J. J. Kim, G. Siravegna, D. A. Laheru, C. Lauricella, M. Lim, E. J. Lipson, S. K. N. Marie, G. J. Netto, K. S. Oliner, A. Olivi, L. Olsson, G. J. Riggins, A. Sartore-Bianchi, K. Schmidt, I.-M. Shih, S. M. Oba-Shinjo, S. Siena, D. Theodorescu, J. Tie, T. T. Harkins, S. Veronese, T.-L. Wang, J. D. Weingart, C. L. Wolfgang, L. D. Wood, D. Xing, R. H. Hruban, J. Wu, P. J. Allen, C. M. Schmidt, M. A. Choti, V. E. Velculescu, K. W. Kinzler, B. Vogelstein, N. Papadopoulos, L. A. Diaz, Detection of Circulating Tumor DNA in Early- and Late-Stage Human Malignancies, *Sci. Transl. Med.* 6, 224ra24-224ra24 (2014).
7. F. Diehl, M. Li, D. Dressman, Y. He, D. Shen, S. Szabo, L. A. Diaz, S. N. Goodman, K. A. David, H. Juhl, K. W. Kinzler, B. Vogelstein, Detection and quantification of mutations in the plasma of patients with colorectal tumors, *Proc. Natl. Acad. Sci.* 102, 16368-16373 (2005).
8. S.-J. Dawson, D. W. Y. Tsui, M. Murtaza, H. Biggs, O. M. Rueda, S.-F. Chin, M. J. Dunning, D. Gale, T. Forshew, B. Mahler-Araujo, S. Rajan, S. Humphray, J. Becq, D. Halsall, M. Wallis, D. Bentley, C. Caldas, N. Rosenfeld, Analysis of Circulating Tumor DNA to Monitor Metastatic Breast Cancer, *N. Engl. J. Med.* 368, 1199-1209 (2013).
9. F. Diehl, K. Schmidt, M. A. Choti, K. Romans, S. Goodman, M. Li, K. Thornton, N. Agrawal, L. Sokoll, S. A. Szabo, K. W. Kinzler, B. Vogelstein, L. A. Diaz, Circulating mutant DNA to assess tumor dynamics., *Nat. Med.* 14, 985-90 (2008).
10. J. Tie, Y. Wang, C. Tomasetti, L. Li, S. Springer, I. Kinde, N. Silliman, M. Tacey, H.-L. Wong, M. Christie, S. Kosmider, I. Skinner, R. Wong, M. Steel, B. Tran, J. Desai, I. Jones, A. Haydon, T. Hayes, T. J. Price, R. L. Strausberg, L. A. Diaz, N. Papadopoulos, K. W. Kinzler, B. Vogelstein, P. Gibbs, Circulating tumor DNA analysis detects minimal residual disease and predicts recurrence in patients with stage II colon cancer., *Sci. Transl. Med.* 8, 346ra92 (2016).
11. A. A. Chaudhuri, J. J. Chabon, A. F. Lovejoy, A. M. Newman, H. Stehr, T. D. Azad, M. S. Khodadoust, M. S.

Esfahani, C. L. Liu, L. Zhou, F. Scherer, D. M. Kurtz, C. Say, J. N. Carter, D. J. Merriott, J. C. Dudley, M. S. Binkley, L. Modlin, S. K. Padda, M. F. Gensheimer, R. B. West, J. B. Shrager, J. W. Neal, H. A. Wakelee, B. W. Loo, A. A. Alizadeh, M. Diehn, Early Detection of Molecular Residual Disease in Localized Lung Cancer by Circulating Tumor DNA Profiling., *Cancer Discov.* 7, 1394-1403 (2017).

12. J. D. Cohen, L. Li, Y. Wang, C. Thoburn, B. Afsari, L. Danilova, C. Douville, A. A. Javed, F. Wong, A. Mattox, R. H. Hruban, C. L. Wolfgang, M. G. Goggins, M. Dal Molin, T.-L. Wang, R. Roden, A. P. Klein, J. Ptak, L. Dobbyn, J. Schaefer, N. Silliman, M. Popoli, J. T. Vogelstein, J. D. Browne, R. E. Schoen, R. E. Brand, J. Tie, P. Gibbs, H.-L. Wong, A. S. Mansfield, J. Jen, S. M. Hanash, M. Falconi, P. J. Allen, S. Zhou, C. Bettegowda, L. A. Diaz, C. Tomasetti, K. W. Kinzler, B. Vogelstein, A. M. Lennon, N. Papadopoulos, Detection and localization of surgically resectable cancers with a multi-analyte blood test., *Science* 359, 926-930 (2018).

13. I. S. Haque, O. Elemento, Challenges in Using ctDNA to Achieve Early Detection of Cancer, *bioRxiv,* 237578 (2017).

14. A. M. Newman, A. F. Lovejoy, D. M. Klass, D. M. Kurtz, J. J. Chabon, F. Scherer, H. Stehr, C. L. Liu, S. V Bratman, C. Say, L. Zhou, J. N. Carter, R. B. West, G. W. Sledge Jr, J. B. Shrager, B. W. Loo, J. W. Neal, H. A. Wakelee, M. Diehn, A. A. Alizadeh, Integrated digital error suppression for improved detection of circulating tumor DNA, *Nat. Biotechnol.* 34, 547-555 (2016).

15. P. Ulz, G. G. Thallinger, M. Auer, R. Graf, K. Kashofer, S. W. Jahn, L. Abete, G. Pristauz, E. Petru, J. B. Geigl, E. Heitzer, M. R. Speicher, Inferring expressed genes by whole-genome sequencing of plasma DNA, *Nat. Genet.* 48, 1273-1278 (2016).

16. M. W. Snyder, M. Kircher, A. J. Hill, R. M. Daza, J. Shendure, Cell-free DNA Comprises an In Vivo Nucleosome Footprint that Informs Its Tissues-Of-Origin., *Cell* 164, 57-68 (2016).

17. P. Burnham, M. S. Kim, S. Agbor-Enoh, H. Luikart, H. A. Valantine, K. K. Khush, I. De Vlaminck, Single-stranded DNA library preparation uncovers the origin and diversity of ultrashort cell-free DNA in plasma, *Sci. Rep.* 6, 27859 (2016).

18. G. Genovese, A. K. Kahler, R. E. Handsaker, J. Lindberg, S. A. Rose, S. F. Bakhoum, K. Chambert, E. Mick, B. M. Neale, M. Fromer, S. M. Purcell, O. Svantesson, M. Landén, M. Höglund, S. Lehmann, S. B. Gabriel, J. L. Moran, E. S. Lander, P. F. Sullivan, P. Sklar, H. Grönberg, C. M. Hultman, S. A. McCarroll, Clonal Hematopoiesis and Blood-Cancer Risk Inferred from Blood DNA Sequence, *N. Engl. J. Med.* 371, 2477-2487 (2014).

19. Y. Hu, B. Ulrich, J. Supplee, Y. Kuang, P. H. Lizotte, N. Feeney, N. Guibert, M. M. Awad, K.-K. Wong, P. A. Janne, C. P. Paweletz, G. R. Oxnard, False positive plasma genotyping due to clonal hematopoiesis., *Clin. Cancer Res.*, clincanres.0143.2018 (2018).

20. A. J. Bronkhorst, J. F. Wentzel, J. Aucamp, E. van Dyk, L. du Plessis, P. J. Pretorius, Characterization of the cell-free DNA released by cultured cancer cells, *Biochim. Biophys. Acta—Mol. Cell Res.* 1863, 157-165 (2016).

21. S. Jahr, H. Hentze, S. Englisch, D. Hardt, F. O. Fackelmayer, R. D. Hesch, R. Knippers, DNA fragments in the blood plasma of cancer patients: quantitations and evidence for their origin from apoptotic and necrotic cells., *Cancer Res.* 61, 1659-65 (2001).

22. Y. M. D. Lo, K. C. A. Chan, H. Sun, E. Z. Chen, P. Jiang, F. M. F. Lun, Y. W. Zheng, T. Y. Leung, T. K. Lau, C. R. Cantor, R. W. K. Chiu, Maternal plasma DNA sequencing reveals the genome-wide genetic and mutational profile of the fetus., *Sci. Transl. Med.* 2, 61ra91 (2010).

23. D. Chandrananda, N. P. Thorne, M. Bahlo, L.-S. Tam, G. Liao, E. Li, High-resolution characterization of sequence signatures due to non-random cleavage of cell-free DNA, *BMC Med. Genomics* 8, 29 (2015).

24. P. Jiang, Y. M. D. Lo, The Long and Short of Circulating Cell-Free DNA and the Ins and Outs of Molecular Diagnostics, *Trends Genet.* 32, 360-371 (2016).

25. S. C. Y. Yu, K. C. A. Chan, Y. W. L. Zheng, P. Jiang, G. J. W. Liao, H. Sun, R. Akolekar, T. Y. Leung, A. T. J. I. Go, J. M. G. van Vugt, R. Minekawa, C. B. M. Oudejans, K. H. Nicolaides, R. W. K. Chiu, Y. M. D. Lo, Size-based molecular diagnostics using plasma DNA for noninvasive prenatal testing., *Proc. Natl. Acad. Sci. U.S.A* 111, 8583-8 (2014).

26. F. M. F. Lun, N. B. Y. Tsui, K. C. A. Chan, T. Y. Leung, T. K. Lau, P. Charoenkwan, K. C. K. Chow, W. Y. W. Lo, C. Wanapirak, T. Sanguansermsri, C. R. Cantor, R. W. K. Chiu, Y. M. D. Lo, Noninvasive prenatal diagnosis of monogenic diseases by digital size selection and relative mutation dosage on DNA in maternal plasma., *Proc. Natl. Acad. Sci. U.S.A* 105, 19920-5 (2008).

27. G. Minarik, G. Repiska, M. Hyblova, E. Nagyova, K. Soltys, J. Budis, F. Duris, R. Sysak, M. Gerykova Bujalkova, B. Vlkova-Izrael, O. Biro, B. Nagy, T. Szemes, Utilization of Benchtop Next Generation Sequencing Platforms Ion Torrent PGM and MiSeq in Noninvasive Prenatal Testing for Chromosome 21 Trisomy and Testing of Impact of In Silico and Physical Size Selection on Its Analytical Performance., *PLoS One* 10, e0144811 (2015).

28. M. B. Giacona, G. C. Ruben, K. A. Iczkowski, T. B. Roos, D. M. Porter, G. D. Sorenson, Cell-Free DNA in Human Blood Plasma, *Pancreas* 17, 89-97 (1998).

29. N. Umetani, A. E. Giuliano, S. H. Hiramatsu, F. Amersi, T. Nakagawa, S. Martino, D. S. B. Hoon, Prediction of breast tumor progression by integrity of free circulating DNA in serum., *J. Clin. Oncol.* 24, 4270-6 (2006).

30. F. Mouliere, B. Robert, E. Arnau Peyrotte, M. Del Rio, M. Ychou, F. Molina, C. Gongora, A. R. Thierry, T. Lee, Ed. High Fragmentation Characterizes Tumour-Derived Circulating DNA, *PLoS One* 6, e23418 (2011).

31. F. Mouliere, S. El Messaoudi, D. Pang, A. Dritschilo, A. R. Thierry, Multi-marker analysis of circulating cell-free DNA toward personalized medicine for colorectal cancer, *Mol. Oncol.* 8, 927-941 (2014).

32. P. Jiang, C. W. M. Chan, K. C. A. Chan, S. H. Cheng, J. Wong, V. W.-S. Wong, G. L. H. Wong, S. L. Chan, T. S. K. Mok, H. L. Y. Chan, P. B. S. Lai, R. W. K. Chiu, Y. M. D. Lo, Lengthening and shortening of plasma DNA in hepatocellular carcinoma patients., *Proc. Natl. Acad. Sci. U.S.A* 112, E1317-25 (2015).

33. H. R. Underhill, J. O. Kitzman, S. Hellwig, N. C. Welker, R. Daza, D. N. Baker, K. M. Gligorich, R. C. Rostomily, M. P. Bronner, J. Shendure, D. J. Kwiatkowski, Ed. Fragment Length of Circulating Tumor DNA, *PLOS Genet.* 12, e1006162 (2016).

34. O. A. Zill, K. C. Banks, S. R. Fairclough, S. A. Mortimer, J. V Vowles, R. Mokhtari, D. R. Gandara, P. C. Mack, J. I. Odegaard, R. J. Nagy, A. M. Baca, H. Eltoukhy, D. I. Chudova, R. B. Lanman, A. Talasaz, The Landscape of Actionable Genomic Alterations in Cell-Free Circulating Tumor DNA from 21,807 Advanced Cancer Patients., *Clin. Cancer Res.*, clincanres.3837.2017 (2018).

35. G. Macintyre, T. E. Goranova, D. De Silva, D. Ennis, A. M. Piskorz, M. Eldridge, D. Sie, L.-A. Lewsley, A. Hanif, C. Wilson, S. Dowson, R. M. Glasspool, M. Lockley, E. Brockbank, A. Montes, A. Walther, S. Sundar, R. Edmondson, G. D. Hall, A. Clamp, C. Gourley, M. Hall, C. Fotopoulou, H. Gabra, J. Paul, A. Supernat, D. Millan, A. Hoyle, G. Bryson, C. Nourse, L. Mincarelli, L. N. Sanchez, B. Ylstra, M. Jimenez-Linan, L. Moore, O. Hofmann, F. Markowetz, I. A. McNeish, J. D. Brenton, Copy number signatures and mutational processes in ovarian carcinoma, *Nat. Genet.*, 1 (2018).

36. C. A. Parkinson, D. Gale, A. M. Piskorz, H. Biggs, C. Hodgkin, H. Addley, S. Freeman, P. Moyle, E. Sala, K. Sayal, K. Hosking, I. Gounaris, M. Jimenez-Linan, H. M. Earl, W. Qian, N. Rosenfeld, J. D. Brenton, E. R. Mardis, Ed. Exploratory Analysis of TP53 Mutations in Circulating Tumour DNA as Biomarkers of Treatment Response for Patients with Relapsed High-Grade Serous Ovarian Carcinoma: A Retrospective Study, *PLOS Med.* 13, e1002198 (2016).

37. T. Forshew, M. Murtaza, C. Parkinson, D. Gale, D. W. Y. Tsui, F. Kaper, S.-J. Dawson, A. M. Piskorz, M. Jimenez-Linan, D. Bentley, J. Hadfield, A. P. May, C. Caldas, J. D. Brenton, N. Rosenfeld, Noninvasive identification and monitoring of cancer mutations by targeted deep sequencing of plasma DNA., *Sci. Transl. Med.* 4, 136ra68 (2012).

38. A. R. Thierry, S. El Messaoudi, P. B. Gahan, P. Anker, M. Stroun, Origins, structures, and functions of circulating DNA in oncology, *Cancer Metastasis Rev.* 35, 347-376 (2016).

39. M. G. Best, N. Sol, B. A. Tannous, P. Wesseling, T. Wurdinger, RNA-Seq of Tumor-Educated Platelets Enables Blood-Based Pan-Cancer, Multiclass, and Molecular Pathway Cancer Diagnostics, *Cancer Cell* 28, 666-676 (2015).

40. M. G. Best, N. Sol, S. G. J. G. In't Veld, A. Vancura, M. Muller, A.-L. N. Niemeijer, A. V Fejes, L.-A. Tjon Kon Fat, A. E. Huis In't Veld, C. Leurs, T. Y. Le Large, L. L. Meijer, I. E. Kooi, F. Rustenburg, P. Schellen, H. Verschueren, E. Post, L. E. Wedekind, J. Bracht, M. Esenkbrink, L. Wils, F. Favaro, J. D. Schoonhoven, J. Tannous, H. Meijers-Heijboer, G. Kazemier, E. Giovannetti, J. C. Reijneveld, S. Idema, J. Killestein, M. Heger, S. C. de Jager, R. T. Urbanus, I. E. Hoefer, G. Pasterkamp, C. Mannhalter, J. Gomez-Arroyo, H.-J. Bogaard, D. P. Noske, W. P. Vandertop, D. van den Broek, B. Ylstra, R. J. A. Nilsson, P. Wesseling, N. Karachaliou, R. Rosell, E. Lee-Lewandrowski, K. B. Lewandrowski, B. A. Tannous, A. J. de Langen, E. F. Smit, M. M. van den Heuvel, T. Wurdinger, Swarm Intelligence-Enhanced Detection of Non-Small-Cell Lung Cancer Using Tumor-Educated Platelets., *Cancer Cell* 32, 238-252.e9 (2017).

41. A. L. Riediger, S. Dietz, U. Schirmer, M. Meister, I. Heinzmann-Groth, M. Schneider, T. Muley, M. Thomas, H. Sültmann, Mutation analysis of circulating plasma DNA to determine response to EGFR tyrosine kinase inhibitor therapy of lung adenocarcinoma patients, *Sci. Rep.* 6, 33505 (2016).

42. J. Belic, M. Koch, P. Ulz, M. Auer, T. Gerhalter, S. Mohan, K. Fischereder, E. Petru, T. Bauernhofer, J. B. Geigl, M. R. Speicher, E. Heitzer, Rapid Identification of Plasma DNA Samples with Increased ctDNA Levels by a Modified FAST-SeqS Approach, *Clin. Chem.* 61, 838-849 (2015).

43. D. G. Stover, H. A. Parsons, G. Ha, S. S. Freeman, W. T. Barry, H. Guo, A. D. Choudhury, G. Gydush, S. C. Reed, J. Rhoades, D. Rotem, M. E. Hughes, D. A. Dillon, A. H. Partridge, N. Wagle, I. E. Krop, G. Getz, T. R. Golub, J. C. Love, E. P. Winer, S. M. Tolaney, N. U. Lin, V. A. Adalsteinsson, Association of Cell-Free DNA Tumor Fraction and Somatic Copy Number Alterations With Survival in Metastatic Triple-Negative Breast Cancer., *J. Clin. Oncol.* 36, 543-553 (2018).

44. B. Routy, E. Le Chatelier, L. Derosa, C. P. M. Duong, M. T. Alou, R. Daillere, A. Fluckiger, M. Messaoudene, C. Rauber, M. P. Roberti, M. Fidelle, C. Flament, V. Poirier-Colame, P. Opolon, C. Klein, K. Iribarren, L. Mondragon, N. Jacquelot, B. Qu, G. Ferrere, C. Clémenson, L. Mezquita, J. R. Masip, C. Naltet, S. Brosseau, C. Kaderbhai, C. Richard, H. Rizvi, F. Levenez, N. Galleron, B. Quinquis, N. Pons, B. Ryffel, V. Minard-Colin, P. Gonin, J.-C. Soria, E. Deutsch, Y. Loriot, F. Ghiringhelli, G. Zalcman, F. Goldwasser, B. Escudier, M. D. Hellmann, A. Eggermont, D. Raoult, L. Albiges, G. Kroemer, L. Zitvogel, Gut microbiome influences efficacy of PD-1-based immunotherapy against epithelial tumors., *Science* 359, 91-97 (2018).

45. C. Abbosh, N. J. Birkbak, G. A. Wilson, M. Jamal-Hanjani, T. Constantin, R. Salari, J. Le Quesne, D. A. Moore, S. Veeriah, R. Rosenthal, T. Marafioti, E. Kirkizlar, T. B. K. Watkins, N. McGranahan, S. Ward, L. Martinson, J. Riley, F. Fraioli, M. Al Bakir, E. Grönroos, F. Zambrana, R. Endozo, W. L. Bi, F. M. Fennessy, N. Sponer, D. Johnson, J. Laycock, S. Shafi, J. Czyzewska-Khan, A. Rowan, T. Chambers, N. Matthews, S. Turajlic, C. Hiley, S. M. Lee, M. D. Forster, T. Ahmad, M. Falzon, E. Borg, D. Lawrence, M. Hayward, S. Kolvekar, N. Panagiotopoulos, S. M. Janes, R. Thakrar, A. Ahmed, F. Blackhall, Y. Summers, D. Hafez, A. Naik, A. Ganguly, S. Kareht, R. Shah, L. Joseph, A. Marie Quinn, P. A. Crosbie, B. Naidu, G. Middleton, G. Langman, S. Trotter, M. Nicolson, H. Remmen, K. Kerr, M. Chetty, L. Gomersall, D. A. Fennell, A. Nakas, S. Rathinam, G. Anand, S. Khan, P. Russell, V. Ezhil, B. Ismail, M. Irvin-Sellers, V. Prakash, J. F. Lester, M. Kornaszewska, R. Attanoos, H. Adams, H. Davies, D. Oukrif, A. U. Akarca, J. A. Hartley, H. L. Lowe, S. Lock, N. Iles, H. Bell, Y. Ngai, G. Elgar, Z. Szallasi, R. F. Schwarz, J. Herrero, A. Stewart, S. A. Quezada, K. S. Peggs, P. Van Loo, C. Dive, C. J. Lin, M. Rabinowitz, H. J. W. L. Aerts, A. Hackshaw, J. A. Shaw, B. G. Zimmermann, TRACERx consortium, PEACE consortium, C. Swanton, Phylogenetic ctDNA analysis depicts early-stage lung cancer evolution., *Nature* 545, 446-451 (2017).

46. D. Hanahan, R. A. Weinberg, Hallmarks of cancer: the next generation., *Cell* 144, 646-74 (2011).

47. K. M. Patel, K. E. van der Vos, C. G. Smith, F. Mouliere, D. Tsui, J. Morris, D. Chandrananda, F. Marass, D. van den Broek, D. E. Neal, V. J. Gnanapragasam, T. Forshew, B. W. van Rhijn, C. E. Massie, N. Rosenfeld, M. S. van der Heijden, Association Of Plasma And Urinary Mutant DNA With Clinical Outcomes In Muscle Invasive Bladder Cancer, *Sci. Rep.* 7, 5554 (2017).

48. H. Li, R. Durbin, Fast and accurate short read alignment with Burrows-Wheeler transform, *Bioinformatics* 25, 1754-1760 (2009).

49. I. Scheinin, D. Sie, H. Bengtsson, M. A. van de Wiel, A. B. Olshen, H. F. van Thuijl, H. F. van Essen, P. P. Eijk, F. Rustenburg, G. A. Meijer, J. C. Reijneveld, P. Wesseling, D. Pinkel, D. G. Albertson, B. Ylstra, DNA copy number analysis of fresh and formalin-fixed specimens by shallow whole-genome sequencing with identification and exclusion of problematic regions in the genome assembly, *Genome Res.* 24, 2022-2032 (2014).

The invention claimed is:

1. A computer-implemented method for detecting variant nucleic acid from a cell-free nucleic acid-containing sample from a subject, wherein the variant nucleic acid is circulating tumor DNA (ctDNA), the method comprising:
   a) providing data representing fragment sizes of nucleic acid fragments obtained from said sample;
   b) causing a processor to process the data from step a) according to a classification algorithm that has been trained on a training set comprising a plurality of samples of cell-free nucleic acid containing the variant nucleic acid and a plurality of samples not containing the variant nucleic acid, wherein said classification algorithm operates to classify sample data into one of at least two classes, the at least two classes comprising a first class containing the variant nucleic acid and a second class not containing the variant nucleic acid, wherein said classification algorithm operates to classify sample data into one of said at least two classes based on at least a plurality of cell-free DNA (cfDNA) fragment size features selected from the group consisting of:
      (i) a proportion of fragments in a 20-150 bp size range (P(20-150));
      (ii) a proportion of fragments in a 100-150 bp size range (P(100-150));
      (iii) a proportion of fragments in a 160-180 bp size range (P(160-180));
      (iv) a proportion of fragments in a 180-220 bp size range (P(180-220));
      (v) a proportion of fragments in a 250-320 bp size range (P(250-320));
      (vi) a ratio of the proportions P(20-150)/P(160-180);
      (vii) a ratio of the proportion P(100-150) divided by the proportion of fragments in a 163-169 bp size range;
      (viii) a ratio of the proportions P(20-150)/P180-220); and
      (ix) amplitude oscillations in fragment size density with 10 bp periodicity,
   wherein the data representing fragment sizes of nucleic acid fragments in step a) includes the plurality of cfDNA fragment size features used by the classification algorithm; and
   c) outputting the classification of the sample from step b) and thereby determining whether the sample contains ctDNA,
   wherein the classification of the sample as containing ctDNA or not is used to predict whether said sample or a further sample from the subject will be susceptible to further ctDNA analysis,
   wherein said sample is classified as containing ctDNA, said further ctDNA analysis comprises sequencing to a greater sequencing depth and/or targeted sequencing of ctDNA in said sample or said further sample, and the sample or further sample is subjected to said further ctDNA analysis.

2. The method of claim 1, wherein the data representing fragment sizes of the nucleic acid fragments comprise fragment sizes inferred from sequence reads, fragment sizes determined by fluorimetry, or fragment sizes determined by densitometry, or wherein the fragment sizes of cfDNA fragments are inferred from sequence reads using mapping locations of read ends in a reference genome of a species from which the sample was obtained following alignment of the sequence reads with the reference genome.

3. The method of claim 1, wherein the plurality of cfDNA fragment size features comprise: P(160-180), P(180-220), P(250-320) and the amplitude oscillations in fragment size density with 10 bp periodicity.

4. The method of claim 1, wherein said classification algorithm operates to classify sample data into one of said at least two classes based on said plurality of cell-free DNA (cfDNA) fragment size features and a deviation from copy number neutrality feature which is a trimmed Median Absolute Deviation from copy number neutrality (t-MAD) score or an ichorCNA score.

5. The method of claim 4, wherein the t-MAD score is determined by trimming regions of genome that exhibit high copy number variability in whole genome datasets derived from healthy subjects and then calculating a median absolute deviation from $\log_2 R=0$ of non-trimmed regions of the genome.

6. The method of claim 1, wherein the classification algorithm performs Random Forests (RF) analysis, logistic regression (LR) analysis, or support vector machine (SVM) analysis, wherein the performance of the classification algorithm when trained on the training set is assessed by an area under the curve (AUC) value from a receiver operating characteristic (ROC) analysis, or wherein the classification algorithm that has been trained on a training set comprising at least 10 samples from healthy subjects and at 10 samples from subjects known to have a cancer.

7. The method according to claim 1, wherein the data provided in step a) represent whole-genome sequence (WGS) reads, Tailored Panel Sequencing (TAPAS) sequence reads, Tagged-Amplicon Deep Sequencing (Tam-Seq) reads, hybrid-capture sequence reads, focused-exome sequence reads or whole-exome sequence reads.

8. The method according to claim 7, wherein the data provided in step a) represent shallow whole-genome sequence (sWGS) reads, optionally 0.4× depth WGS reads.

9. The method according to claim 1,
   wherein the data provided in step a) represent fragment sizes of multiple DNA fragments from a substantially cell-free liquid sample from a subject having or suspected as having a cancer selected from melanoma, lung cancer, cholangiocarcinoma, bladder cancer, oesophageal cancer, colorectal cancer, ovarian cancer, glioma, pancreatic cancer, renal cancer and breast cancer, or
   wherein the sample is a plasma sample, a urine sample, a saliva sample, a cerebrospinal fluid sample, a serum sample, or other DNA-containing biological liquid sample.

10. The method of claim 1, wherein the method is for detecting a presence of, growth of, prognosis of, regression of, treatment response of, or recurrence of a cancer in a subject from which the sample has been obtained.

11. The method of claim 10, wherein the presence of ctDNA in the sample is distinguished from cfDNA containing somatic mutations of non-cancerous origin, wherein the non-cancerous origin comprises clonal expansions of normal epithelia or clonal hematopoiesis of indeterminate potential (CHIP).

12. The method of claim 10, wherein the fragment size data provided in step a) represent sequence reads of multiple DNA fragments from a substantially cell-free liquid sample from a subject and wherein the method is for determining whether the sample contains ctDNA or contains cfDNA from CHIP, wherein the classification algorithm has been trained on a training set further comprising a plurality of samples of cfDNA obtained from subjects having CHIP, and wherein said at least two classes further comprise a third class containing CHIP-derived cfDNA.

13. The method of claim 1, further comprising:
analysing the cell-free nucleic acid-containing sample, or a library derived from the cell-free nucleic acid-containing sample, wherein the sample has been obtained from the subject, to determine fragment sizes of nucleic acid fragments in said sample or said library;
wherein said analysing comprises:
sequencing nucleic acids from the nucleic acid-containing sample or the library to obtain sequence reads and inferring the fragment sizes from the sequence reads;
measuring the fragment sizes of nucleic acids from the nucleic acid-containing sample or the library by fluorimetry; or
measuring the fragment sizes of nucleic acids from the nucleic acid-containing sample or the library by densitometry.

14. The method of claim 1, further comprising:
sequencing the cell-free nucleic acid-containing sample, or a library derived from the cell-free nucleic acid-containing to obtain a plurality of sequence reads; and
processing the plurality of sequence reads to determine sequence data representing fragment sizes of cfDNA fragments obtained from said sample and/or representing a measure of deviation from copy number neutrality of the cfDNA fragments obtained from said sample.

15. The method of claim 14, wherein the sequencing comprises generating a sequencing library from the sample and performing whole-genome sequencing, Tailored Panel Sequencing (TAPAS) sequencing, hybrid-capture sequencing, TAm-Seq sequencing, focused-exome sequencing, whole-exome sequencing, or wherein the sequencing comprises generating an indexed sequencing library and performing shallow whole genome sequencing (sWGS), optionally sWGS to a depth of 0.4×, or wherein processing the sequence reads comprises one or more of the following steps:
aligning sequence reads to a reference genome of a species of the subject;
removal of contaminating adapter sequences;
removal of PCR and optical duplicates;
removal of sequence reads of low mapping quality; and
if multiplex sequencing, de-multiplexing by excluding mismatches in sequencing barcodes.

16. The method of claim 1, wherein the sample is a plasma sample, a urine sample, a saliva sample, a cerebrospinal fluid sample, a serum sample, or other DNA-containing biological liquid sample.

17. The method of claim 14,
wherein the method is for detecting a presence of, growth of, prognosis of, regression of, treatment response of, or recurrence of a cancer in a subject from which the sample has been obtained, wherein the presence of ctDNA is distinguished from the presence of cfDNA containing somatic mutations of non-cancerous origin, wherein a somatic mutation containing cfDNA fragment is classified as being of tumour origin or being of CHIP origin based on a plurality of fragment size features determined from the plurality of sequence reads.

18. The method of claim 1, wherein:
said sample is a plasma sample and wherein a probability that the sample contains ctDNA as determined by the classification algorithm is used to determine whether ctDNA will be detectable in a urine sample; or
said sample is a urine sample and wherein a probability that the sample contains ctDNA as determined by the classification algorithm is used to determine whether ctDNA will be detectable in a plasma sample.

\* \* \* \* \*